United States Patent
Adachi et al.

(10) Patent No.: US 6,455,528 B1
(45) Date of Patent: Sep. 24, 2002

(54) PIPERAZINE COMPOUNDS AND MEDICINAL USE THEREOF

(75) Inventors: Kunitomo Adachi, Fukuoka; Yoshiyuki Aoki, Hirakata; Tokushi Hanano, Iruma; Hiroshi Morimoto; Masao Hisadome, both of Fukuoka, all of (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/529,491

(22) PCT Filed: Oct. 13, 1998

(86) PCT No.: PCT/JP98/04613

§ 371 (c)(1),
(2), (4) Date: Apr. 14, 2000

(87) PCT Pub. No.: WO99/19301

PCT Pub. Date: Apr. 22, 1999

(30) Foreign Application Priority Data

Oct. 14, 1997 (JP) .............................. 9-280880
Sep. 16, 1998 (JP) ........................... 10-261100

(51) Int. Cl.$^7$ ................... A61K 31/506; A61K 31/495; C07D 403/04; C07D 295/155
(52) U.S. Cl. ................... 514/252.14; 544/295; 544/357; 544/360; 544/369; 544/370; 544/392; 544/393; 514/252.11; 514/253.12; 514/253.01; 514/253.13; 514/254.02; 514/254.05; 514/255.03
(58) Field of Search ................ 544/295, 360, 544/357; 514/252.11, 252.14, 253.12

(56) References Cited

U.S. PATENT DOCUMENTS

| | | | |
|---|---|---|---|
| 5,286,728 A | 2/1994 | Ferrini ..................... 514/255 |
| 5,563,141 A | * 10/1996 | Wayne et al. ............... 514/252 |
| 5,563,143 A | 10/1996 | Cohan et al. ............... 514/256 |
| 5,569,659 A | 10/1996 | Reitz ........................ 514/253 |
| 5,670,503 A | 9/1997 | Kawai et al. ............... 514/243 |
| 5,789,409 A | 8/1998 | Ogata et al. ............... 514/252 |
| 5,827,513 A | 10/1998 | Bonda et al. ............... 424/85.2 |

FOREIGN PATENT DOCUMENTS

JP 52-156879 * 12/1977
WO WO 92/12154 7/1992

OTHER PUBLICATIONS

Reitz et al., "N–Aryl–N'–Benzylpiperazines as Potential Antipsychotic Agents", *Journal of Medicinal Chemistry*, vol. 38, No. 21 (1995), pp. 4211–4222.
Derwent Abtract for JP 52–15687 (Dec. 27, 1977).

* cited by examiner

Primary Examiner—Emily Bernhardt
(74) Attorney, Agent, or Firm—Crowell & Moring LLP

(57) ABSTRACT

The present invention relates to a piperazine compound of the formula

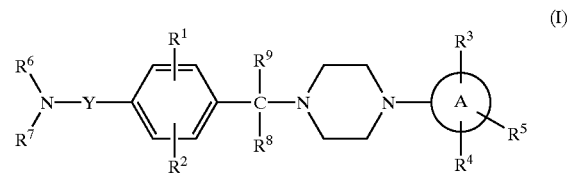

wherein $R^1$ and $R^2$ are each hydrogen, halogen, lower alkyl, lower alkoxy, amino, substituted amino, nitro, hydroxy or cyano, $R^3$, $R^4$ and $R^5$ are each hydrogen, halogen, lower alkyl, lower alkoxy, nitro, amino, substituted amino or hydroxy, $R^6$ and $R^7$ are each hydrogen, lower alkyl, lower alkyl substituted by halogen, aralkyl, acyl or lower acyl substituted by halogen, $R^8$ and $R^9$ are each hydrogen or lower alkyl, Y is lower alkylene and the like, and ring A is phenyl, pyrimidyl, thiazolyl, pyridyl, pyrazyl or imidazolyl, a pharmaceutically acceptable salt thereof and pharmaceutical agents containing these compounds. The compound of the present invention has superior TNF-α production inhibitory effect and/or IL-10 production promoting effect, and, since it is free of or shows only strikingly reduced expression of an effect on the central nervous system, the compound is useful as a highly safe and superior TNF-α production inhibitor an/or IL-10 production promoter and is useful as an agent for the prophylaxis or treatment of various diseases caused by abnormal TNF-α production, diseases curable with IL-10, such as chronic inflammatory diseases, acute inflammatory diseases, inflammatory diseases due to infection, autoimmune diseases, allergic diseases, and TNF-α mediated diseases.

22 Claims, No Drawings

PIPERAZINE COMPOUNDS AND MEDICINAL USE THEREOF

TECHNICAL FIELD

The present invention relates to a pharmaceutical agent, particularly, a piperazine compound useful as a TNF-α production inhibitor and/or an IL-10 production promoter, and use thereof as a pharmaceutical agent.

BACKGROUND ART

There are a number of cytokines that have been found as proteins involved in the expression of biological functions, such as biological immune responses, inflammatory reactions and the like. Of such cytokines, tumor necrosis factor alpha (hereinafter to be referred to as TNF-α) was first found as a cytokine having an anti-tumor effect. Subsequent studies have characterized it as a cytokine involved in inflammations. In recent years, TNF-α has been recognized as a cytokine broadly involved in biophylaxis through inflammation and immune responses.

For example, TNF-α has been reported to show a promoting effect on the production of interleukin-1 (hereinafter to be referred to as IL-1), which is an inflammatory cytokine, and the like, an endotoxin shock induction effect, a fibroblast proliferation effect, a bone resorption effect, and an action to cause arthritis, such as cartilage destruction effect and the like [Beutler, B., et al., Nature, 316, 552–554 (1985):Peetre, C., et al., J. Clin. Invest., 78, 1694–1700 (1986):Bevilacqua, M. P., et al., Science, 241, 1160–1165 (1989)].

In rheumatoid arthritis, TNF-α activity has been found in synovial fluid and sera [Macnaul, K. L., et al., J. Immunol., 145, 4154–4166 (1990):Brennan, F. M., et al., J. Immunol., 22, 1907–1912 (1992)]. Since an anti-TNF-α chimera antibody has been recently reported to be effective against rheumatoid arthritis and Crohn's disease, the importance of TNF-α in these diseases has been recognized [Elliott, M. J, et al., Arthritis Rheum., 36, 1681–1690 (1993): VanDullemen, H. M. et al., Gastroenterology 109, 129–135 (1995)].

Increased TNF-α concentrations have been reported in the expectoration of patients with adult respiratory distress syndrome (ARDS), which is a serious respiratory disease, and TNF-α is considered to be involved in ARDS [Marks, J. D. et al., Am. Rev. Respir. Dis. 141, 94–97 (1990), Millar, A. B. et al., Nature, 324, 73 (1986)]. TNF-α is also considered to be involved in viral hepatitis and fulminant viral hepatitis [Sheron, N. et al., Lancet 336, 321–322 (1990), Muto, Y. et al., Lancet, ii, 72–74 (1986)].

In the case of myocardial ischemia, such as acute myocardial infarction, the TNF-α concentration in blood has been reported to increase [Latini, R., et al., J. Cardiovasc. Pharmacol., 23, 1–6 (1990)], thereby suggesting the involvement of TNF-α in such disease state [Squadrito, F. et al., Inflammation Res., 45, 14–19 (1996), Lefer, A. M. et al., Science, 249, 61–64 (1990)]. More recently, TNF-α has been reported to inhibit myocardial contraction [Finkel, M. S., et al., Science, 257, 387–389 (1992); Pagani, D. F., et al., J. Clin. Invest., 90, 389–398 (1992)].

In addition, TNF-α has been found to be equivalent to cachectin which is a cachexia inducer that hypercatabolizes the systemic metabolism in cancer and infectious diseases and causes utmost exhaustion [B. Beutler, D. Greenwald, J. D. Hulmes et al., Nature, 316, 552–554 (1985)].

TNF-α is listed as one of the causes of sepsis [Starnes, H. F. Jr. et al., J. Immunol., 145, 4185–4191 (1990), Lechner, A. J. et al., Am. J. Physiol., 263, 526–535 (1992)], and an inhibitory effect on septic shock has been acknowledged in an experiment using a TNF-α antibody [Starnes, H. F. Jr., et al., J. Immunol., 145, 4185–4191 (1990); Beutler, B., et al., Science, 229, 869–871 (1985)].

Other than the above-mentioned, possible involvement of TNF-α has been suggested in osteoarthritis [Lewis, A. J. et al., Immunopharm. Immunotoxicol., 17, 607–613 (1995), Venn, G., et al., Arthritis Rheum., 36(6), 819–826 (1993)], multiple sclerosis [Sharief, M. K., etal., Engl. J. Med., 325(7), 467–472 (1991), Beck, J. et al., Acta. Neurol. Scand., 78, 318–323 (1988), Franciotta, D. M. et al., Ann. Neurol., 26, 787–789 (1989), Hofmann, F. M. et al., J. Exp. Med., 170, 607–612 (1989), Gallo, P. et al., J. Neuroimmunol., 23, 41–44 (1989)], Kawasaki disease [Matsubara, T., et al., Clin. Immunol., Immunopathol., 56, 29–36 (1990)], inflammatory bowel diseases such as ulcerative colitis, Crohn's disease and the like [Murch, S. et al., Arch. Dis. Child, 66, 561 (1991), Van Dullemen et al., Gastroenterology, 109, 129–135 (1995)], Behqet's disease [Akoglu, T., et al., J. Rheumatol., 17, 1107–1108(1990)], systemic lupus erythematosus (SLE) [Maury, C. P. J., et al., Arthritis Rheum., 32, 146–150(1989)], graft versus host disease (GvHD) [Piruet et al., J. Exp. Med., 170, 655–663 (1987), Holler et al., Blood, 75, 1011–1016 (1990), Irle et al., Bone Marrow Transplant., 3, 127 (1988), Symington et al., Transplantation, 50, 518–521 (1990), Herve et al., Blood, 79, 3362–3368 (1992), Herve et al., Immunol. Rev., 129, 31–55 (1992), Nestel, F. P., et al., J. Exp. Med., 175, 405–413 (1992)], allograft rejection [Imagawa et al., Transplantation, 50, 189–193 (1990)], malaria [Grau, G. E., et al., Science, 237, 1210–1212 (1987), Grau et al., N. Engl. J. Med., 320, 1586–1591 (1989), Kwiatkowski et al., Q. J. Med., 86, 91–98 (1993)], acquired immunodeficiency syndrome (AIDS) [Lahdevirt et al., Am. J. Med., 85, 289–291 (1988), Tracy, Cancer. Cell, 1, 62–63 (1989), odeh, J. Intern. Med., 228, 549–556 (1990), Bromberg et al., J. Immunol., 148, 3412–3417 (1992), Wllaurie et al., AIDS, 6, 1265–1268 (1992), Ayehunie et al., Clin. Exp. Immunol., 91, 37–42 (1993)], meningitis [Waage, A., et al., Lancet I, 355–357 (1987) diabetes [Held, W. et al., Proc. Natl. Acad. Sci. USA, 87, 2239–2243 (1990), Hotamisligil, G. S., et al., Science, 259, 87–91 (1993)], thermal burn [Marano, M. A. et al., Surg. Gynecol. Obstet., 170, 32–38 (1990)], ischemia-reperfusion injury [Squadrito, F. et al., J. Lipid Mediators 8, 53–65 (1993)], chronic heart failure [Levine, B. et al., New Engl. J. Med., 323, 236–241 (1990)], infection [Chang et al., Immunol. Infect. Dis., 2, 61–68 (1992), Harvell, J. Immunol., 143, 2894–2899 (1989), Kindler et al., Cell, 56,731–740 (1989), Liew et al., Immunology, 69, 570–573 (1990), Nakane et al., Infect. Immun., 57, 3331–3337 (1989), Nakano et al., J. Immunol., 144, 1935–1941 (1990), Opal etal., J. Infect. Dis., 161, 1148–1152 (1990)], contact dermatitis [Piguet et al., J. Exp. Med., 173, 673–679 (1991)], bacterial shock [Exley et al., Lancet, 335, 1275–1277 (1990)], endotoxemia [Beutler et al., Science, 229, 860–871 (1985)], demyelinating disease [Probert et al., Proc. Natl. Acad. Sic. U.S.A., 92, 11294–11298 (1995)], fibroid lung [Piguet et al., J. Exp. Med., 170, 655–663 (1989), Piguet et al., Nature, 344, 245–247 (1990)], osteoporosis [Ishimi et al., J. Immunol., 145, 3297–3303 (1990), MacDonald et al., Br. J. Rheumatol., 31, 149–155 (1992)], thrombus due to disseminated intravascular coagulation (DIC) and the like [Tracy et al., Surg. Gen. Obstet., 164, 415–422 (1987), Van et al., N. Engl. J. Med., 322, 1622–1629 (1990)] and the like.

Interleukin-10 (hereinafter to be referred to as IL-10) is a cytokine mainly produced by type 2 helper T cells. IL-10 potentiates activity of B cells and mast cells, but for macrophages, it is one of the inhibitory cytokines that strongly inhibit the function of type 1 helper T cell involved in cellular immunity, because they inhibit antigen presenting ability or cytokine (TNF-α, IL-1 and the like) production capability of macrophages. Thus, IL-10 plays an important role in the immune response system. For example, IL-10 has been reported to inhibit TNF-α production by joint synovial cells in rheumatoid arthritis [Isomaki, P, et al., Arthritis Rheum., 39, 386–395 (1996)]. It has been also reported that, when IL-10 is intravenously injected to a healthy subject and hemocytes of the subject are stimulated by endotoxin, TNF-α production is inhibited [Chernoff, A.E, et al., J. Immunol., 154, 5492–5499 (1995)]. Moreover, a report has been documented that, in IL-10 gene knockout mice, chronic colitis spontaneously occurs and, when compared to normal mice, inflammatory cytokine (TNF-α, IL-1 and the like) concentration in colon tissue significantly increases, but that administration of IL-10 inhibits incidence of colitis and progress of the disease [Breg D. J. et al., J. Clin. Invest., 98, 1010 (1996)]. In the tumor cells, into which IL-10 gene has been transferred, the tumor growth can be inhibited and metastasis of the tumor can be also inhibited [Kundu N. et al., Int. J. Cancer, 76, 713 (1998)]. At present, a gene recombinant human IL-10 has been under development as a therapeutic drug of septic shock, Crohn's disease, rheumatoid arthritis and malignant tumor.

JP-A-52-156879 discloses a piperazine derivative useful as an analgesic and antiphlogistic agent, psychotropic, anti-anxiety drug and hypotensive agent, and JP-A-9-208570 discloses a benzylpiperazine derivative useful as an anti-allergic agent and anti-inflammatory agent. U.S. Pat. No. 5,569,659 discloses a 4-arylpiperazine compound and a 4-arylpiperidine compound useful as an antipsychotic drug, and J. Med. Chem., vol. 38, pp. 4211–4222 (1995) discloses an N-aryl-N'-benzylpiperazine compound which is useful as an antipsychotic drug. Moreover, WO92/12154 discloses an imidazotriazine compound, and WO94/19350 discloses a pyrazolotriazine compound, respectively as an IL-1 and TNF-α production inhibitor.

As mentioned above, it has become clear that hyperproduction of TNF-α causes intense effect on normal cells and various disease states. Thus, a TNF-α production inhibitor that can cure such disease states has been desired. However, the anti-TNF-α antibody currently under development is associated with therapeutic problems such as availability only as an injection, easy generation of antibody and the like, and therefore, it is not entirely satisfactory as a TNF-α production inhibitor.

A pharmaceutical agent that promotes the production of IL-10 is expected to be a therapeutic agent of the diseases in which TNF-α is involved, because IL-10 inhibits production of TNF-α. However, such pharmaceutical agent is not commercially available at the moment. A gene recombinant human IL-10 now being developed is a biological preparation, which is subject to therapeutic problems such as availability only as an injection, easy generation of antibody and the like, as in the case of anti-TNF-α antibody, and therefore, it is insufficient.

The compound disclosed in the above-mentioned JP-A-52-156879 has lower alkylene between phenyl and piperazine ring wherein the lower alkylene may be methylene, ethylene, propylene, trimethylene or ethylidene. Specific examples include only the compounds wherein lower alkylene is ethylene or propylene. These disclosed compounds have an analgesic and antiphlogistic effect but simultaneously have an effect on the central nervous system. Because of the side effects due to the effect on the central nervous system, the development of the compound as an analgesic or antiphlogistic agent is difficult. In addition, the compounds disclosed in WO92/12154 and WO94/19350 do not show sufficient TNF-α production inhibitory effect, and are not satisfactory.

It is therefore an object of the present invention to provide a compound which has a superior TNF-α production inhibitory effect and/or IL-10 production promoting effect, has no effect on the central nervous system, and which is useful for the prophylaxis or treatment of autoimmune diseases, inflammatory diseases and the like.

The present inventors have conducted intensive studies with the purpose of solving the above-mentioned problems and found that, of the compounds described in JP-A-52-156879, a compound wherein lower alkylene between phenyl and piperazine ring is methylene or methylene substituted by lower alkyl, which compound is not concretely disclosed therein, has superior TNF-α production inhibitory effect and/or IL-10 production promoting effect and is free of or shows only strikingly reduced expression of an effect on the central nervous system, which resulted in the completion of the present invention.

DISCLOSURE OF THE INVENTION

Accordingly, the present invention provides the following.
(1) A piperazine compound of the formula

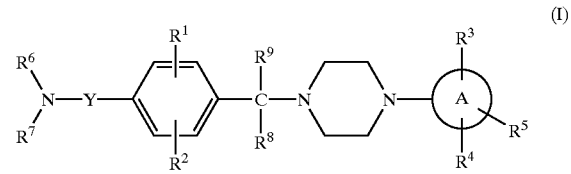

wherein
$R^1$ and $R^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;
$R^3$, $R^4$ and $R^5$ are the same or different and each is hydrogen, halogen, lower alkyl, lower alkoxy, nitro, amino, hydroxy or amino mono- or di-substituted by a group selected from the group consisting of lower alkyl and lower acyl;
$R^6$ and $R^7$ are the same or different and each is hydrogen, lower alkyl, lower alkyl substituted by 1 to 3 halogen(s), aralkyl, acyl or lower acyl substituted by 1 to 3 halogen(s);
$R^8$ and $R^9$ are the same or different and each is hydrogen or lower alkyl;
Y is a group of the formula

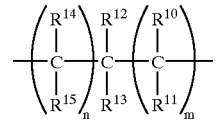

wherein $R^{10}$ and $R^{11}$ are the same or different and each is hydrogen or lower alkyl, $R^{12}$ and $R^{13}$ are the same or different and each is hydrogen or lower alkyl, or $R^{12}$ and $R^{13}$ in combination form alkylene, $R^{14}$ and $R^{15}$ are the same or different and each is hydrogen or lower alkyl, m is an integer of 0–2, n is an integer of 0–2, and $0 \leq m+n \leq 2$; and ring A is phenyl, pyrimidyl, thiazolyl, pyridyl, pyrazyl or imidazolyl, provided that when one of $R^6$ and $R^7$ is hydrogen and the other is butyl, in Y, both $R^{12}$ and $R^{13}$ are hydrogen, m and n are 0, $R^1$, $R^2$, $R^8$ and $R^9$ are hydrogen, and ring A is phenyl, one of $R^3$, $R^4$ and $R^5$ should not be 2-isopropoxy and the remaining two should not be hydrogen, and a pharmaceutically acceptable salt thereof.

(2) The piperazine compound of the above-mentioned (1), which has the following formula (I-a)

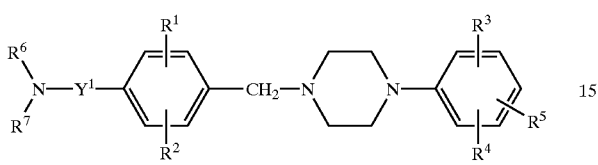

wherein
  $R^1$ and $R^2$ are the same or different and each is hydrogen, halogen, lower alkyl, lower alkoxy, amino, amino mono- or di-substituted by a group selected from the group consisting of lower alkyl. and lower acyl, nitro, hydroxy or cyano;
  $R^3$, $R^4$ and $R^5$ are the same or different and each is hydrogen, halogen, lower alkyl, lower alkoxy, nitro, amino, hydroxy or amino mono- or di-substituted by a group selected from the group consisting of lower alkyl and lower acyl;
  $R^6$ and $R^7$ are the same or different and each is hydrogen, lower alkyl, lower alkyl substituted by 1 to 3 halogen (s), aralkyl, acyl or lower acyl substituted by 1 to 3 halogen(s); and
  $Y^1$ is a group of the formula

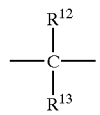

wherein $R^{12}$ and $R^{13}$ are the same or different and each is hydrogen or lower alkyl, or $R^{12}$ and $R^{13}$ in combination form alkylene,
  provided that when one of $R^6$ and $R^7$ is hydrogen and the other is butyl, in $Y^1$, both $R^{12}$ and $R^{13}$ are hydrogen and $R^1$ and $R^2$ are hydrogen, one of $R^3$, $R^4$ and $R^5$ should not be 2-isopropoxy and the remaining two should not be hydrogen, and a pharmaceutically acceptable salt thereof.

(3) The piperazine compound of the above-mentioned (1), which has the following formula (I-b)

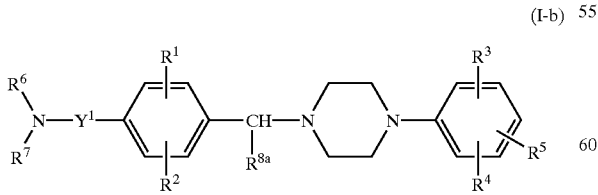

wherein
  $R^1$ and $R^2$ are the same or different and each is hydrogen, halogen, lower alkyl, lower alkoxy, amino, amino mono-or di-substituted by a group selected from the group consisting of lower alkyl and lower acyl, nitro, hydroxy or cyano;
  $R^3$, $R^4$ and $R^5$ are the same or different and each is hydrogen, halogen, lower alkyl, lower alkoxy, nitro, amino, hydroxy or amino mono-or di-substituted by a group selected from the group consisting of lower alkyl and lower acyl;
  $R^6$ and $R^7$ are the same or different and each is hydrogen, lower alkyl, lower alkyl substituted by 1 to 3 halogen (s), aralkyl, acyl or lower acyl substituted by 1 to 3 halogen(s);
  $R^{8a}$ is lower alkyl; and
  $Y^1$ is a group of the formula

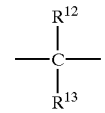

wherein $R^{12}$ and $R^{13}$ are the same or different and each is hydrogen or lower alkyl, or $R^{12}$ and $R^{13}$ in combination form alkylene, and a pharmaceutically acceptable salt thereof.

(4) The piperazine compound of the above-mentioned (3), wherein-$R^{8a}$ is methyl and a pharmaceutically acceptable salt thereof.

(5) The piperazine compound of the above-mentioned (1), which has the following formula (I-c)

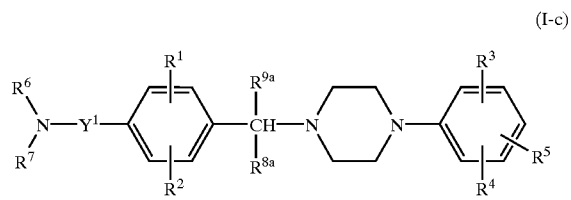

wherein
  $R^1$ and $R^2$ are the same or different and each is hydrogen, halogen, lower alkyl, lower alkoxy, amino, amino mono-or di-substituted by a group selected from the group consisting of lower alkyl and lower acyl, nitro, hydroxy or cyano;
  $R^3$, $R^4$ and $R^5$ are the same or different and each is hydrogen, halogen, lower alkyl, lower alkoxy, nitro, amino, hydroxy or amino mono-or di-substituted by a group selected from the group consisting of lower alkyl and lower acyl;
  $R^6$ and $R^7$ are the same or different and each is hydrogen, lower alkyl, lower alkyl substituted by 1 to 3 halogen (s), aralkyl, acyl or lower acyl substituted by 1 to 3 halogen(s);
  $R^{8a}$ and $R^{9a}$ are the same or different and each is lower alkyl; and
  $Y^1$ is a group of the formula

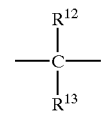

wherein $R^{12}$ and $R^{13}$ are the same or different and each is hydrogen or lower alkyl, or $R^{12}$ and $R^{13}$ in combination form alkylene, and a pharmaceutically acceptable salt thereof.

(6) The piperazine compound of the above-mentioned (5), wherein $R^{8a}$ and $R^{9a}$ are both methyl, and a pharmaceutically acceptable salt thereof.

(7) The piperazine compound of any of the above-mentioned (1) to (6), wherein $R^3$, $R^4$ and $R^5$ are the same or different and each is hydrogen, halogen or lower alkoxy, and a pharmaceutically acceptable salt thereof.

(8) The piperazine compound of the above-mentioned (1), which has the following formula

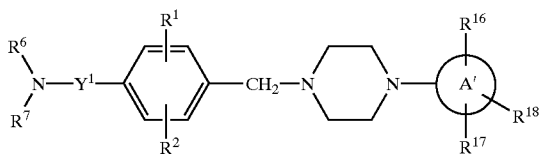

(I-d)

wherein $R^1$ and $R^2$ are the same or different and each is hydrogen, halogen, lower alkyl, lower alkoxy, amino, amino mono-or di-substituted by a group selected from the group consisting of lower alkyl and lower acyl, nitro, hydroxy or cyano;

ring A' is a group of the formula

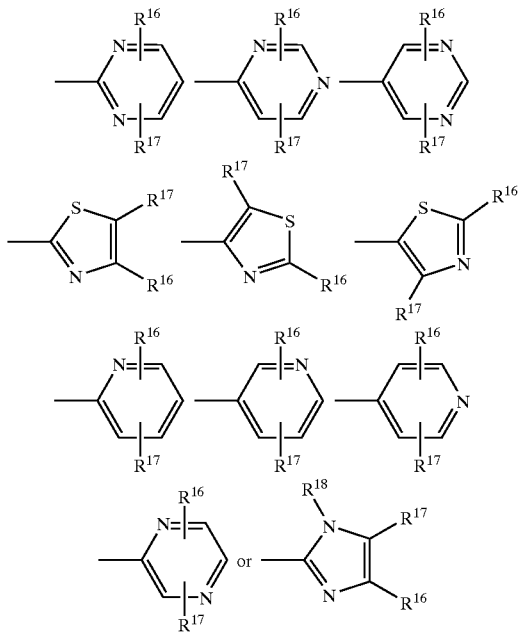

wherein $R^{16}$ and $R^{17}$ are the same or different and each is hydrogen, halogen, lower alkyl, lower alkoxy or amino mono- or di-substituted by a group selected from the group consisting of lower alkyl and lower acyl, and $R^{18}$ is hydrogen or lower alkyl;

$R^6$ and $R^7$ are the same or different and each is hydrogen, lower alkyl, lower alkyl substituted by 1 to 3 halogen(s), aralkyl, acyl or lower acyl substituted by 1 to 3 halogen(s); and $Y^1$ is a group of the formula

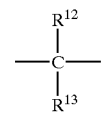

wherein $R^{12}$ and $R^{13}$ are the same or different and each is hydrogen or lower alkyl, or $R^{12}$ and $R^{13}$ in combination form alkylene, and a pharmaceutically acceptable salt thereof.

(9) The piperazine compound of the above-mentioned (1), which has the following formula

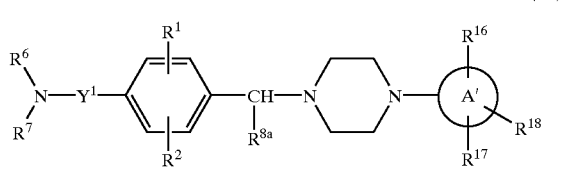

(I-e)

wherein $R^1$ and $R^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;

ring A' is a group of the formula

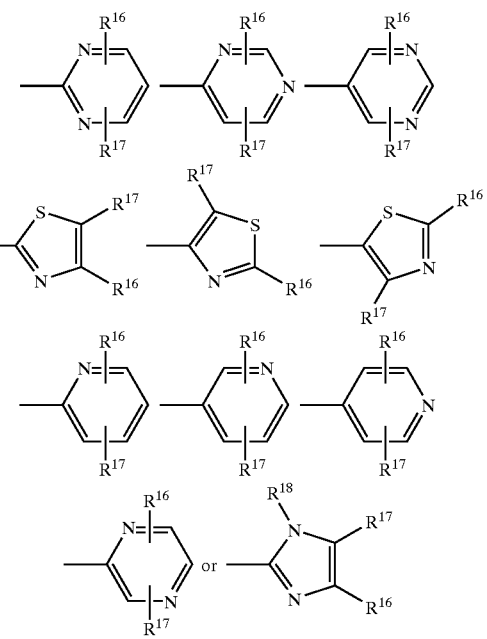

wherein $R^{16}$ and $R^{17}$ are the same or different and each is hydrogen, halogen, lower alkyl, lower alkoxy, amino mono- or di-substituted by a group selected from the group consisting of lower alkyl and lower acyl, and $R^{18}$ is hydrogen or lower alkyl;

$R^6$ and $R^7$ are the same or different and each is hydrogen, lower alkyl, lower alkyl substituted by 1 to 3 halogen(s), aralkyl, acyl or lower acyl substituted by 1 to 3 halogen(s);

$R^{8a}$ is lower alkyl; and $Y^1$ is a group of the formula $$-\overset{R^{12}}{\underset{R^{13}}{C}}-$$

wherein $R^{12}$ and $R^{13}$ are the same or different and each is hydrogen or lower alkyl, or $R^{12}$ and $R^{13}$ in combination form alkylene,
and a pharmaceutically acceptable salt thereof.
(10) The piperazine compound of the above-mentioned (9), wherein $R^{8a}$ is methyl, and a pharmaceutically acceptable salt thereof.
(11) The piperazine compound of the above-mentioned (1), which has the following formula (I-f)

[Structure of formula I-f showing: $R^6$, $R^7$, N, $Y^1$, phenyl with $R^1$, $R^2$, C with $R^{9a}$, $R^{8a}$, N-piperazine-N, ring A' with $R^{16}$, $R^{17}$, $R^{18}$]

wherein
$R^1$ and $R^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;
ring A' is a group of the formula

[Nine heterocyclic ring structures with $R^{16}$, $R^{17}$, $R^{18}$ substituents including pyrazine, pyrimidine, thiazole, pyridine, and imidazole variants]

or wherein $R^{16}$ and $R^{17}$ are the same or different and each is hydrogen, halogen, lower alkyl, lower alkoxy or amino mono- or di-substituted by a group selected from the group consisting of lower alkyl and lower acyl, and $R^{18}$ is hydrogen or lower alkyl;

$R^6$ and $R^7$ are the same or different and each is hydrogen, lower alkyl, lower alkyl substituted by 1 to 3 halogen (s), aralkyl, acyl or lower acyl substituted by 1 to 3 halogen(s);
$R^{8a}$ and $R^{9a}$ are the same or different and each is lower alkyl; and
$Y^1$ is a group of the formula $$-\overset{R^{12}}{\underset{R^{13}}{C}}-$$

wherein $R^{12}$ and $R^{13}$ are the same or different and each is hydrogen or lower alkyl, or $R^{12}$ and $R^{13}$ in combination form alkylene,
and a pharmaceutically acceptable salt thereof.
(12) The piperazine compound of the above-mentioned (11), wherein $R^{8a}$ and $R^{9a}$ are both methyl, and a pharmaceutically acceptable salt thereof.
(13) The piperazine compound of any of the above-mentioned (1) to (12), wherein one of $R^6$ and $R^7$ is hydrogen and the other is acyl, and a pharmaceutically acceptable salt thereof.
(14) The piperazine compound of any of the above-mentioned (1) to (13), wherein $R^{12}$ and $R^{13}$ are the same or different and each is hydrogen or methyl, $R^{12}$ and $R^{13}$ in combination form ethylene, and a pharmaceutically acceptable salt thereof.
(15) The piperazine compound of the above-mentioned (1), (2), (7), (13) or (14), which is a member selected from the group consisting of N-(4-((4-phenylpiperazin-1-yl) methyl)phenylmethyl)acetamide, N-(4-((4-(4-fluorophenyl)piperazin-1-yl)methyl)phenylmethyl)-acetamide, N-(4-((4-(2-fluorophenyl)piperazin-1-yl) methyl)phenylmethyl)-acetamide, N-(4-((4-(2,4-difluorophenyl)piperazin-1-yl)methyl)phenylmethyl)-acetamide, N-(2-(4-((4-phenylpiperazin-1-yl)methyl) phenyl)ethyl)acetamide, N-(2-(4-((4-(4-fluorophenyl) piperazin-1-yl)methyl)phenyl)ethyl)-acetamide, N-(1-(4-((4-phenylpiperazin-1-yl)methyl)phenyl)ethyl) acetamide, N-(1-(4-((4-(4-fluorophenyl)piperazin-1-yl) methyl)phenyl)ethyl)-acetamide, N-(1-(4-((4-(2,4-difluorophenyl)piperazin-1-yl)methyl)phenyl)-ethyl) acetamide, N-(1-(4-((4-(4-fluorophenyl)piperazin-1-yl) methyl)phenyl)-1-methylethyl)acetamide, N-(1-(4-((4-phenylpiperazin-1-yl)methyl)phenyl)cyclopropyl)-acetamide and N-(1-(4-((4-(4-fluorophenyl)piperazin-1-yl)methyl)phenyl)-cyclopropyl)acetamide,
and a pharmaceutically acceptable salt thereof.
(16) The piperazine compound of the above-mentioned (1), (3), (4), (7),
(13) or (14), which is a member selected from the group consisting of N-(4-(1-( 4-phenylpiperazin-1-yl) ethyl) phenylmethyl )acetamide, N-(4-(1-(4-(4-fluorophenyl) piperazin-1-yl)ethyl)phenylmethyl)-acetamide and N-(4-(1-(4-(2,4-difluorophenyl)piperazin-1-yl)ethyl) phenylmethyl)-acetamide,
and a pharmaceutically acceptable salt thereof.
(17) The piperazine compound of the above-mentioned (1), (5)–(7), (13) or (14), which is N-(4-(1-(4-(4-fluorophenyl)piperazin-1-yl)-1-methylethyl) phenylmethyl) acetamide, and a pharmaceutically acceptable salt thereof.
(18) The piperazine compound of the above-mentioned (1), (7), (8), (13) or (14), which is a member selected from the group consisting of N-(4-((4-(pyrimidin-2-yl)piperazin-1-yl)methyl)phenylmethyl)-acetamide, N-(1-(4-((4-(pyrimidin-2-yl)piperazin-1-yl)methyl)phenyl)ethyl)-acetamide, N-(1-(4-((4-(pyrimidin-2-yl)piperazin-1-yl)methyl)phenyl)-cyclopropyl)acetamide, N-(4-((4-(pyrimidin-2-yl)piperazin-1-yl)methyl)phenylmethyl)-formamide, N-(4-((4-(pyrimidin-2-yl)piperazin-1-yl)methyl)phenylmethyl)-propionamide, N-(4-((4-(thiazol-2-yl)piperazin-1-yl)methyl)phenylmethyl)acetamide and N-(4-((4-(pyridin-2-yl)piperazin-1-yl)methyl)phenylmethyl)acetamide, and a pharmaceutically acceptable salt thereof.

(19) The piperazine compound of the above-mentioned (1), (7), (9), (10), (13) or (14), which is N-(1-(4-(1-(4-(pyrimidin-2-yl)piperazin-1-yl)ethyl)phenyl)cyclopropyl)acetamide, and a pharmaceutically acceptable salt thereof.

(20) A pharmaceutical composition containing the piperazine compound of any of the above-mentioned (1) to (19) or a pharmaceutically acceptable salt thereof as an active ingredient.

(21) A TNF-α production inhibitor and/or IL-10 production promoter containing the piperazine compound of any of the above-mentioned (1) to (19) or a pharmaceutically acceptable salt thereof as an active ingredient.

(22) An agent for the prophylaxis or treatment of diseases caused by abnormal TNF-α production, TNF-α mediated diseases or diseases curable with IL-10, which contains the piperazine compound of any of the above-mentioned (1) to (19) or a pharmaceutically acceptable salt thereof as an active ingredient.

(23) An agent for the prophylaxis or treatment of an inflammatory disease, which contains the piperazine compound of any of the above-mentioned (1) to (19) or a pharmaceutically acceptable salt thereof as an active ingredient.

(24) An agent for the prophylaxis or treatment of an autoimmune disease, which contains the piperazine compound of any of the above-mentioned (1) to (19) or a pharmaceutically acceptable salt thereof as an active ingredient.

(25) An agent for the prophylaxis or treatment of rheumatoid arthritis, which contains the piperazine compound of any of the above-mentioned (1) to (19) or a pharmaceutically acceptable salt thereof as an active ingredient.

(26) An agent for the prophylaxis or treatment of an allergic disease, which contains the piperazine compound of any of the above-mentioned (1) to (19) or a pharmaceutically acceptable salt thereof as an active ingredient.

The groups shown by respective symbols in the specification are explained in the following.

Halogen at $R^1$ and $R^2$ is fluorine, chlorine, bromine or iodine.

Lower alkyl at $R^1$ and $R^2$ is alkyl having 1 to 4 carbon atoms, such as methyl, ethyl, propyl, isopropyl, butyl, isobutyl, tert-butyl and the like.

Lower alkoxy at $R^1$ and $R^2$ is alkoxy having 1 to 4 carbon atoms, such as methoxy, ethoxy, propoxy, isopropoxy, butoxy, tert-butoxy and the like.

With regard to the amino mono- or di-substituted by a group selected from lower alkyl and lower acyl at $R^1$ and $R^2$, lower alkyl as a substituent means alkyl having 1 to 4 carbon atoms, such as methyl, ethyl, propyl, isopropyl, butyl, isobutyl, tert-butyl and the like. Lower acyl as a substituent means lower alkanoyl having 1 to 4 carbon atoms, lower alkoxycarbonyl having 1 to 4 carbon atoms or $C_1$–$C_4$ lower alkanoyl substituted by phenyl. Examples thereof include formyl, acetyl, propionyl, butyryl, methoxycarbonyl, ethoxycarbonyl, propoxycarbonyl, isopropoxycarbonyl, butoxycarbonyl, isobutoxycarbonyl, tert-butoxycarbonyl, benzoyl, phenylacetyl and phenylpropionyl. Amino mono- or di-substituted by these substituents means methylamino, dimethylamino, ethylamino, diethylamino, propylamino, butylamino, acetylamino, diacetylamino, propionylamino, dipropionylamino, butyrylamino, N-methyl-N-acetylamino, N-ethyl-N-acetylamino, N-methyl-N-propionylamino, methoxycarbonylamino, ethoxycarbonylamino, propoxycarbonylamino, tert-butoxycarbonylamino, benzoylamino, phenylacetylamino and the like.

Halogen at $R^3$, $R^4$ and $R^5$ is fluorine, chlorine, bromine or iodine.

Lower alkyl at $R^3$, $R^4$ and $R^5$ means alkyl having 1 to 4 carbon atoms, such as methyl, ethyl, propyl, isopropyl, butyl, isobutyl, tert-butyl and the like.

Lower alkoxy at $R^3$, $R^4$ and $R^5$ means alkoxy having 1 to 4 carbon atoms, such as methoxy, ethoxy, propoxy, isopropoxy, butoxy, tert-butoxy and the like.

With regard to the amino mono- or di-substituted by a group selected from lower alkyl and lower acyl at $R^3$, $R^4$ and $R^5$, lower alkyl as a substituent means alkyl having 1 to 4 carbon atoms, such as methyl, ethyl, propyl, isopropyl, butyl, isobutyl, tert-butyl and the like. Lower acyl as a substituent means lower alkanoyl having 1 to 4 carbon atoms, lower alkoxycarbonyl having 1 to 4 carbon atoms or $C_1$–$C_4$ lower alkanoyl substituted by phenyl. Examples thereof include formyl, acetyl, propionyl, butyryl, methoxycarbonyl, ethoxycarbonyl, propoxycarbonyl, isopropoxycarbonyl, butoxycarbonyl, isobutoxycarbonyl, tert-butoxycarbonyl, benzoyl, phenylacetyl and phenylpropionyl. The amino mono- or di-substituted by these substituents may be methylamino, dimethylamino, ethylamino, diethylamino, propylamino, butylamino, acetylamino, diacetylamino, propionylamino, dipropionylamino, butyrylamino,- N-methyl-N-acetylamino, N-ethyl-N-acetylamino, N-methyl-N-propionylamino, methoxycarbonylamino, ethoxycarbonylamino, propoxycarbonylamino, tert-butoxycarbonylamino, benzoylamino, phenylacetylamino and the like.

Lower alkyl at $R^6$ and $R^7$ means alkyl having 1 to 4 carbon atoms, such as methyl, ethyl, propyl, isopropyl, butyl, isobutyl, tert-butyl and the like.

The lower alkyl substituted by 1 to 3 halogen(s) at $R^6$ and $R^7$ is $C_1$-$C_4$ lower alkyl substituted by halogen (e.g., fluorine, chlorine, bromine and the like). Examples thereof include fluoromethyl, trifluoromethyl, chloromethyl, bromomethyl, 2-fluoroethyl, 2,2,2-trifluoroethyl, 2-chloroethyl, 2-bromoethyl, 3-fluoropropyl, 3-chloropropyl, 4-fluorobutyl, 4-chlorobutyl and the like.

Aralkyl at $R^6$ and $R^7$ means benzyl, 2-phenylethyl, 3-phenylpropyl.

Acyl at $R^6$ and $R^7$ means alkanoyl having 1 to 5 carbon atoms, lower alkoxycarbonyl having 1 to 4 carbon atoms, $C_1$-$C_4$ lower alkanoyl substituted by phenyl or pyridyl, or $C_1$-$C_4$ lower alkylsulfonyl. Examples thereof include formyl, acetyl, propionyl, butyryl, valeryl, isovaleryl, trimethylacetyl, methoxycarbonyl, ethoxycarbonyl, propoxycarbonyl, isopropoxycarbonyl, butoxycarbonyl, isobutoxycarbonyl, tert-butoxycarbonyl, benzoyl, nicotinoyl, isonicotinoyl, picolinoyl, phenylacetyl, phenylpropionyl, methanesulfonyl and the like.

Lower acyl substituted by 1 to 3 halogen(s) at $R^6$ and $R^7$ is $C_1$-$C_4$ lower acyl substituted by halogen (e.g., fluorine, chlorine, bromine and the like). Examples thereof include fluoroacetyl, trifluoroacetyl, chloroacetyl, bromoacetyl, 3-chloropropionyl, 3-bromopropionyl, 4-chlorobutyryl, 4-bromobutyryl and the like.

Lower alkyl at $R^8$ and $R^9$ means alkyl having 1 to 4 carbon atoms, such as methyl, ethyl, propyl, isopropyl, n-butyl, isobutyl, sec-butyl, tert-butyl and the like.

Lower alkyl at $R^{10}$ and $R^{11}$ means alkyl having 1 to 4 carbon atoms, such as methyl, ethyl, propyl, isopropyl, butyl and the like.

Lower alkyl at $R^{12}$ and $R^{13}$ means alkyl having 1 to 4 carbon atoms, such as methyl, ethyl, propyl, isopropyl, butyl and the like.

The alkylene formed by $R^{12}$ and $R^{13}$ in combination means methylene, ethylene, trimethylene, tetramethylene, pentamethylene.

Lower alkyl at $R^{14}$ and $R^{15}$ means alkyl having 1 to 4 carbon atoms, such as methyl, ethyl, propyl, isopropyl, butyl and the like.

Halogen at $R^{16}$ and $R^{17}$ means fluorine, chlorine, bromine or iodine.

Lower alkyl at $R^{16}$ and $R^{17}$ means alkyl having 1 to 4 carbon atoms, such as methyl, ethyl, propyl, isopropyl, butyl, isobutyl, tert-butyl and the like. Lower alkoxy at $R^{16}$ and $R^{17}$ means alkoxy having 1 to 4 carbon atoms, such as methoxy, ethoxy, propoxy, isopropoxy, butoxy, tert-butoxy and the like.

With regard to the amino mono- or di-substituted by a group selected from lower alkyl and lower acyl at $R^{16}$ and $R^{17}$, lower alkyl as a substituent means alkyl having 1 to 4 carbon atoms, such as methyl, ethyl, propyl, isopropyl, butyl, isobutyl, tert-butyl and the like. Lower acyl as a substituent means lower alkanoyl having 1 to 4 carbon atoms, lower alkoxycarbonyl having 1 to 4 carbon atoms or $C_1$–$C_4$ lower alkanoyl substituted by phenyl. Examples thereof include formyl, acetyl, propionyl, butyryl, methoxycarbonyl, ethoxycarbonyl, propoxycarbonyl, isopropoxycarbonyl, butoxycarbonyl, isobutoxycarbonyl, tert-butoxycarbonyl, benzoyl, phenylacetyl and phenylpropionyl. The amino mono- or di-substituted by these substituents is exemplified by methylamino, dimethylamino, ethylamino, diethylamino, propylamino, butylamino, acetylamino, diacetylamino, propionylamino, dipropionylamino, butyrylamino, N-methyl-N-acetylamino, N-ethyl-N-acetylamino, N-methyl-N-propionylamino, methoxycarbonylamino, ethoxycarbonylamino, propoxycarbonylamino, tert-butoxycarbonylamino, benzoylamino, phenylacetylamino and the like.

Lower alkyl at $R^{18}$ means alkyl having 1 to 4 carbon atoms, such as methyl, ethyl, propyl, isopropyl, butyl, isobutyl, tert-butyl and the like.

Ring A is

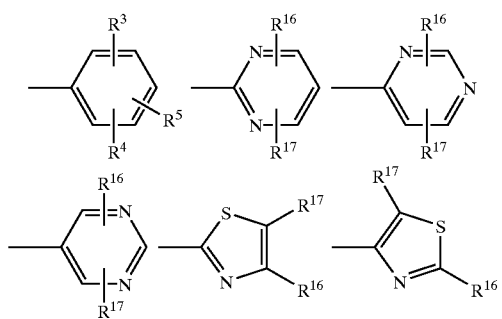

-continued

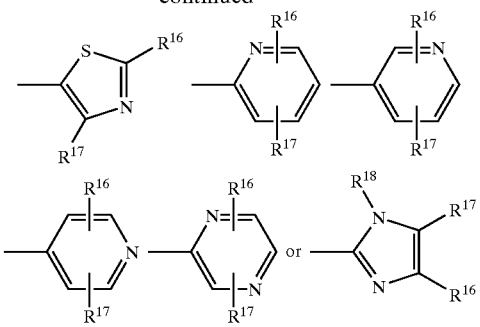

wherein each symbol is as defined in the above. Ring A' is 2-pyrimidyl, 4-pyrimidyl, 5-pyrimidyl, 2-thiazolyl, 4-thiazolyl, 5-thiazolyl, 2-pyridyl, 3-pyridyl, 4-pyridyl, 2-pyrazyl or 2-imidazolyl, mentioned above, with preference given to the above-mentioned 2-pyrimidyl, 2-thiazolyl, 2-pyridyl or 2-imidazolyl.

The pharmaceutically acceptable salt of the compound (I) of the present invention is, for example, a salt with inorganic acid such as hydrochloric acid, hydrobromic acid, hydroiodic acid, sulfuric acid, nitric acid, phosphoric acid and the like, a salt with organic acid such as acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, 10-camphorsulfonic acid and the like. The compound of the present invention can be converted to a quaternary ammonium salt. The compound of the present invention (I) and a pharmaceutically acceptable salt thereof may be a hydrate (monohydrate, 1/2 hydrate, 1/4 hydrate, 1/5 hydrate, dihydrate, 3/2 hydrate, 3/4 hydrate and the like) or a solvate. When the inventive compound (I) has an asymmetric carbon, at least two optical isomers exist. The present invention encompasses these optical isomers and racemates thereof.

The compound of the present invention can be produced by, for example, the following methods.

Method A

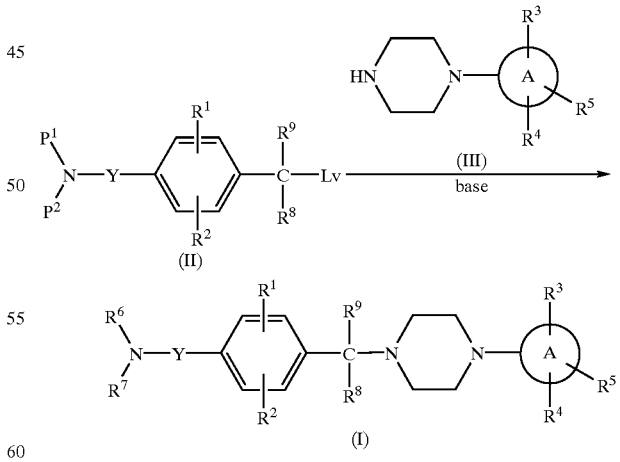

wherein Lv is a leaving group widely used in the organic synthetic chemistry, suchas halogen (e.g, fluorine, chlorine, bromineor iodine), mnethanesulfonyloxy, p-toluenesulfonyloxy and trifluoromethane-sulfonyloxy, $P^1$ and $P^2$ encompass $R^6$ and $R^7$ defined earlier, and further mean an amino-protecting group widely used in the organic synthetic chemistry, such as benzyloxycarbonyl, $P^1$ and $P^2$ may form an imido group, such as phthalimide, together with the adjacent nitrogen atom and other symbols are as defined above. When $R^3$, $R^4$ and $R^5$ have a functional group such as amino, hydroxy and the like, they may be protected as necessary.

The base to be used for the condensation of compound (II) and compound (III) may be, for example, potassium carbonate, potassium hydrogencarbonate, sodium carbonate, sodium hydrogencarbonate, sodium hydroxide, sodium methoxide, sodium ethoxide, sodium hydride, potassium hydride, lithium diisopropylamide, butyl lithium, lithium hexamethyldisilazane, triethylamine, diisopropylethylamine, 1,8-diazabicyclo[5.4.0]undeca-7-ene, pyridine and 4-dimethylaminopyridine.

The solvent to be used for the condensation may be, for example, methanol, ethanol, 1-propanol, 2-propanol, tert-butyl alcohol, tetrahydrofuran, dioxane, diethyl ether, ethylene glycol dimethyl ether, benzene, dichloromethane, dichloroethane, chloroform, toluene, xylene, hexane, dimethylformamide, dimethyl sulfoxide, water and a mixture thereof.

The reaction temperature of condensation is generally from $-80°$ C. to $150°$ C., and a temperature above or under this range can be employed as necessary.

The reaction time of condensation is generally from 30 minutes to 2 days, and a time longer or shorter than this range can be employed as necessary.

After condensation under the above-mentioned reaction conditions, a protecting group(s) is/are removed as necessary, after which compound (I) can be purified by a method known in the field of organic synthetic chemistry, such as solvent extraction, recrystallization, chromatography, and a method using an ion exchange resin.

The compound (III) may be a commercially available one or may be synthesized from bis(2-chloro or bromoethyl) amine and substituted aromatic amine according to the method disclosed in Journal of Medicinal Chemistry (J. Med. Chem.), vol. 29, pp. 630–634 (1986) or Tetrahedron Letters, vol. 37, pp. 319–322 (1996). Alternatively, it can be synthesized by treating bis(2-hydroxyethyl)amine and substituted aromatic amine in an aqueous hydrochloric acid solution.

Method B

Compound (I) wherein one of $R^6$ and $R^7$ is acyl and the other is hydrogen is hydrolyzed to give compound (I-1) wherein $R^6$ and $R^7$ of compound (I) are hydrogen

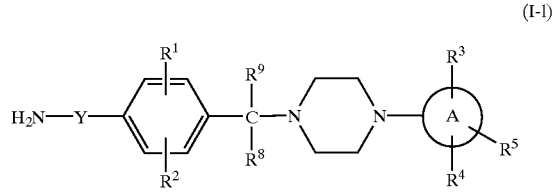

(I-1)

wherein each symbol is as defined above.

Hydrolysis can be performed under both acidic conditions and basic conditions. When acidic conditions are employed, mineral acid (e.g., hydrochloric acid, sulfuric acid and the like), preferably a concentrated or diluted aqueous hydrochloric acid solution, is used and, Cas an organic co-solvent, for example, methanol, ethanol, tert-butyl alcohol, tetrahydrofuran, ethylene glycol dimethyl ether, dimethylformamide, dimethyl sulfoxide, acetonitrile or a mixture thereof is used. When basic conditions are employed, the base to be used may be, for example, sodium hydroxide, potassium hydroxide, lithium hydroxide or barium hydroxide. The solvent used may be, for example, water, methanol, ethanol, tert-butyl alcohol, tetrahydrofuran, dimethylformamide, dimethyl sulfoxide, acetonitrile or a mixture thereof.

The reaction temperature of hydrolysis is generally from $-20°$ C. to $150°$ C., and a temperature above or under this range can be employed as necessary.

The reaction time of hydrolysis is generally from 30 minutes to 2 days, and a time longer or shorter than this range can be employed as necessary.

After hydrolysis under the above-mentioned reaction conditions and, where necessary, removal of protecting group (s), compound (I-1) can be purified by a method known in the field of organic synthetic chemistry, such as solvent extraction, recrystallization, chromatography, and a method using an ion exchange resin.

The methods (Method B1 to Method B8) for modifying the amino group of compound (I-1) are explained in the following.

Method B1

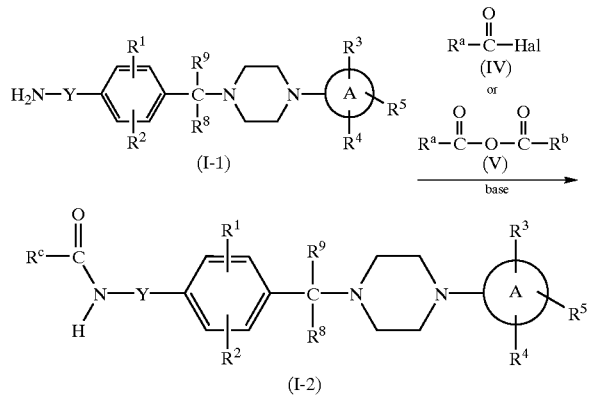

wherein $R^a$ is $C_1$–$C_4$ alkyl optionally substituted by 1 to 3 halogen(s) (e.g., fluorine, chlorine, bromine and the like), Hal is halogen (e.g., chlorine, bromine, iodine and the like), $R^b$ is $C_1$–$C_4$ alkyl optionally substituted by 1 to 3 halogen(s) (e.g., fluorine, chlorine, bromine and the like), $R^c$ is $C_1$–$C_4$ alkyl optionally substituted by 1 to 3 halogen(s) (e.g., fluorine, chlorine, bromine and the like), and the other symbols are as defined above.

The base to be used for condensation of compound (I-1) may be, for example, triethylamine, diisopropylethylamine, potassiumcarbonate, potassium hydrogencarbonate, sodium carbonate, sodium hydrogencarbonate, sodium hydroxide, sodiummethoxide, sodium ethoxide, pyridine and 4-dimethylaminopyridine.

The solvent to be used for condensation may be, for example, water, methanol, ethanol, 1-propanol, 2-propanol, tert-butyl alcohol, tetrahydrofuran, dioxane, diethyl ether, ethylene glycol dimethyl ether, benzene, dichloromethane, dichloroethane, chloroform, ethyl acetate, toluene, xylene, hexane, dimethylformamide, dimethyl sulfoxide and a mixture thereof.

The reaction temperature of condensation is generally from $-20°$ C. to $80°$ C., and a temperature above or under this range can be employed as necessary.

The reaction time of condensation is generally from 30 minutes to 2 days, and a time longer or shorter than this range can be employed as necessary.

After reduction under the above-mentioned reaction conditions and, where necessary, removal of protecting group (s), compound (I-2) can be purified by a method known in the field of organic synthetic chemistry, such as solvent extraction, recrystallization, chromatography, and a method using an ion exchange resin.

Method B2

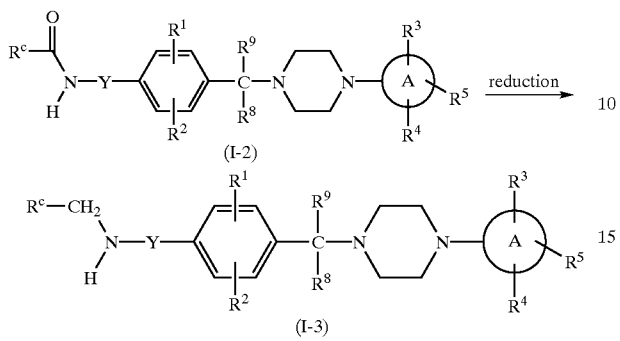

wherein each symbol is as defined above.

The reducing agent to be used for reduction of amide group in compound (I-2) may be, for example, metallic reducing reagent such as aluminum lithium hydride, sodium borohydride, lithium borohydride and the like, or diborane.

The solvent to be used for reduction of amide group may be, for example, tetrahydrofuran, dioxane, diethyl ether, methanol, ethanol, 1-propanol, 2-propanol, tert-butyl alcohol, ethylene glycol dimethyl ether, a mixture thereof and the like.

The reaction temperature of reduction of amino group is generally from $-20°$ C. to $80°$ C., and a temperature above or under this range can be employed as necessary.

The reaction time of reduction of amide group is generally from 30 minutes to 10 hours, and a time longer or shorter than this range can be employed as necessary.

After reduction under the above-mentioned reaction conditions and, where necessary, removal of protecting group (s), compound (I-3) can be purified by a method known in the field of organic synthetic chemistry, such as solvent extraction, recrystallization, chromatography, and a method using an ion exchange resin.

Method B3

Compound (I-3) can be also produced by the following method.

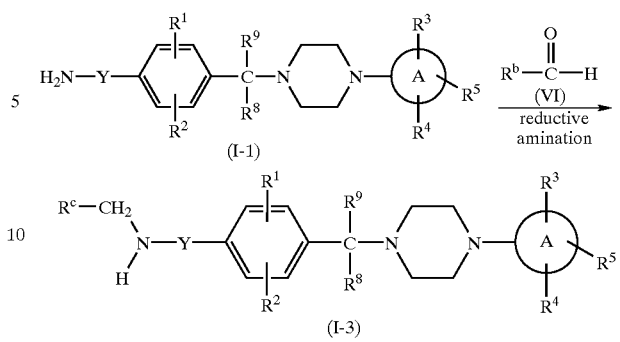

wherein each symbol is as defined above.

The reducing agent to be used for reductive amination of compound (I-1) may be, for example, sodium borohydride or sodium cyanoborohydride, and catalytic reduction using transition metal (e.g., palladium-carbon, platinum oxide, Raney nickel, rhodium, ruthenium) is also effective.

The solvent to be used for reductive amination may be, for example, water, methanol, ethanol, 1-propanol, 2-propanol, tert-butyl alcohol, tetrahydrofuran, dioxane, diethyl ether, ethylene glycol dimethyl ether, acetone, ethyl acetate, acetic acid, benzene, toluene, xylene, dimethylformamide, dimethyl sulfoxide or a mixture thereof.

The reaction temperature of reductive amination is generally from $-20°$ C. to $150°$ C., and a temperature above or under this range can be employed as necessary.

The reaction time of reductive amination is generally from 30 minutes to 2 days, and a time longer or shorter than this range can be employed as necessary.

After reduction under the above-mentioned reaction conditions and, where necessary, removal of protecting group (s), compound (I-3) can be purified by a method known in the field of organic synthetic chemistry, such as solvent extraction, recrystallization, chromatography, and a method using an ion exchange resin.

Method B4

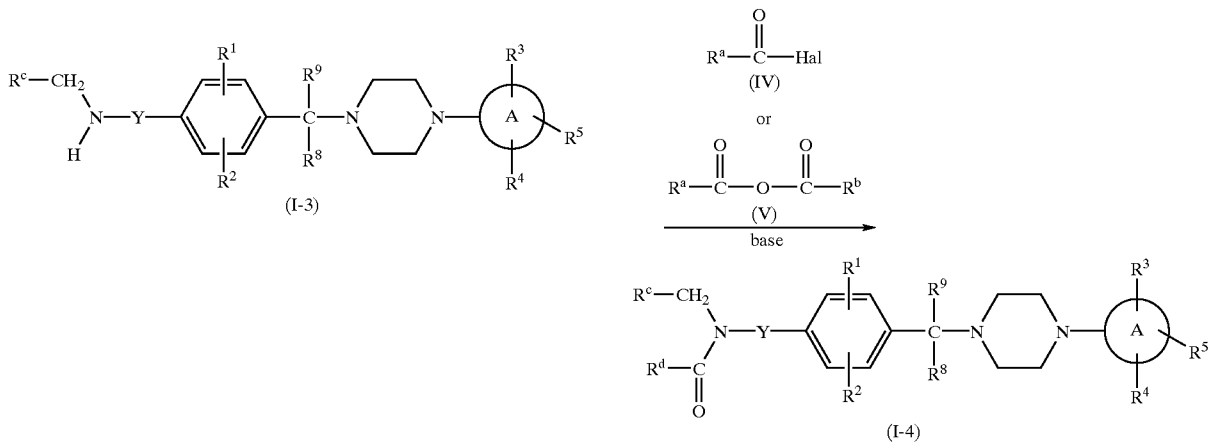

wherein $R^d$ is hydrogen or $C_1$–$C_4$ alkyl optionally substituted by 1 to 3 halogen(s) (e.g., fluorine, chlorine, bromine and the like), and the other symbols are as defined above.

The reaction conditions (reagent, reaction solvent, reaction time) of acylation are the same as in Method B1.

After acylation under the above-mentioned reaction conditions and, where necessary, removal of protecting group (s), compound (I-4) can be purified by a method known in the field of organic synthetic chemistry, such as solvent extraction, recrystallization, chromatography, and a method using an ion exchange resin.

Method B5

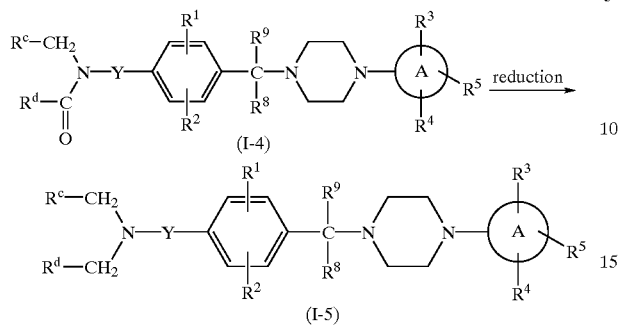

wherein each symbol is as defined above.

The reaction conditions (reagent, reaction solvent, reaction time) of reduction are the same as in Method B2.

After reduction under the above-mentioned reaction conditions and, where necessary, removal of protecting group (s), compound (I-5) can be purified by a method known in the field of organic synthetic chemistry, such as solvent extraction, recrystallization, chromatography, and a method using an ion exchange resin.

Method B6

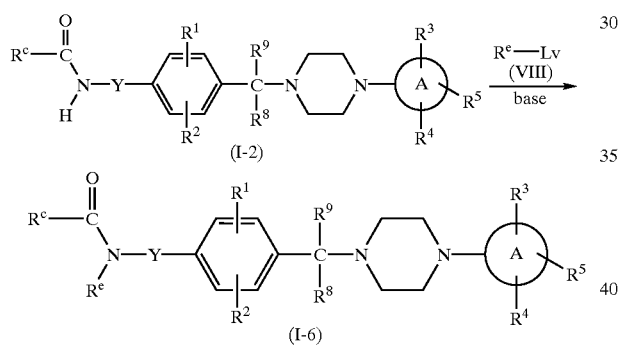

wherein $R^e$ is $C_1$–$C_4$ alkyl optionally substituted by 1 to 3 halogen(s) (e.g., fluorine, chlorine, bromine and the like), and the other symbols to are as defined above.

In this reaction, the acyl moiety ($R^c$—C=O) is preferably electron-withdrawing group such as trifluoroacetyl and the like.

The base to be used for condensation of compound (I-2) may be, for example, sodium hydroxide, sodium methoxide, sodium ethoxide, sodium hydride, potassium hydride, lithium diisopropylamide, butyl lithium, phenyl lithium, lithium hexamethyldisilazane, triethylamine, diisopropylethylamine or 1,8-diazabicyclo[5.4.0]undeca-7-ene.

The solvent to be used for condensation may be, for example, methanol, ethanol, 1-propanol, 2-propanol, tert-butyl alcohol, tetrahydrofuran, dioxane, diethyl ether, ethylene glycol dimethyl ether, dichloromethane, dichloroethane, chloroform, benzene, toluene, xylene, hexane, dimethylformamide, dimethyl sulfoxide or a mixture thereof.

The reaction temperature of condensation is generally from −80° C. to 150° C., and a temperature above or under this range can be employed as necessary.

The reaction time of condensation is generally from 30 minutes to 2 days, and a time longer or shorter than this range can be employed as necessary.

After condensation under the above-mentioned reaction conditions and, where necessary, removal of protecting group(s), compound (I-6) can be purified by a method known in the field of organic synthetic chemistry, such as solvent extraction, recrystallization, chromatography, and a method using an ion exchange resin.

Method B7

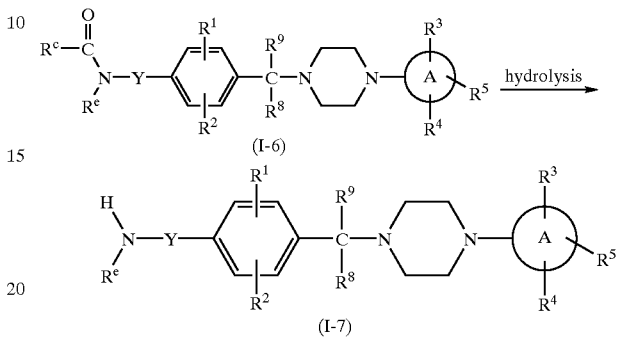

wherein each symbol is as defined above.

Hydrolysis is performed under the same reaction conditions as in Method B.

After hydrolysis under the above-mentioned reaction conditions and, where necessary, removal of protecting group (s), compound (I-7) can be purified by a method known in the field of organic synthetic chemistry, such as solvent extraction, recrystallization, chromatography, and a method using an ion exchange resin.

Method B8

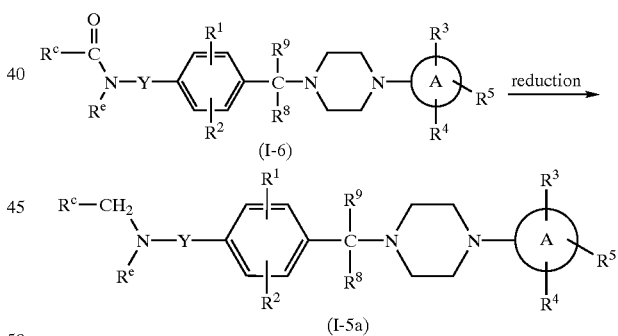

wherein each symbol is as defined above.

The reduction is performed under the same reaction conditions as in Method B2.

After reduction under the above-mentioned reaction conditions and, where necessary, removal of protecting group (s), compound (I-5a) can be purified by a method known in the field of organic synthetic chemistry, such as solvent extraction, recrystallization, chromatography, and a method using an ion exchange resin.

Method C

Compound (I) can be also produced by the following method.

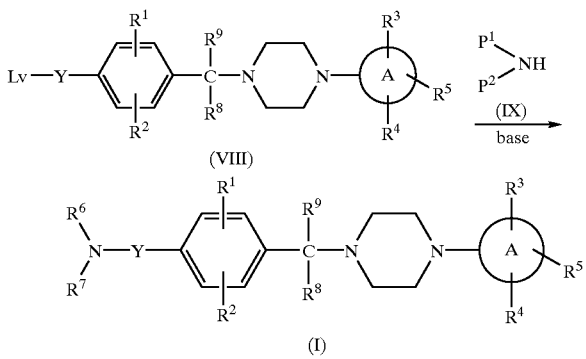

wherein each symbol is as defined above.

The reaction conditions (reagent, reaction solvent, reaction time) of condensation are the same as in the condensation in Method A.

After condensation under the above-mentioned reaction conditions and, where necessary, removal of protecting group(s), compound (I) can be purified by a method known in the field of organic synthetic chemistry, such as solvent extraction, recrystallization, chromatography, and a method using an ion exchange resin.

Method D

Compound (I-1) can be also produced by the following method.

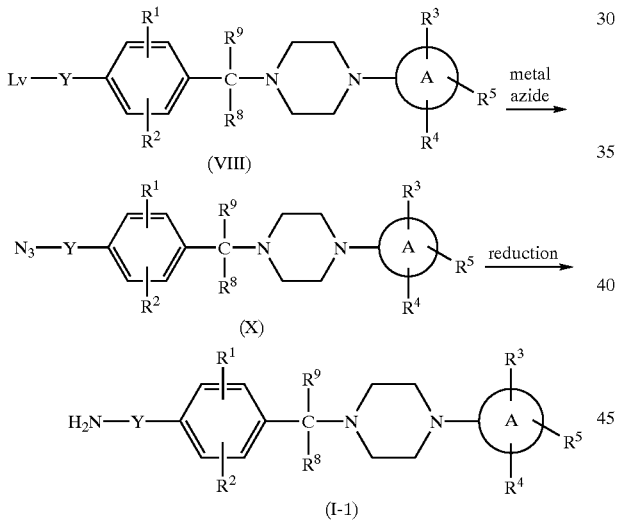

wherein each symbol is as defined above.

The metal azide compound to be used for the azidation of compound (VIII) is exemplified by sodium azide, lithium azide and the like.

The solvent to be used for azidation may be, for example, water, methanol, ethanol, 1-propanol, 2-propanol, tert-butyl alcohol, tetrahydrofuran, dioxane, diethyl ether, ethylene glycol dimethyl ether, acetone, ethyl acetate, acetic acid, benzene, toluene, xylene, dimethylformamide, dimethyl sulfoxide or a mixture thereof.

The reaction temperature of azidation is generally from 0° C. to 150° C., and a temperature above or under this range can be employed as necessary.

The reaction time of azidation is generally from 30 minutes to 2 days, and a time longer or shorter than this range can be employed as necessary.

The reducing agent to be used for reduction of the azide group in compound (X) may be, for example, a metallic reducing reagent such as aluminum lithium hydride, sodium borohydride, lithium borohydride, sodium cyanoborohydride and the like, diborane or triphenylphosphine, and catalytic reduction using transition metal (e.g., palladium-carbon, platinum oxide, Raney nickel, rhodium, ruthenium) is also effective.

The solvent to be used for reduction of the azide group may be, for example, water, methanol, ethanol, 1-propanol, 2-propanol, tert-butyl alcohol, tetrahydrofuran, dioxane, diethyl ether, ethylene glycol dimethyl ether, acetone, ethyl acetate, acetic acid, benzene, toluene, xylene, dimethylformamide, dimethyl sulfoxide or a mixture thereof.

The reaction temperature of reduction of the azide group is generally from −20° C. to 150° C., and a temperature above or under this range can be employed as necessary.

The reaction time of reduction of the azide group is generally from 30 minutes to 2 days, and a time longer or shorter than this range can be employed as necessary.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method E

Compound (I-1) can be also produced by the following method.

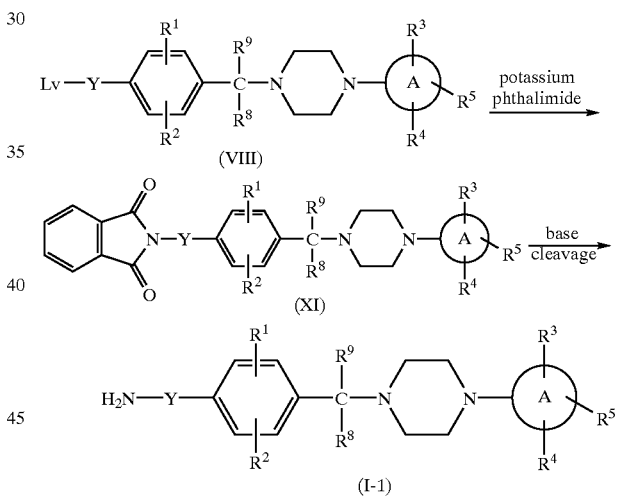

wherein each symbol is as defined above.

The solvent to be used for condensation of compound (VIII) may be, for example, water, methanol, ethanol, 1-propanol, 2-propanol, tert-butyl alcohol, tetrahydrofuran, dioxane, diethyl ether, ethylene glycol dimethyl ether, acetone, ethyl acetate, acetic acid, benzene, toluene, xylene, dimethylformamide, dimethyl sulfoxide or a mixture thereof.

The reaction temperature of condensation is generally from 0° C. to 150° C., and a temperature above or under this range can be employed as necessary.

The reaction time of condensation is generally from 30 minutes to 2 days, and a time longer or shorter than this range can be employed as necessary.

The base to be used for cleavage of compound (XI) may be, for example, hydrazine hydrate, methyl hydrazine, phenyl hydrazine, sodium hydroxide, potassium hydroxide, barium hydroxide or lithium hydroxide.

The solvent to be used for cleavage may be, for example, water, methanol, ethanol, 1-propanol, 2-propanol, tert-butyl alcohol, tetrahydrofuran, dioxane, diethyl ether, ethylene glycol dimethyl ether, acetone, dimethylformamide, dimethyl sulfoxide or a mixture thereof.

The reaction temperature of cleavage is generally from 0° C. to 150° C., and a temperature above or under this range can be employed as necessary.

The reaction time of cleavage is generally from 30 minutes to 2 days, and a time longer or shorter than this range can be employed as necessary.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method F

Compound (XI) can be also produced by the following method.

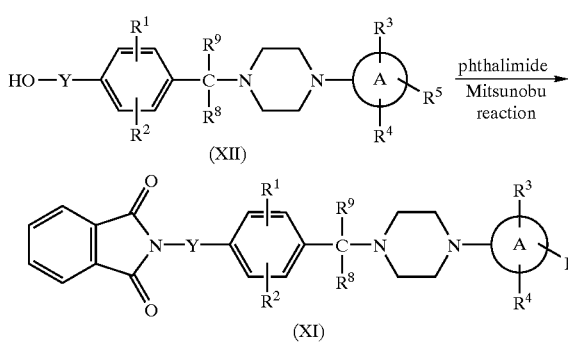

wherein each symbol is as defined above.

The reagent to be used for Mitsunobu reaction may be, for example, dialkyl azodicarboxylate (wherein alkyl means lower alkyl such as ethyl, propyl, isopropyl, butyl, isobutyl and the like) and triphenylphosphine.

The solvent to be used for Mitsunobu reaction may be, for example, methanol, ethanol, 1-propanol, 2-propanol, tert-butyl alcohol, tetrahydrofuran, dioxane, diethyl ether, ethylene glycol dimethyl ether, acetone, dimethylformamide, dimethyl sulfoxide or a mixture thereof.

The reaction temperature of Mitsunobu reaction is generally from –80° C. to 100° C., and a temperature above or under this range can be employed as necessary.

The reaction time of Mitsunobu reaction is generally from 30 minutes to 2 days, and a time longer or shorter than this range can be employed as necessary.

After Mitsunobu reaction under the above-mentioned reaction conditions and, where necessary, removal of protecting group(s), compound (XI) can be purified by a method known in the field of organic synthetic chemistry, such as solvent extraction, recrystallization, chromatography, and a method using an ion exchange resin.

Method G

Compound (I) can be also produced by the following method.

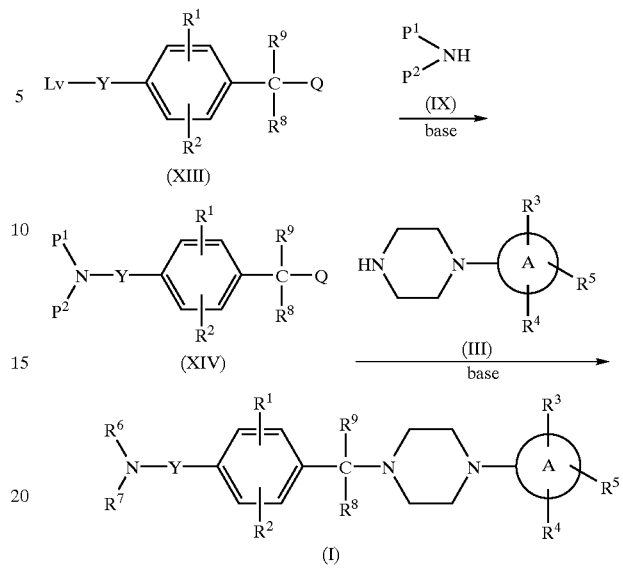

wherein Q is the aforementioned leaving group, Lv and its precursor hydroxyl group with or without protection with a suitable protecting group, which can be easily converted to Lv by a method known in the field of organic synthetic chemistry, and other symbols are as defined above.

The reaction conditions of the condensation of compound (XIII) and compound (IX) are the same as in the conditions for Method C, Method D and Method E. The group Q of the obtained compound (XIV) is converted to a leaving group Lv as necessary by a method known in the field of organic synthetic chemistry, and condensed with compound (III) in the same manner as in Method A, which is followed by, where necessary, removal of protecting group(s) to produce compound (I).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method H

Compound (I) can be also produced by the following method.

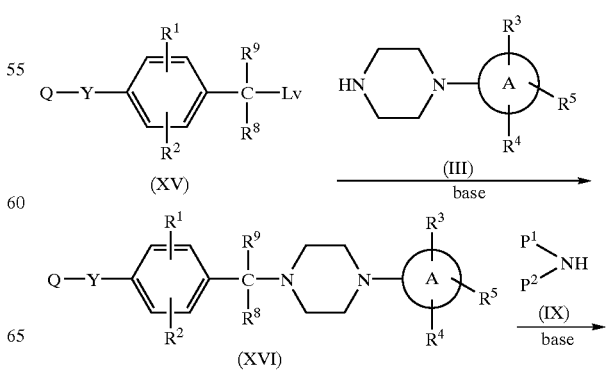

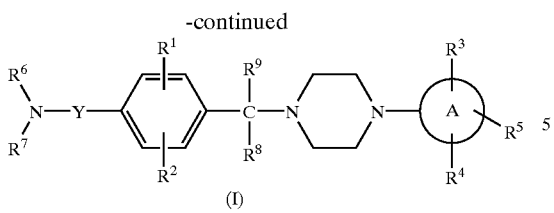

(I)

wherein each symbol is as defined above.

The reaction conditions of the condensation of compound (XV) and compound (III) are the same as in the conditions for Method A. The group Q of the obtained compound (XVI) is converted to a leaving group Lv by a method known in the field of organic synthetic chemistry. Then, in the same manner as in Method C, Method D and Method E, it is condensed with compound (IX) and, where necessary, the protecting group(s) is/are removed to produce compound (I).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method I

Compound (I) can be also produced by the following method.

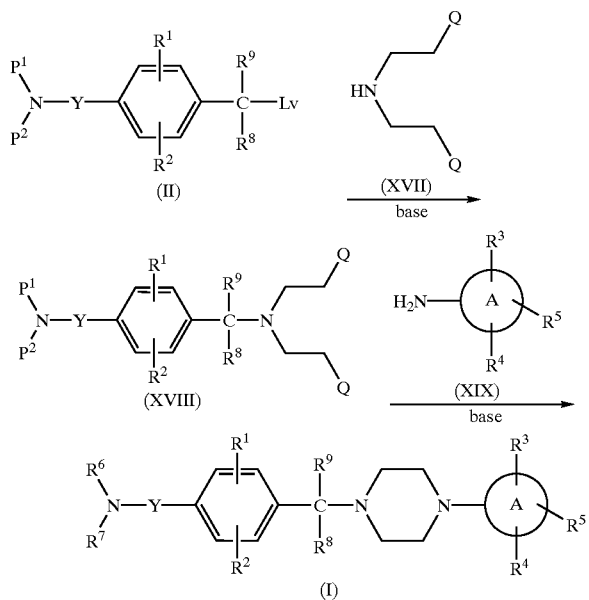

wherein each symbol is as defined above.

The reaction conditions (reagent, reaction solvent, reaction time) of condensation of compound (II) and compound (XVII) are the same as in Method A.

The group Q of the obtained compound (XVIII) is converted to a leaving group Lv as necessary by a method known in the field of organic synthetic chemistry. In the same manner as in Method A, it is condensed with compound (XIX) and, where necessary, the protecting group(s) is/are removed to produce compound (I).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method J

Compound (I) can be also produced by the following method.

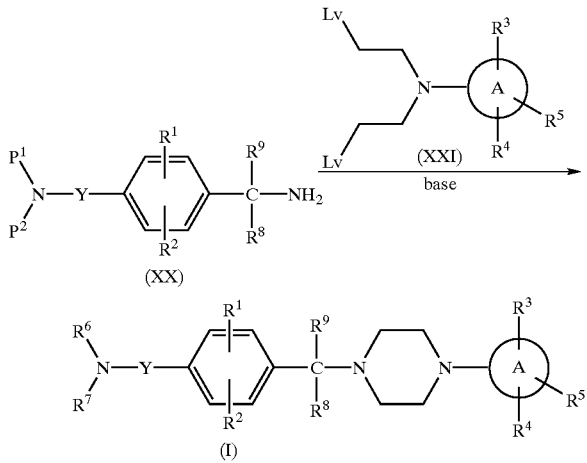

wherein each symbol is as defined above.

The reaction conditions (reagent, reaction solvent, reaction time) of condensation in this method are the same as in Method A.

After condensation under the above-mentioned reaction conditions and, where necessary, removal of protecting group(s), compound (I) can be purified by a method known in the field of organic synthetic chemistry, such as solvent extraction, recrystallization, chromatography, and a method using an ion exchange resin.

The compound (XXI) can be produced by condensing compound (XIX) with compound (XXIIa)

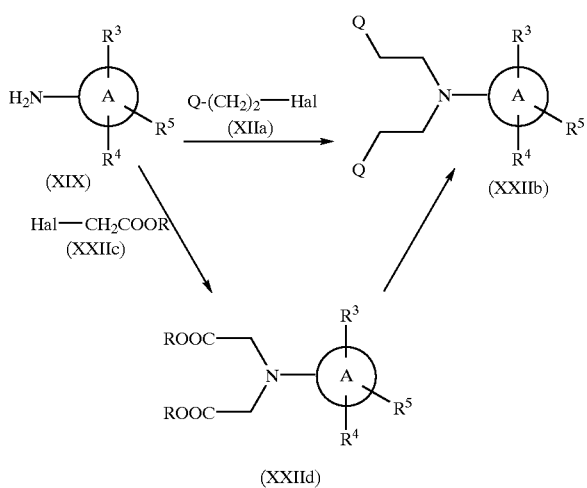

wherein Q, Hal and R are as defined above, in the same manner as in Method A to give compound (XXIIb) (wherein each symbol is as defined above), and converting the group Q of compound (XXIIb) to a leaving group Lv as necessary by a method known in the field of organic synthetic chemistry. The compound (XXIIb) can be produced by condensing compound (XIX) with compound (XXIIc) (wherein R is lower alkyl having 1 to 4 carbon atoms and Hal is as defined above) in the same manner as in Method A to give compound (XXIId) (wherein each symbol is as defined above), and converting the resulting compound by a method known in the field of organic synthetic chemistry.

The reaction conditions (reagent, reaction solvent, reaction time) of condensation are the same as in Method A.

The reducing agent to be used for reduction of the ester group in compound (XXIId) may be, for example, a metallic reducing reagent such as aluminum lithium hydride, sodium borohydride, lithium borohydride and the like, or diborane.

The solvent to be used for reduction of the ester group may be, for example, tetrahydrofuran, dioxane, diethyl ether, methanol, ethanol, 1-propanol, 2-propanol, tert-butyl alcohol, ethylene glycol dimethyl ether or a mixture thereof.

The reaction temperature of reduction of the ester group is generally from −20° C. to 80° C., and a temperature above or under this range can be employed as necessary.

The reaction time of reduction of the ester group is generally from 30 minutes to 10 hours, and a time longer or shorter than this range can be employed as necessary.

After reduction under the above-mentioned reaction conditions and, where necessary, removal of protecting group (s), compound (XXIIb) can be purified by a method known in the field of organic synthetic chemistry, such as solvent extraction, recrystallization, chromatography, and a method using an ion exchange resin.

Method K

Compound (I) can be also produced by the following method.

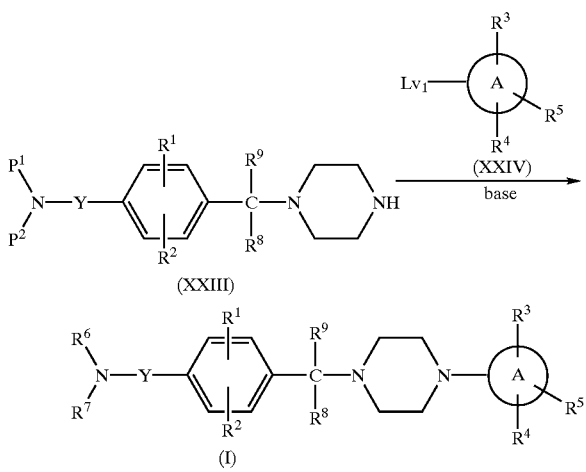

wherein $L_{v1}$ is a leaving group widely used in aromatic nucleophilic substitution reaction, such as halogen (e.g., fluorine, chlorine, bromine or iodine), nitro, p-toluenesulfonyloxy, methanesulfonyloxy, trifluoromethanesulfonyloxy, benzenesulfenyl, benzenesulfonyl, azido, aryloxy, alkoxy, alkylthio or amino, and the other symbols are as defined above.

The solvent to be used for aromatic nucleophilic substitution reaction of compound (XXIII) may be, for example, methanol, ethanol, 1-propanol, 2-propanol, tert-butyl alcohol, tetrahydrofuran, dioxane, diethyl ether, ethylene glycol dimethyl ether, benzene, dichloromethane, dichloroethane, chloroform, toluene, xylene, hexane, dimethylformamide, dimethyl sulfoxide, acetonitrile or a mixture thereof.

For aromatic nucleophilic substitution reaction, a catalyst such as copper powder, copper oxide and the like can be added as necessary.

The reaction temperature of aromatic nucleophilic substitution reaction is generally from 0° C. to 150° C., and a temperature above or under this range can be employed as necessary.

The reaction time of aromatic nucleophilic substitution reaction is generally from 30 minutes to 2 days, and a time longer or shorter than this range can be employed as necessary.

After aromatic nucleophilic substitution reaction under the above-mentioned reaction conditions and, where necessary, removal of protecting group(s), compound (I) can be purified by a method known in the field of organic synthetic chemistry, such as solvent extraction, recrystallization, chromatography, and a method using an ion exchange resin.

Method L

Compound (II) wherein $R^8$ and $R^9$ are both hydrogen can be produced by the following method.

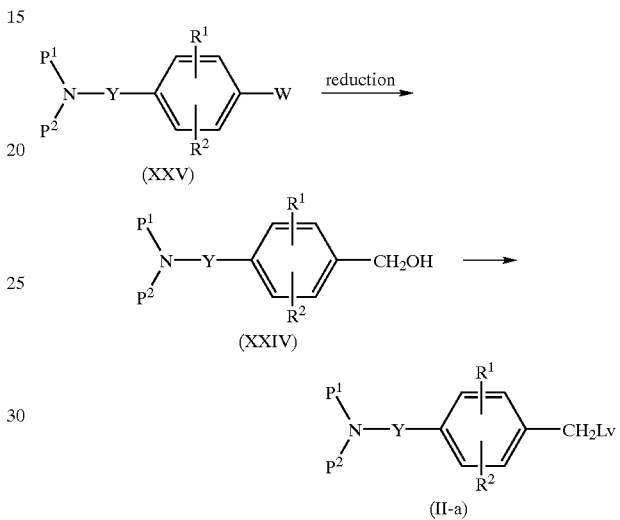

wherein W is carboxylic acid derivative that can be easily converted to each other by a method basic and widely used in the field of organic synthetic chemistry, such as carboxylic acid, carboxylic acid ester (COOR; wherein R is lower alkyl having 1 to 4 carbon atoms), carboxamide or carbonitrile, and the other symbols are as defined above.

The compound (XXV) is converted to an ester group as necessary by a method known in the field of organic synthetic chemistry and subjected to reduction.

The reducing agent to be used for reduction of the ester group may be, for example, a metallic reducing reagent (e.g., aluminum lithium hydride, sodium borohydride, lithium borohydride and the like) or diborane.

The solvent to be used for reduction of the ester group may be, for example, water, tetrahydrofuran, dioxane, diethyl ether, methanol, ethanol, 1-propanol, 2-propanol, tert-butyl alcohol, ethylene glycol dimethyl ether, a mixture thereof, and the like.

The reaction temperature of reduction of the ester group is generally from −20° C. to 80° C., and a temperature above or under this range can be employed as necessary.

The reaction time of reduction of the ester group is generally from 30 minutes to 10 hours, and a time longer or shorter than this range can be employed as necessary.

After reduction under the above-mentioned reaction conditions, the hydroxyl group of compound (XXVI) is converted to a group Lv by a method known in the field of organic synthetic chemistry, and where necessary, the protecting group(s) is/are removed. The compound (II-a) can be purified by a method known in the field of organic synthetic chemistry, such as solvent extraction, recrystallization, chromatography, and a method using an ion exchange resin.

The compound (II-a) and compound (III) are condensed in the same manner as in Method A, and, where necessary, the protecting group(s) is/are removed to give compound (I) wherein RB and R⁹ are both hydrogen, namely, compound (I-8)

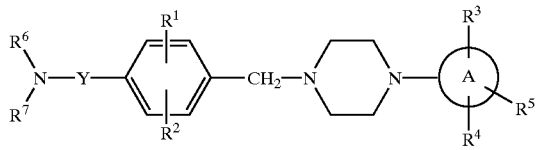

(I-8)

wherein each symbol is as defined above.
Method M

Compound (XIV) wherein $R^8$ is lower alkyl and $R^9$ is hydrogen can be produced by the following method.

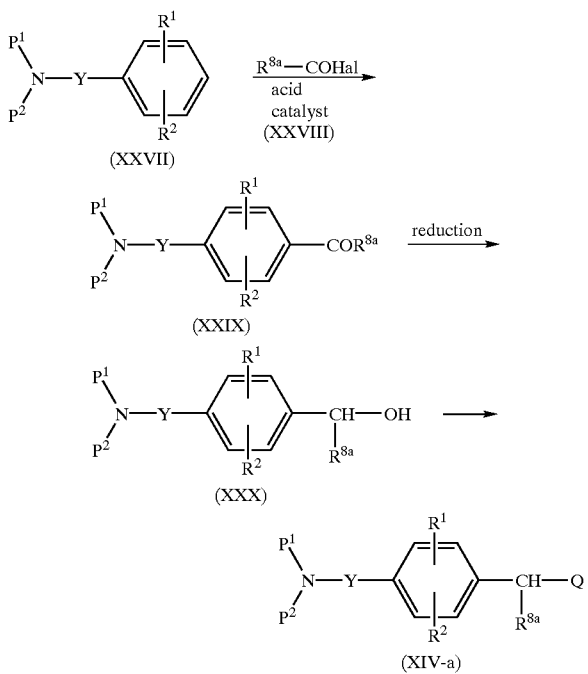

wherein $R^{8a}$ is lower alkyl, and the other symbols are as defined above.

The acid catalyst used for Friedel-Crafts reaction of compound (XXVII) is, for example, aluminum chloride, aluminum bromide, titanium chloride, sulfuric acid, zinc chloride, iron chloride or hydrogen fluoride, phosphoric acid.

The solvent to be used for the Friedel-Crafts reaction may be, for example, tetrahydrofuran, dioxane, diethyl ether, dichloromethane, dichloroethane, chloroform, ethylene glycol dimethyl ether, acetonitrile, nitromethane, carbon disulfide or a mixture thereof. Where necessary, the solvent may not be used.

The reaction temperature of the Friedel-Crafts reaction is generally from –20 C. to 100° C., and a temperature above or under this range can be employed as necessary.

The reaction time of reduction of the Friedel-Crafts reaction is generally from 30 minutes to 24 hours, and a time longer or shorter than this range can be employed as necessary.

The reducing agent to be used for reduction of the carbonyl group in compound (XXIX) may be, for example, a metallic reducing reagent such as aluminum lithium hydride, sodium borohydride, lithium borohydride and the like, or diborane.

The solvent to be used for reduction of the carbonyl group may be, for example, water, tetrahydrofuran, dioxane, diethyl ether, methanol, ethanol, 1-propanol, 2-propanol, tert-butyl alcohol, ethylene glycol dimethyl ether, a mixture thereof, and the like.

The reaction temperature of reduction of the carbonyl group is generally from –20° C. to 80° C., and a temperature above or under this range can be employed as necessary.

The reaction time of reduction of the carbonyl group is generally from 30 minutes to 10 hours, and a time longer or shorter than this range can be employed as necessary.

The obtained compound (XXX) is converted to a group Q by a method known in the field of organic synthetic chemistry to produce compound (XIV-a).

The group Q of compound (XIV-a) is converted to a group Lv as necessary by a method known in the field of organic synthetic chemistry and condensed with compound (III) in the same manner as in Method A. Where necessary, the protecting group(s) is/are removed to produce compound (I) wherein $R^9$ is hydrogen, namely, compound (I-9)

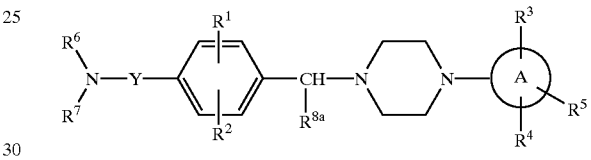

(I-9)

wherein each symbol is as defined above.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method N

Compound (II) wherein $R^8$ and $R^9$ are both hydrogen and Lv is particularly halogen can be produced by the following method.

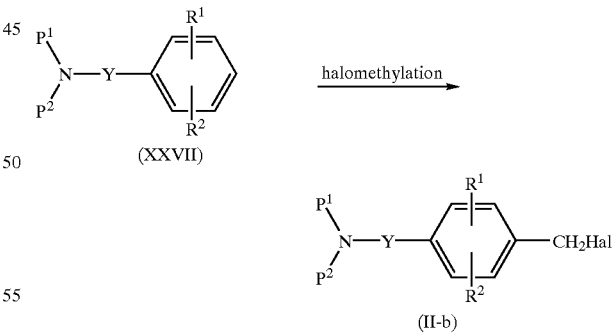

wherein each symbol is as defined above.

The reagent to be used for halomethylation of compound (XXVII) is exemplified by formaldehyde and hydrogen chloride, formaldehyde and hydrogen bromide, formaldehyde and hydrogen iodide, chloromethyl methyl ether, bis(chloromethyl) ether, methoxyacetyl chloride and 1-chloro-4-(chloromethoxy)butane.

The catalyst to be used for halomethylation is, for example, zinc chloride, aluminum chloride, aluminum bromide, titanium chloride or iron chloride.

The solvent to be used for halomethylation may be, for example, tetrahydrofuran, dioxane, diethyl ether, dichloromethane, dichloroethane, chloroform, ethylene glycol dimethyl ether, acetonitrile, nitromethane, carbon disulfide or a mixture thereof.

The reaction temperature of halomethylation is generally from −20° C. to 100° C., and a temperature above or under this range can be employed as necessary.

The reaction time of halomethylation is generally from 30 minutes to 24 hours, and a time longer or shorter than this range can be employed as necessary.

After halomethylation under the above-mentioned reaction conditions and, where necessary, removal of protecting group(s), compound (II-b) can be purified by a method known in the field of organic synthetic chemistry, such as solvent extraction, recrystallization, chromatography, and a method using an ion exchange resin.

Moreover, compound (II-b) and compound (III) are condensed in the same manner as in Method A to produce compound (I-8).

Method O

Compound (XXVI) can be also produced by the following method.

nitromethane, carbon disulfide and the like. Where necessary, a solvent may not be used.

The temperature of reaction with dichloromethyl methyl ether is generally from −50° C. to 50° C., and a temperature above or under this range can be employed as necessary.

The time of reaction with dichloromethyl methyl ether is generally from 30 minutes to 24 hours, and a time longer or shorter than this range can be employed as necessary.

The reducing agent to be used for reduction of the formyl group in compound (XXXI) may be, for example, a metallic reducing reagent such as aluminum lithium hydride, sodium borohydride, lithium borohydride and the like, or diborane.

The solvent to be used for reduction of the formyl group may be, for example, water, tetrahydrofuran, dioxane, diethyl ether, methanol, ethanol, 1-propanol, 2-propanol, tert-butyl alcohol, ethylene glycol dimethyl ether, a mixture thereof, and the like.

The reaction temperature of reduction of the formyl group is generally from −20° C. to 80° C., and a temperature above or under this range can be employed as necessary.

The reaction time of reduction of the formyl group is generally from 30 minutes to 10 hours, and a time longer or shorter than this range can be employed as necessary.

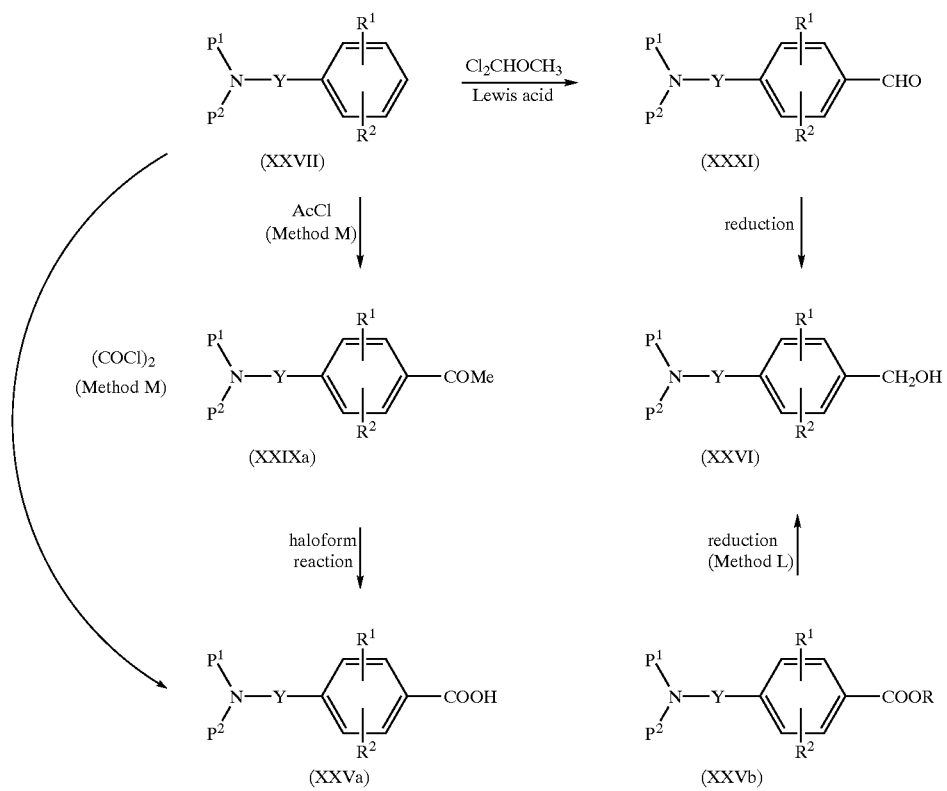

wherein each symbol is as defined above.

The Lewis acid to be used for the reaction with dichloromethyl methyl ether may be, for example, aluminum chloride, titanium tetrachloride, tin tetrachloride, antimony (v)chloride, iron(III) chloride, boron trifluoride, bismuth(III) chloride, zinc chloride, mercury(II) chloride and the like.

The organic solvent to be used for the reaction with dichloromethyl methyl ether may be, for example, tetrahydrofuran, diethyl ether, ethylene glycol dimethyl ether, dimethylformamide, dimethyl sulfoxide, methylene chloride, chloroform, dichloroethane, acetonitrile, The compound (XXVI) can be produced using a haloform reaction as the key reaction.

The acylation of compound (XXVII) with acetyl chloride is performed under the same reaction conditions as in Method M.

The reagent to be used for the haloform reaction of compound (XXIXa) may be, for example, base (e.g., sodium hydroxide, potassium hydroxide and the like), and a halogenating agent (e.g., bromine, chlorine, sodium (potassium) hypochlorite, sodium (potassium) hypobromite and the like).

The solvent to be used for haloform reaction may be, for example, water, methanol, ethanol, 1-propanol, 2-propanol, tert-butyl alcohol, tetrahydrofuran, dioxane, a mixture thereof, and the like.

The temperature of haloform reaction is generally from −20° C. to 100° C., and a temperature above or under this range can be employed as necessary.

The reaction time of haloform reaction is generally from 30 minutes to 24 hours, and a time longer or shorter than this range can be employed as necessary.

Conversion of compound (XXVa) via compound (XXVb) to compound (XXVI) is performed under the reaction conditions described for Method L.

The compound (XXVa) can be also produced by directly from compound (XXVII) by Friedel-Crafts reaction using oxalyl chloride. The Friedel-Crafts reaction using oxalyl chloride is performed under the reaction conditions described for Method M.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

The compound (XXXI) can be also produced from compound (XXVII) using known Friedel-Crafts type reaction widely used in the field of organic synthetic chemistry, such as Gattermann-Koch method, Gattermann method, Vilsmeier method, Duff method.

Method P

The compound (XIV), compound (II-a), compound (XV) can be converted to compound (XX) by introducing an amino group described in, for example, Method D, Method E and Method F.

Method Q

Compound (I-1) and compound (XII) wherein $R^8$ and $R^9$ are both hydrogen can be also produced by the following method.

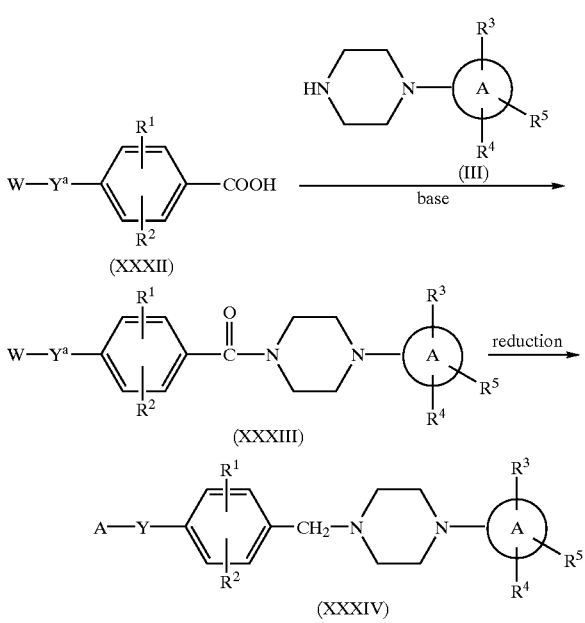

wherein $Y^a$ is single bond or alkyl having one less carbon atoms than Y defined above, A is hydroxy or amino, and the other symbols are as defined above.

For condensation of compound (XXXII) and compound (III), for example, 1) acid chloride method and 2) mixed acid anhydride method widely used in the field of organic synthetic chemistry are particularly effective.

The reagent used for the acid chloride method may be, for example, thionyl chloride and oxazolyl chloride.

The solvent to be used for acid chloride method may be, for example, tetrahydrofuran, dioxane, diethyl ether, ethylene glycol dimethyl ether, benzene, dichloromethane, dichloroethane, chloroform, toluene, xylene and hexane.

The reaction temperature of acid chloride method is generally from 0° C. to 80° C., and a temperature above or under this range can be employed as necessary.

The reaction time of acid chloride method is generally from 30 minutes to 2 days, and a time longer or shorter than this range can be employed as necessary.

The reagent used for the mixed acid anhydride method may be, for example, methyl chlorocarbonate, ethyl chlorocarbonate, isopropyl chlorocarbonate, isobutyl chlorocarbonate or phenyl chlorocarbonate.

The base to be used for mixed acid anhydride method may be, for example, triethylamine, diisopropylethylamine, potassium carbonate, potassium hydrogencarbonate, sodium carbonate, sodium hydrogencarbonate, sodium hydroxide, sodium methoxide or sodium ethoxide.

The solvent to be used for acid anhydride method may be, for example, tetrahydrofuran, dioxane, acetone, diethyl ether, ethylene glycol dimethyl ether, benzene, dichloromethane, dichloroethane, chloroform, toluene, xylene or hexane.

The reaction temperature of mixed acid anhydride method is generally from −80° C. to 20° C., and a temperature above or under this range can be employed as necessary.

The reaction time of acid anhydride method is generally from 30 minutes to 2 days, and a time longer or shorter than this range can be employed as necessary.

The reducing agent to be used for compound (XXXIII) may be, for example, a metallic reducing reagent (e.g., aluminum lithium hydide, sodium borohydride, lithium borohydride and the like), or diborane.

The solvent to be used for reduction may be, for example, water, tetrahydrofuran, dioxane, diethyl ether, methanol, ethanol, 1-propanol, 2-propanol, tert-butyl alcohol, ethylene glycol dimethyl ether, a mixture thereof, and the like.

The reaction temperature of reduction is generally from −20° C. to 80° C., and a temperature above or under this range can be employed as necessary.

The reaction time of reduction is generally from 30 minutes to 10 hours, and a time longer or shorter than this range can be employed as necessary.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method R

Compound (I-1) can be also produced by the following method.

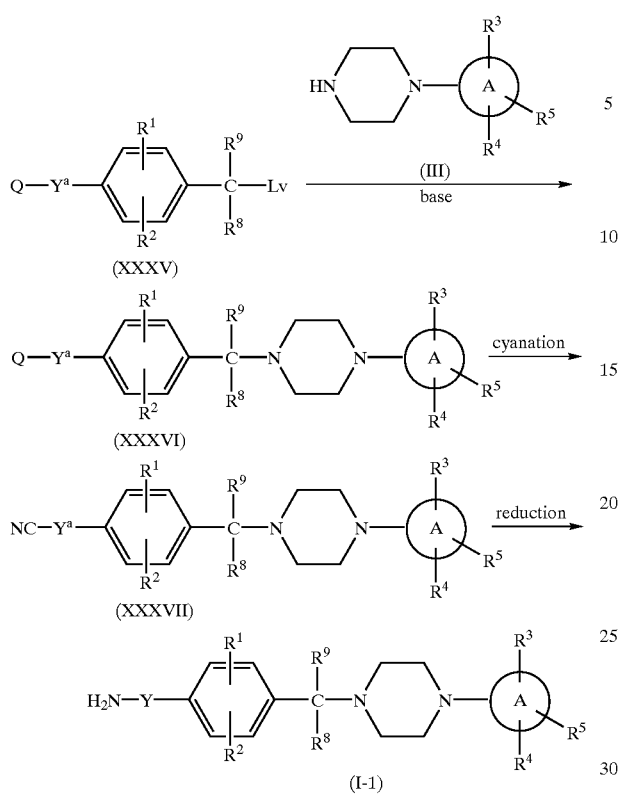

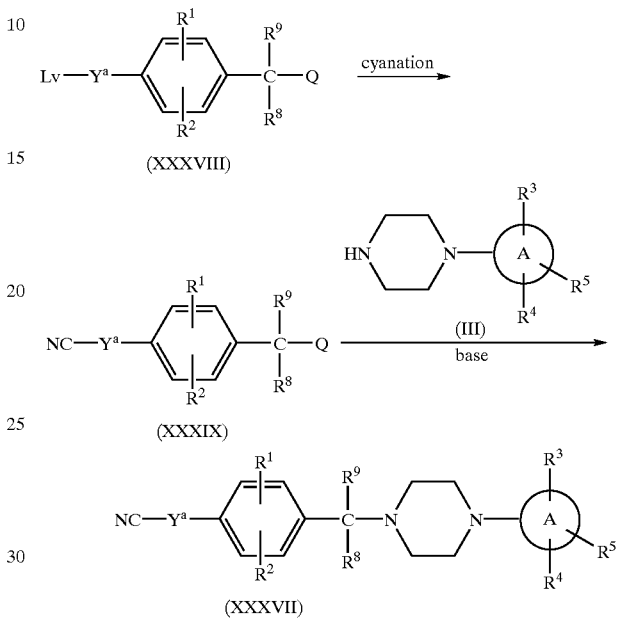

wherein each symbol is as defined above.

The compound (XXXV) and compound (III) are condensed under the same reaction conditions as in Method A.

The group Q of compound (XXXVI) is converted to a leaving group Lv as necessary by a method known in the field of organic synthetic chemistry and then subjected to cyanation.

The reagent to be used for cyanation may be, for example, sodium cyanide or potassium cyanide.

The solvent to be used for cyanation may be, for example, methanol, ethanol, 1-propanol, 2-propanol, tert-butyl alcohol, tetrahydrofuran, dimethylformamide, dimethyl sulfoxide or a mixture thereof.

The reaction temperature of cyanation is generally from 0° C. to 150° C., and a temperature above or under this range can be employed as necessary.

The reaction time of cyanation is generally from 30 minutes to 2 days, and a time longer or shorter than this range can be employed as necessary.

The reducing agent to be used for reduction of the cyano group in compound (XXXVII) may be, for example, a metallic reducing reagent such as aluminum lithium hydide, sodium borohydride and lithium borohydride, or diborane.

The solvent to be used for cyanation may be, for example, tetrahydrofuran, dioxane, diethyl ether, methanol, ethanol, 1-propanol, 2-propanol, tert-butyl alcohol, ethylene glycoldimethyl ether, a mixture thereof, and the like.

The reaction temperature of reduction of the cyano group is generally from −20° C. to 80° C., and a temperature above or under this range can be employed as necessary.

The reaction time of reduction of the cyano group is generally from 30 minutes to 10 hours, and a time longer or shorter than this range can be employed as necessary.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method S

Compound (XXXVII) can be also produced by the following method.

wherein each symbol is as defined above.

In this method, the conditions of cyanation are the same as in Method R and those of condensation are the same as in Method A.

After cyanation and condensation under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method T

Compound (XXV) wherein $R^1$ is hydrogen and $R^2$ is nitro can be produced by the following method.

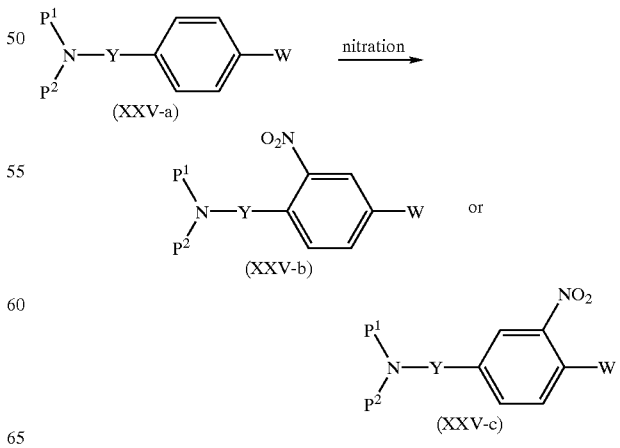

wherein each symbol is as defined above.

By this nitration, compound (XXV-b) is mainly produced.

The reagent to be used for nitration may be, for example, nitric acid, mixed acid, acetyl nitrate, dinitrogen pentaoxide or nitronium salt.

The solvent to be used for nitration may be, for example, water, acetic acid, acetic anhydride, con. sulfuric acid, chloroform, dichloromethane, carbon disulfide, dichloroethane or a mixture thereof, or the solvent may not be used.

The reaction temperature of nitration is generally from −20° C. to 80° C., and a temperature above or under this range can be employed as necessary.

The reaction time of nitration is generally from 30 minutes to 10 hours, and a time longer or shorter than this range can be employed as necessary.

After nitration under the above-mentioned reaction conditions and, where necessary, removal of protecting group (s), compound (XXV-b), compound (XXV-c) can be purified by a method known in the field of organic synthetic chemistry, such as solvent extraction, recrystallization, chromatography, and a method using an ion exchange resin.

Further, compound (XXV-b) and compound (XXV-c) are reacted in the same manner as in Method L to produce compound (I-8a)

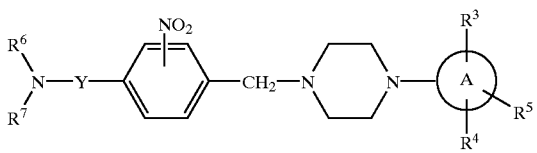

(I-8a)

wherein each symbol is as defined above.

Method U

Compound (I-8) wherein $R^1$ is hydrogen and $R^2$ is amino can be produced by the following method.

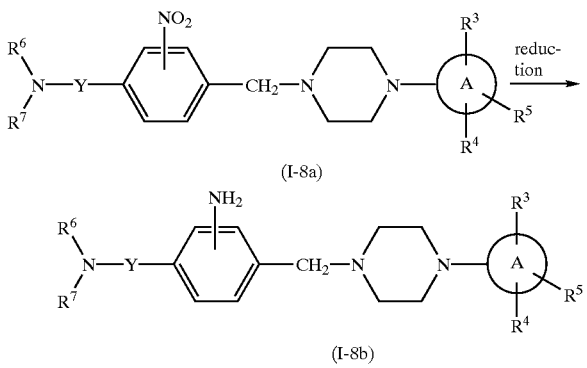

wherein each symbol is as defined above.

The reducing agent to be used for reduction of the nitro group may be, for example, a metallic reducing reagent (e.g., sodium borohydride, lithium borohydride, aluminum lithium hydide and the like), reduction using metal (e.g., iron, zinc, tin and the like), and catalytic reduction using transition metal (e.g., palladium-carbon, platinum oxide, Raney-nickel, rhodium, ruthenium and the like). When catalytic reduction is applied, ammonium formate, sodium dihydrogenphosphate, hydrazine and the like can be used as the hydrogen source.

The solvent to be used for reduction of the nitro group may be, for example, water, methanol, ethanol, tert-butyl alcohol, tetrahydrofuran, diethyl ether, dioxane, acetone, ethyl acetate, acetic acid, benzene, toluene, xylene, dimethylformamide, dimethyl sulfoxide or a mixture thereof.

The reaction temperature of reduction of nitro is generally from −20° C. to 150° C., and a temperature above or under this range can be employed as necessary.

The reaction time of reduction of nitro is generally from 30 minutes to 2 days, and a time longer or shorter than this range can be employed as necessary.

After reduction under the above-mentioned reaction conditions and, where necessary, removal of protecting group (s), compound (I-8b) can be purified by a method known in the field of organic synthetic chemistry, such as solvent extraction, recrystallization, chromatography, and a method using an ion exchange resin.

In compound (I-8b), when $R^6$ and $R^7$ are not hydrogen and $R^3$, $R^4$ and $R^5$ are not amino, the functional group (hydroxy and the like) are protected as necessary, and the compound is subjected to the reactions as described in Method B1 to Method B8 to produce a compound wherein the amino group on the corresponding phenylene ring has been alkylated and/or acylated.

Method V

Compound (I-8) wherein $R^1$ is hydrogen, $R^2$ is hydrogen, halogen (e.g., fluorine, chlorine, bromine or iodine), hydroxy or cyano can be produced by the following method.

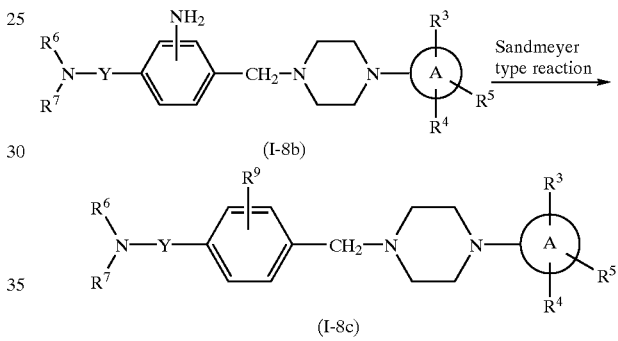

wherein Rg is hydrogen, halogen (e.g., fluorine, chlorine, bromine or iodine), hydroxy or cyano, and the other symbols are as defined above.

As the Sandmeyer type reaction, Sandmeyer reaction, Gattermann reaction, Schiemann reaction and the like are exemplified. The Sandmeyer type reaction comprises processes of diazotization of amine and nucleophilic substitution of the resulting diazonium salt using various nucleophiles.

For diazotization, an aqueous sodium nitrite solution, nitrous acid and organic nitrite ester (e.g., isopentyl nitrite) are generally used.

The solvent to be used for diazotization may be, for example, water, hydrochloric acid, hydrobromic acid, nitric acid, dilute sulfuric acid, benzene, toluene or a mixture thereof.

The reaction temperature of diazotization is generally from −20° C. to 100° C., and a temperature above or under this range can be employed as necessary.

The reaction time of diazotization is generally from 10 minutes to 5 hours, and a time longer or shorter than this range can be employed as necessary.

The reagent to be used for nucleophilic substitution may be, for example, hypophosphorous acid, fluoroboric acid, hydrochloric acid—copper(I) chloride, hydrochloric acid—Gattermann copper, hydrobromic acid—copper(I) bromide, hydrobromic acid—Gattermann copper, iodine, potassium iodide, sodium iodide, trimethylsilyl iodide, water, copper(I) cyanide, sodium cyanide, potassium cyanide and the like.

The solvent to be used for nucleophilic substitution may be, for example, water, hydrochloric acid, hydrobromic acid, nitric acid, dilute sulfuric acid, benzene, toluene, chloroform, dichloromethane, acetonitrile or a mixture thereof.

The reaction temperature of nucleophilic substitution is generally from −20° C. to 100° C., and a temperature above or under this range can be employed as necessary.

The reaction time of nucleophilic substitution is generally from 30 minutes to 5 hours, and a time longer or shorter than this range can be employed as necessary.

After nucleophilic substitution under the above-mentioned reaction conditions and, where necessary, removal of protecting group(s), compound (I-8c) can be purified by a method known in the field of organic synthetic chemistry, such as solvent extraction, recrystallization, chromatography, and a method using an ion exchange resin.

Method W

Compound (XXV) wherein $R^1$ is hydrogen and $R^2$ is amino can be produced by the following method.

(XXV-b)

(XXV-c)

reduction (XXV-d)

wherein each symbol is as defined above.

The reaction conditions of reduction of nitro are the same as in Method U.

After reduction under the above-mentioned reaction conditions and, where necessary, removal of protecting group(s), compound (XXV-d) can be purified by a method known in the field of organic synthetic chemistry, such as solvent extraction, recrystallization, chromatography, and a method using an ion exchange resin.

Further, the amino group of compound (XXV-d) is protected and reacted in the same manner as in Method L to produce compound (I-8b).

Method X

Compound (XXV) wherein $R^1$ is hydrogen, $R^2$ is hydrogen, halogen (e.g., fluorine, chlorine, bromine or iodine), hydroxy or cyano can be produced by the following method.

(XXV-d)

Sandmeyer type reaction (XXV-e)

wherein each symbol is as defined above.

The reaction conditions of Sandmeyer type reaction are the same as in Method V.

After Sandmeyer type reaction under the above-mentioned reaction conditions and, where necessary, removal of protecting group(s), compound (XXV-e) can be purified by a method known in the field of organic synthetic chemistry, such as solvent extraction, recrystallization, chromatography, and a method using an ion exchange resin.

Further, compound (XXV-e) is reacted in the same manner as in Method L to produce compound (I-8c).

Method Y

Compound (XXIX) wherein $R^1$ is hydrogen and $R^2$ is nitro can be produced by the following method.

(XXIX-a)

nitration (XXIX-b)

wherein each symbol is as defined above.

The reaction conditions of nitration are the same as in Method T.

After nitration under the above-mentioned reaction conditions and, where necessary, removal of protecting group(s), compound (XXIX-b) can be purified by a method known in the field of organic synthetic chemistry, such as solvent extraction, recrystallization, chromatography, and a method using an ion exchange resin.

Further, compound (XXIX-b) is reacted in the same manner as in Method M, Method G or Method I to produce compound (I-9a)

(I-9a)

wherein each symbol is as defined above.

Method Z

Compound (I-9) wherein $R^1$ is hydrogen and $R^2$ is amino can be produced by the following method.

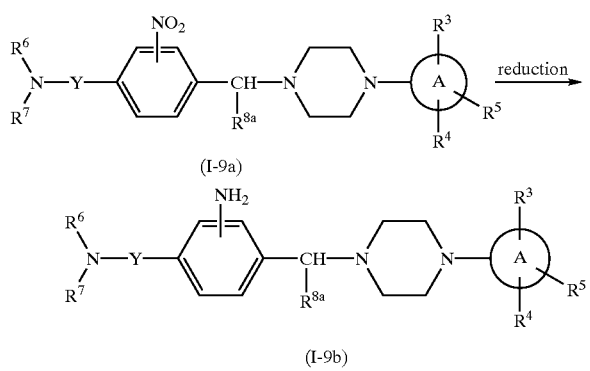

(I-9a)

(I-9b)

wherein each symbol is as defined above.

The reaction conditions of reduction are the same as in Method U.

After reduction under the above-mentioned reaction conditions and, where necessary, removal of protecting group(s), compound (I-9b) can be purified by a method known in the field of organic synthetic chemistry, such as solvent extraction, recrystallization, chromatography, and a method using an ion exchange resin.

In compound (I-9b), when $R^6$ and $R^7$ are not hydrogen and $R^3$, $R^4$ and $R^5$ are not amino, the functional group (hydroxy and the like) are protected as necessary, and the compound is subjected to the reactions as described in Method B1 to Method B8 to produce a compound wherein the amino group on the corresponding phenylene ring has been alkylated and/or acylated.

Method AA

Compound (I-9) wherein $R^1$ is hydrogen and $R^2$ is hydrogen, halogen (e.g., fluorine, chlorine, bromine or iodine), hydroxy or cyano can be produced by the following method.

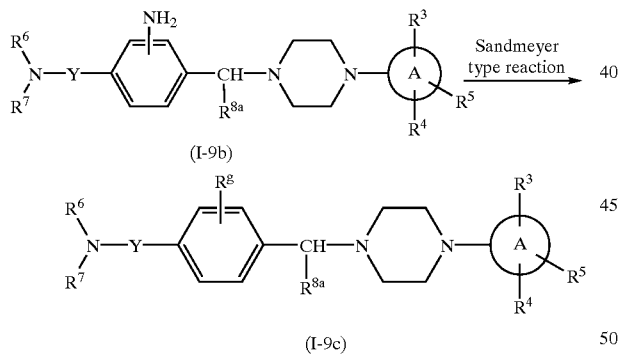

(I-9b)

(I-9c)

wherein each symbol is as defined above.

The reaction conditions of Sandmeyer type reaction are the same as in Method V.

After Sandmeyer type reaction under the above-mentioned reaction conditions and, where necessary, removal of protecting group(s), compound (I-9c) can be purified by a method known in the field of organic synthetic chemistry, such as solvent extraction, recrystallization, chromatography, and a method using an ion exchange resin.

Method BB

The compound (X) can be produced by subjecting compound (XII) to Mitsunobu reaction in the same manner as in Method F using hydrogen azide.

The reaction conditions (reagent, solvent, reaction temperature, reaction time) of Mitsunobu reaction are the same as in Method F.

After Mitsunobu reaction under the above-mentioned reaction conditions, the protecting group(s) is/are removed as necessary, and compound (X) can be purified by a method known in the field of organic synthetic chemistry, such as solvent extraction, recrystallization, chromatography, and a method using an ion exchange resin.

Method CC

Compound (I) wherein Y is methylene and $R^8$ and $R^9$ are both hydrogen can be produced by the following method.

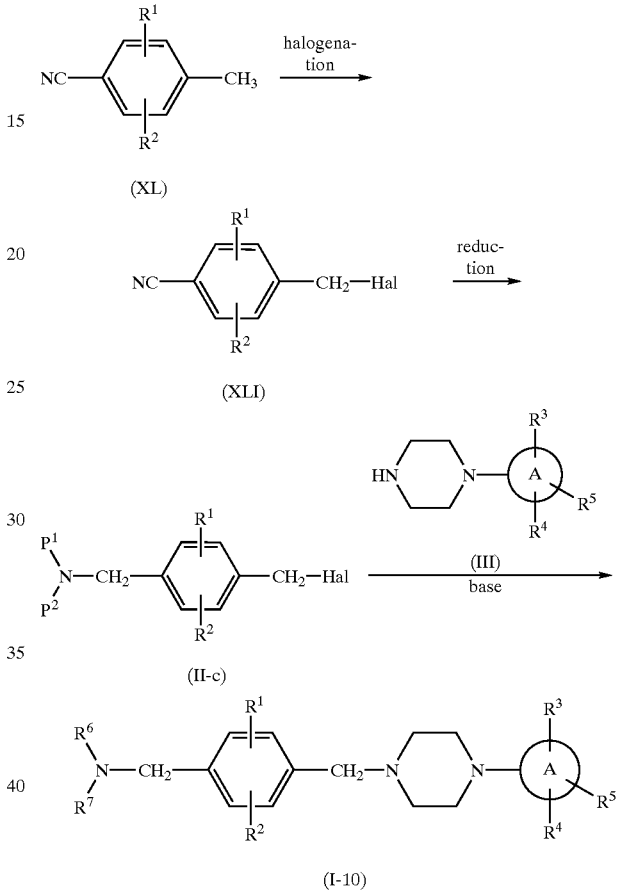

(XL)

(XLI)

(II-c)

(I-10)

wherein Hal is halogen such as chlorine, bromine, iodine and the like, and the other symbols are as defined above.

The halogenizing agent to be used for the halogenation of compound (XL) may be, for example, halogen (e.g., chlorine, bromine, iodine and the like), N-bromosuccinimide, N-chlorosuccinimide, sulfuryl chloride, hypohalite tert-butyl and the like. For acceleration of the reaction, a radical initiator such as dibenzoyl peroxide, azobisisobutyronitrile and the like can be used. In addition, the reaction may be carried out under heat or light for acceleration of the reaction.

The solvent to be used for halogenation is preferably carbon tetrachloride.

The reaction temperature of halogenization is generally from 0° C. to 100° C., and a temperature above or under this range can be employed as necessary.

The reaction time of halogenization is generally 1 to 12 hours, and a time longer or shorter than this range can be employed as necessary.

The reducing agent to be used for reduction of compound (XLI) may be, for example, those used in catalytic reduction such as diisobutylaluminum hydride, sodium borohydride— cobalt (II) chloride, aluminum lithium hydride—aluminum chloride, lithium trimethoxyaluminum hydride, borane—methyl sulfide and transition metal (e.g., palladium-carbon, platinum oxide, Raney-nickel, rhodium, ruthenium and the like).

The solvent to be used for reduction may be, for example, methanol, ethanol, tert-butyl alcohol, tetrahydrofuran, diethyl ether, dioxane, ethyl acetate, benzene, toluene, xylene, dimethylformamide, dimethyl sulfoxide and the like.

The reaction temperature of reduction is generally from −20° C. to 80° C., and a temperature above or under this range can be employed as necessary.

The reaction time of reduction is generally from 30 minutes to 24 hours, and a time longer or shorter than this range can be employed as necessary.

The compound resulting from reduction is alkylated, aralkylated, acylated or protected by a protecting group as necessary by a method known in the field of organic synthetic chemistry to live compound (II-c).

Further, compound (II-c) and compound (III) are condensed in the same manner as in Method A to produce compound (I-10).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method DD

Compound (III) can be produced by the following method.

The reaction temperature of hydrolysis is generally from −20° C. to 100° C., and a temperature above or under this range can be employed as necessary.

The reaction time of hydrolysis is generally from 30 minutes to 2 days, and a time longer or shorter than this range can be employed as necessary.

The solvent to be used for condensation to directly obtain compound (III) from compound (XLII) and piperazine may be, for example, methanol, ethanol, 1-propanol, 2-propanol, tert-butyl alcohol, tetrahydrofuran, dioxane, diethyl ether, ethylene glycol dimethyl ether, benzene, dichloromethane, dichloroethane, chloroform, toluene, xylene, hexane, dimethylformamide, dimethyl sulfoxide, acetonitrile or a mixture thereof, or the solvent may not be used.

The reaction temperature of condensation is generally from 0° C. to 150° C., and a temperature above or under this range can be employed as necessary.

The reaction time of condensation is generally from 30 minutes to 2 days, and a time longer or shorter than this range can be employed as necessary.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

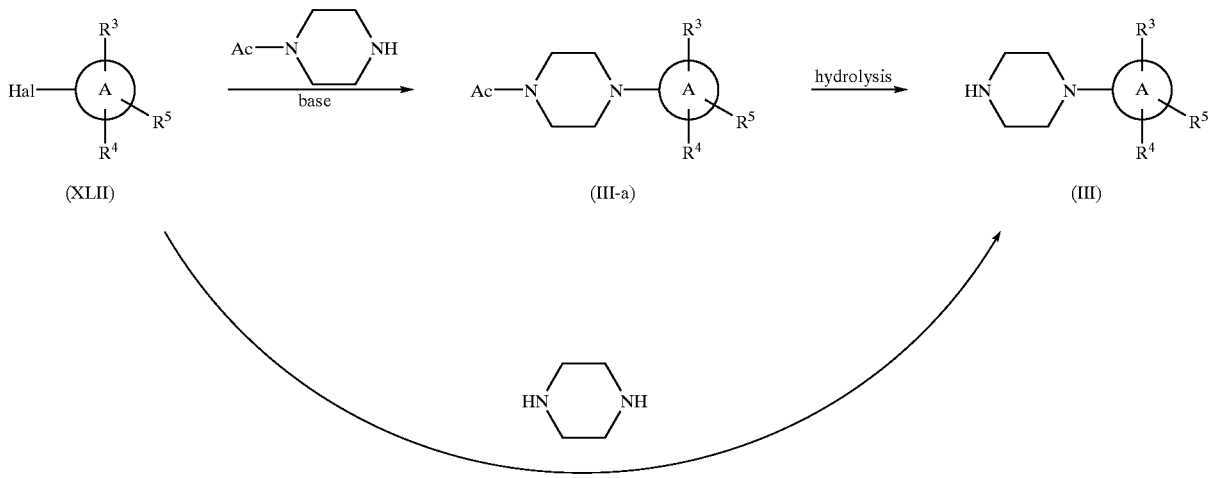

wherein Ac is acetyl, and the other symbols are as defined above.

The compound (XLII) and 1-acetylpiperazine are condensed under the same reaction conditions as in Method K.

The reagent used for hydrolysis of compound (III-a) may be, for example, hydrochloric acid, sulfuric acid, acetic acid, trifluoroacetic acid, sodium hydroxide, potassium hydroxide, barium hydroxide, lithium hydroxide and the like.

The solvent to be used for hydrolysis may be, for example, water, methanol, ethanol, isopropyl alcohol, tert-butyl alcohol, acetone, tetrahydrofuran, ethylene glycol dimethyl ether, dimethylformamide, dimethyl sulfoxide or a mixture thereof.

Method EE

Compound (III) can be also produced by the following method.

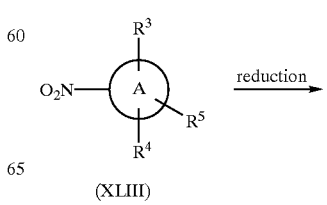

(XLIII)

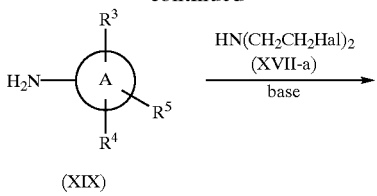

(XIX)

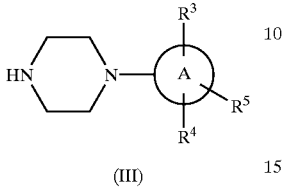

(III)

wherein each symbol is as defined above.

The reducing agent to be used for reduction of the nitro group in compound (XLIII) may be, for example, a metallic reducing reagent such as sodium borohydride, lithium borohydride, aluminum lithium hydide and the like, reduction with metal (e.g., iron, zinc, tin and the like), and catalytic reduction using transition metal (e.g., palladium-carbon, platinum oxide, Raney nickel, rhodium, ruthenium and the like). When catalytic reduction is applied, ammonium formate, sodium dihydrogenphosphate, hydrazine and the like can be used as the hydrogen source.

The solvent to be used for reduction of the nitro group may be, for example, water, methanol, ethanol, tert-butyl alcohol, tetrahydrofuran, diethyl ether, dioxane, acetone, ethyl acetate, acetic acid, benzene, toluene, xylene, dimethylformamide, dimethyl sulfoxide or a mixture thereof.

The reaction temperature of reduction of nitro is generally from −20° C. to 80° C., and a temperature above or under this range can be employed as necessary.

The reaction time of reduction is generally 1 to 24 hours, and a time longer or shorter than this range can be employed as necessary.

The compound (XIX) and compound (XVII-a) are condensed under the same reaction conditions as in Method A to produce compound (III).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method FF

The compound (I) wherein Y is a group of the formula

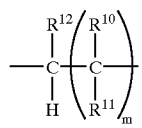

wherein each symbol is as defined above, and $R^9$ is hydrogen, can be produced by the following method.

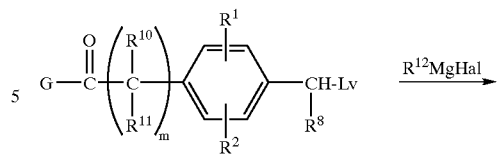

(XLIV)

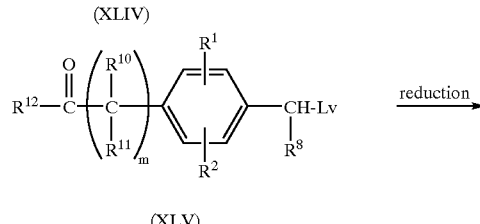

(XLV)

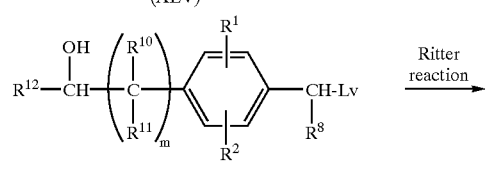

(XLVI)

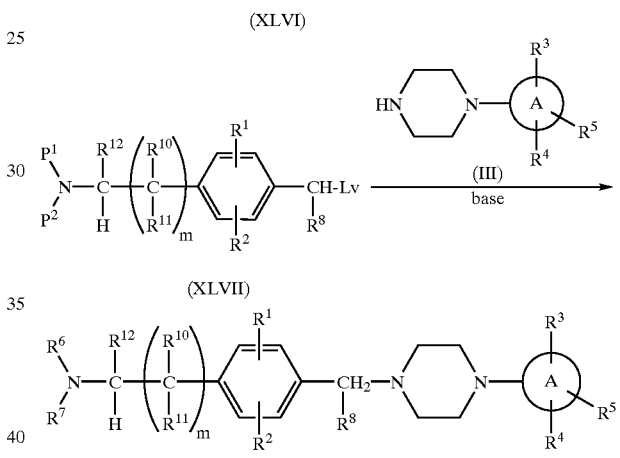

(I-11)

wherein G is a hydroxyl group or lower alkoxy, and the other symbols are as defined above.

The organic solvent to be used for addition reaction of compound (XLIV) may be, for example, tetrahydrofuran, diethyl ether, ethylene glycoldimethyl ether, dimethylformamide, dimethyl sulfoxide, benzene, toluene, xylene, dioxane, methylene chloride, chloroform, dichloroethane and the like.

The reaction temperature of addition is generally from −20° C. to 100° C., and a temperature above or under this range can be employed as necessary.

The reaction time of addition is generally from 30 minutes to 2 days, and a time longer or shorter than this range can be employed as necessary.

The reducing agent to be used for reduction of compound (XLV) may be, for example, sodium borohydride, lithium borohydride, aluminum lithium hydride, diisobutylaluminum hydride, lithium trimethoxyaluminum hydride, lithium tri-tert-butoxyaluminum hydride, diborane and the like.

The organic solvent to be used for reduction may be, for example, methanol, ethanol, tert-butyl alcohol, tetrahydrofuran, diethyl ether, ethylene glycol dimethyl ether, acetone and methyl ethyl ketone.

The reaction temperature of reduction is generally from −100° C. to 80° C., and a temperature above or under this range can be employed as necessary.

The reaction time of reduction is generally from 30 minutes to 10 hours, and a time longer or shorter than this range can be employed as necessary.

The organic solvent to be used for Ritter reaction of compound (XLVI) may be, for example, hydrogen cyanide, acetonitrile, benzonitrile and the like.

The organic solvent to be used for Ritter reaction may be, for example, acetic acid, tetrahydrofuran, diethyl ether, ethylene glycol dimethyl ether, dimethylformamide, dimethyl sulfoxide, benzene, toluene, xylene, dioxane, methylene chloride, chloroform, dichloroethane and the like.

The acid catalyst to be used for Ritter reaction may be, for example, strong acid such as sulfuric acid, trifluoroacetic acid and the like.

The reaction temperature of Ritter reaction is generally from −20° C. to 80° C., and a temperature above or under this range can be employed as necessary.

The reaction time of Ritter reaction is generally from 30 minutes to 24 hours, and a time longer or shorter than this range can be employed as necessary.

The compound obtained by Ritter reaction is hydrolyzed, alkylated, aralkylated, acylated or protected by a protecting group as necessary by a method known in the field of organic synthetic chemistry to produce compound (XLVII).

The compound (XLVII) and compound (III) are condensed under the same reaction conditions as in Method A to produce compound (I-11).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method GG

The compound (I) wherein Y is a group of the formula

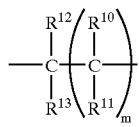

wherein each symbol is as defined above, and $R^9$ is hydrogen, can be produced by the following method.

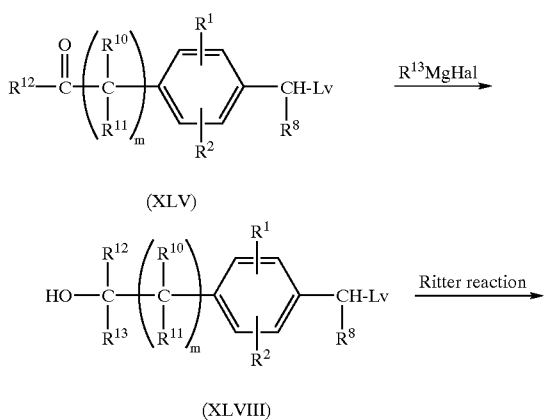

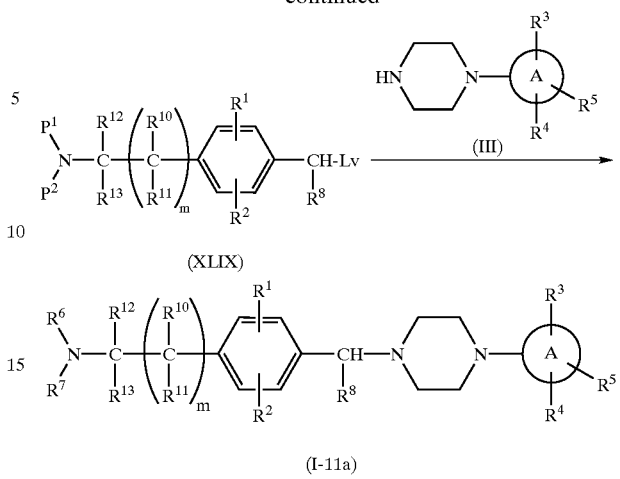

wherein each symbol is as defined above.

The addition reaction of compound (XLV) and Ritter reaction of compound (XLVIII) can be carried out under the same reaction conditions as in Method FF.

The compound (XLIX) and compound (III) are condensed under the same reaction conditions as in Method A.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method HH

Compound (XXIX) and compound (XXX) can be also produced by the following method.

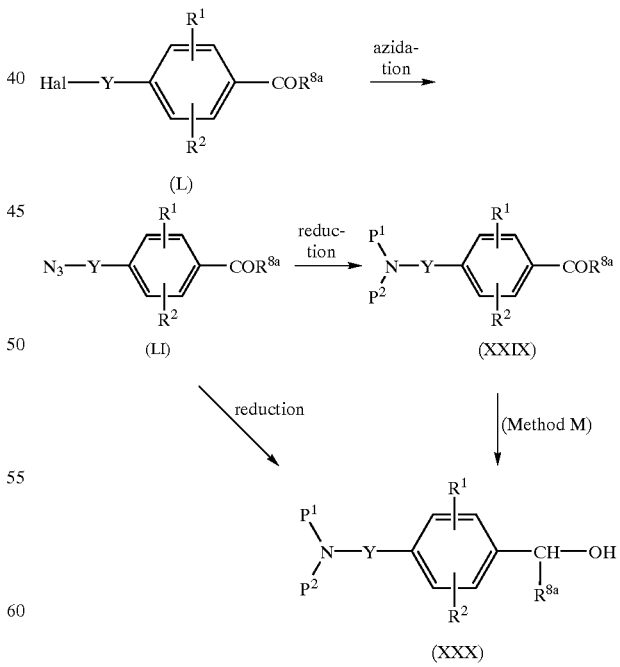

wherein each symbol is as defined above.

The azidating agent to be used for azidation of compound (L) is exemplified by metal azide (e.g., sodium azide, lithium azide and the like) and the like.

The reaction temperature of azidation is generally from 0° C. to 100° C., and a temperature above or under this range can be employed as necessary.

The reaction time of azidation is generally 1 to 24 hours, and a time longer or shorter than this range can be employed as necessary.

The reducing agent to be used for reduction of compound (LI) may be, for example, a metallic reducing reagent such as sodium borohydride, lithium borohydride, aluminum lithium hydride and the like, triphenylphosphine, and catalytic reduction using transition metal (Lindlar catalyst (palladium, calcium carbonate), palladium-carbon, Raney nickel, platinum oxide, rhodium, ruthenium and the like). For the selective reduction of the azide group alone of compound (LI), catalytic reduction using triphenylphosphine or transition metal is particularly effective.

The organic solvent to be used for reduction may be, for example, methanol, ethanol, tert-butyl alcohol, tetrahydrofuran, diethyl ether, dioxane, acetone, ethyl acetate, acetic acid, benzene, toluene, xylene, dimethylformamide, dimethyl sulfoxide and the like.

The reaction temperature of reduction is generally from $-20°$ C. to $80°$ C., and a temperature above or under this range can be employed as necessary.

The reaction time of reduction is generally 1 to 24 hours, and a time longer or shorter than this range can be employed as necessary.

The compound obtained by reduction is alkylated, aralkylated, acylated or protected by a protecting group as necessary by a method known in the field of organic synthetic chemistry to produce compound (XXIX).

After reaction under the above-mentioned reaction conditions and, where necessary, removal of protecting group (s), the synthetic intermediate in each step and the objective compound can be purified by a method known in the field of organic synthetic chemistry, such as solvent extraction, recrystallization, chromatography, and a method using an ion exchange resin.

Method II

Compound (I) wherein Y is methylene and $R^8$ and $R^9$ are the same or different and each is lower alkyl can be produced by the following method.

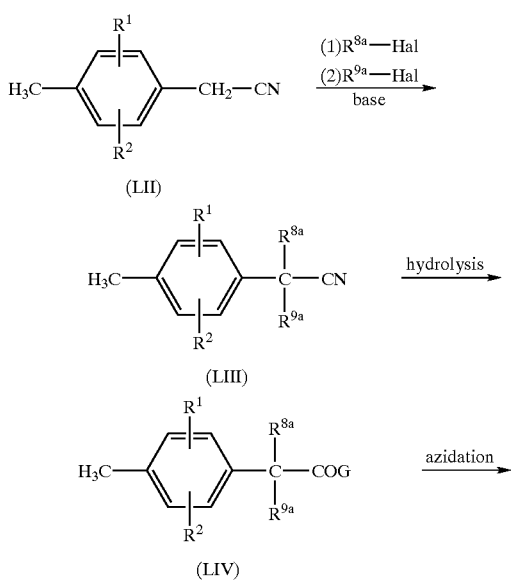

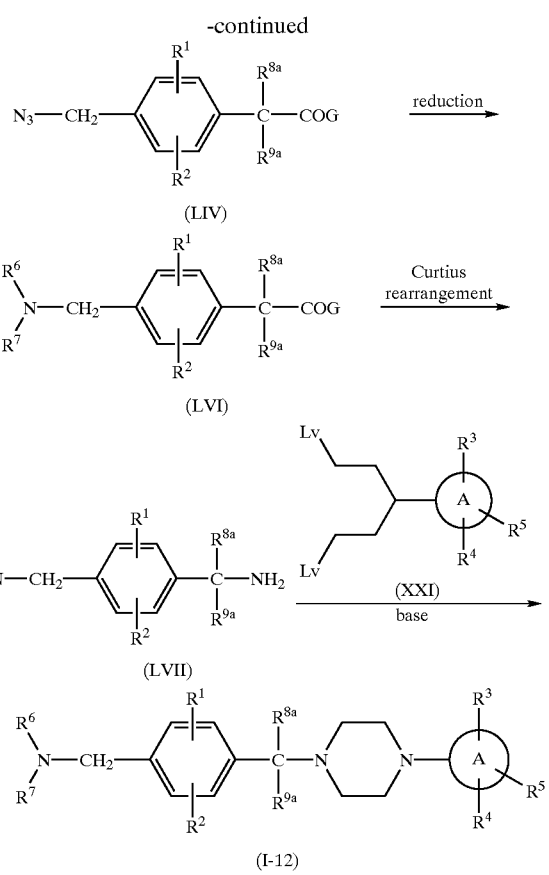

wherein $R^{9a}$ is lower alkyl, and the other symbols are as defined above.

The base to be used for condensation of compound (LII) may be, for example, sodium methoxide, sodium ethoxide, sodium hydride, potassium hydride, lithium diisopropylamide, lithium hexamethyldisilazane, diisopropylethylamine, 1,8-diazabicyclo[4.3.0]undeca-5-ene, sodium amide and the like.

The organic solvent to be used for condensation may be, for example, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane, acetonitrile and the like.

The reaction temperature of condensation is generally from $-20°$ C. to $150°$ C., and a temperature above or under this range can be employed as necessary.

The reaction time of condensation is generally from 30 minutes to 2 days, and a time longer or shorter than this range can be employed as necessary.

The base to be used for hydrolysis of compound (LIII) may be, for example, acid such as hydrochloric acid, sulfuric acid, formic acid, acetic acid and the like, or alkali such as sodium hydroxide, potassium hydroxide and the like.

The solvent to be used for hydrolysis may be, for example, water, methanol, ethanol, isopropyl alcohol, tert-butyl alcohol, ethylene glycol, diethylene glycol, a mixture thereof, and the like.

The reaction temperature of hydrolysis is generally from $-20°$ C. to $150°$ C., and a temperature above or under this range can be employed as necessary.

The reaction time of hydrolysis is generally from 30 minutes to 2 days, and a time longer or shorter than this range can be employed as necessary.

After halogenation of compound (LIV), the compound is subjected to azidation to produce compound (LIX). The halogenation of compound (LIV) can be performed under the same reaction conditions as in Method CC. The obtained halogenated compound is subjected to azidation under the same reaction conditions as in Method HH.

The compound (LV) is reduced under the same reaction conditions as in Method HH.

The base to be used for curtius rearrangement of compound (LVI) may be, for example, Hünig base such as triethylamine, diisopropylethylamine and the like. When the substrate of this reaction, carboxylic acid, is a salt, a base is not necessary.

The activator to be used for Curtius rearrangement is exemplified by methyl chlorocarbonate, ethyl chlorocarbonate, isopropyl chlorocarbonate, isobutyl chlorocarbonate, phenyl chlorocarbonate and the like.

The azidating agent to be used for Curtius rearrangement is exemplified by sodium azide, diphenylphosphoryl azide (when this reagent is used, base or activator is not necessary) and the like.

The solvent to be used for Curtius rearrangement may be, for example, aprotic solvent in the former half of the reaction, such as tetrahydrofuran, acetone, diethyl ether, ethylene glycol dimethyl ether, dimethylformamide, dimethyl sulfoxide, dioxane, methylene chloride, chloroform, dichloroethane, acetonitrile and the like, and in the latter half of the reaction, for example, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane, acetonitrile or benzyl alcohol is used.

The reaction temperature of Curtius rearrangement is generally from −20° C. to 150° C., and a temperature above or under this range can be employed as necessary.

The reaction time of Curtius rearrangement is generally from 30 minutes to 10 hours, and a time longer or shorter than this range can be employed as necessary.

The carbamic acid compound obtained by Curtius rearrangement is treated with benzyl alcohol and subjected to catalytic reduction to produce compound (LVII). When carbamic acid compound is treated with an alcohol solution of acid (e.g., hydrochloric acid, sulfuric acid and the like) or alkali (e.g., sodium hydroxide, potassium hydroxide and the like), or trimethylsilyl iodide, compound (LVII) can be produced.

The compound (LVII) and compound (XXI) are condensed under the same reaction conditions as in Method J.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method JJ

Compound (XVIII) can be produced by the following method.

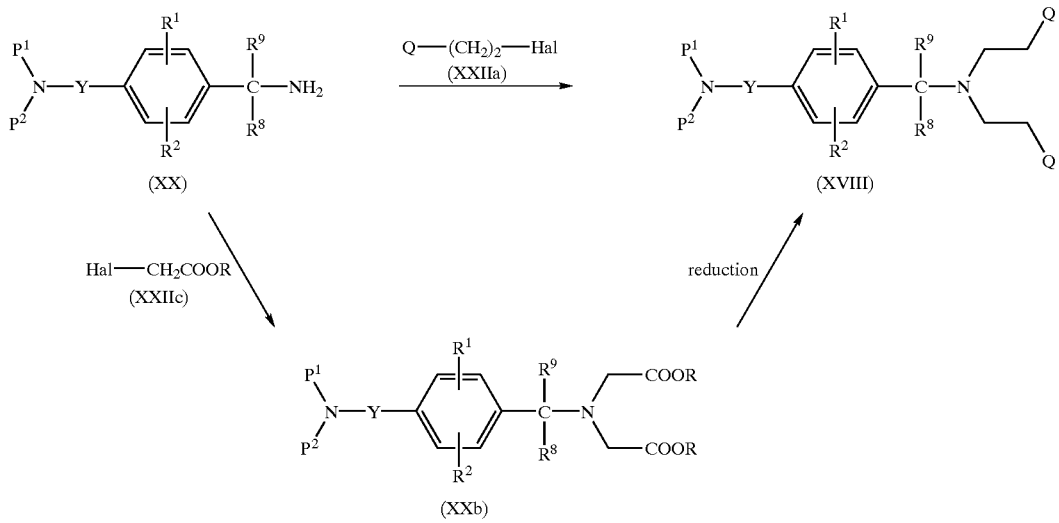

wherein each symbol is as defined above.

The compound (XX) and compound (XXIIa) are condensed under the same reaction conditions as in Method J.

The compound (XX) and compound (XXIIc) are condensed under the same reaction conditions as in Method J. The compound (XXb) is reduced under the same reaction conditions as in Method J.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method KK

Compound (I) wherein m=n=0, $R^{12}$ and $R^{13}$ in combination form ethylene and $R^8$ and $R^9$ are both hydrogen can be produced by the following method.

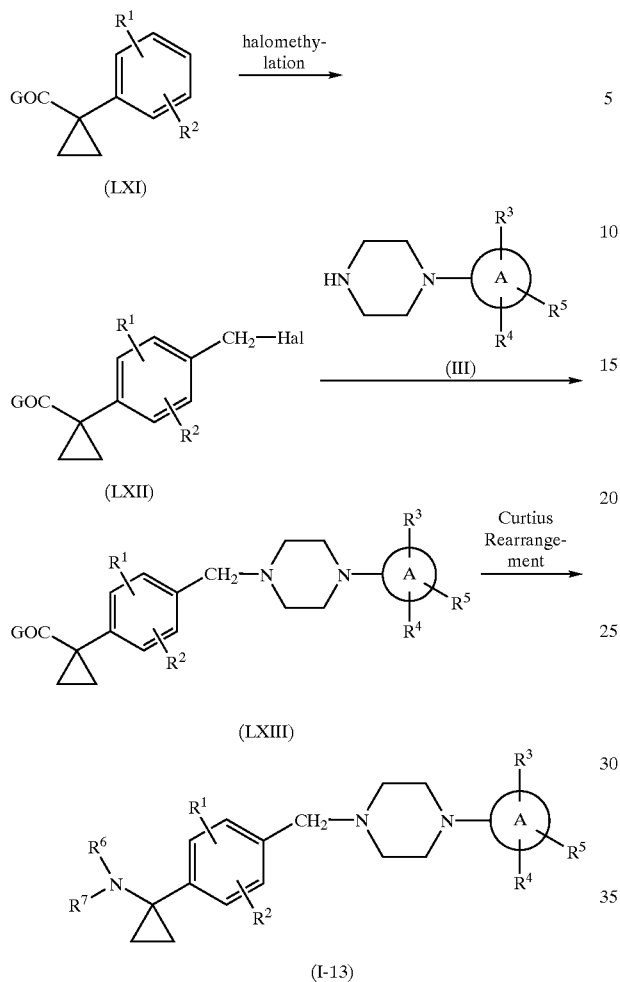

(LXI)

(LXII)

(LXIII)

(I-13)

wherein each symbol is as defined above.

The compound (LXI) is halomethylated under the same reaction conditions as in Method N.

The compound (LXII) and compound (III) are condensed under the same reaction conditions as in Method A.

The compound (LXIII) is subjected to Curtius rearrangement under the same reaction conditions as in Method II. The carbamic acid compound obtained by Curtius rearrangement is reacted with a Grignard reagent to produce compound (I-13) wherein $R^6$ or $R^7$ is acylated. The amine compound obtained by Curtius rearrangement is alkylated, aralkylated or acylated by a method known in the field of organic synthetic chemistry to produce compound (I-13).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method LL

Compound (I) wherein m=n=0, $R^{12}$ and $R^{13}$ in combination form ethylene and $R^9$ is hydrogen can be produced by the following method.

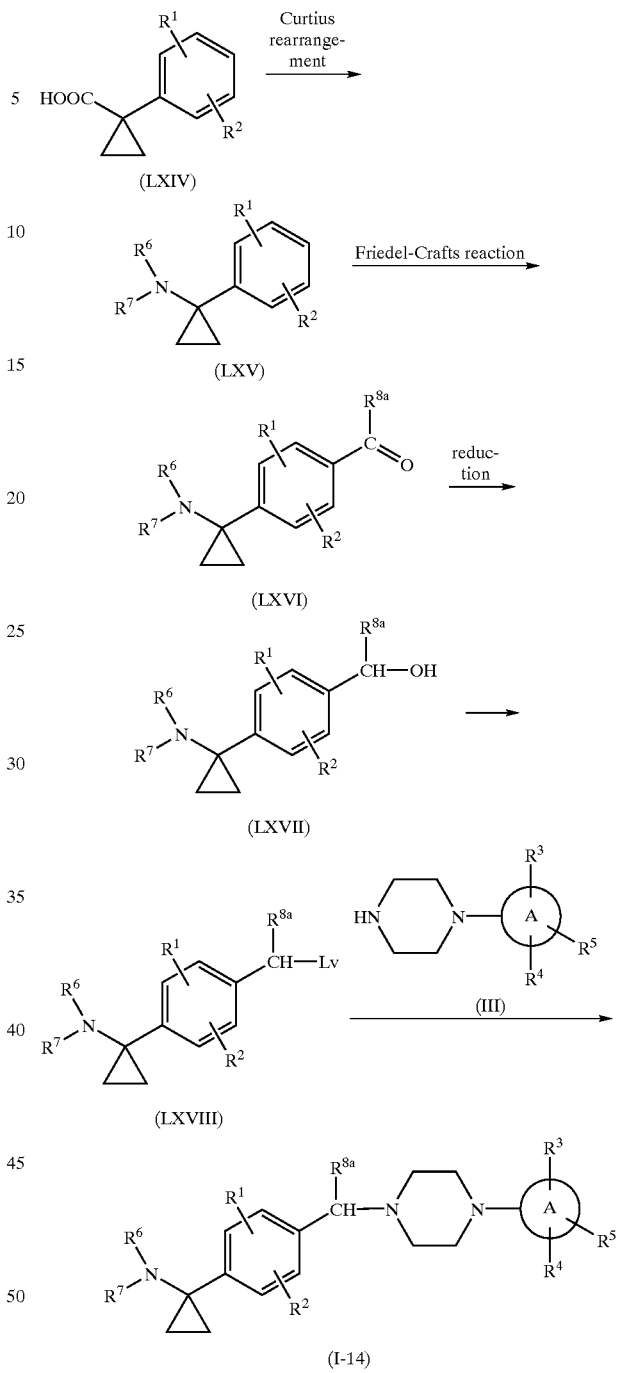

(LXIV)

(LXV)

(LXVI)

(LXVII)

(LXVIII)

(I-14)

wherein each symbol is as defined above.

The compound (LXIV) is subjected to Curtius rearrangement under the same reaction conditions as in Method KK.

The Friedel-Crafts reaction of compound (LXV) and reduction of compound (LXVI) can be carried our under the same reaction conditions as in Method M. The hydroxyl group of compound (LXVII) is converted to a leaving group Lv by a method known in the field of organic synthetic chemistry to give compound (LXVIII), which is then condensed with compound (III) in the same manner as in Method A to produce compound (I-14).

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

Method MM

Compound (XXIV) wherein $Lv_1$ is chlorine or bromine can be produced by the following method.

(XIX) → Sandmeyer type reaction → (XXIV)

wherein each symbol is as defined above.

The compound (XIX) is subjected to Sandmeyer type reaction under the same reaction conditions as in Method V.

After Sandmeyer type reaction under the above-mentioned reaction conditions and, where necessary, removal of protecting group(s), compound (XXIV) can be purified by a method known in the field of organic synthetic chemistry, such as solvent extraction, recrystallization, chromatography, and a method using an ion exchange resin.

Method NN

Compound (XXIV) wherein $Lv_1$ is chlorine can be produced by the following method.

(LXIX) → POCl₃ → (XXIV)

wherein each symbol is as defined above.

This method is particularly effective for converting the hydroxyl group of hetero ring derivative, such as 2-hydroxypyrimidine, 2-hydroxypyridine and the like, to chloride.

The reagent to be used for chlorination of compound (LXIX) may be, for example, phosphorous oxychloride.

The solvent to be used for chlorination may be, for example, dichloromethane, dichloroethane, chloroform, carbon tetrachloride or a mixture thereof, or the reaction proceeds without solvent.

The reaction temperature of chlorination is generally from 0° C. to 150° C., and a temperature above or under this range can be employed as necessary.

The reaction time of chlorination is generally from 30 minutes to 2 days, and a time longer or shorter than this range can be employed as necessary.

After chlorination under the above-mentioned reaction conditions and, where necessary, removal of protecting group(s), compound (XXIV) can be purified by a method known in the field of organic synthetic chemistry, such as solvent extraction, recrystallization, chromatography, and a method using an ion exchange resin.

Method OO

Compound (XXVII) wherein m=n=0 at Y can be produced by the following method.

(LXX) → halogenation → (LXXI) → ammonolysis → (LXXII) → Method B1–Method B8 → (XXVII)

wherein each symbol is as defined above.

The reagent to be used for halogenation of compound (LXX) may be, for example, N-bromosuccimide and N-chlorosuccimide.

For the halogenation, a radical initiator such as 2,2'-azobisisobutyronitrile (AIBN), benzoyl peroxide and the like can be used as necessary.

The solvent to be used for halogenation may be, for example, carbon tetrachloride, chloroform, dichloromethane or benzene.

The reaction temperature of halogenation is generally from 0° C. to 150° C., and a temperature above or under this range can be employed as necessary.

The reaction time of halogenation is generally from 30 minutes to 2 days, and a time longer or shorter than this range can be employed as necessary.

The reagent to be used for ammonolysis of compound (LXXI) may be, for example, liquid ammonia.

The solvent to be used for ammonolysis may be, for example, water, methanol, ethanol, 1-propanol, tetrahydrofuran, dioxane or a mixture thereof.

The reaction temperature of ammonolysis is generally from 0° C. to 150° C., and a temperature above or under this range can be employed as necessary.

The reaction time of ammonolysis is generally from 30 minutes to 2 days, and a time longer or shorter than this range can be employed as necessary.

The compound (LXXII) can be converted to compound (XXVII) according to Methods B1 to B8.

After each reaction under the above-mentioned reaction conditions and, where necessary, removal of protecting group(s), the synthetic intermediate in each step and the objective compound can be purified by a method known in the field of organic synthetic chemistry, such as solvent extraction, recrystallization, chromatography, and a method using an ion exchange resin.

The compound (I) of the present invention can be treated with an acid (e.g., hydrochloric acid, hydrobromic acid, hydroiodic acid, sulfuric acid, nitric acid, phosphoric acid, acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, 10-camphorsulfonic acid and the like), as necessary, in a suitable solvent (e.g., water, methanol, ethanol, diethyl ether, tetrahydrofuran, dioxane and the like) to convert to a pharmaceutically acceptable salt. The compound (I) of the present invention can be converted to a quaternary ammonium salt by treating with lower alkyl halide (e.g., methyl iodide, methyl bromide, ethyl iodide, ethyl bromide and the like) in the presence of a base. When the obtained crystals of the compound of the present invention are anhydride, the compound of the present invention is treated with water, a water-containing solvent or a different solvent to give a hydrate (e.g., monohydrate, 1/2 hydrate, 1/4 hydrate, 1/5 hydrate, dihydrate, 3/2 hydrate, 3/4 hydrate and the like) or solvate.

The compound of the present invention thus obtained can be isolated and purified by a conventional method such as recrystallization, column chromatography and the like. When the resulting product is a racemate, for example, a desired optically active compound can be resolved by fractional recrystallization of a salt with an optically active acid or by passing the racemate through a column packed with an optically active carrier. Individual diastereomers can be separated by fractional crystallization, chromatography and the like. These can be also obtained by using an optically active starting compound.

The compound of the present invention has a TNF-α production inhibitory effect and/or IL-10 production promoting effect, and is useful for the prophylaxis and treatment of various diseases caused by abnormal TNF-α production, diseases treatable with IL-10, such as chronic inflammatory disease, acute inflammatory disease, inflammatory disease due to infection, autoimmune diseases, allergic diseases, and other TNF-α mediated diseases.

The chronic inflammatory diseases include osteoarthritis, psoriatic arthritis, inflammatory dermal disease (psoriasis, eczematoid dermatitis, seborrheic dermatitis, lichen planus, pemphigus, bullous pemphigoid, epidermolysis bullosa, urticaria, vascular edema, angiitis, erythema, dermal eosinophilia, acne, alopecia areata, eosinophilic fasciitis, atherosclerosis and the like), inflammatory bowel disease (ulcerative colitis, Crohn's disease and the like) and the like.

The acute inflammatory diseases include contact dermatitis, adult respiratory distress syndrome (ARDS), sepsis (inclusive of organ disorders etc. caused by sepsis), septic shock, and the like.

The inflammatory diseases due to infection include endotoxin shock, acquired immunodeficiency syndrome (AIDS), meningitis, cachexia, viral hepatitis, fulminant hepatitis, other inflammatory responses due to infection with bacteria, virus, mycoplasma and the like (inclusive of fever, pain, organ disorders caused by influenzal or non-influenzal cold and the like) and the like.

The autoimmune diseases include rheumatoid arthritis, ankylosing spondylitis, systemic lupus erythematosus, glomerular nephritis (nephrotic syndrome (idiopathic nephrotic syndrome, minimal-change nephropathy and the like) and the like), multiple sclerosis, polychondritis, scleroderma, dermatomyositis, wegener's granulomatosis, active chronic hepatitis I, primary biliary cirrhosis, myasthenia gravis, idiopathic sprue, Graves' disease, sarcoidosis, Reiter's syndrome, juvenile diabetes (type I diabetes mellitus), autoimmune ophthalmic disease (endocrine ophthalmopathy, uveitis, keratitis (keratoconjunctivitis sicca, vernal keratoconjunctivitis and the like) and the like), Behqet's disease, autoimmune hemopathy (hemolytic anemia, aplastic anemia, idiopathic thrombocytopenia and the like), various malignant tumors (adenocarcinoma and the like), matastatic carcinoma and the like.

The allergic diseases include atopic dermatitis, asthmatic diseases (bronchial asthma, infantile asthma, allergic asthma, intrinsic asthma, extrinsic asthma, dust asthma, late-onset asthma, bronchial hypersensitivity, bronchitis and the like), allergic rhinitis, allergic conjunctivitis and the like.

Other TNF-α mediated diseases include resistant responses in organ or tissue transplantation (e.g., allograft or xenograft of heart, kidney, liver, lung, bone marrow, cornea, pancreas, pancreatic cell, small intestine, duodenum, limbs, muscle, nerve, fatty marrow, skin and the like) in mammals such as human, dog, cat, cow, horse, swine, monkey, mice and the like, i.e., rejection and graft versus host disease (GvHD), osteoporosis, cancer cachexia, thermal burn, trauma, scald, inflammatory response (inclusive of shock) and the like against plant and animal components (inclusive of snake venom and the like) and administration of drug and the like, myocardial infarction, chronic heart failure, congestive heart failure, ischemia-reperfusion injury, Kawasaki disease, pneumonia, malaria, meningitis, peritonitis, fibroid lung and disseminated intravascular coagulation (DIC). In addition to these, the inventive compound is useful for the prophylaxis and treatment of hepatopathy.

The compound of the present invention is characteristically void of effect on the central nervous system, because it has no or extremely weak affinity for the receptors distributed in the central nervous system. Moreover, the compound of the present invention having a TNF-α production inhibitory effect and an IL-10 production promoting effect is expected to show superior prophylactic and therapeutic effects on the above-mentioned diseases, particularly chronic diseases such as rheumatoid arthritis, chronic inflammatory diseases and the like, by the synergistic action of these two effects. In the present invention, a compound having these two effects is preferable.

When the compound (I) of the present invention is used as a TNF-α production inhibitor and/or an IL-10 production promoter, it is prepared into a typical pharmaceutical preparation. For example, the compound of the present invention (I) is prepared into a dosage form suitable for oral or parenteral administration upon admixing with a pharmaceutically acceptable carrier (excipient, binder, disintegrant, corrigent, flavor, emulsifier, diluent, solubilizer and the like) to give a pharmaceutical composition or preparation, such as tablet, pill, powder, granule, capsule, troche, syrup, liquid, emulsion, suspension, injection (liquid, suspension and the like), suppository, inhalent, transdermal absorber, eye drop, nose drop, eye ointment and the like.

When a solid preparation is produced, an additive is used, such as sucrose, lactose, cellulose sugar, D-mannitol, maltitol, dextran, starches, agar, arginates, chitins, chitosans, pectins, tragacanth, acacia, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethylene glycol, sodium hydrogencarbonate, magnesium stearate, talc and the like. The tablets can be made into those having typical tablet film, as necessary, such as sugar-coated tablet, enteric coated tablet, film coating tablet, or two-layer tablet, or multi-laye tablet.

When a semi-solid preparation is produced, plant and animal fats and oils (olive oil, corn oil, castor oil and the like), mineral oils (petrolatum, white petrolatum, solid paraffin and the like), wax (jojoba oil, carnauba wax, bee wax and the like), partially synthesized or completely synthesized glycerol fatty acid ester (lauric acid, myristic acid, palmitic acid and the like), and the like are used. Commercially available products of these are, for example, Witepsol (manufactured by Dynamitnovel Ltd.), pharmasol (manufactured by Japan Oil & Fat Co. Ltd.) and the like.

When a liquid preparation is produced, an additive is used, such as sodium chloride, glucose, sorbitol, glycerol, olive oil, propylene glycol, ethyl alcohol and the like. In particular, when an injection is prepared, sterile aqueous solution, such as physiological saline, isotonic liquid and oily liquid (e.g., sesame oil and soybean oi) are used. Where necessary, a suitable suspending agent, such as sodium carboxymethylcellulose, nonionic surfactant and solubilizer (e.g., benzyl benzoate, benzyl alcohol and the like) may be used concurrently. Further, when an eye drop or nasal drop is given, an aqueous liquid or aqueous solution is used, particularly, sterile aqueous solution for injection. The liquid for eye drop or nasal drop may contain various additives as appropriate, such as buffer (borate buffer, acetate buffer, carbonate buffer and the like are preferable for reducing irritation), isotonicity agent, solubilizer, preservative, viscous agent, chelating agent, pH adjusting agent (pH is preferably adjusted generally to about 6–8.5) and aromatic.

The amount of the active ingredient in these preparations is 0.1–100 wt %, suitably 1–50 wt %, of the preparation. The dose varies depending on the condition, body weight, age and the like of patients. In the case of oral administration, it is generally about 0.01–50 mg per day for an adult, which is administered once or in several doses.

EXAMPLES

The present invention is explained in detail in the following by way of Examples which do not limit the present invention. Of the symbols used in the chemical structures, Ac means acetyl, Me means methyl and Et means ethyl.

Example 1

Synthesis of N-(4-((4-Phenylpiperazin-1-yl)methyl) phenylmethyl)acetamide (1) 4-Acetamidomethylbenzoic Acid

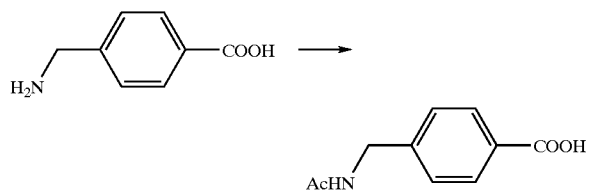

To a solution of 4-(aminomethyl)benzoic acid (20.46 g) in ethyl acetate (100 ml) was added an aqueous sodium hydroxide (12 g) solution (100 ml) and acetic anhydride (14 ml) was further added at 5–7° C. This reaction mixture was stirred at room temperature for 1 hr and made acidic with 10% hydrochloric acid and extracted with ethyl acetate:ethanol (10:1) (100 ml×5). The extract was washed with saturated brine and dried over anhydrous sodium sulfate. The solvent was evaporated to give a pale-yellow solid (27.2 g). The obtained solid was crystallized from ethyl acetate:ethanol (1:1,500 ml) to give the objective compound (16.7 g) as white crystals, m.p. 200–202° C.

$^1$H-NMR(DMSO-d$_6$) δ: 1.89(3H, s), 4.32(2H, d, J=5.9 Hz), 7.36(2H, d, J=7.9 Hz), 7.89(2H, d, J=8.6 Hz), 8.41(1H, m), 12.84(1H, br.s); IR(KBr): 3298, 1691, 1646, 1539 cm$^{-1}$; MS(EI): 193(M$^+$); Elemental analysis: Calculated: C; 62.17, H; 5.74, N; 7.25; Found: C; 62.01, H; 5.71, N; 7.21.

(2) Methyl 4-Acetamidomethylbenzoate

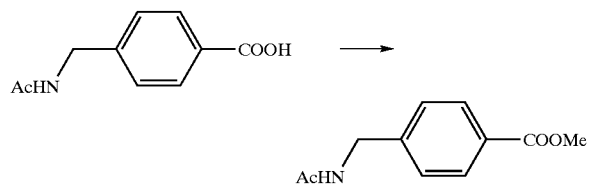

4-Acetamidomethylbenzoic acid(4.0 g) was dissolved in 0.5% hydrochloric acid—methanol solution (100 ml). The mixture was stirred at 40° C. for 3.5 hr, and poured into ice water (300 ml) and extracted with ethyl acetate (100 ml×4). The extract was washed with saturated sodium hydrogencarbonate solution and saturated brine, and dried over anhydrous sodium sulfate. The solvent was evaporated to give a pale-yellow solid (4.3 g). The obtained solid was crystallized from ethyl acetate (50 ml) to give the title compound (3.2 g) as pale-yellow white crystals, m.p.=110–111° C.

$^1$H-NMR(DMSO-d$_6$) δ: 1.90(3H, s), 3.84(3H, s), 4.33 (2H, d, J=5.9 Hz), 7.39(2H, d, J=8.6 Hz), 7.92(2H, d, J=7.9 Hz), 8.43(1H, m); IR(KBr): 3277, 1727, 1643, 1556 cm$^{-1}$; MS(EI): 207(M$^+$); Elemental analysis: Calculated: C; 63.76, H; 6.32, N; 6.76; Found: C; 63.76, H; 6.38, N; 6.76.

(3) N-(4-Hydroxymethylphenylmethyl)acetamide

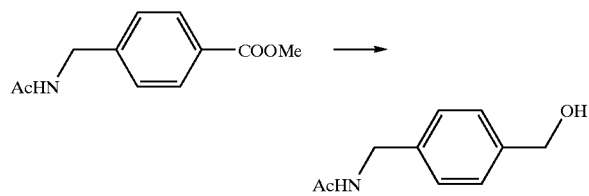

To a suspension of aluminum lithium hydride (570 mg) in tetrahydrofuran (80 ml) was added a solution of methyl 4-acetamidomethylbenzoate (3.1 g) in tetrahydrofuran (20 ml) under ice-cooling. The mixture was stirred at room temperature for 1.5 hr and a saturated aqueous sodium sulfate solution (7 ml) was added at 100° C. The mixture was stirred at room temperature for 1 hr. The sediment was filtrated and the solvent was evaporated to give the title substance (2.8 g) as a white solid.

$^1$H-NMR(DMSO-d$_6$) δ: 1.86(3H, s), 4.22(2H, d, J=5.9 Hz), 4.46(2H, s), 5.13(1H, br.s), 7.19(2H, d, J=7.9 Hz), 7.25(2H, d, J=8.6 Hz), 8.30(1H, m); MS(EI): 179(M$^+$).

(4) N-(4-Chloromethylphenylmethyl)acetamide

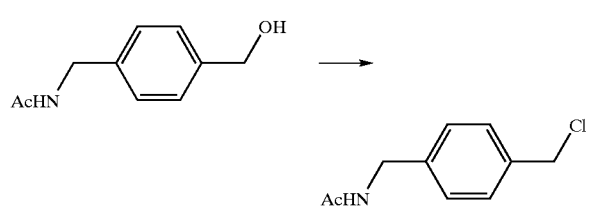

To a solution of N-(4-hydroxymethylphenylmethyl) acetamide (1.5 g) in chloroform (50 ml) was added thionyl chloride (0.73 ml) and the mixture was refluxed under heating for 1 hr. The solvent was evaporated and the obtained residue was crystallized from ethyl acetate to give the title compound (1.8 g) as pale-yellow crystals.

m.p.=116–118° C.; $^1$H-NMR(CDCl$_3$) δ: 2.01(3H, s), 4.40 (2H, d, J=5.9 Hz), 4.56(2H, s), 6.20(1H, br.s), 7.26(2H, d, J=8.6 Hz), 7.34(2H, d, J=7.9 Hz); MS(EI): 197(M$^+$).

(5) N-(4-((4-Phenylpiperazin-1-yl)methyl)phenylmethyl) acetamide

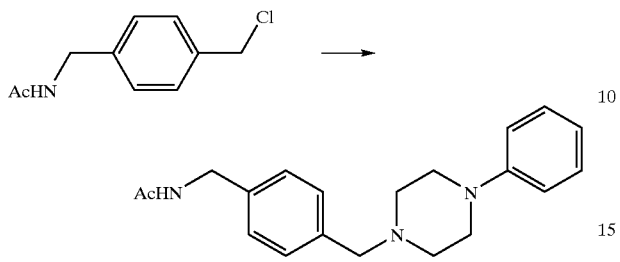

A solution of N-(4-chloromethylphenylmethyl)acetamide (1.65 g), 1-phenylpiperazine (1.3 ml) and potassium carbonate (1.2 g) in dimethylformamide (50 ml) was stirred at 60° C. for 1 hr. The reaction mixture was poured into water (200 ml) and extracted with ethyl acetate (100 ml×3). The extract was washed with saturated brine and dried over anhydrous sodium sulfate. The solvent was evaporated to give a brown solid (4.4 g). The obtained solid was purified by silica gel column chromatography (developing solvent; chloroform:methanol=10:1) to give a pale-brown solid (3.45 g). The obtained solid was crystallized from ethyl acetate and the crystals were recrystallized from a mixture of ethyl acetate, ethanol and hexane to give the title compound (1.4 g) as white crystals, m.p.=135–136° C.

$^1$H-NMR(DMSO-d$_6$) δ: 1.87(3H, s), 2.50(4H, m), 3.11 (4H, m), 3.49(2H, s), 4.23(2H, d, J=5.9 Hz), 6.76(1H, t, J=7.3 Hz), 6.90(2H, d, J=7.9 Hz), 7.15–7.29(6H, m), 8.30 (1H, t, J=5.9 Hz); IR(KBr): 3318, 2813, 1645, 1538 cm$^{-1}$; MS(EI): 323(M$^+$); Elemental analysis: Calculated: C; 74.27, H; 7.79, N; 12.99; Found: C; 74.01, H; 7.88, N; 12.77.

Example 2

Synthesis of 4-((4-(Aminomethyl)phenyl)methyl)-1-phenylpiperazine

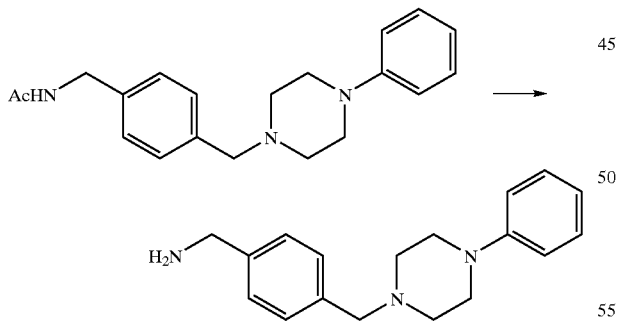

N-(4-((4-Phenylpiperazin-1-yl)methyl)phenylmethyl) acetamide (2.6 g) was dissolved in 10% hydrochloric acid (50 ml) and the mixture was refluxed under heating for 6 hr. To the mixture was added 10% aqueous sodium hydroxide solution to make it alkaline and the mixture was extracted with ethyl acetate (100 ml×3). The extract was washed with saturated brine and dried over anhydrous sodium sulfate. The solvent was evaporated and the obtained residue was crystallized from water-ethanol to give the title compound (1.34 g) as white crystals, m.p.=68–70° C.

$^1$H-NMR(DMSO-d$_6$) δ: 2.40–2.50(4H, m), 3.05–3.15 (4H, m), 3.10–3.45(2H, br.s), 3.48(2H, s), 3.69(2H, s), 6.76(1H, t, J=7.3 Hz), 6.90(2H, d, J=7.9 Hz), 7.15–7.30(6H, m); IR(KBr): 3359, 2805, 1602, 1506 cm$^{-1}$; MS(EI): 281 (M$^+$); Elemental analysis: Calculated: C; 76.83, H; 8.24, N; 14.93; Found: C; 76.60, H; 8.21, N; 14.59.

Example 3

Synthesis of N-(4-((4-Phenylpiperazin-1-yl)methyl) phenylmethyl)formamide

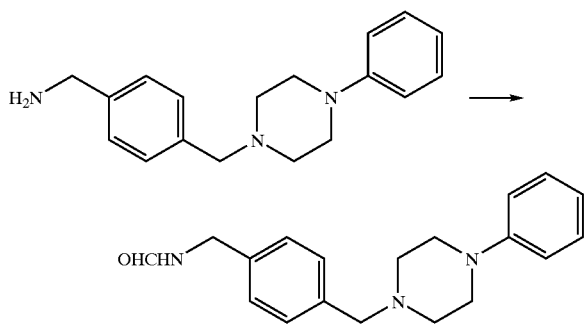

A mixture of acetic anhydride (0.36 ml) and formic acid (0.15 ml) was stirred at 50–60° C. for 2 hr, and to the obtained acetic acid and formic acid anhydride was added a solution of 4-((4-(aminomethyl)phenyl)methyl)-1-phenylpiperazine (0.5 g) in methylene chloride (10 ml) under ice-cooling. This reaction mixture was stirred at 5–10° C. for 2.5 hr and left standing at room temperature for 14 hr. To this reaction mixture were added ethanol (20 ml) and ethyl acetate (150 ml) and the mixture was washed with saturated sodium hydrogencarbonate solution and saturated brine, and dried over anhydrous sodium sulfate. The solvent was evaporated to give a brown solid (0.56 g). The obtained solid was purified by silica gel column chromatography (developing solvent; chloroform:methanol=9:1) to give a pale-brown solid (0.55 g). The obtained solid was crystallized from ethyl acetate-hexane (2:1) to give the title compound (0.41 g) as pale-yellow white crystals, m.p.= 108–109° C.

$^1$H-NMR(DMSO-d$_6$) δ: 2.45–2.53(4H, m), 3.05–3.15 (4H, m), 3.49(2H, s), 4.29(2H, d, J=5.9 Hz), 6.76(1H, t, J=7.3 Hz), 6.90(2H, d, J=8.6 Hz), 7.15–7.30(6H, m), 8.13 (1H, d, J=1.3 Hz), 8.47(1H, m); IR(KBr): 3315, 2846, 2821, 1658, 1522 cm$^{-1}$; MS(EI): 309(M$^+$) Elemental analysis: Calculated: C; 73.76, H; 7.49, N; 13.58; Found: C; 73.36, H; 7.53, N; 13.47.

Example 4

Synthesis of N-(4-((4-Phenylpiperazin-1-yl)methyl) phenylmethyl)propionamide

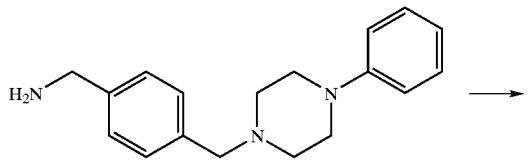

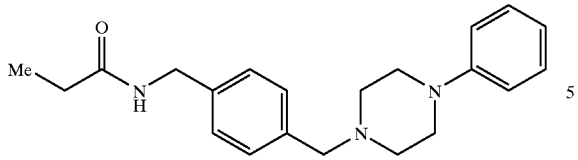

A solution of 4-((4-(aminomethyl)phenyl)methyl)-1-phenylpiperazine (0.62 g), propionyl chloride (0.23 ml) and triethylamine (0.37 ml) in methylene chloride (20 ml) was stirred at room temperature for 4 hr. To this reaction mixture was added chloroform (100 ml), and the mixture was washed with saturated brine and dried over anhydrous sodium sulfate. The solvent was evaporated to give a pale-brown solid (0.9 g). The obtained solid was crystallized from ethyl acetate (50 ml) to give the title compound (0.5 g) as pale-yellow white crystals, m.p.=140–141° C.

$^1$H-NMR(DMSO-d$_6$) δ: 1.03(3H, t, J=7.9 Hz), 2.14(2H, q, J=7.9 Hz), 2.45–2.55(4H, m), 3.05–3.15(4H, m), 3.49(2H, s), 4.24(2H, d, J=5.9 Hz), 6.76(1H, t, J=7.3 Hz), 6.90(2H, d, J=7.9 Hz), 7.15–7.30(6H, m), 8.24(2H, t, J=5.9 Hz); IR(KBr): 3318, 2940, 2819, 1645, 1535 cm$^{-1}$; MS(EI): 337(M$^+$); Elemental analysis: Calculated: C; 74.74, H; 8.06, N; 12.45; Found: C; 74.66, H; 8.11, N; 12.16.

Example 5

Synthesis of N-(4-((4-(4-fluorophenyl)piperazin-1-yl)methyl)phenylmethyl)acetamide

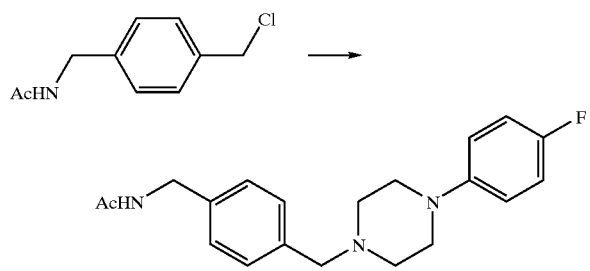

By similar reaction and treatment to that in Example 1(5) using (4-fluorophenyl)piperazine dihydrochloride instead of phenylpiperazine, the title compound was obtained as white crystals, m.p.=164–166° C.

$^1$H-NMR(DMSO-d$_6$) δ: 1.87(3H, s), 2.45–2.55(4H, m), 3.00–3.10(4H, m), 3.49(2H, s), 4.23(2H, d, J=5.9 Hz), 6.89–6.95(2H, m), 6.95–7.06(2H, m), 7.19–7.39(4H, m), 8.30(1H, t, J=5.9 Hz); IR(KBr): 3317, 2920, 2832, 1643, 1513 cm$^{-1}$; MS(EI): 341(M$^+$) Elemental analysis: Calculated: C; 70.36, H; 7.09, N; 12.31; Found: C; 70.08, H; 7.06, N; 12.13.

Example 6

Synthesis of N-(4-((4-(2-Chlorophenyl)piperazin-1-yl)methyl)phenylmethyl)acetamide·Dihydrochloride

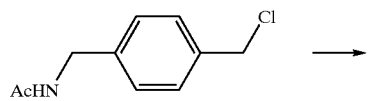

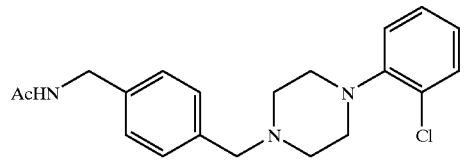

By similar reaction using (2-chlorophenyl)piperazine instead of phenylpiperazine to that in Example 1(5) and treatment with 4M hydrochloric acid—dioxane in ethanol, the title compound was obtained as pale-brown crystals.

m.p.=235–238° C. (decomposition).

$^1$H-NMR(DMSO-d$_6$) δ: 1.89(3H, s), 3.10–3.40(8H, m), 4.28(2H, d, J=5.9 Hz), 4.37(2H, m), 7.05–7.20(1H, m), 7.30–7.35(3H, m), 7.44(1H, dd, J=1.3, 7.9 Hz), 7.63(2H, d, J=7.9 Hz), 8.45(1H, t, J=5.9 Hz), 11.43(1H, br.s); IR(KBr): 3282, 2591, 1664, 1543 cm$^{-1}$; MS(EI): 357(M$^+$); Elemental analysis: Calculated: C; 60.76, H; 6.23, N; 10.63; Found: C; 60.49, H; 6.34, N; 10.63.

Example 7

Synthesis of N-(4-((4-(2,3-Dimethylphenyl) piperazin-1-yl)methyl)phenylmethyl) acetamide·Hydrochloride

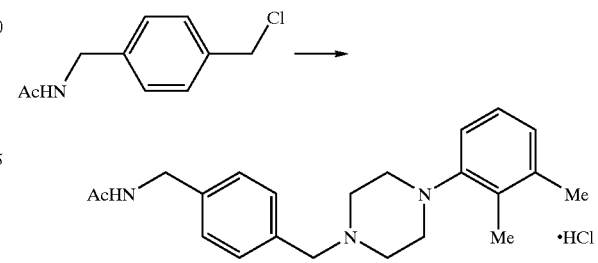

By similar reaction using (2,3-dimethylphenyl)piperazine hydrochloride instead of phenylpiperazine to that in Example 1(5) and treatment with 4M hydrochloric acid-dioxane in ethanol, the title compound was obtained as white crystals.

m.p.=253–255° C. (decomposition); $^1$H-NMR(DMSO-d$_6$) δ: 1.89(3H, s), 2.15(3H, s), 2.21(3H, s), 3.00–3.35(8H, m), 4.28(2H, d, J=5.9 Hz), 4.35(2H, s), 6.88(1H, d, J=7.9 Hz), 6.92(1H, d, J=7.3 Hz), 7.06(1H, dd, J=7.3, 7.9 Hz), 7.33(2H, d, J=8.6 Hz), 7.63(2H, d, J=8.6 Hz), 8.45(1H, m), 11.33(1H, br.s); IR(KBr): 3253, 2465, 1649, 1556 cm$^{-1}$; MS(EI): 351(M$^+$); Elemental analysis: Calculated: C; 68.11, H; 7.79, N; 10.83; Found: C; 67.74, H; 7.94, N; 10.67.

Example 8

Synthesis of N-(4-((4-(2-Methoxyphenyl)piperazin-1-yl)methyl)phenylmethyl)acetamide·Dihydrochloride

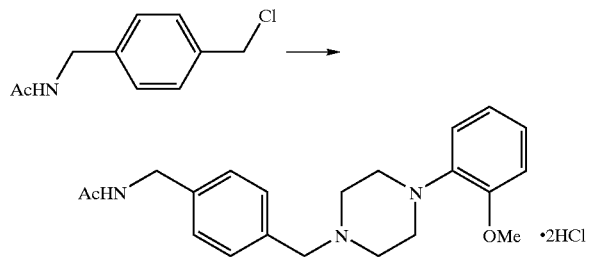

In Example 1(5), (2-methoxyphenyl)piperazine was used for reaction instead of phenylpiperazine, which was followed by treatment with hydrochloric acid-ether and recrystallization from methanol-ethyl acetate to give the title compound as white crystals.

m.p.=221–223° C.; $^1$H-NMR(DMSO-d$_6$) δ: 1.89(3H, s), 3.06–3.27(4H, m), 3.31–3.35(2H, m), 3.44–3.57(2H, m), 3.78(3H, s), 4.28(2H, d, J=5.9 Hz), 4.34(2H, br.s), 6.86–7.05 (4H, m), 7.33(2H, d, J=8.4 Hz), 7.61(2H, d, J=8.5 Hz), 8.45(1H, t, J=5.9 Hz), 11.33(1H, br.s); IR(KBr): 3263, 2487, 1666, 1535 cm$^{-1}$; MS(EI): 353(M$^+$); Elemental analysis: Calculated: C; 58.88, H; 7.29, N; 9.81; Found: C; 58.45, H; 6.91, N; 9.75.

Example 9

Synthesis of N-(4-((4-(3-Methylphenyl)piperazin-1-yl)methyl)phenylmethyl)acetamide

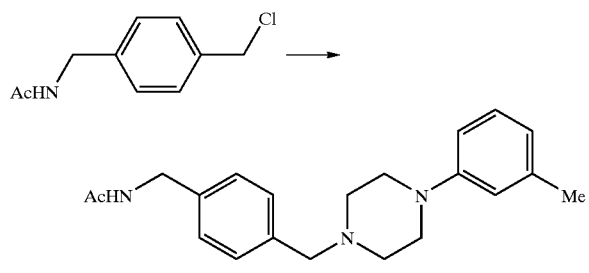

By similar reaction and treatment to that in Example 1(5) using (3-methylphenyl)piperazine instead of phenylpiperazine, the title compound was obtained as pale-yellow crystals, m.p.=80–81° C.

$^1$H-NMR(CDCl$_3$) δ: 2.02(3H, s), 2.31(3H, s), 2.58(4H, dt, J=5.3, 4.7 Hz), 3.18(4H, dd, J=5.3, 4.7 Hz), 3.55(2H, s), 4.42(2H, d, J=5.3 Hz), 5.72(1H, br.s), 6.67(1H, d, J=7.3 Hz), 6.72(1H, d, J=7.3 Hz), 6.74(1H, s), 7.13(1H, t, J=7.3 Hz), 7.24(2H, d, J=7.9 Hz), 7.33(2H, d, J=7.9 Hz); IR(KBr): 3317, 2815, 1633, 1537 cm$^{-1}$; MS(EI): 337(M$^+$); Elemental analysis: Calculated: C; 74.74, H; 8.06, N; 12.54; Found: C; 74.60, H; 8.04, N; 12.47.

Example 10

Synthesis of N-(4-((4-(3-Methoxyphenyl)piperazin-1-yl)methyl)phenylmethyl)acetamide Hydrochloride 3/4 Hydrate

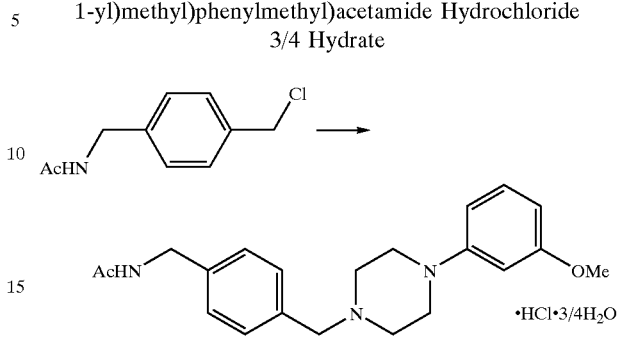

In Example 1(5), (3-methoxyphenyl)piperazine was used for reaction instead of phenylpiperazine, which was followed by treatment with hydrochloric acid—ether and recrystallization from methanolethyl acetate to give the title compound as white crystals, m.p.=201.5–202.5° C.

$^1$H-NMR(DMSO-d$_6$) δ: 1.89(3H, s), 3.07–3.29(4H, m), 3.33–3.39(2H, m), 3.72(3H, s), 3.77–3.81(2H, m), 4.28(2H, d, J=5.9 Hz), 4.34(2H, d, J=3.3 Hz), 6.45(1H, ddd, J=8.6, 7.9, 2.0 Hz), 6.49(1H, s), 6.52(1H, ddd, J=8.6, 7.9, 2.0 Hz), 7.14(1H, ddd, J=8.6, 7.9 Hz), 7.33(2H, d, J=7.9 Hz), 7.70 (2H, d, J=7.9 Hz), 8.44(1H, t, J=5.9 Hz), 11.33(1H, br.s); IR(KBr): 3280, 2464, 1643, 1556 cm$^{-1}$ MS(EI): 353(M$^+$); Elemental analysis: Calculated: C; 62.52, H; 7.37, N; 10.42; Found: C; 62.64, H; 7.34, N; 10.44.

Example 11

Synthesis of N-(4-((4-(4-Chlorophenyl)piperazin-1-yl)methyl)phenylmethyl)acetamide

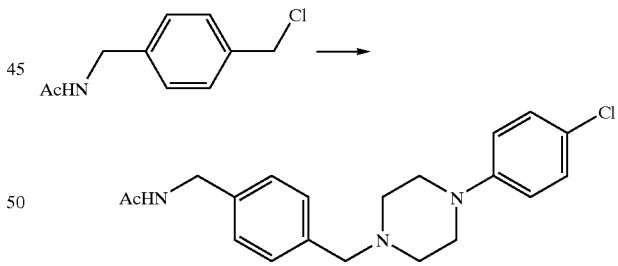

By similar reaction and treatment to that in Example 1(5) using (4-chlorophenyl)piperazine instead of phenylpiperazine, the title compound was obtained as pale-yellow crystals, m.p.=180.5–182° C.

$^1$H-NMR(CDCl$_3$) δ: 2.02(3H, s), 2.58(4H, dd, J=5.3, 4.6 Hz), 3.15(4H, dd, J=5.3, 4.6 Hz), 3.54(2H, s), 4.42(2H, d, J=5.9 Hz), 5.74(1H, br.s), 6.82(2H, ddd, J=9.2, 3.3, 2.0 Hz), 7.19(2H, ddd, J=9.2, 3.3, 2.0 Hz), 7.24(2H, d, J=7.9 Hz), 7.32(2H, d, J=7.9 Hz); IR(KBr): 3315, 2890, 1645, 1542 cm$^{-1}$; MS(EI): 357(M$^+$); Elemental analysis: Calculated: C; 67.12, H; 6.76, N; 11.45; Found: C; 67.08, H; 6.73, N; 11.75.

Example 12

Synthesis of N-(4-((4-(2-Fluorophenyl)piperazin-1-yl)methyl)phenylmethyl)acetamide Hydrochloride 1/4 Hydrate

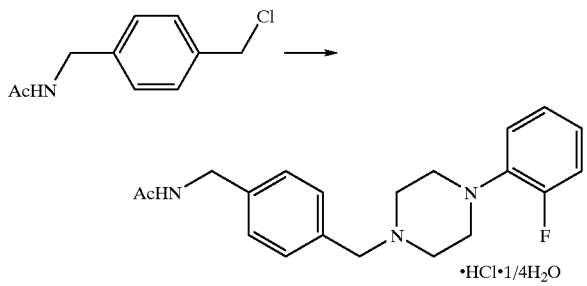

In Example 1(5), (2-fluorophenyl)piperazine was used for reaction instead of phenylpiperazine, which was followed by treatment with hydrochloric acid—ether and recrystallization from a mixture of ethanol-ethyl acetate-hexane to give the title compound as pale-brown crystals, m.p.=250–252° C. (decomposition).

$^1$H-NMR(DMSO-d$_6$) δ: 1.89(3H, s), 3.15–3.60(8H, m), 4.28(2H, d, J=5.9 Hz), 4.35(2H, br.s), 7.15(4H, m), 7.33(2H, d, J=7.9 Hz), 7.62(2H, d, J=7.9 Hz), 8.46(1H, t, J=5.9 Hz), 11.43(1H, br.s); IR(KBr): 3265, 2679, 1664, 1504 cm$^{-1}$; MS(EI): 341(M$^+$); Elemental analysis: Calculated: C; 62.82, H; 6.72, N; 10.99; Found: C; 62.60, H; 6.56, N; 11.00.

Example 13

Synthesis of N-(4-((4-(4-Methoxyphenyl)piperazin-1-yl)methyl)phenylmethyl)acetamide

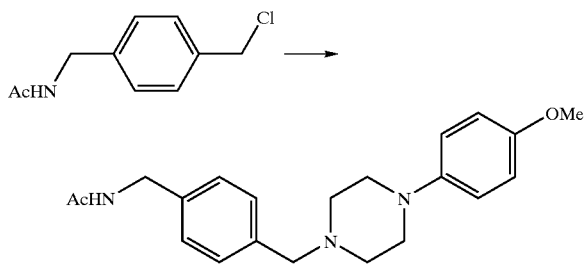

By similar reaction and treatment to that in Example 1(5) using (4-methoxyphenyl)piperazine instead of phenylpiperazine, the title compound was obtained as white crystals, m.p.=137–138° C.

$^1$H-NMR(CDCl$_3$) δ: 1.87(3H, s), 2.50(4H, m), 2.99(4H, m), 3.48(2H, s), 3.67(3H, s), 4.23(2H, d, J=5.9 Hz), 6.79 (2H, d, J=9.2 Hz), 6.86(2H, d, J=9.2 Hz), 7.21. (2H, d, J=8.6 Hz), 7.27(2H, d, J=7.9 Hz), 8.30(1H, t, J=5.6 Hz); IR(KBr): 3325, 1649, 1514 cm$^{-1}$; MS(EI): 353(M$^+$); Elemental analysis: Calculated: C; 71.36, H; 7.70, N; 11.89; Found: C; 71.19, H; 7.70, N; 11.77.

Example 14

Synthesis of N-(2-(4-((4-Phenylpiperazin-1-yl)methyl)phenyl)ethyl)acetamide (1) N-(2-(4-Chloromethylphenyl)ethyl)acetamide

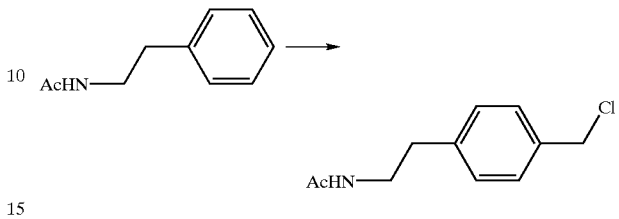

To a solution of N-(2-phenylethyl)acetamide (5.0 g) in dichloromethane (31 ml) was added titanium tetrachloride (17 ml) at 0–5° C. over 30 min. Thereto was added dichloromethyl methyl ether (8.4 ml) at 0–5° C. over 30 min. This reaction mixture was stirred at room temperature for 3 hr and was poured into ice water (1000 ml). The mixture was extracted with ethyl acetate (200 ml×2). The ethyl acetate layer was washed with aqueous sodium hydroxide and saturated brine, and dried over anhydrous sodium sulfate. The solvent was evaporated to give a mixture (1.4 g) containing N-(2-(4-formylphenyl)ethyl)acetamide and N-(2-(2-formylphenyl) ethyl) acetamide at about 8:1 as a pale-brown oil.

To a solution of this mixture (1.4 g) in ethanol (7.3 ml) was added sodium borohydride (0.56 g) and the mixture was stirred at 50° C. for 3 hr. Thereto was added 2N hydrochloric acid (ca. 20 ml) at below 10° C. This mixture was poured into water (300 ml) and extracted with ethyl acetate (250 ml×2). The ethyl acetate layer was washed with aqueous sodium hydroxide (200 ml) and saturated brine (200 ml), and dried over anhydrous sodium sulfate. The solvent was evaporated and the obtained residue was purified by silica gel column chromatography (developing solvent; ethyl acetate:methanol:chloroform=3:1:12) to give a mixture (0.58 g) containing N-(2-(4-hydroxymethylphenyl)ethyl)-acetamide and N-(2-(2-hydroxymethylphenyl)ethyl) acetamide at about 8:1 as a yellow oil.

A solution of this mixture (0.58 g) and thionyl chloride (0.30 ml) in dichloromethane (15 ml) was refluxed under heating for 2 hr. The solvent was evaporated and the obtained residue was purified by silica gel column chromatography (developing solvent; ethyl acetate) to give a mixture (0.40 g) containing the title compound and N-(2-(2-chloromethylphenyl)ethyl)acetamide at about 8:1 as white crystals.

In the same manner as in the above, white crystals (0.70 g) containing the title compound and N-(2-(2-chloromethylphenyl)ethyl)acetamide at about 8:1 was obtained. The crystals were combined with the crystals (0.40 g) obtained earlier and recrystallized from a mixture of ethyl acetate-isopropyl ether-hexane to give the title compound (0.58 g) as white crystals, m.p.=86–88° C.

$^1$H-NMR(CDCl$_3$) δ: 1.94(3H, s), 2.82(2H, dd, J=7.3, 6.6 Hz), 3.50(2H, dd, J=7.3, 6.6 Hz), 4.57(2H, s), 5.49(1H, br.s), 7.19(2H, d, J=8.6 Hz), 7.34(2H, d, J=7.9 Hz); IR(KBr): 3297, 1633, 1543 cm$^{-1}$; MS(EI): 211((M+1)+); Elemental analysis: Calculated: C; 62.41, H; 6.67, N; 6.62; Found: C; 62.34, H; 6.80, N; 6.70.

(2) N-(2-(4-((4-Phenylpiperazin-1-yl)methyl)phenyl)ethyl)acetamide

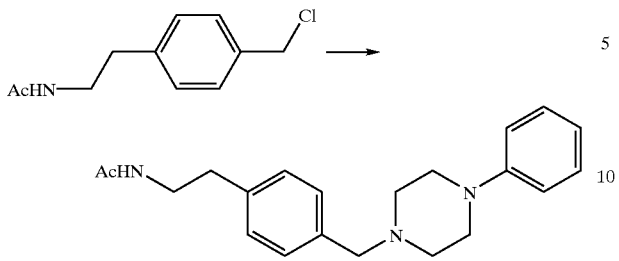

By similar reaction and treatment to that in Example 1(5) using N-(2-(4-chloromethylphenyl)ethyl)acetamide instead of N-(4-chloromethylphenylmethyl)acetamide, the title compound was obtained as white crystals, m.p.=117–118° C.

$^1$H-NMR(CDCl$_3$) δ: 1.94(3H, s), 2.61(4H, t, J=5.3 Hz), 3.15(2H, dd, J=7.3, 6.6 Hz), 3.20(2H, t, J=5.3 Hz), 3.15(2H, dd, J=6.6, 5.9 Hz), 3.55(2H, s), 5.46(1H, br.s), 6.84(1H, t, J=7.3 Hz), 6.92(2H, d, J=7.9 Hz), 7.16(1H, d, J=7.9 Hz), 7.23(2H, d, J=7.9 Hz), 7.30(2H, d, J=7.9 Hz); IR(KBr): 3352, 3302, 1647, 1535 cm$^{-1}$; MS(EI): 337((M−1)+); Elemental analysis: Calculated: C; 74.74, H; 8.06, N; 12.45; Found: C; 74.49, H; 8.05, N; 12.40.

Example 15

Synthesis of N-(3-(4-((4-Phenylpiperazin-1-yl)methyl)phenyl)propyl)acetamide 1/4 Hydrate (1) N-(3-(4-Chloromethylphenyl)propyl)acetamide

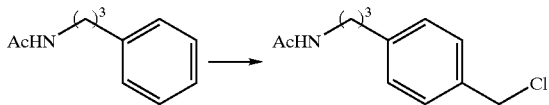

To a solution of N-(3-phenylpropyl)acetamide (10.14 g) in dichloromethane (130 ml) was added titanium tetrachloride (28 ml) at 5–7° C. over 30 mm. There to was added a solution of dichloromethyl methyl ether (18 ml) in dichloromethane (20 ml) at 5–8° C. over 30 min. This reaction mixture was stirred at room temperature for 3 hr, and poured into ice water (1000 ml). The mixture was extracted with chloroform (500 ml×2). The chloroform layer was washed with saturated aqueous sodium hydrogencarbonate, and dried over anhydrous sodium sulfate. The solvent was evaporated and the obtained residue was purified by silica gel column chromatography (developing solvent; hexane::ethyl acetate=2:1→methanol:chloroform=3:97) to give a mixture (10.85 g) containing N-(3-(4-formylphenyl)propyl)acetamide and N-(3-(2-formylphenyl)propyl)acetamide at about 6:1 as a yellow oil.

To a solution of this mixture (10.85 g) in ethanol (100 ml) was added sodium borohydride (2.0 g) at 5° C. over 15 min. This mixture was stirred at room temperature for 1 hr and 2N hydrochloric acid (ca. 20 ml) was added at below 10° C. This mixture was poured into water (300 ml) and extracted with ethyl acetate (250 ml×2). The ethyl acetate layer was washed with saturated sodium hydrogencarbonate solution (200 ml) and saturated brine (200 ml), and dried over anhydrous sodium sulfate. The solvent was evaporated and the obtained residue was purified by silica gel column chromatography (developing solvent; methanol:chloroform=4:96) to give a mixture (4.36 g) containing N-(3-(4-hydroxymethylphenyl)propyl)acetamide and N-(3-(2-hydroxymethylphenyl)propyl)acetamide at about 6:1 as white crystals.

A solution of this mixture (1.428 g) and thionyl chloride (0.60 ml) in chloroform (50 ml) was refluxed under heating for 2 hr. The solvent was evaporated and the obtained residue was purified by silica gel column chromatography (developing solvent; methanol:chloroform=3:97) to give a mixture (1.26 g) containing the title compound and N-(3-(2-chloromethylphenyl)propyl)acetamide at about 6:1 as white crystals. The crystals (0.98 g) were recrystallized from ethyl acetate-hexane to give the title compound (0.23 g) as white crystals. m.p.=89–90° C.

$^1$H-NMR(CDCl$_3$) δ: 1.82(2H, tt, J=7.4, 7.4 Hz), 1.94(3H, s), 2.65(2H, t, J=7.6 Hz), 3.27(2H, dt, J=6.8 Hz), 4.56(2H, s), 5.55(1H, br.s), 7.17(2H, d, J=8.6 Hz), 7.29(2H, d, J=7.9 Hz); IR(KBr): 3298, 1639, 1551 cm$^{-1}$; MS(EI): 226((M+1)+); Elemental analysis: Calculated: C; 63.85, H; 7.14, N; 6.21; Found: C; 63.69, H; 7.17, N; 6.20.

(2) N-(3-(4-((4-Phenylpiperazin-1-yl)methyl)phenyl)propyl)acetamide 1/4 Hydrate

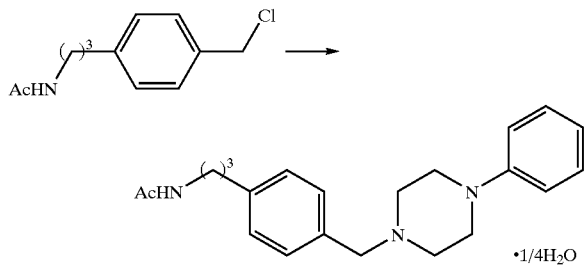

By similar reaction and treatment to that in Example 1(5) using N-(3-(4-chloromethylphenyl)propyl)acetamide instead of N-(4-chloromethylphenylmethyl) acetamide, the title compound was obtained as white crystals, m.p.= 117–118° C.

$^1$H-NMR(CDCl$_3$) δ: 1.83(2H, tt, J=7.4, 7.4 Hz), 1.94(3H, s), 2.62(6H, m), 3.19(4H, t, J=4.9 Hz), 3.27(2H, dt, J=6.8, 6.8 Hz), 3.53(2H, s), 5.48(1H, br.s), 6.84(1H, t, J=7.2 Hz), 6.91(2H, d, J=7.1 Hz), 7.14(2H, d, J=7.9 Hz), 7.25(4H, m); IR(KBr): 3323, 2941, 1641, 1601, 1537 cm$^{-1}$; MS(EI): 351((M+1)+); Elemental analysis: Calculated: C; 74.23, H; 8.35, N; 11.80; Found: C; 74.27, H; 8.26, N; 11.89.

Example 16

Synthesis of N-(4-(1-(4-Phenylpiperazin-1-yl)ethyl)phenylmethyl)acetamide Dihydrochloride (1) N-Phenylmethylacetamide

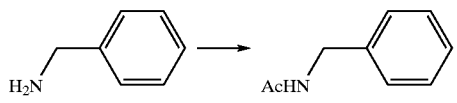

To a solution of benzylamine (98.1 g) in methylene chloride (100 ml) was added an aqueous solution (200 ml) of sodium hydroxide (44 g). While further stirring the mixture, acetyl chloride (78 ml) was added at 15–20° C. over 1 hr. This reaction mixture was stirred at room temperature for 30 min and extracted with chloroform (100 ml×2). The chloroform layer was washed with water and dried over anhydrous magnesium sulfate. The solvent was evaporated to give a white solid (160 g). The obtained solid was crystallized from hexane: ethyl acetate (2:1, 750 ml) to give the title compound (125.7 g) as white crystals, m.p.=61–62° C.

$^1$H-NMR(CDCl$_3$) δ: 2.00(3H, s), 4.41(2H, d, J=5.3 Hz), 5.95(1H, br.s), 7.20–7.35(5H, m); IR(KBr): 3298, 1645, 1552 cm$^{-1}$; MS(EI): 149(M$^+$); Elemental analysis: Calculated: C; 72.46, H; 7.43, N; 9.39; Found: C; 72.40, H; 7.32, N; 9.35.

(2) N-[(4-Acetylphenyl)methyl]acetamide

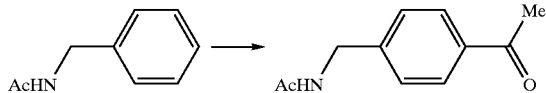

To a suspension of aluminum chloride (22.3 g) in dichloroethane (40 ml) was added acetylchloride (7.1 ml). Thereto was added a solution of N-phenylmethylacetamide (10 g) in dichloroethane (20 ml) at 10–15° C. over 20 min. This reaction mixture was stirred at room temperature for 6 hr and poured into ice water (100 ml). The mixture was extracted with chloroform (100 ml×3). The chloroform layer was washed with saturated brine and dried over anhydrous sodium sulfate. The solvent was evaporated to give a black brown oil (15.5 g). The obtained residue was purified by silica gel column chromatography (developing solvent; chloroform:methanol=20:1) to give the title compound (6.48 g) as a black brown solid.

$^1$H-NMR(CDCl$_3$) δ: 2.04(3H, s), 2.57(3H, s), 4.46(2H, d, J=5.9 Hz), 6.30(1H, br.s), 7.34(2H, d, J=7.9 Hz), 7.88(2H, d, J=7.9 Hz); MS(EI): 191(M$^+$);

(3) N-{[4-(1-Hydroxyethyl)phenyl]methyl}acetamide

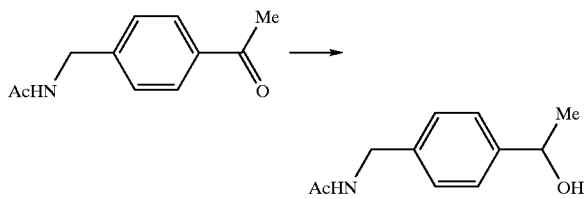

To a solution of N-[(4-acetylphenyl)methyl]acetamide (6.1 g) in methanol (50 ml) was added sodium borohydride (1.2 g) under ice-cooling. This reaction mixture was stirred at 5–7° C. for 2 hr. Thereto was added 2% hydrochloric acid and extracted with ethyl acetate (100 ml×3). The ethyl acetate layer was washed with saturated brine and dried over anhydrous sodium sulfate. The solvent was evaporated to give a brown oil (6.3 g). The obtained brown oil was purified by silica gel column chromatography (developing solvent; chloroform:methanol=9:1) to give the title compound (5.98 g) as a pale-brown oil, m.p.=61–62° C.

$^1$H-NMR(CDCl$_3$) δ: 1.46(3H, d, J=6.6 Hz), 1.97(3H, s), 2.55(1H, br.s), 4.35(2H, d, J=5.9 Hz), 4.85(1H, q, J=6.6 Hz), 6.15(1H, br.s), 7.21(2H, d, J=7.9 Hz), 7.31(2H, d, J=7.9 Hz); IR(neat): 3302, 2971, 1651, 1556 cm$^{-1}$; MS(EI): 193(M$^+$);

(4) N-{[4-(1-Chloroethyl)phenyl]methyl}acetamide

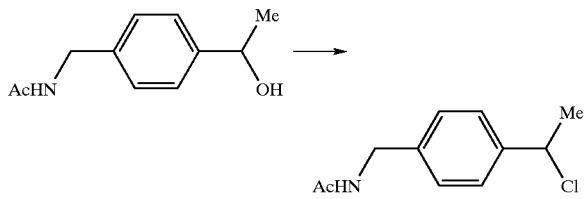

A solution of N-{[4-(1-hydroxyethyl)phenyl] methyl}acetamide (5.7 g) and thionyl chloride (2.6 ml) in chloroform (50 ml) was refluxed under heating for 1.5 hr. The solvent was evaporated to give a brown oil (6.7 g). The obtained brown oil was purified by silica gel column chromatography (developing solvent; chloroform:methanol= 20:1) to give the title compound (5.5 g) as a pale-brown oil.

$^1$H-NMR(CDCl$_3$) δ: 1.83(3H, d, J=7.3 Hz), 2.01(3H, s), 4.40(2H, d, J=4.6 Hz), 5.07(1H, q, J=7.3 Hz), 6.12(1H, br.s), 7.26(2H, d, J=8.6 Hz), 7.38(2H, d, J=8.6 Hz); MS(EI): 211(M$^+$);

(5) N-(4-(1-(4-Phenylpiperazin-1-yl)ethyl)phenylmethyl) acetamide Dihydrochloride

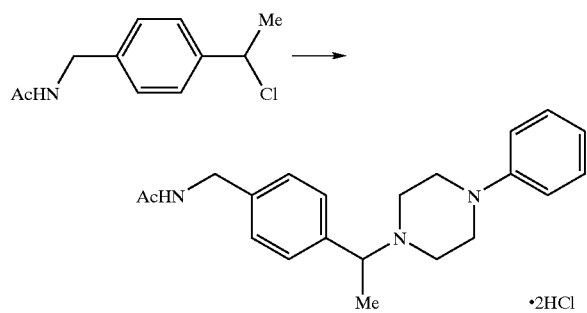

In Example 1(5), N-{[4-(1-chloroethyl)phenyl] methyl}acetamide was used for reaction instead of N-(4-chloromethylphenylmethyl)acetamide, which was followed by treatment with 4M hydrochloric acid-dioxane in ethanol to give the title compound as white crystals.

m.p.=233–235° C. (decomposition); $^1$H-NMR(DMSO-d$_6$) δ: 1.74(3H, d, J=6.6 Hz), 1.89(3H, s), 2.80–3.20(4H, m), 3.38(1H, m), 3.65–3.85(3H, m), 4.27(2H, d, J=5.9 Hz), 4.51(1H, m), 6.86(1H, t, J=7.3 Hz), 6.96(2H, d, J=7.9 Hz), 7.25(2H, dd, J=7.3, 8.6 Hz), 7.34(2H, d, J=7.9 Hz), 7.65(2H, d, J=7.9 Hz), 8.47(1H, m), 11.71(1H, br.s); IR(KBr): 3296, 3061, 2397, 1668, 1542 cm$^{-1}$; MS(EI): 337(M$^+$); Elemental analysis: Calculated: C; 61.46, H; 7.12, N; 10.24; Found: C; 61.41, H; 7.20, N; 10.32.

Example 17

Synthesis of N-((2,6-Dimethyl-4-((4-phenylpiperazin-1-yl)methyl)phenyl)methyl) acetamide 1/5 Hydrate (1) 4-Nitromesitylenic Acid

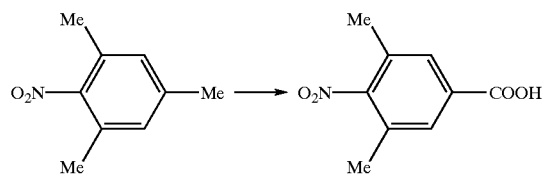

To a solution of chromic anhydride (40 g) in acetic acid (450 ml) was added a solution of nitromesitylene (20 g) in acetic acid (50 ml) at 65–70° C. over 20 min. This reaction mixture was stirred at 65–70° C. for 30 min and isopropyl alcohol (45 ml) was added. This reaction mixture was further stirred at 50° C. for 30 min. Water was added to the reaction mixture to make the total amount 500 ml and the mixture was ice-cooled. The precipitated crystals were collected by filtration to give the title compound (13 g) as pale-green crystals.

$^1$H-NMR(CDCl$_3$) δ: 2.37(6H, s), 7.89(2H, s); IR(KBr): 2968, 2930, 1696, 1602, 1535 cm$^{-1}$; MS(EI): 195(M$^+$)

(2) Ethyl 4-Nitromesitylenate

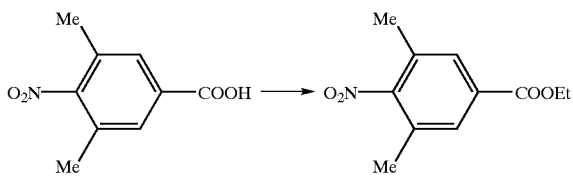

To a solution of 4-nitromesitylenecarboxylic acid (13 g) in ethanol (50 ml) was added a solution of 28% hydrochloric acid-ethanol (50 ml) and the mixture was refluxed under heating for 2 hr. There action mixture was concentrated and ethyl acetate was added. The mixture was washed with water and saturated brine, and dried over anhydrous magnesium sulfate. The solvent was evaporated and the obtained residue was purified by silica gel column chromatography (developing solvent; hexane:ethyl acetate=9:1) to give the title compound (7.7 g) as pale-brown crystals.

$^1$H-NMR(CDCl$_3$) δ: 1.41(3H, t, J=4 Hz), 2.35(6H, s), 4.40(2H, q, J=4 Hz), 7.81(2H, s); IR(KBr): 3077, 2998, 1725, 1606, 1524 cm$^{-1}$; MS(EI): 223(M$^+$).

(3) Ethyl 4-Aminomesitylenate

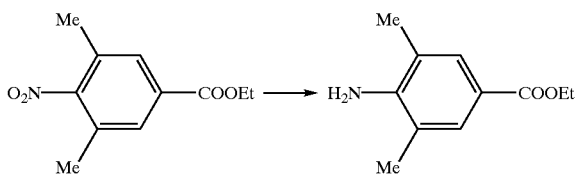

To a solution of ethyl 4-nitromesitylenate (7.7 g) in ethyl acetate (300 ml) was added 10% palladium-carbon (3 g) and the mixture was stirred for 3.5 hr under a hydrogen atmosphere. The catalyst was filtered off from the reaction mixture and the filtrate was washed with water and saturated brine, and dried over anhydrous sodium sulfate. The solvent was evaporated to give the title compound (6.6 g) as pale-brown crystals.

$^1$H-NMR(CDCl$_3$) δ: 1.37(3H, t, J=4 Hz), 2.20(6H, s), 3.96(2H, br.s), 4.32(2H, q, J=4 Hz), 7.66(2H, s); IR(KBr): 3506, 3398, 1692, 1627 cm$^{-1}$; MS(EI): 193(M$^+$).

(4) Ethyl 4-Cyanomesitylenate

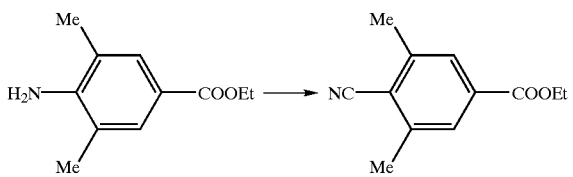

To a solution of ethyl 4-aminomesitylenate (6.6 g) in conc. hydrochloric acid (50 ml) was added a solution of sodium sulfite (2.6 g) in water (15 ml) at 0–5° C. over 30 min. This reaction mixture was stirred at 0° C. for 1 hr. To this reaction mixture was neutralized by adding sodium carbonate and then ethyl acetate (100 ml) was added. To a solution of copper cyanide (6.8 g) in water (100 ml) was added potassium cyanide (18 g) and the mixture was stirred at 0° C. for 30 min. The above-mentioned reaction mixture was added at 0–5° C. and the mixture was stirred at 0° C. for 1 hr. The reaction mixture was extracted with ethyl acetate, washed with aqueous sodium hydrogencarbonate and saturated brine, and dried over anhydrous magnesium sulfate. The solvent was evaporated and the obtained residue was recrystallized from ethyl acetate-hexane to give the title compound (5.5 g) as pale-brown crystals.

$^1$H-NMR(CDCl$_3$) δ: 1.39(3H, t, J=4 Hz), 2.57(6H, s), 4.37(2H, q, J=4 Hz), 7.76(2H, s). IR(KBr): 3056, 2222, 1716, 1585 cm$^{-1}$; MS(EI): 203(M$^+$).

(5) 4-Aminomethyl-3,5-dimethylbenzyl Alcohol

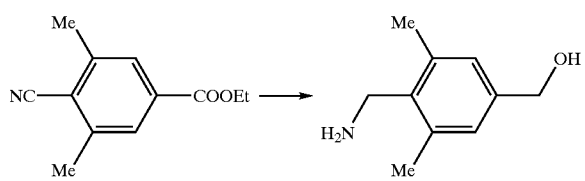

To a solution of aluminum lithium hydride (2.1 g) in tetrahydrofuran (20 ml) was added a solution of ethyl 4-cyanomesitylenate (2.9 g) in tetrahydrofuran (30 ml) at 0° C. and the mixture was refluxed under heating for 6 hr. To this reaction mixture was added 50% (v/v) tetrahydrofuran in water under ice-cooling. This mixture was stirred at room temperature for 30 min and the catalyst was filtered off using Celite. The solvent was evaporated and the obtained residue was recrystallized from methanol-isopropyl ether to give the title compound (5.5 g) as white crystals.

$^1$H-NMR(CDCl$_3$) δ: 1.52(3H, br.s), 2.39(6H, s), 3.85(2H, s), 4.59(2H, s), 7.03(2H, s); IR(KBr): 3294, 2927, 2858, 1647, 1554 cm$^{-1}$; MS(EI): 164(M$^+$);

(6) N-((4-Hydroxymethyl-2,6-dimethylphenyl)methyl) acetamide

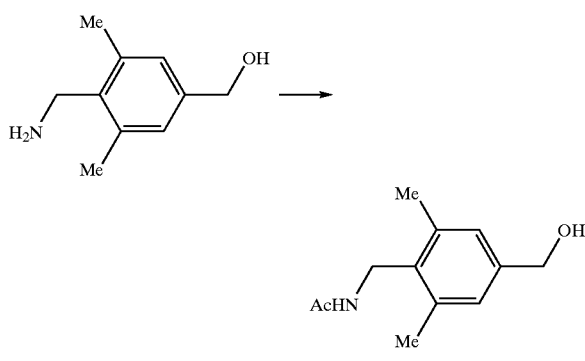

To a solution of 4-aminomethyl-3,5-dimethylbenzyl alcohol (2.3 g) in ethyl acetate (70 ml) was added a solution of potassium carbonate (2.0 g) in water (35 ml). To this solution was added acetyl chloride (0.95 ml) under ice-cooling. This mixture was stirred at room temperature for 1 hr. The reaction mixture was extracted with ethyl acetate, washed with saturated brine and dried over anhydrous magnesium sulfate. The solvent was evaporated and the obtained residue was recrystallized from methanol-ethyl acetate to give the title compound (2.0 g) as white crystals, m.p.=193.5–194.5° C.

$^1$H-NMR(CDCl$_3$) δ: 1.97(3H, s), 2.36(6H, s), 4.44(2H, d, J=4.6 Hz), 4.62(2H, s), 5.27(1H, br.s), 7.06(2H, s); IR(KBr): 3286, 2951, 1632, 1537 cm$^{-1}$; MS(EI): 207(M$^+$);

(7) N-((4-Chloromethyl-2,6-dimethylphenyl)methyl)acetamide

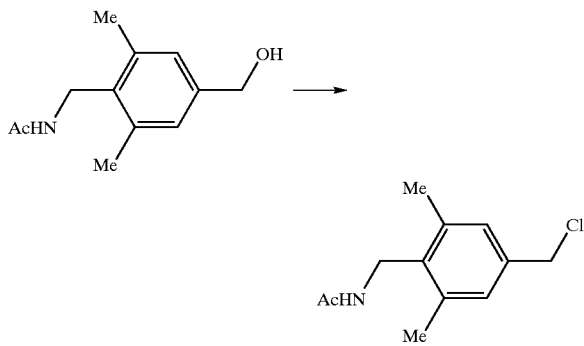

To a solution of N-((4-hydroxymethyl-2,6-dimethylphenyl)methyl)acetamide (1.0 g) in dichloromethane (12 ml) was added thionyl chloride (0.88 ml). This mixture was stirred at room temperature for 3 hr. The reaction mixture was poured into water and extracted with ethyl acetate. The extract was washed with aqueous sodium hydrogencarbonate and saturated brine, and dried over anhydrous magnesium sulfate. The solvent was evaporated and the obtained residue was recrystallized from ethyl acetate-isopropyl ether to give the title compound (1.0 g) as white crystals.

m.p.=193–194.5° C. $^1$H-NMR(CDCl$_3$) δ: 1.97(3H, s), 2.36(6H, s), 4.44(2H, d, J=4.6 Hz), 4.50(2H, s), 5.26(1H, br.s), 7.06(2H, s); IR(KBr): 3284, 1633, 1538 cm$^{-1}$; MS(EI): 225(M$^+$).

(8) N-(4-(4-Phenylpiperazin-1-ylmethyl)-2,6-dimethylphenylmethyl)acetamide 1/5 Hydrate

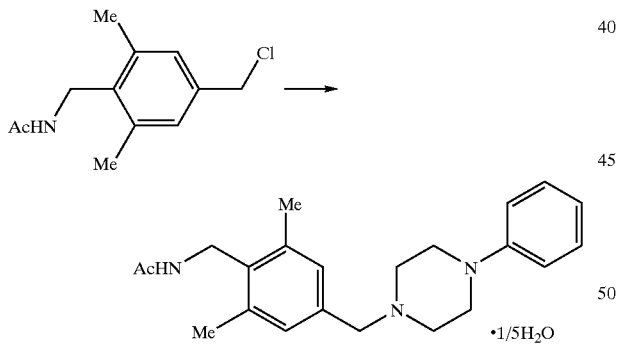

By similar reaction and treatment to that in Example 1(5) using N-((4-chloromethyl-2,6-dimethylphenyl)methyl)acetamide instead of N-(4-chloromethylphenylmethyl)acetamide, the title compound was obtained as white crystals, m.p.=159–160.5° C.

$^1$H-NMR(CDCl$_3$) δ: 1.97(3H, s), 2.36(6H, s), 2.60(4H, dd, J=5.3, 4.6 Hz), 3.20(4H, dd, J=5.3, 4.6 Hz), 3.48(2H, s), 4.46(2H, d, J=4.6 Hz), 5.27(1H, br.s), 6.86(1H, dt, J=7.3, 1.3 Hz), 6.92(2H, dd, J=7.3, 1.3 Hz), 7.04(2H, s), 7.21–7.29(2H, m); IR(KBr): 3269, 2952, 1600, 1546 cm$^{-1}$; MS(EI): 351 (M$^+$); Elemental analysis: Calculated: C; 74.41, H; 8.35, N; 11.83; Found: C; 74.63, H; 8.32, N; 11.79.

Example 18

Synthesis of N-(4-(4-(4-Fluorophenyl)piperazin-1-ylmethyl)-2,6-dimethylphenylmethyl)acetamide

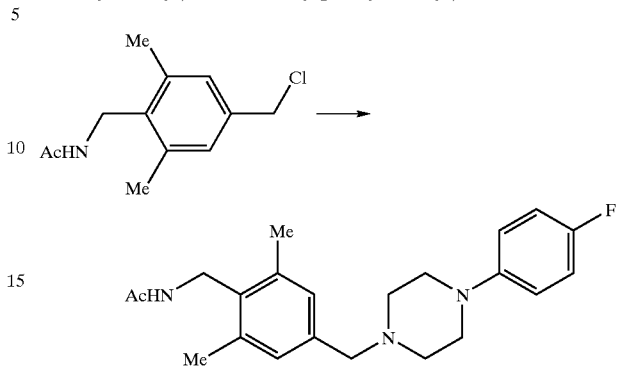

By similar reaction and treatment to that in Example 17(8) using 1-(4-fluorophenyl)piperazine instead of 1-phenylpiperazine, the title compound was obtained as white crystals, m.p.=163–164° C.

$^1$H-NMR(CDCl$_3$) δ: 1.98(3H, s), 2.36(6H, s), 2.60(4H, dd, J=5.3, 4.6 Hz), 3.12(4H, dd, J=5.3, 4.6 Hz), 3.48(2H, s), 4.45(2H, d, J=4.6 Hz), 5.25(1H, br.s), 6.83–6.98(4H, m), 7.03(2H, s); IR(KBr): 3323, 2947, 1645, 1531 cm$^{-1}$; MS(EI): 369(M$^+$); Elemental analysis: Calculated: C; 71.52, H; 7.64, N; 11.37; Found: C; 71.22, H; 7.71, N; 11.28.

Example 19

Synthesis of N-(4-(1-(4-(2-Methoxyphenyl)piperazin-1-yl)ethyl)phenylmethyl)acetamide Dihydrochloride

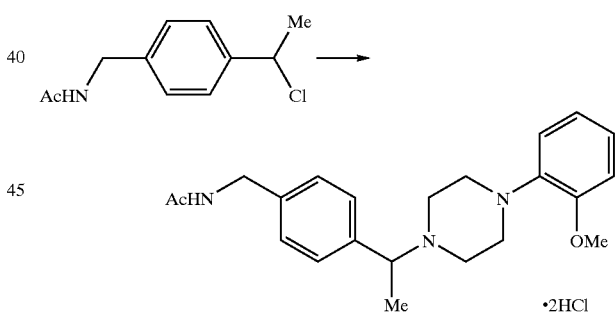

In Example 1(5), N-((4-(1-chloroethyl)phenyl)methyl)acetamide was used for reaction instead of N-(4-chloromethylphenylmethyl)acetamide and 1-(2-methoxyphenyl)piperazine instead of 1-phenylpiperazine, which was followed by treatment with 4M hydrochloric acid-dioxane in ethanol to give the title compound as white crystals.

m.p.=220–223° C. (decomposition); $^1$H-NMR(DMSO-d$_6$) δ: 1.75(3H, d, J=6.6 Hz), 1.90(3H, s), 2.90–3.25(4H, m), 3.40–3.60(3H, m), 3.77(3H, s), 3.82(1H, m), 4.28(1H, d, J=5.3 Hz), 4.53(1H, m), 6.85–7.10(4H, m), 7.35(2H, d, J=7.9 Hz), 7.68(2H, d, J=8.6 Hz), 8.53(1H, t, J=5.3 Hz), 11.81(1H, br.s); IR(KBr): 3286, 3253, 2983, 2404, 1668 cm$^{-1}$; MS(EI): 367(M$^+$); Elemental analysis: Calculated: C; 60.00, H; 7.09, N; 9.54; Found: C; 60.07, H; 7.19, N; 9.61.

Example 20

Synthesis of N-(4-((4-(2,4-Difluorophenyl)piperazin-1-yl)methyl)phenylmethyl)acetamide

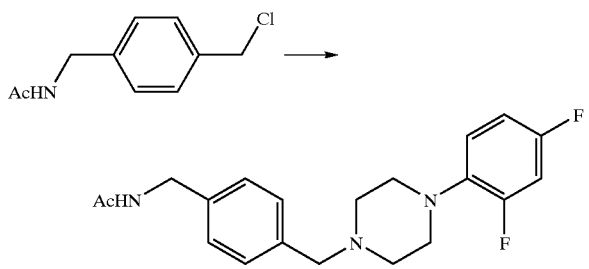

By similar reaction and treatment to that in Example 1(5) using (2,4-difluorophenyl)piperazine dihydrochloride instead of phenylpiperazine, the title compound was obtained as pale-brown crystals, m.p.=94–95° C.

$^1$H-NMR(CDCl$_3$) δ: 2.02(3H, s), 2.61(4H, dd, J=5.28, 4.62 Hz), 3.04(4H, dd, J=5.3, 4.6 Hz), 3.56(2H, s), 4.42(2H, d, J=5.9 Hz), 5.71(1H, br.s), 6.73–6.93(3H, m), 7.24(2H, d, J=7.9 Hz), 7.32(2H, d, J=7.9 Hz); IR(KBr): 3307, 2939, 2821, 1645, 1556 cm$^{-1}$; MS(EI): 359(M$^+$); Elemental analysis: Calculated: C; 66.84, H; 6.45, N; 11.69; Found: C; 66.84, H; 6.43, N; 11.66.

Example 21

Synthesis of N-(2-Nitro-4-((4-phenylpiperazin-1-yl)methyl)phenylmethyl)acetamide (1) Methyl 4-Acetamidomethyl-3-nitrobenzoate

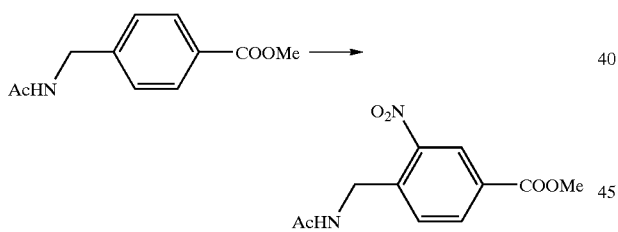

To a mixture (mixed acid) of fuming nitric acid (70 ml) and conc. sulfuric acid (70 ml) was added methyl 4-acetamidomethylbenzoate (54 g) at 7–15° C. for 1.5 hr. This reaction mixture was stirred at room temperature for 1 hr and poured into ice water (600 ml). The mixture was extracted with chloroform (300 ml×3). The extract was washed with water, saturated sodium hydrogencarbonate solution and saturated brine, and dried over anhydrous sodium sulfate. The solvent was evaporated to give a yellow oil (75 g). The obtained yellow oil was crystallized from ethyl acetate (50 ml) and recrystallized from hexane/ethyl acetate (1:1, 600 ml) to give the title compound (45.5 g) as pale-yellow crystals.

m.p.=100–102° C.; $^1$H-NMR(CDCl$_3$)δ: 2.02(3H, s), 3.97 (3H, s), 4.71(2H, d, J=6.6 Hz), 6.38(1H, m), 7.76(1H, d, J=7.9 Hz), 8.24(1H, dd, J=1.3, 7.9 Hz), 8.67(1H, d, J=1.3 Hz); IR(KBr): 3280, 1735, 1648, 1533, 1434 cm$^{-1}$; MS(EI): 253((M+1)+); Elemental analysis: Calculated: C; 52.38, H; 4.80, N; 11.11; Found: C; 52.33, H; 4.79, N; 11.11.

(2) N-(4-Hydroxymethyl-2-nitrophenylmethyl)acetamide

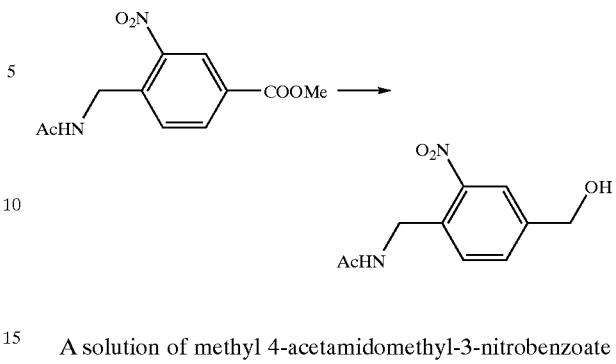

A solution of methyl 4-acetamidomethyl-3-nitrobenzoate (20 g) and lithium borohydride (1.7 g) in tetrahydrofuran (200 ml) was stirred at 40–50° C. for 2.5 hr. The reaction mixture was poured into water (150 ml) and extracted with ethylacetate (100 ml×3). The extract was washed with saturated brine and dried over anhydrous sodium sulfate. The solvent was evaporated to give a yellow oil (15.5 g). The obtained yellow oil was purified by silica gel column chromatography (developing solvent; chloroform:methanol=9:1) to give a pale-brown solid (13.5 g). The obtained solid was crystallized from ethyl acetate/ethanol/hexane (30:2:5) to give the title compound (12 g) as yellow white crystals.

m.p.=133–135° C.; $^1$H-NMR(DMSO-d$_6$)δ: 1.90(3H, s), 4.51(2H, d, J=5.9 Hz), 4.58(2H, d, J=5.3 Hz), 5.47(1H, t, J=5.3 Hz), 7.49(1H, d, J=7.9 Hz), 7.64(1H, d, J=7.9 Hz), 7.96(1H, s), 8.39(1H, m) IR(KBr): 3290, 1656, 1558, 1529 cm$^{-1}$; MS(EI): 225((M+1)+).

(3) N-(4-Chloromethyl-2-nitrophenylmethyl)acetamide

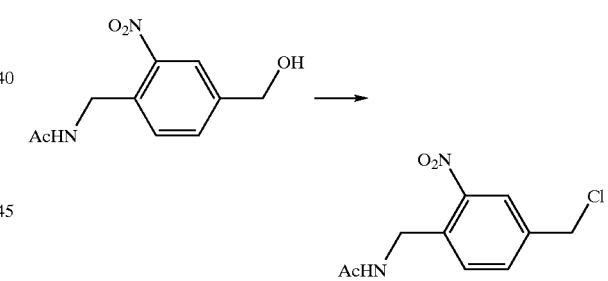

To a solution of N-(4-hydroxymethyl-2-nitrophenylmethyl)acetamide (9.1 g), triethylamine (6.2 ml) and dimethylaminopyridine (0.99 g) in dichloromethane (150 ml)-tetrahydrofuran (50 ml) was added p-toluenesulfonyl chloride (8.5 g) under ice-cooling. This mixture was stirred at room temperature for 3 hr. The reaction mixture was washed with water and saturated brine, and dried over anhydrous sodium sulfate. The solvent was evaporated to give a yellow oil (15.5 g). The obtained yellow oil was purified by silica gel column chromatography (developing solvent; chloroform:methanol=20:1) to give the title compound (12 g) as a pale-brown solid (7.8 g).

$^1$H-NMR(DMSO-d$_6$)δ: 1.90(3H, s), 4.52(2H, d, J=5.9 Hz), 4.87(2H, s), 7.54(1H, d, J=8.6 Hz), 7.79(1H, dd, J=1.3, 8.6 Hz), 8.12(1H, d, J=1.3 Hz), 8.43(1H, m); MS(EI): 243(M$^+$).

(4) N-(2-Nitro-4-((4-phenylpiperazin-1-yl)methyl)phenylmethyl)acetamide

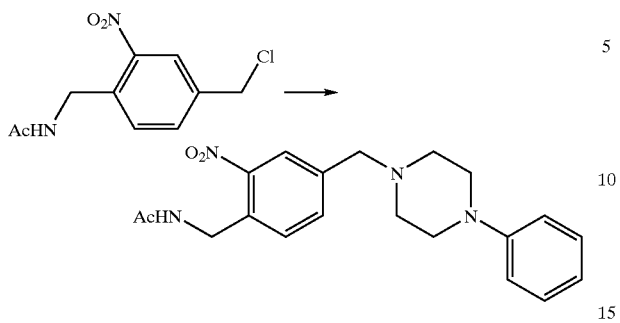

A solution of N-(4-chloromethyl-2-nitrophenylmethyl)acetamide (1.4 g), phenylpiperazine (0.8 ml) and potassium carbonate (0.6 g) in dimethylformamide (20 ml) was stirred at 60° C. for 4 hr. The reaction mixture was poured into water (150 ml) and extracted with ethyl acetate. The extract was washed with saturated brine and dried over anhydrous sodium sulfate. The solvent was evaporated to give a pale-yellow solid. The obtained pale-yellow solid was crystallized from ethyl acetate to give the title compound (1.3 g) as pale-yellow white crystals, m.p.=135–136° C.

$^1$H-NMR(DMSO-$d_6$) δ: 1.90(3H, s), 2.50–2.60(4H, m), 3.10–3.15(4H, m), 3.62(2H, s), 4.51(2H, d, J=5.9 Hz), 6.77(1H, m), 6.91(2H, d, J=7.9 Hz), 7.20(2H, m), 7.50(1H, d, J=7.9 Hz), 7.68(1H, dd, J=1.3, 7.9 Hz), 7.97(1H, d, J=1.3 Hz), 8.40(1H, t, J=5.9 Hz); IR(KBr): 3251, 3080, 2823, 1641, 1599 cm$^{-1}$; MS(EI): 368(M$^+$); Elemental analysis: Calculated: C; 65.20, H; 6.57, N; 15.21; Found: C; 65.17, H; 6.58, N; 15.12.

Example 22

Synthesis of N-(2-Amino-4-((4-phenylpiperazin-1-yl)methyl)phenylmethyl)acetamide

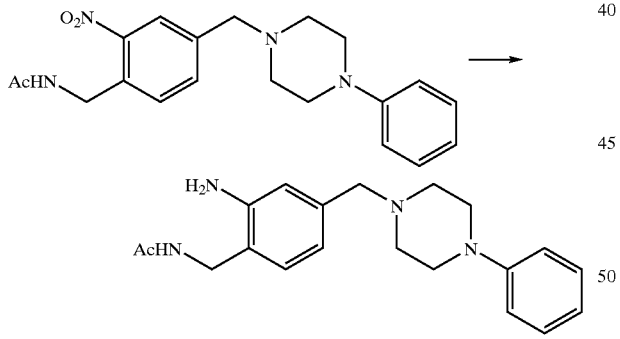

To a solution of N-(2-nitro-4-((4-phenylpiperazin-1-yl)methyl)phenylmethyl)acetamide (0.5 g) and water-containing Raney-nickel (0.5 g) in ethanol (8 ml) was added dropwise hydrazine monohydrate (0.7 ml) and the mixture was refluxed under heating at room temperature for 1 hr. Raney-nickel was removed by passing the mixture through Celite and the solvent was evaporated to give a white solid (0.48 g). The obtained white solid was crystallized from hexane/ethyl acetate (1:1, 100 ml) to give the title compound (45.5 g) as white crystals, m.p.=148–149° C.

$^1$H-NMR(DMSO-$d_6$)δ: 1.85(3H, s), 2.40–2.55(4H, m), 3.05–3.15(4H, m), 3.35(2H, s), 4.08(2H, d, J=5.9 Hz), 5.05(2H, s), 6.46(1H, dd, J=1.3, 5.9Hz), 6.62(1H, d, J=1.3 Hz), 6.76(1H, t, J=7.3 Hz), 6.89–6.93(3H, m), 7.15–7.25(2H, m), 8.21(1H, t, J=5.9 Hz); IR(KBr): 3336, 3239, 2809, 1623, 1523 cm$^{-1}$; MS(EI): 338(M$^+$); Elemental analysis: Calculated: C; 70.98, H; 7.74, N; 16.55; Found: C; 70.85, H; 7.77, N; 16.33.

Example 23

Synthesis of N-(4-((4-(4-Fluorophenyl)piperazin-1-yl)methyl)-2-nitrophenylmethyl)acetamide

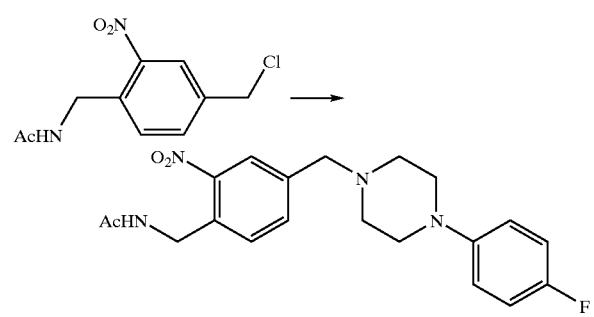

In Example 21(4), (4-fluorophenyl)piperazine dihydrochloride was used instead of phenylpiperazine to give the title compound as yellow crystals, m.p.=112–114° C.

$^1$H-NMR(DMSO-$d_6$)δ: 1.91(3H, s), 2.45–2.55(4H, m), 3.05–3.15(4H, m), 3.62(2H, s), 4.52(2H, d, J=5.9 Hz), 6.90–7.00(2H, m), 7.00–7.07(2H, m), 7.51(1H, d, J=7.9 Hz), 7.68(1H, dd, J=1.3, 7.9 Hz), 7.97(1H, d, J=1.3 Hz), 8.40(1H, t, J=5.9 Hz); IR(KBr): 3253, 2831, 1639, 1562 cm$^{-1}$; MS(EI): 386(M$^+$); Elemental analysis: Calculated: C; 62.16, H; 6.00, N; 14.50; Found: C; 61.80, H; 5.97, N; 14.13.

Example 24

Synthesis of N-(2-Amino-4-((4-(4-fluorophenyl)piperazin-1-yl)methyl)phenylmethyl)acetamide

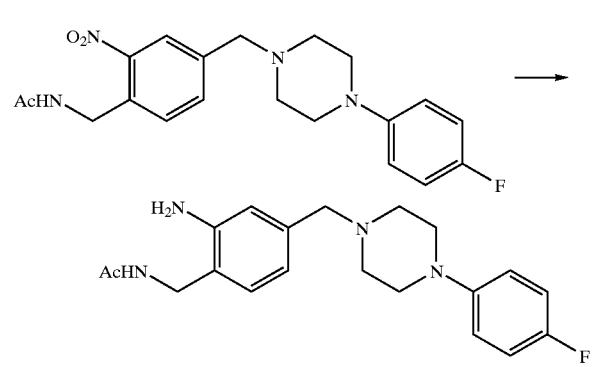

In Example 22, N-(4-((4-(4-fluorophenyl)piperazin-1-yl)methyl)-2-nitrophenylmethyl)acetamide was used instead of N-(2-nitro-4-((4-phenylpiperazin-1-yl)methyl)phenylmethyl)acetamide to give the title compound as yellow white crystals, m.p.=163–164° C.

$^1$H-NMR(DMSO-$d_6$)δ: 1.85(3H, s), 2.45–2.55(4H, m), 3.00–3.10(4H, m), 3.33(2H, s), 4.08(2H, d, J=6.6 Hz), 5.05(2H, s), 6.46(1H, dd, J=1.3, 7.3 Hz), 6.61(1H, d, J=1.3 Hz), 6.89–6.95(3H, m), 6.99–7.06(2H, m), 8.21(1H, t, J=5.9 Hz); IR(KBr): 3311, 3241, 2836, 1626, 1510 cm$^{-1}$; MS(EI): 356(M$^+$); Elemental analysis: Calculated: C; 67.39, H; 7.07, N; 15.72; Found: C; 67.56, H; 7.14, N; 15.59.

Example 25

Synthesis of N-(2-Acetamide-4-((4-(4-fluorophenyl)-piperazin-1-yl)methyl)phenylmethyl)acetamide

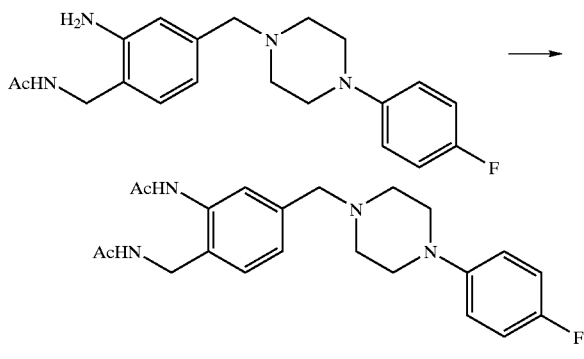

A solution of N-(2-amino-4-((4-(4-fluorophenyl)piperazin-1-yl)methyl)phenylmethyl)acetamide (1.65 g), acetic anhydride (0.52 ml) and triethylamine (0.77 ml) in methylene chloride (20 ml) was refluxed under heating for 3 hr. The reaction mixture was poured into water (150 ml) and extracted with chloroform. The extract was washed with saturated brine and dried over anhydrous sodium sulfate. The solvent was evaporated to give a brown oil. The obtained brown oil was purified by silica gel column chromatography (developing solvent; chloroform:methanol=20:1) to give a pale-brown solid (1.5 g). This pale-brown solid was crystallized from ethyl acetate to give the title compound (1.1 g) as pale-yellow crystals, m.p.=145–146° C.

$^1$H-NMR(DMSO-$d_6$)δ: 1.89(3H, s), 2.07(3H, s), 2.45–2.55(4H, m), 3.00–3.10(4H, m), 3.47(2H, s), 4.20(2H, d, J=5.9 Hz), 6.88–6.98(2H, m), 6.99–7.07(3H, m), 7.20(1H, d, J=7.9 Hz), 7.66(1H, s), 8.48(1H, t, J=5.9 Hz), 9.82(1H, s); IR(KBr): 3288, 2819, 1673, 1626, 1587 cm$^{-1}$; MS(EI): 398(M$^+$); Elemental analysis: Calculated: C; 66.31, H; 6.83, N; 14.06; Found: C; 66.06, H; 6.78, N; 13.94.

Example 26

Synthesis of N-(2-Chloro-4-((4-(4-fluorophenyl)-piperazin-1-yl)methyl)phenylmethyl)acetamide

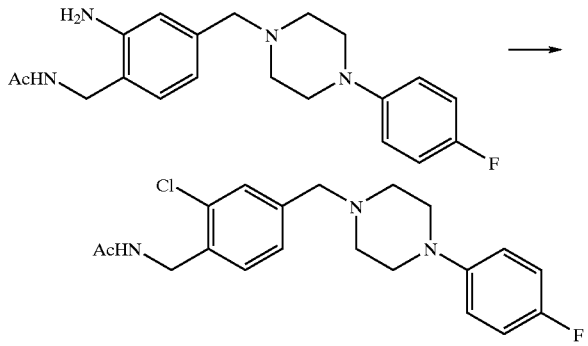

To an aqueous solution (2 ml) of sodium nitrite (213 mg) was added a solution of N-(2-amino-4-((4-(4-fluorophenyl)piperazin-1-yl)methyl)phenylmethyl)acetamide (1.1 g) in conc. hydrochloric acid (5 ml) under ice-cooling. This mixture was stirred at the same temperature for 40 min. The reaction mixture was added to a solution of copper(I) chloride (183 mg) in conc. hydrochloric acid (2 ml) over 10 min. The mixture was stirred at room temperature for 2 hr. The reaction mixture was poured into aqueous sodium hydroxide solution and extracted with ethyl acetate. The extract was washed with saturated brine and dried over anhydrous sodium sulfate. The solvent was evaporated to give a green oil (1.4 g). The obtained green oil was purified by silica gel column chromatography (developing solvent; chloroform:methanol=20:1) to give a pale-brown solid (0.9 g). This pale-brown solid was crystallized from ethyl acetate/hexane to give the title compound (0.75 g) as yellow crystals.

m.p.=141–142° C.; $^1$H-NMR(DMSO-$d_6$)δ: 1.90(3H, s), 2.45–2.55(4H, m), 3.00–3.10(4H, m), 3.51(2H, s), 4.30(2H, d, J=5.9 Hz), 6.85–6.95(2H, m), 6.95–7.05(2H, m), 7.22–7.32(2H, m), 7.38(1H, s), 8.32(1H, t, J=5.9 Hz); IR(KBr): 3267, 2827, 1653, 1554, 1512 cm$^{-1}$; MS(EI): 375(M$^+$); Elemental analysis: Calculated: C; 63.91, H; 6.17, N; 11.18; Found: C; 63.85, H; 6.16, N; 11.23.

Example 27

Synthesis of N-(2-(4-((4-(4-Fluorophenyl)piperazin-1-yl)methyl)phenyl)ethyl)acetamide (1) 4-((4-Chloromethylphenyl)methyl)-1-(4-fluorophenyl)piperazine

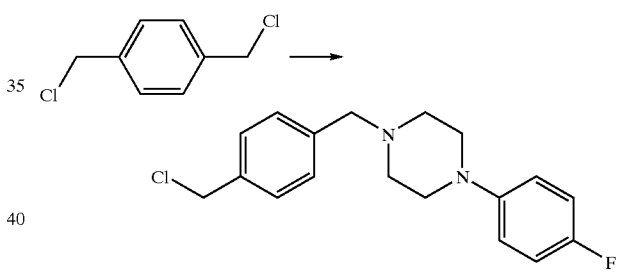

To an aqueous solution (100 ml) of 1-(4-fluorophenyl)piperazine dihydrochloride was added an aqueous solution (50 ml) of sodium hydroxide (10 g) and the mixture was extracted with ethyl acetate. The organic layer was washed with saturated brine and dried over anhydrous sodium sulfate. The solvent was evaporated to give a white solid (ca. 20 g). A solution of this solid (1-(4-fluorophenyl)piperazine), α,α'-dichloro-p-xylene (20.0 g) and potassium carbonate in dimethylformamide (150 ml) was stirred at 75° C. for 2 hr and poured into ice water (500 ml). The mixture was extracted with ethyl acetate (400 ml×2). The ethyl acetate layer was washed with saturated brine and dried over anhydrous sodium sulfate. The obtained residue was purified by silica gel column chromatography (developing solvent; ethyl acetate:hexane=1:3) and recrystallized from ethyl acetate-hexane to give the title compound (10.66 g) as white crystals.

m.p.=81–83° C.; $^1$H-NMR(CDCl$_3$)δ: 2.60(4H, t, J=5.3 Hz), 3.11(4H, t, J=4.9 Hz), 3.56(2H, s), 4.58(2H, s), 6.90 (4H, m), 7.35(4H, s); IR(KBr): 2947, 2839, 2773, 1514 cm$^{-1}$; MS(EI): 318(M$^+$); Elemental analysis: Calculated: C; 67.81, H; 6.32, N; 8.79; Found: C; 67.80, H; 6.34, N; 8.75.

(2) 2-(4-(4-(4-Fluorophenyl)piperazin-1-ylmethyl)phenyl)acetonitrile

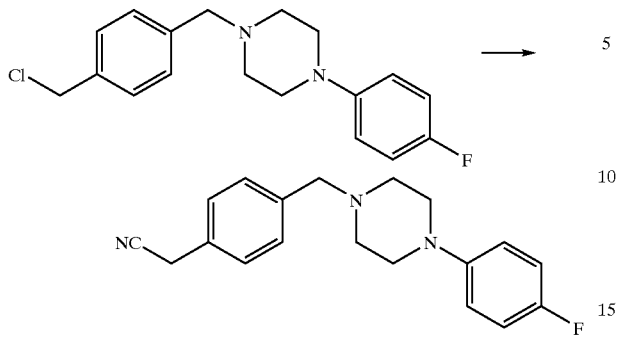

A solution of 4-((4-chloromethylphenyl)methyl)-1-(4-fluorophenyl)piperazine (10.0 g), sodium cyanide (1.72 g) and a catalytic amount of sodium iodide in dimethylformamide (50 ml) was stirred at 70° C. for 3 hr, and poured into ice water (200 ml) and extracted with ethyl acetate (300 ml×2). The ethyl acetate layer was washed with saturated brine and dried over anhydrous sodium sulfate. The obtained residue was purified by silica gel column chromatography (developing solvent; ethyl acetate:hexane=1:2) and recrystallized from ethyl acetate-hexane to give the title compound (6.50 g) as pale-yellow crystals.

m.p.=111–113° C.; $^1$H-NMR(CDCl$_3$)δ: 2.60(4H, t, J=5.0 Hz), 3.11(4H, t, J=4.9 Hz), 3.56(2H, s), 3.73(2H, s), 6.89 (4H, m), 7.29(2H, d, J=7.9 Hz), 7.37(2H, d, J=7.9 Hz); IR(KBr): 2946, 2816, 2775, 2248, 1514 cm$^{-1}$; MS(EI): 291((M−F)+); Elemental analysis: Calculated: C; 73.76, H; 6.52, N; 13.58; Found: C; 73.98, H; 6.52, N; 13.52.

(3) N-(2-(4-((4-(4-Fluorophenyl)piperazin-1-yl)methyl)phenyl)ethyl)acetamide

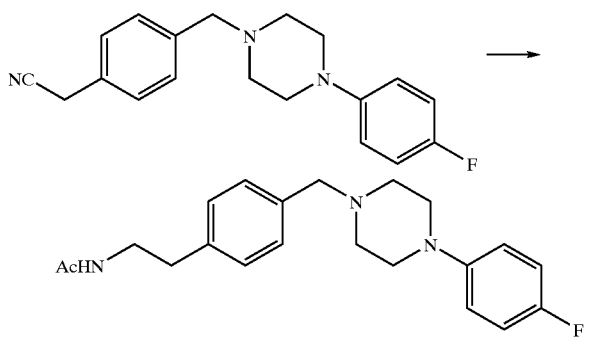

To a solution of aluminum lithium hydride (0.74 g) in tetrahydrofuran (30 ml) was added 2-(4-(4-(4-fluorophenyl)-piperazin-1-ylmethyl)phenyl)acetonitrile (2.0 g) in tetrahydrofuran (30 ml) at 5–10° C., and the mixture was refluxed under heating for 4 hr. To this reaction mixture was added saturated aqueous sodium sulfate solution (10 ml) under ice-cooling. The insoluble matter was filtered off and the solvent was evaporated to give the obtained residue as purified by silica gel column chromatography (developing solvent; ethyl acetate:hexane=3:1; methanol:chloroform= 1:9, later 1:6) to give 4-(4-(2-aminoethyl)phenyl)-1-(4-fluorophenyl)piperazine (0.59 g). To this compound in a dichloromethane solution (20 ml) were added triethylamine (0.24 ml) and acetic anhydride (0.21 ml) and the mixture was left standing at room temperature for 10 min and poured into ice water (100 ml) and extracted with ethyl acetate (100 ml×2). The ethyl acetate layer was washed with saturated brine (100 ml) and dried over anhydrous sodium sulfate. The obtained crude crystals were recrystallized from ethyl acetate/hexane to give the title compound (416 mg) as pale-brown crystals, m.p.=121–123° C.

$^1$H-NMR(CDCl$_3$)δ: 1.94(3H, s), 2.61(4H, t, J=5.0 Hz), 2.81(2H, t, J=6.9 Hz), 3.12(4H, t, J=4.9 Hz), 3.51(2H, q, J=6.4 Hz), 3.54(2H, s), 5.50(1H, br.s), 6.89(4H, m), 7.16 (2H, d, J=7.9 Hz), 7.29(2H, d, J=7.9 Hz); IR(KBr): 3292, 2819, 1647, 1514 cm$^{-1}$; MS(EI): 355(M$^+$); Elemental analysis: Calculated: C; 70.96, H; 7.37, N; 11.82; Found: C; 70.81, H; 7.41, N; 11.68.

Example 28

Synthesis of N-(2-Bromo-4-(((4-(4-fluorophenyl)-piperazin-1-yl)methyl)phenylmethyl)acetamide

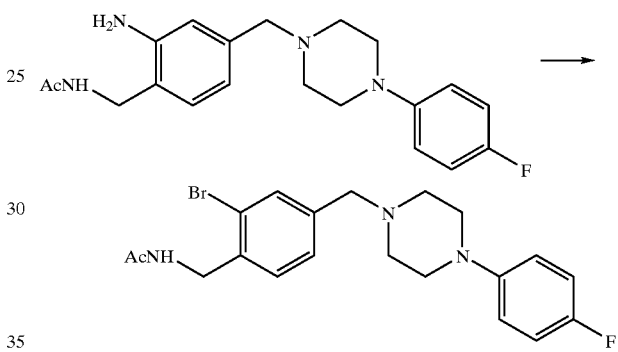

To an aqueous solution (4 ml) of sodium nitrite (387 mg) was added a solution of N-(2-amino-4-((4-(4-fluorophenyl)piperazin-1-yl)methyl)phenylmethyl)acetamide (2.0 g) in 48% hydrobromic acid (10 ml) under ice-cooling. This reaction mixture was stirred at the same temperature for 45 min and added to a solution of copper(I) bromide (483 mg) in 48% hydrobromic acid (6 ml) over 15 min. This reaction mixture was stirred at room temperature for 5 hr and poured into aqueous sodium hydroxide solution. The mixture was passed through Celite and extracted with ethyl acetate. The extract was washed with saturated brine and dried over anhydrous sodium sulfate. The solvent was evaporated to give a brown oil (1.7 g). The obtained brown oil was purified by silica gel column chromatography (developing solvent; chloroform:methanol=20:1) to give a brown oil (1.4 g). This brown oil was crystallized from ethyl acetate-hexane and recrystallized from ethyl acetate-hexane to give the title compound (0.9 g) as yellow white crystals, m.p.=149–150° C.

$^1$H-NMR(DMSO-d$_6$)δ: 1.91(3H, s), 2.45–2.55(4H, m), 3.00–3.10(4H, m), 3.50(2H, s), 4.27(2H, d, J=5.9 Hz), 6.85–6.95(2H, m), 6.95–7.05(2H, m), 7.22–7.35(2H, m), 7.55(1H, s), 8.33(1H, t, J=5.9 Hz); IR(KBr): 3269, 2827, 1653, 1550, 1512 cm$^{-1}$; MS(EI): 420(M$^+$); Elemental analysis: Calculated: C; 57.15, H; 5.52, N; 10.00; Found: C; 56.92, H; 5.39, N; 9.92.

Example 29

Synthesis of N-(3-Nitro-4-(((4-( 4-fluorophenyl)-piperazin-1-yl)methyl)phenylmethyl)acetamide Dihydrochloride 1/2 Hydrate (1) 4-Methyl-3-nitrobenzonitrile

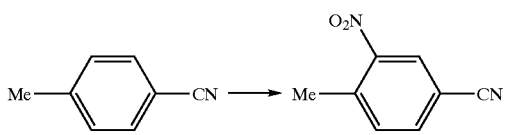

To conc. sulfuric acid (50 ml) was added p-tolunitrile (50 g) under ice-cooling and fuming nitric acid (38 ml) was added at the same temperature over 1 hr. The reaction mixture was poured into ice water (700 g) and the precipitated crystals were collected by filtration. The obtained crystals were washed with water to give yellow white crystals (90 g). The yellow white crystals were recrystallized from ethanol:water (9:1) to give the title compound (61 g) as white crystals.

m.p.=102–103° C.; $^1$H-NMR(DMSO-d$_6$)δ: 2.58(3H, s), 7.73(1H, d, J=7.9 Hz), 8.09(1H, dd, J=1.3, 7.9 Hz), 8.50(1H, d, J=1.3 Hz); IR(KBr): 3088, 2235, 1616, 1525 cm$^{-1}$; MS(EI): 163(M$^+$); Elemental analysis: Calculated: C; 59.26, H; 3.73, N; 17.28; Found: C; 59.05, H; 3.53, N; 16.86.

(2) 4-Bromomethyl-3-nitrobenzonitrile

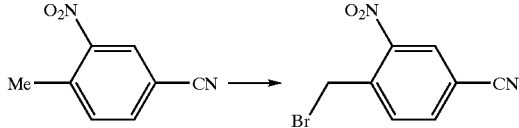

A solution of 4-methyl-3-nitrobenzonitrile (30 g), N-bromosuccinimide (37 g) and azobisisobutyronitrile (3.1 g) in carbon tetrachloride (300 ml) was refluxed under heating for 8 hr. To the reaction mixture was added water (100 ml) and the mixture was extracted with chloroform. The extract was washed with saturated brine and dried over anhydrous sodium sulfate. The solvent was evaporated under reduced pressure and the obtained residue was purified by silica gel column chromatography (developing solvent; ethyl acetate:hexane=1:4) and recrystallized from ethyl acetate-hexane to give the title compound (23.7 g) as pale-yellow crystals, m.p.=85–89° C.

$^1$H-NMR(DMSO-d$_6$)δ: 4.96(2H, s), 7.97(1H, d, J=7.9 Hz), 8.22(1H, dd, J=1.3, 7.9 Hz), 8.61(1H, d, J=1.3 Hz); IR(KBr): 3082, 2235, 1614, 1530 cm$^{-1}$; MS(EI): 241(M$^+$); Elemental analysis: Calculated: C; 39.86, H; 2.09, N; 11.62; Found: C; 40.64, H; 2.15, N; 11.85.

(3) N-(4-Bromomethyl-3-nitrophenylmethyl)acetamide

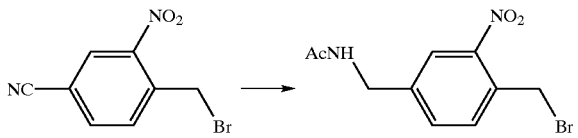

To a solution of 4-bromomethyl-3-nitrobenzonitrile (25.7 g) in tetrahydrofuran (250 ml) was added a 2.0 M tetrahydrofuran solution (59 ml) of a borane-methylsulfide complex and the mixture was refluxed under heating for 4.5 hr. To the reaction mixture was added hydrochloric acid-methanol and the mixture was refluxed under heating for 1.5 hr. The solvent was evaporated under reduced pressure to give a brown oil. The obtained brown oil was crystallized from ethyl acetate to give yellow white crystals. To a mixed solution of the obtained yellow white crystals, acetic anhydride (12.1 ml), water (50 ml) and ethyl acetate (100 ml) was added an aqueous solution (50 ml) of sodium hydroxide (12.8 g) under ice-cooling. This reaction mixture was stirred at room temperature for 2.5 hr and extracted with ethyl acetate. The extract was washed with saturated brine and dried over anhydrous sodium sulfate. The solvent was evaporated under reduced pressure. The obtained residue was purified by silica gel column chromatography (developing solvent; chloroform:methanol=20:1) to give the title compound (21.4 g) as a brown oil.

$^1$H-NMR(CD3OD)δ: 2.03(3H, s), 4.45(2H, s), 4.94(2H, d, J=2.0 Hz), 7.55–7.65(2H, m), 7.96(1H, s); MS(EI): 287 (M$^+$).

(4) N-(3-Nitro-4-(((4-(4-fluorophenyl)piperazin-1-yl) methyl)phenylmethyl)acetamide Dihydrochloride 1/2 Hydrate

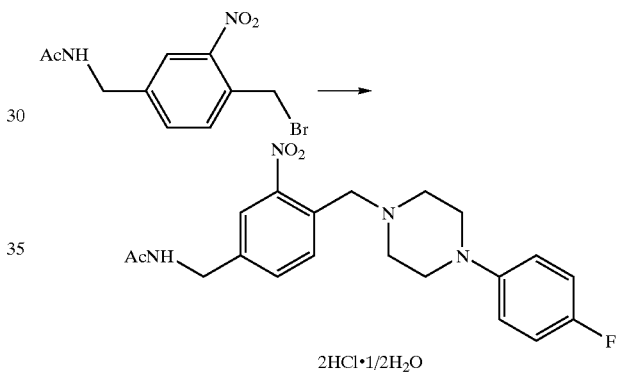

A solution of N-(4-bromomethyl-3-nitrophenylmethyl) acetamide (21 g), 1-(4-fluorophenyl)piperazine dihydrochloride (20.4 g) and potassium carbonate (40.4 g) in dimethylformamide (200 ml) was stirred at 85° C. for 8.5 hr. The reaction mixture was poured into water (300 ml) and extracted with ethyl acetate. The extract was washed with saturated brine and dried over anhydrous sodium sulfate. The solvent was evaporated to give a brown oil (37 g). The obtained residue was purified by silica gel column chromatography (developing solvent; ethyl acetate:hexane=1:1) to give a brown oil (15.5 g). To a solution of this brown oil (1.0 g) in ethanol (20 ml) was added 1M hydrochloric acid-ether (6.5 ml). The solvent was evaporated under reduced pressure. The residue was crystallized from ethanol-ethyl acetate to give the title compound (1.1 g) as pale-brown crystals.

m.p.=202–204° C. (decomposition); $^1$H-NMR(DMSO-d$_6$)δ: 1.92(3H, s), 3.20–3.50(8H, m), 4.39(2H, d, J=5.9 Hz), 4.70(2H, s), 4.70–4.90(2H, brs), 6.95–7.15(4H, m), 7.75 (1H, m), 8.05–8.10(2H, m), 8.72(1H, t, 5.9 Hz); IR(KBr): 3255, 2337, 2157, 1627, 1537 cm$^{-1}$; MS(EI): 241(M$^+$); Elemental analysis: Calculated: C; 51.29, H; 5.60, N; 11.96; Found: C; 51.56, H; 5.58, N; 11.91.

Example 30

Synthesis of N-(3-Amino-4-(((4-(4-fluorophenyl)-piperazin-1-yl)methyl)phenylmethyl)acetamide

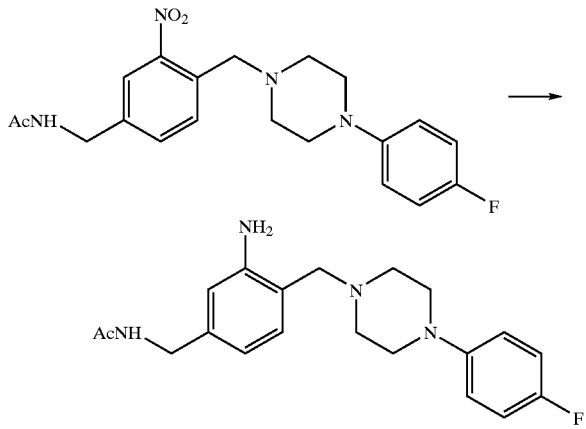

To a solution of N-(3-nitro-4-((4-phenylpiperazin-1-yl)methyl)phenylmethyl)acetamide (14.5 g) and water-containing Raney-nickel (5.0 g) in ethanol (150 ml) was added dropwise hydrazine monohydrate (18.2 ml) at room temperature and the mixture was refluxed under heating for 4 hr. Raney-nickel was removed by passing the mixture through Celite and the solvent was evaporated to give a brown oil (18.0 g). The obtained brown oil was purified by silica gel column chromatography (developing solvent; chloroform:methanol=20:1) to give a brown oil (11.6 g). The obtained brown oil was crystallized from hexane:ethyl acetate (2:1) to give the title compound (7.4 g) as yellow white crystals.

m.p.=131–132° C.; $^1$H-NMR(DMSO-d$_6$)δ: 1.86(3H, s), 2.45–2.55(4H, m), 3.05–3.10(4H, m), 3.40(2H, s), 4.11(2H, d, J=5.9 Hz), 5.25(2H, s), 6.41(1H, dd, J=1.3, 5.9 Hz), 6.53(1H, d, J=1.3 Hz), 6.88–6.95(3H, m), 7.00–7.06(2H, m), 8.20(1H, t, J=5.3 Hz); IR(KBr): 3305, 2819, 1625, 1512 cm$^{-1}$; MS(EI): 356(M$^+$); Elemental analysis: Calculated: C; 67.39, H; 7.07, N; 15.72; Found: C; 67.06, H; 7.19, N; 15.40.

Example 31

Synthesis of N-(3-Chloro-4-(((4-(4-fluorophenyl)piperazin-1-yl)methyl)phenylmethyl)acetamide Dihydrochloride 1/2 Hydrate

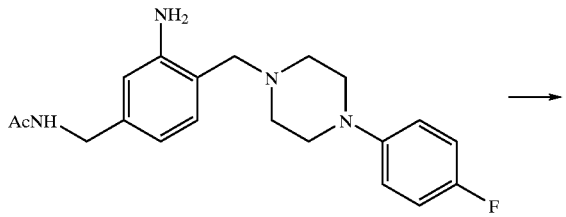

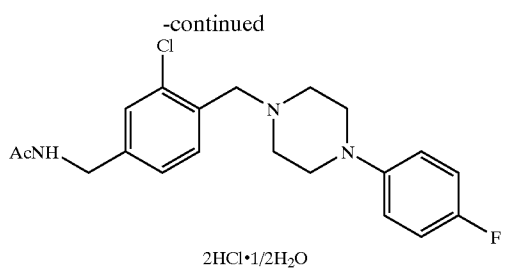

2HCl·1/2H$_2$O

To an aqueous solution (2 ml) of sodium nitrite (213 mg) was added a solution of N-(3-amino-4-((4-(4-fluorophenyl)piperazin-1-yl)methyl)phenylmethyl)acetamide (1.0 g) in conc. hydrochloric acid (5 ml) under ice-cooling. This reaction mixture was stirred at the same temperature for 1 hr and added to a solution of copper(I) chloride (167 mg) in conc. hydrochloric acid (3 ml). The reaction mixture was stirred at room temperature for 3 hr, poured into an aqueous sodium hydroxide solution and extracted with ethyl acetate. The extract was washed with saturated brine and dried over anhydrous sodium sulfate and the solvent was evaporated to give a brown oil (1.4 g). The obtained brown oil was purified by silica gel column chromatography (developing solvent; chloroform:methanol=10:1) to give a brown oil (1.2 g). The brown oil was treated with 1M hydrochloric acid-ether (10 ml) in ethanol and concentrated under reduced pressure to give a brown solid. The obtained brown solid was crystallized from ethyl acetate-ethanol to give the title compound (0.7 g) as pale-yellow crystals, m.p.=200–205° C. (decomposition).

$^1$H-NMR(DMSO-d$_6$)δ: 1.91(3H, s), 3.10–3.50(6H, m), 3.60–3.70(2H, m), 4.29(2H, d, J=5.9 Hz), 4.51(2H, s), 4.90–5.10(2H, m), 6.95–7.15(4H, m), 7.33(1H, d, J=7.3 Hz), 7.45(1H, s), 8.00(1H, d, J=7.9 Hz), 8.60(1H, t, J=5.9 Hz), 11.69(1H, brs); IR(KBr): 3282, 2493, 2443, 2418, 2063, 1676, 1542 cm$^{-1}$; MS(EI): 376(M$^+$); Elemental analysis: Calculated: C; 52.47, H; 5.72, N; 9.18; Found: C; 52.76, H; 5.57, N; 9.58.

Example 32

Synthesis of N-(3-Bromo-4-(((4-(4-fluorophenyl)piperazin-1-yl)methyl)phenylmethyl)acetamide

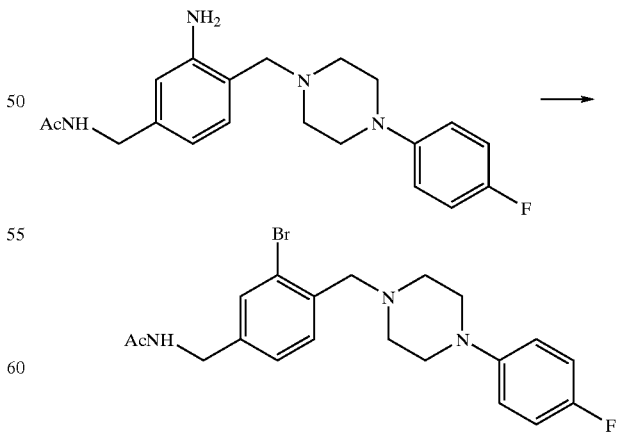

To an aqueous solution (3 ml) of sodium nitrite (290 mg) was added a solution of N-(3-amino-4-((4-(4-fluorophenyl)piperazin-1-yl)methyl)phenylmethyl)acetamide (1.5 g) in 48% hydrobromic acid (8 ml) under ice-cooling. This reaction mixture was stirred at the same temperature for 45 min and added to a solution of copper(I) bromide (362 mg) in 48% hydrobromic acid (4 ml) over 15 min. The reaction mixture was stirred at room temperature for 4.5 hr and poured into an aqueous sodium hydroxide solution. After passing through Celite, the mixture was extracted with ethyl acetate. The extract was washed with saturated brine and dried over anhydrous sodium sulfate and the solvent was evaporated to give a brown solid (1.8 g). The obtained brown solid was crystallized from ethyl acetate to give the title compound (1.3 g) as yellow crystals, m.p.=125–127° C.

$^1$H-NMR(DMSO-d$_6$)δ: 1.88(3H, s), 2.50–2.60(4H, m), 3.05–3.10(4H, m), 3.57(2H, s), 4.23(2H, d, J=5.9 Hz), 6.85–6.95(2H, m), 6.95–7.05(2H, m), 7.25(1H, dd, J=1.3, 7.9 Hz), 7.44(1H, d, J=7.9 Hz), 7.48(1H, d, J=1.3 Hz), 8.36(1H, t, J=5.9 Hz); IR(KBr): 3304, 2823, 1649, 1508 cm$^{-1}$; MS(EI): 420(M$^+$); Elemental analysis: Calculated: C; 57.15, H; 5.52, N; 10.00; Found: C; 57.15, H; 5.54, N; 10.05.

Example 33

Synthesis of N-(4-((4-(4-Nitrophenyl)piperazin-1-yl)methyl)phenylmethyl)acetamide

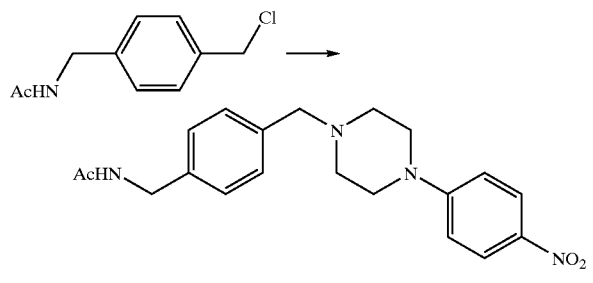

By similar reaction and treatment to that in Example 1(5) using (4-nitrophenyl)piperazine instead of phenylpiperazine, the title compound was obtained as yellow crystals, m.p.=151.5–153.5° C.

$^1$H-NMR(CDCl$_3$)δ: 2.03(3H, s), 2.58(4H, dd, J=5.3, 4.6 Hz), 3.42(4H, dd, J=5.3, 4.6 Hz), 3.55(2H, s), 4.42(2H, d, J=5.9 Hz), 5.77(1H, br.s), 6.80(2H, d, J=9.9 Hz), 7.25(2H, d, J=7.9 Hz), 7.31(2H, d, J=7.9 Hz), 8.16(2H, d, J=9.2 Hz). IR(KBr): 3307, 2922, 2848, 1641, 1540 cm$^{-1}$; MS(EI): 368(M$^+$); Elemental analysis: Calculated: C; 65.20, H; 6.57, N; 15.21; Found: C; 65.06, H; 6.58, N; 15.19.

Example 34

Synthesis of N-(4-((4-(4-Aminophenyl)piperazin-1-yl)methyl)phenylmethyl)acetamide 3 Hydrochloride 3/2 Hydrate

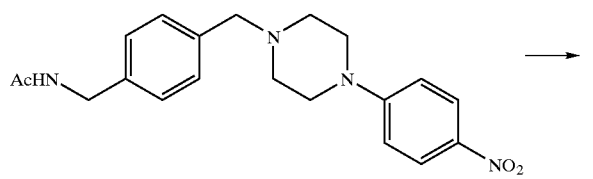

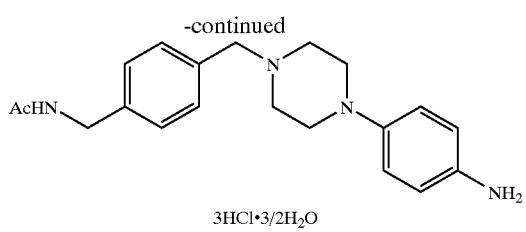

To a solution of N-(4-((4-(4-nitrophenyl)piperazin-1-yl)methyl)phenylmethyl)acetamide (6.1 g) and Raney-nickel (0.6 g) in ethanol (166 ml) was added dropwise hydrazine monohydrate (4 ml) at 2° C.–3° C. over 30 min. This reaction mixture was stirred at room temperature for 1 hr, then at 35° C. for 30 min, and subsequently refluxed under heating at 50° C. for 6 hr and 40 min. To this solution was again added hydrazine monohydrate (4 ml) and the mixture was refluxed under stirring at 50° C. for 8 hr. The reaction mixture was passed through Celite and the filtrate was concentrated under reduced pressure and the residue was poured into water, which was followed by extraction with ethyl acetate. The extract was washed with saturated brine and dried over anhydrous magnesium sulfate and the solvent was evaporated to give a purple solid (5.0 g). To the obtained solid were added methanol and hydrochloric acid, and the mixture was concentrated to dryness under reduced pressure. The obtained solid was recrystallized from methanol-ethyl acetate to give the title compound (1.3 g) as purple crystals.

m.p.=198–200° C.; $^1$H-NMR(DMSO-d$_6$)δ: 1.89(3H, s), 3.05–3.40(6H, m), 3.75–3.85(2H, m), 4.28(2H, d, J=5.9 Hz), 4.34(2H, s), 7.06(2H, d, J=8.6 Hz), 7.29(2H, d, J=7.9 Hz), 7.33(2H, d, J=8.6 Hz), 7.62(2H, d, J=7.9 Hz), 8.47(1H, t, J=5.9 Hz), 10.30(3H, br.s), 11.61(1H, br.s). IR(KBr): 3437, 3278, 2985, 2846, 1626, 1560 cm$^{-1}$; MS(EI): 338(M$^+$); Elemental analysis: Calculated: C; 50.59, H; 6.86, N; 11.80; Found: C; 50.62, H; 6.69, N; 11.79.

Example 35

Synthesis of N-(4-((4-(4-Acetamidophenyl)piperazin-1-yl)methyl)phenylmethyl)acetamide

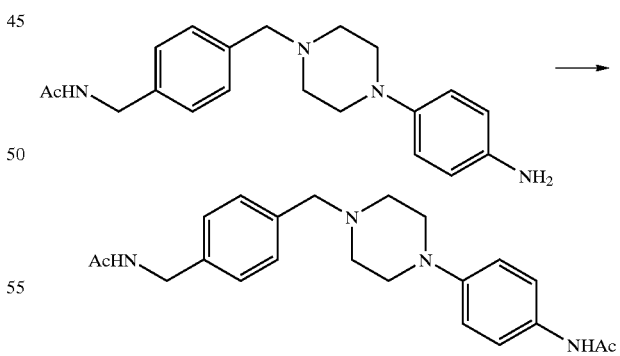

To a solution of N-(4-((4-(4-aminophenyl)piperazin-1-yl)methyl)phenylmethyl)acetamide (1.8 g) and potassium carbonate (3.1 g) in a mixed solvent of water (50 ml) and ethyl acetate (50 ml) was added dropwise acetyl chloride (0.43 ml) at room temperature over 10 min. This reaction mixture was stirred at room temperature for 4 hr and poured into saturated brine, which was followed by extraction with chloroform. The extract was washed with saturated brine and dried over anhydrous magnesium sulfate and the solvent was evaporated to give a purple solid (5.0 g). The obtained solid was subjected to column chromatography (elution solvent; chloroform:methanol=9:1) to give a pale-brown solid. The solid was recrystallized from methanol-water to give the title compound (0.75 g) as pale-red crystals, m.p.= 225–226° C.

$^1$H-NMR(DMSO-$d_6$)δ: 1.87(3H, s), 1.98(3H, s), 2.46–2.51(4H, m), 3.03–3.06(4H, m), 3.48(2H, s), 4.23(2H, d, J=5.9 Hz), 6.84(2H, d, J=8.6 Hz), 7.20(2H, d, J=8.6 Hz), 7.27(2H, d, J=7.9 Hz), 7.39(2H, d, J=9.2 Hz), 8.29(1H, t, J=5.9 Hz), 9.66(1H, s). IR(KBr): 3311, 2933, 2819, 1655, 1516 cm$^{-1}$; MS(EI): 380(M$^+$); Elemental analysis: Calculated: C; 69.45, H; 7.42, N; 14.73; Found: C; 69.19, H; 7.48, N; 14.68.

Example 36

Synthesis of N-(4-((4-(4-Hydroxyphenyl)piperazin-1-yl)methyl)phenylmethyl)acetamide Dihydrochloride

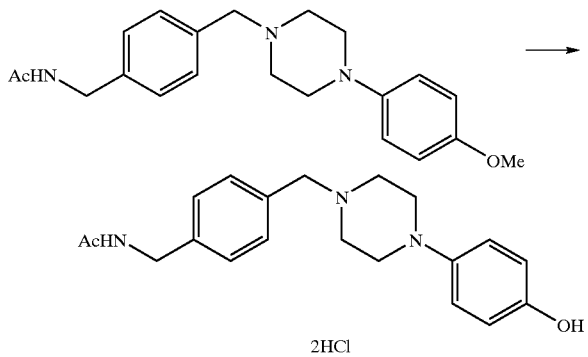

To a solution of N-(4-((4-(4-methoxyphenyl)piperazin-1-yl)methyl)phenylmethyl)acetamide (2.0 g) in methylene chloride (27 ml) was added dropwise a solution of boron tribromide (2.2 ml) in methylene chloride (10 ml) at −70° C. over 15 min. The temperature of this solution was gradually raised and the mixture was left standing overnight at room temperature. The reaction mixture was poured into ice water and stirred at 40° C. for 30 min. After the reaction, the reaction mixture was neutralized by adding an aqueous sodium hydroxide solution and extracted with chloroform. The extract was dried over anhydrous sodium sulfate and the solvent was evaporated to give a brown solid (1.6 g). The obtained solid was subjected to column chromatography (elution solvent; chloroform:methanol=8:1) to give a pale-brown solid (1.4 g). This solid was dissolved in methanol and converted to hydrochloride with 1 M hydrochloric acid-ether solution. The solvent was evaporated and the residue was recrystallized from methanol-ether to give the title compound (0.81 g) as white crystals, m.p.=218–220° C.

$^1$H-NMR(DMSO-$d_6$)δ: 1.89(3H, s), 3.15–3.80(8H, m), 4.28(2H, d, J=5.9 Hz), 4.35(2H, s), 6.72(2H, d, J=9.2 Hz), 6.93(2H, d, J=8.5 Hz), 7.33(2H, d, J=7.9 Hz), 7.60(2H, d, J=9.2 Hz), 8.44(1H, t, J=5.9 Hz), 11.30(1H, br.s). IR(KBr): 3367, 2987, 2628, 1637, 1552, 1517 cm$^{-1}$; MS(EI): 339 (M$^+$); Elemental analysis: Calculated: C; 58.25, H; 6.60, N; 10.19; Found: C; 57.88, H; 6.71, N; 9.90.

Example 37

Synthesis of N-(4-((4-(4-Fluoro-2-nitrophenyl)-piperazin-1-yl)methyl)phenylmethyl)acetamide (1) Synthesis of 1-Acetyl-4-(4-fluoro-2-nitrophenyl)piperazine

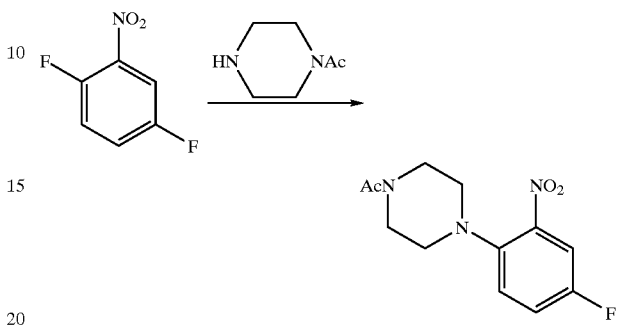

To a solution of 1-acetylpiperazine (48 g) in acetonitrile (100 ml) were added 2,5-difluoronitrobenzene (50 g) and potassium carbonate (44 g) and the mixture was refluxed under heating for 5 hr. The reaction mixture was poured into water and extracted with ethyl acetate. The extract was washed with saturated brine and dried over anhydrous magnesium sulfate and the solvent was evaporated to give the title compound (88 g) as a red solid.

$^1$H-NMR(CDCl$_3$)δ: 2.13(3H, s), 2.98–3.03(4H, m), 3.61 (2H, dd, J=5.28, 4.62 Hz), 3.76(2H, dd, J=5.28, 4.62 Hz), 7.17–7.31(2H, m), 7.53(1H, dd, J=7.91, 3.30 Hz). IR(KBr): 3087, 2918, 2835, 1633, 1583 cm$^{-1}$; MS(EI): 267(M$^+$);

(2) Synthesis of 1-(4-Fluoro-2-nitrophenyl)piperazine

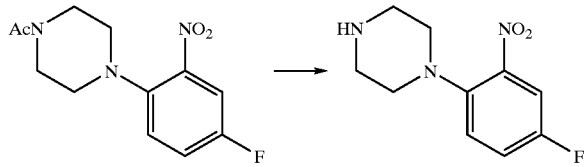

To 1-acetyl-4-(4-fluoro-2-nitrophenyl)piperazine (10 g) was added 1.2N hydrochloric acid (190 ml) and the mixture was refluxed under heating for 17 hr. The reaction mixture was made alkaline (pH 12) with an aqueous sodium hydroxide solution and extracted with ethyl acetate. The extract was washed with saturated brine and dried over anhydrous magnesium sulfate. The solvent was evaporated to give a red oil. The oil was crystallized from ethyl acetate-isopropyl ether-hexane to give the title compound (5.6 g) as a red solid.

m.p.=85–87° C.; $^1$H-NMR(CDCl$_3$)δ: 2.96–3.04(8H, m), 7.15–7.29(2H, m), 7.49(1H, dd, J=7.9, 3.3 Hz). IR(KBr): 3325, 2954, 2815, 1520, 1456 cm$^{-1}$; MS(EI): 225(M$^+$); Elemental analysis: Calculated: C; 53.33, H; 5.37, N; 18.66; Found: C; 53.44, H; 5.40, N; 18.47.

(3) Synthesis of N-(4-((4-(4-Fluoro-2-nitrophenyl) piperazin-1-yl)methyl)phenylmethyl)acetamide

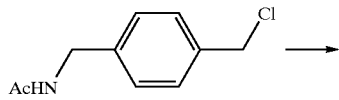

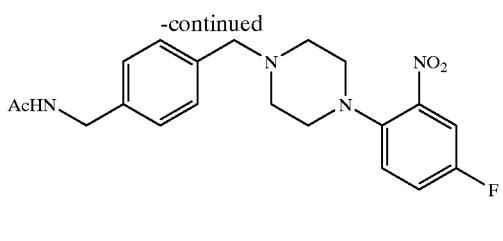

By similar reaction and treatment to that in Example 1(5) using 1-(4-fluoro-2-nitrophenyl)piperazine instead of phenylpiperazine, the title compound was obtained as white crystals, m.p.=94.5–96° C.

$^1$H-NMR(CDCl$_3$)δ: 2.02(3H, s), 2.58(4H, t, J=4.6 Hz), 3.02(4H, t, J=4.6 Hz), 3.55(2H, s), 4.42(2H, d, J=5.3 Hz), 5.76(1H, br.s), 7.14–7.22(2H, m), 7.24(2H, d, J=7.9 Hz), 7.30(2H, d, J=9.2 Hz), 7.48(1H, dd, J=7.9, 2.6 Hz). IR(KBr): 3277, 2943, 2821, 1645, 1529 cm$^{-1}$; MS(EI): 386(M$^+$); Elemental analysis: Calculated: C; 62.16, H; 6.00, N; 14.50; Found: C; 62.15, H; 5.90, N; 14.40.

Example 38

Synthesis of N-(4-((4-(2-Amino-4-fluorophenyl)piperazin-1-yl)methyl)phenylmethyl)acetamide

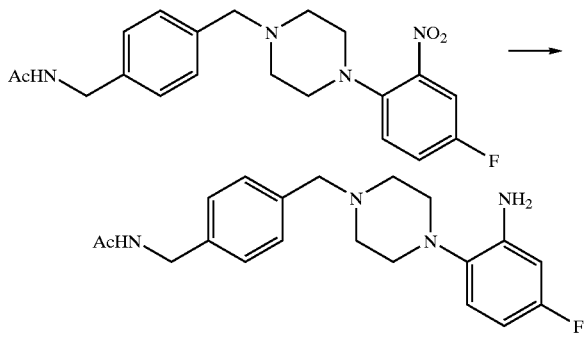

By similar reaction and treatment to that in Example 34 using N-(4-((4-(4-fluoro-2-nitrophenyl)piperazin-1-yl)methyl)-phenylmethyl)acetamide instead of N-(4-((4-(4-nitrophenyl)-piperazin-1-yl)methyl)phenylmethyl) acetamide, the title compound was obtained as pale-brown crystals, m.p.=139–140° C.

$^1$H-NMR(CDCl$_3$)δ: 2.02(3H, s), 2.58(2H, br.s), 5.87(4H, t, J=4.6 Hz), 3.56(2H, s), 4.11(2H, br.s), 5.73(1H, br.s), 6.36–6.44(2H, m), 6.93(2H, dd, J=7.9, 5.9 Hz), 7.24(2H, d, J=7.9 Hz), 7.32(2H, d, J=7.9 Hz). IR(KBr): 3444, 3302, 2829, 1662, 1560 cm$^{-1}$; MS(EI): 356(M$^+$); Elemental analysis: Calculated: C; 67.39, H; 7.07, N; 15.72; Found: C; 67.34, H; 7.08, N; 15.64.

Example 39

Synthesis of N-(4-((4-(2-Acetylamino-4-fluorophenyl)piperazin-1-yl)methyl)phenylmethyl) acetamide

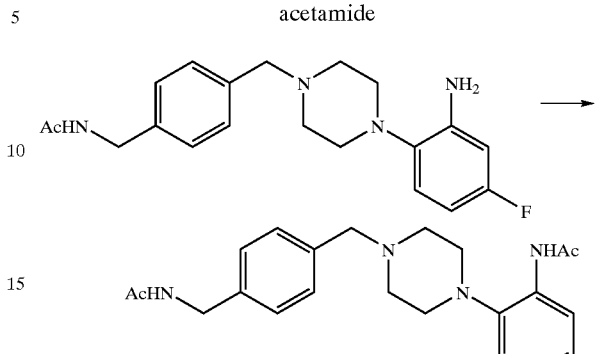

By similar reaction and treatment to that in Example 35 using N-(4-((4-(2-amino-4-fluorophenyl)piperazin-1-yl) methyl)-phenylmethyl)acetamide instead of N-(4-((4-(4-aminophenyl)-piperazin-1-yl)methyl)phenylmethyl) acetamide, the title compound was obtained as white crystals, m.p.=148–149.5° C.

$^1$H-NMR(CDCl$_3$)δ: 2.03(3H, s), 2.20(3H, s), 2.61(4H, br.s), 2.84(4H, t, J=4.6 Hz), 3.57(2H, s), 4.43(2H, d, J=5.9 Hz), 5.77(1H, br.s), 6.72(1H, dt, J=8.6, 2.6 Hz), 7.11(1H, dd, J=8.6, 5.9 Hz), 7.25(2H, d, J=7.9 Hz), 7.32(2H, d, J=7.9 Hz), 8.16(1H, dd, J=11, 2.6 Hz), 8.62(1H, br.s). IR(KBr): 3348, 2935, 2829, 1660, 1603, 1552 cm$^{-1}$; MS(EI): 398(M$^+$); Elemental analysis: Calculated: C; 66.31, H; 6.83, N; 14.16; Found: C; 66.31, H; 6.92, N; 13.87.

Example 40

Synthesis of N-(4-((4-(4-Fluoro-2-methoxyphenyl)-piperazin-1-yl)methyl)phenylmethyl)acetamide Dihydrochloride 1/4 Hydrate (1) Synthesis of 4-Fluoro-2-methoxynitrobenzene

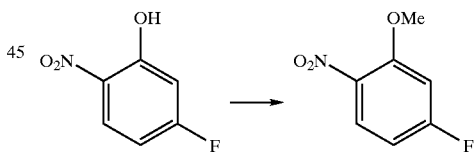

To a suspension of sodium hydride (1.3 g) in dimethylformamide (10 ml) was added a solution of 5-fluoro-2-nitrophenol (5.0 g) in dimethylformamide (20 ml)under ice-cooling. This reaction mixture was stirred at room temperature for 1 hr. To this solution was added methyl iodide (2.0 ml) and the mixture was left standing overnight. The reaction mixture was poured into water and extracted with ethyl acetate. The extract was washed with an aqueous sodium hydroxide solution and saturated brine, and dried over anhydrous magnesium sulfate. The solvent was evaporated to give a red solid. This solid was subjected to silica gel column chromatography (developing solvent; hexane:ethyl acetate=4:1) to give the title compound (4.3 g) as a yellow solid.

$^1$H-NMR(CDCl$_3$)δ: 3.97(3H, s), 6.69–6.82(2H, m), 7.96 (1H, dt, J=3.3, 2.6 Hz). IR(KBr): 3124, 3086, 2994, 1624, 1587 cm$^{-1}$; MS(EI): 171(M$^+$).

(2) Synthesis of 4-Fluoro-2-methoxyaniline

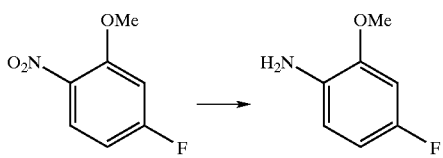

To a solution of 4-fluoro-2-methoxynitrobenzene (4.2 g) in ethanol (50 ml) was added Raney-nickel (0.4 g) at room temperature. To this solution was added dropwise hydrazine monohydrate (6 ml) under ice-cooling. This reaction mixture was stirred at room temperature for 1 hr and passed through Celite. The solvent was evaporated to give an oil. The oil was poured into water and extracted with ethyl acetate. The extract was washed with saturated brine and dried over anhydrous magnesium sulfate and the solvent was evaporated to give a brown oil. The oil was subjected to silica gel column chromatography (developing solvent; hexane:ethyl acetate=1:1) to give the title compound (3.1 g) as a brown oil.

$^1$H-NMR(CDCl$_3$)δ: 3.51(2H, br.s), 3.82(3H, s), 6.45–6.64 (3H, m). IR(KBr): 3452, 3369, 2964, 1612, 1514 cm$^{-1}$; MS(EI): 141(M$^+$).

(3) Synthesis of 1-(4-Fluoro-2-methoxyphenyl)piperazine Dihydrochloride

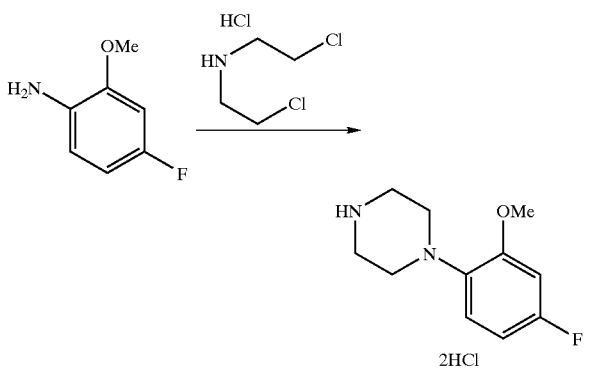

To a solution of 4-fluoro-2-methoxyaniline (3.0 g) in orthoxylene (50 ml) was added bis(2-chloroethyl)amine hydrochloride (3.8 g) and the mixture was refluxed under heating for 13 hr. The reaction mixture was poured into water and washed with isopropyl ether. To the aqueous layer was added an aqueous sodium hydroxide solution to make it alkaline (pH 12) and the mixture was extracted with ethyl acetate. The extract was washed with saturated brine and dried over anhydrous magnesium sulfate and the solvent was evaporated to give a black oil. The oil was dissolved in methanol and conc. hydrochloric acid was added and the mixture was concentrated. To this concentrated solution added tetrahydrofuran to give the title compound (3.1 g) as pale-purple crystals.

$^1$H-NMR(DMSO-d$_6$)δ: 3.20(8H, br.s), 3.82(3H, s), 6.72 (1H, dt, J=8.6, 3.3 Hz), 6.92(1H, dd, J=11, 3.3 Hz), 7.01(1H, dd, J=8.6, 5.9 Hz), 9.51(2H, br.s). IR(KBr): 3352, 2997, 2808, 1625, 1510 cm$^{-1}$; MS(EI): 210(M$^+$).

(4) Synthesis of N-(4-((4-(4-Fluoro-2-methoxyphenyl)piperazin-1-yl )methyl)phenylmethyl)acetamide Dihydrochloride 1/4 Hydrate

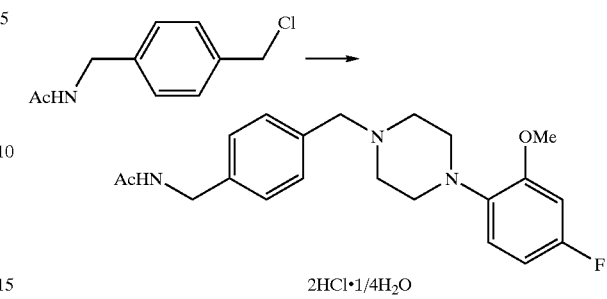

By similar reaction and treatment to that in Example 1(5) using 1-(4-fluoro-2-methoxyphenyl)piperazine dihydrochloride instead of phenylpiperazine, the title compound was obtained as white crystals, m.p.=228–229.5° C.

$^1$H-NMR(DMSO-d$_6$)δ: 1.89(3H, s), 3.06–3.20(4H, m), 3.26–3.43(4H, m), 3.79(3H, s), 4.28(2H, d, J=5.9 Hz), 4.33(2H, d, J=2.6 Hz), 6.70(1H, dt, J=8.6, 2.6 Hz), 6.87–6.95(2H, m), 7.33(2H, d, J=7.9 Hz), 7.62(2H, d, J=7.9 Hz), 7.45(1H, t, J=5.9 Hz), 11.5(1H, br.s). IR(KBr): 3286, 2368, 1664, 1624, 1539 cm$^{-1}$; MS(EI): 371(M$^+$); Elemental analysis: Calculated: C; 56.19, H; 6.40, N; 9.36; Found: C; 56.04, H; 6.66, N; 9.35.

Example 41

Synthesis of N-(4-((4-(2-Ethoxy-4-fluorophenyl)-piperazin-1-yl)methyl)phenylmethyl)acetamide

(1) Synthesis of 2-Ethoxy-4-fluoronitrobenzene

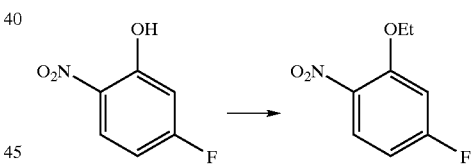

To a solution of ethanol (4.2 ml) in tetrahydrofuran (65 ml) was added a solution of triphenylphosphine (13 g) and 5-fluoro-2-nitrophenol (10 g) in tetrahydrofuran (65 ml). To this solution was added diethyl azodicarboxylate (10 ml) under ice-cooling and the mixture was stirred at room temperature for 4 hr. The reaction mixture was concentrated under reduced pressure and diisopropyl ether was added. The precipitated crystals were collected by filtration and concentrated under reduced pressure. The concentrate was subjected to silica gel column chromatography (developing solvent; hexane:ethyl acetate=4:1) to give a yellow oil. To this oil was added ethyl acetate, washed with an aqueous sodium hydroxide solution, dried over magnesium sulfate and concentrated under reduced pressure to give the title compound (9.6 g) as a yellow oil.

$^1$H-NMR(CDCl$_3$)δ: 1.50(3H, t, J=7.3 Hz), 4.17(2H, q, J=7.3 Hz), 6.67–6.79(2H, m), 7.92(1H, dt, J=3.3, 2.6 Hz). MS(EI): 185(M$^+$).

(2) Synthesis of 2-Ethoxy-4-fluoroaniline

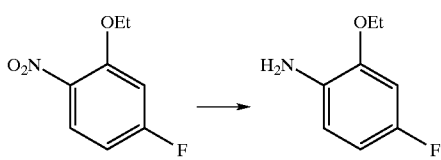

By similar reaction and treatment to that in Example 40(2) using 2-ethoxy-4-fluoronitrobenzene instead of 4-fluoro-2-methoxynitrobenzene, the title compound was obtained as a black oil.

$^1$H-NMR(CDCl$_3$)δ: 1.44(3H, t, J=7.3 Hz), 3.50(2H, br.s), 4.00(2H, q, J=7.3 Hz), 6.27–6.64(3H, m). IR(KBr): 3548, 3369, 2981, 1618, 1512 cm$^{-1}$; MS(EI): 155(M$^+$).

(3) Synthesis of 1-(2-Ethoxy-4-fluorophenyl)piperazine Dihydrochloride

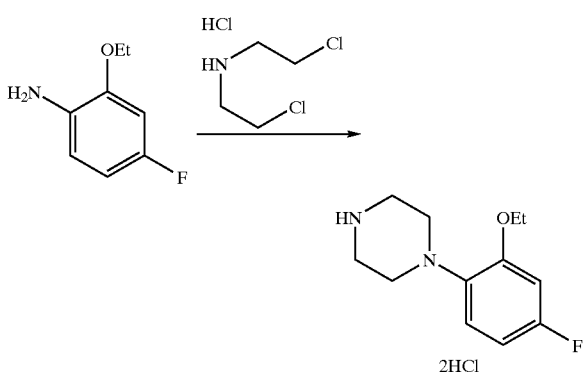

By similar reaction and treatment to that in Example 40(3) using 2-ethoxy-4-fluoroaniline instead of 4-fluoro-2-methoxyaniline, the title compound was obtained as purple crystals.

$^1$H-NMR(DMSO-d$_6$)δ: 1.37(3H, t, J=7.4 Hz), 3.20(8H ,br.s), 4.05(2H, q, J=7.4 Hz), 6.71(1H, dt, J=8.6, 2.6 Hz), 6.89(1H, dd, J=8.6, 2.6 Hz), 7.00(1H, dd, J=3.3, 2.6 Hz), 9.51(2H, br.s). IR(KBr): 3439, 2997, 2841, 1624, 1521 cm$^{-1}$; MS(EI): 224(M$^+$).

(4) Synthesis of N-(4-((4-(2-Ethoxy-4-fluorophenyl) piperazin-1-yl )methyl )phenylmethyl )acetamide

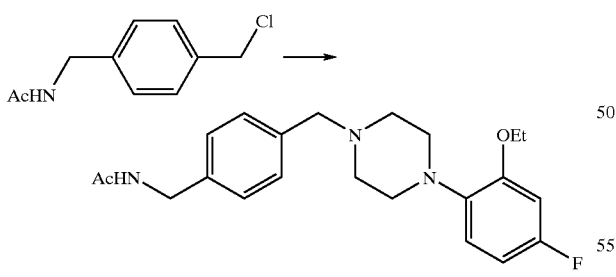

By similar reaction and treatment to that in Example 1(5) using 1-(2-ethoxy-4-fluorophenyl )piperazine dihydrochloride instead of phenylpiperazine, the title compound was obtained as pale-brown crystals.

m.p.=108–109° C.; $^1$H-NMR(CDCl$_3$)δ: 1.45(3H, t, J=6.6 Hz), 2.02(3H, s), 2.62–2.64(4H, m), 3.04(4H, br.s), 3.56(2H, s), 4.02(2H, q, J=6.6 Hz), 4.42(2H, d, J=5.3 Hz), 5.76(1H, br.s), 6.54–6.60(2H, m), 6.81(1H, dd, J=9.2, 5.9 Hz), 7.24 (2H, d, J=7.9 Hz), 7.33(2H, d, J=7.9 Hz). IR(KBr): 3423, 3261, 2929, 1637, 1602, 1560 cm$^{-1}$; MS(EI): 385(M$^+$);

Elemental analysis: Calculated: C; 68.55, H; 7.32, N; 10.90; Found: C; 68.24, H; 7.35, N; 10.70.

Example 42

Synthesis of N-(4-((4-(4-Fluoro-2-isopropoxyphenyl)-piperazin-1-yl)methyl) phenylmethyl)acetamide Hydrochloride 1/4 Ethyl acetate (1) Synthesis of 4-Fluoro-2-isopropoxynitrobenzene

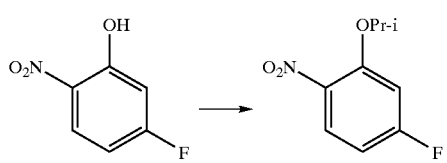

By similar reaction and treatment to that in Example 41(1) using isopropyl alcohol instead of ethanol, the title compound was obtained as an orange oil.

$^1$H-NMR(CDCl$_3$)δ: 1.42(6H, d, J=6.6 Hz), 4.63(1H, septet, J=6.6 Hz), 6.65–6.79(2H, m), 7.45–7.90(1H, m). IR(KBr): 3091, 2983, 1620, 1589 cm$^{-1}$; MS(EI): 199(M$^+$).

(2) Synthesis of 4-Fluoro-2-isopropoxyaniline

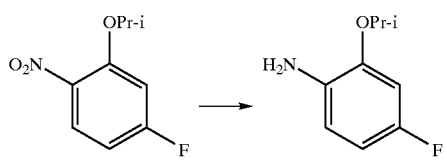

By similar reaction and treatment to that in Example 40(2) using 4-fluoro-2-isopropoxynitrobenzene instead of 4-fluoro-2-methoxynitrobenzene, the title compound was obtained as a black oil. $^1$H-NMR(CDCl$_3$)δ: 1.35(6H, d, J=5.9 Hz), 3.47(2H, br.s), 4.48(1H, septet, J=5.9 Hz), 6.44–6.65(3H, m). IR(KBr): 3460, 3373, 2980, 1614, 1589 cm$^{-1}$; MS(EI): 169(M$^+$);

(3) Synthesis of 1-(4-Fluoro-2-isopropoxyphenyl)piperazine Dihydrochloride

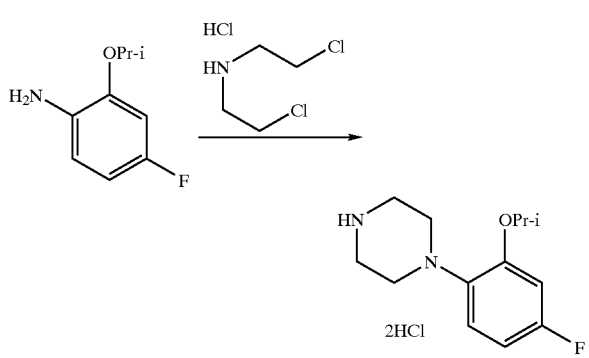

By similar reaction and treatment to that in Example 40(3) using 4-fluoro-2-isopropoxyaniline instead of 4-fluoro-2-methoxyaniline, the title compound was obtained as purple crystals.

$^1$H-NMR(DMSO-d$_6$)δ: 1.31(6H, d, J=5.9 Hz), 3.25(8H, br.s), 4.67(1H, septet, J=5.9 Hz), 6.71(1H, dt, J=8.6, 2.6 Hz), 7.93(1H, dd, J=11, 2.6 Hz), 7.08(1H, dd, J=5.9, 2.6 Hz), 9.61(2H, br.s). IR(KBr): 3442, 2983, 2925, 1626, 1522 cm$^{-1}$; MS(EI): 238(M$^+$).

(4) Synthesis of N-(4-((4-(4-Fluoro-2-isopropoxyphenyl) piperazin-1-yl)methyl)phenylmethyl)acetamide Hydrochloride 1/4 Ethyl Acetate

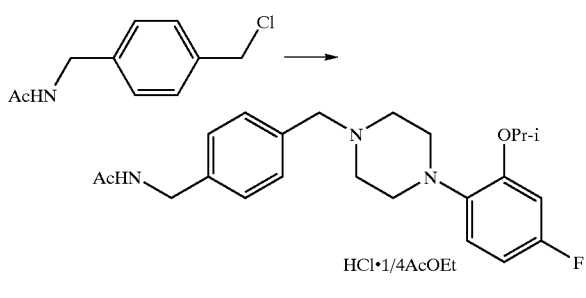

By similar reaction and treatment to that in Example 1(5) using 1-(4-fluoro-2-isopropoxyphenyl)piperazine dihydrochloride instead of phenylpiperazine, the title compound was obtained as white crystals.

m.p.=211.5–213° C.; $^1$H-NMR(DMSO-d$_6$)δ: 1.28(6H, d, J=5.9 Hz), 1.89(3H, s), 3.01–3.24(4H, m), 3.30–3.43(4H, m), 4.28(2H, d, J=5.9 Hz), 4.34(2H, s), 4.64(1H, septet, J=5.9 Hz), 6.67(1H, dd, J=7.9, 2.6 Hz), 6.85–6.92(2H, m), 7.33(2H, d, J=7.9 Hz), 7.61(2H, d, J=7.9 Hz), 8.43(1H, t, J=5.9 Hz), 11.1(1H, br.s). IR(KBr): 3435, 3280, 2931, 1645, 1603, 1541 cm$^{-1}$; MS(EI): 399(M$^+$); Elemental analysis: Calculated: C; 63.36, H; 7.17, N; 9.64; Found: C; 62.94, H; 7.26, N; 9.17.

Example 43

Synthesis of N-(4-((4-(4-Fluoro-2-hydroxyphenyl)-piperazin-1-yl)methyl)phenylmethyl)acetamide Dihydrochloride 1/2 Hydrate (1) Synthesis of 1-Acetyl-4-(4-fluoro-2-nitrophenyl) piperazine

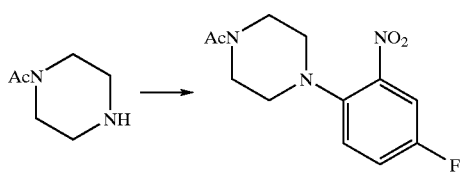

To a solution of 1-acetylpiperazine (20 g) in acetonitrile (50 ml) were added 2,5-difluoronitrobenzene (25 g) and potassium carbonate (22 g) and the mixture was refluxed under heating at room temperature for 4.5 hr. The reaction mixture was poured into water and extracted with ethyl acetate. The extract was washed with saturated brine and dried over anhydrous magnesium sulfate. The solvent was evaporated to give a red oil. The oil was crystallized from ethyl acetate-isopropyl ether to give the title compound (36 g) as a red solid.

$^1$H-NMR(CDCl$_3$)δ: 2.13(3H, s), 2.98–3.01(4H, m), 3.61 (2H, dd, J=5.3, 4.6 Hz), 3.77(2H, dd, J=5.3, 4.6 Hz), 7.16–7.31(2H, m), 7.53(1H, dd, J=7.9, 3.3 Hz). IR(KBr): 3088, 2931, 1641, 1583 cm$^{-1}$; MS(EI): 267(M$^+$).

(2) Synthesis of 1-Acetamido-4-(2-amino-4-fluorophenyl) piperazine

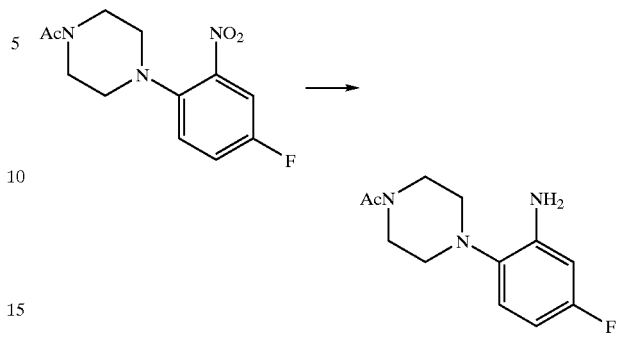

By similar reaction and treatment to that in Example 40(2) using 1-acetamido-4-(4-fluoro-2-nitrophenyl)piperazine instead of 4-fluoro-2-methoxynitrobenzene, the title compound was obtained as a pale-brown solid.

$^1$H-NMR(CDCl$_3$)δ: 2.14(3H, s), 2.78–2.84(4H, m), 3.57–3.59(2H, m), 3.73(1H, br.s), 4.16(1H, br.s), 6.31–6.61 (2H, m), 6.85–7.58(1H, m). IR(KBr): 3429, 3319, 2960, 1626, 1506 cm$^{-1}$; MS(EI): 237(M$^+$).

(3) Synthesis of 1-Acetyl-4-(4-fluoro-2-hydroxyphenyl) piperazine

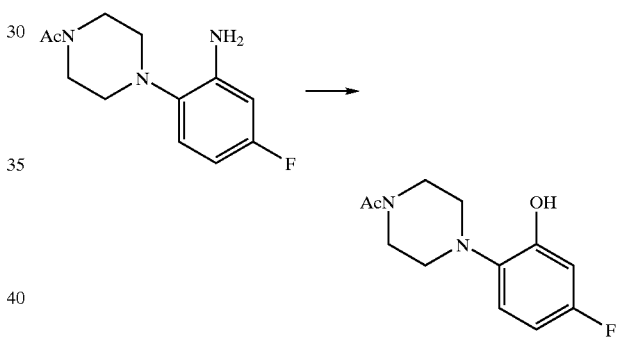

To a solution of 1-acetyl-4-(2-amino-4-fluorophenyl) piperazine (25 g) and conc. sulfuric acid (42 ml) in water (210 ml) was added dropwise a solution of sodium nitrite (13 g) in water (46 ml) under ice-cooling. This reaction mixture was stirred at the same temperature for 4 hr and at room temperature for 6 hr. To the reaction mixture was added an aqueous sodium hydroxide solution to make it alkaline and acetyl chloride was added dropwise. The mixture was stirred at the same temperature for 30 min, passed through Celite and extracted with ethyl acetate. The extract was washed with saturated brine and dried over anhydrous magnesium sulfate. The solvent was evaporated to give a black oil. The oil was subjected to silica gel column chromatography (developing solvent; chloroform:methanol=9:1) to give a black solid. This solid was recrystallized from ethyl acetate-isopropyl ether to give the title compound (0.66 g) as a pale-brown solid, m.p.=183–185° C.

$^1$H-NMR(CDCl$_3$)δ: 2.15(3H, s), 2.80–2.86(4H, m), 3.63 (2H, dd, J=5.3, 4.6 Hz), 3.78(2H, dd, J=5.3, 4.6 Hz), 6.57(1H, dd, J=8.6, 2.6 Hz), 6.69(1H, dd, J=8.9, 2.6 Hz), 7.05(1H, dd, J=8.6, 5.9 Hz), 7.16(1H, br.s). IR(KBr): 3290, 2916, 1630, 1601, 1502 cm$^{-1}$; MS(EI): 238(M$^+$); Elemental analysis: Calculated: C; 60.49, H; 6.35, N; 11.76; Found: C; 60.71, H; 6.27, N; 11.80.

(4) Synthesis of 1-(4-Fluoro-2-hydroxyphenyl)piperazine Dihydrochloride

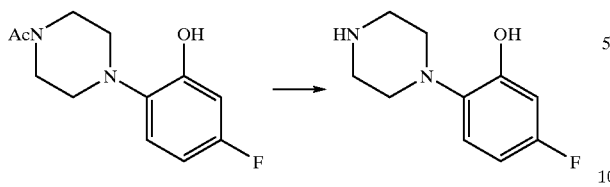

1-Acetyl-4-(4-fluoro-2-hydroxyphenyl)piperazine (0.64 g) was dissolved in a 1.2N aqueous hydrochloric acid solution (16 ml) and refluxed under heating for 7 days. The reaction mixture was concentrated under reduced pressure to give a pale-brown solid. This solid was recrystallized from methanol-ethyl acetate to give the title compound (0.65 g) as pale-brown crystals.

$^1$H-NMR(DMSO-$d_6$)$\delta$: 3.29(8H, br.s), 5.33(1H, br.s), 6.62(1H, dt, J=8.6, 2.6 Hz), 6.80(1H, dd, J=9.9, 2.6 Hz), 7.14–7.20(1H, m), 9.52(2H, br.s). IR(KBr): 3415, 3016, 2995, 1628, 1608 cm$^{-1}$; MS(EI): 169(M$^+$).

(5) Synthesis of N-(4-((4-(4-Fluoro-2-hydroxyphenyl)piperazin-1-yl)methyl)phenylmethyl)acetamide Dihydrochloride 1/2 Hydrate

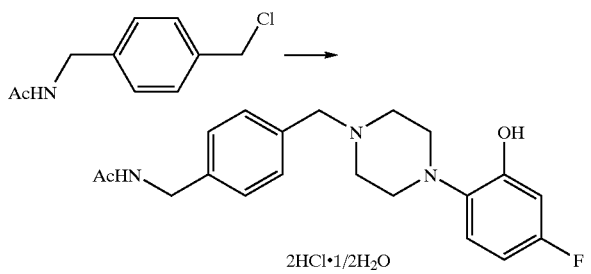

By similar reaction and treatment to that in Example 1(5) using 1-(4-fluoro-2-hydroxyphenyl)piperazine dihydrochloride instead of phenylpiperazine, the title compound was obtained as pale-red crystals.

m.p.=255–257° C.; $^1$H-NMR(DMSO-$d_6$)$\delta$: 1.89(3H, s), 3.04–3.37(9H, m), 4.28(2H, d, J=5.3 Hz), 4.33(2H, s), 6.57(1H, dt, J=8.6, 2.6 Hz), 6.69(1H, dd, J=11, 2.6 Hz), 6.91(1H, dd, J=8.6, 6.6 Hz), 7.33(2H, d, J=7.9 Hz), 7.60(2H, d, J=7.9 Hz), 8.45(1H, t, J=5.9 Hz), 11.2(1H, br.s). IR(KBr): 3246, 3089, 2885, 1618, 1597 cm$^{-1}$; MS(EI): 357(M$^+$); Elemental analysis: Calculated: C; 54.67, H; 6.19, N; 9.56; Found: C; 54.90, H; 6.26, N; 9.47.

Example 44

Synthesis of N-(4-((4-(2-Chloro-4-fluorophenyl)piperazin-1-yl)methyl)phenylmethyl)acetamide (1) Synthesis of 1-(2-Chloro-4-fluorophenyl)piperazine Dihydrochloride

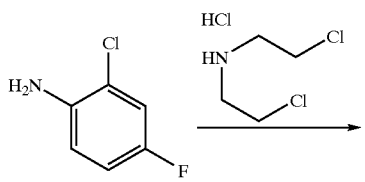

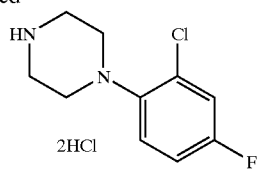

By similar reaction and treatment to that in Example 40(3) using 2-chloro-4-fluoroaniline instead of 4-fluoro-2-methoxyaniline, the title compound was obtained as pale-brown crystals, m.p.=203–204.5° C.

$^1$H-NMR(DMSO-$d_6$)$\delta$: 3.19(8H, dd, J=12, 5.9 Hz), 7.17–7.29(2H, m), 7.43–7.51(1H, m), 9.45(2H, br.s). IR(KBr): 3371, 2956, 2823, 1672, 1569 cm$^{-1}$; MS(EI): 214(M$^+$); Elemental analysis: Calculated: C; 47.83, H; 5.22, N; 11.16; Found: C; 47.58, H; 5.25, N; 11.12.

(2) Synthesis of N-(4-((4-(2-Chloro-4-fluorophenyl)piperazin-1-yl)methyl)phenylmethyl)acetamide

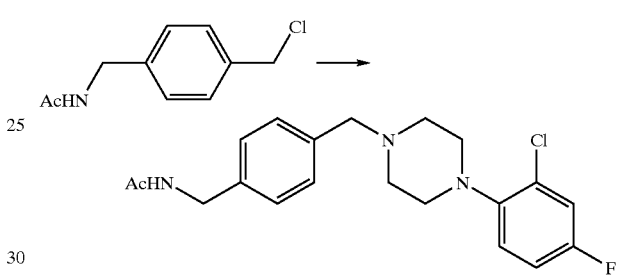

By similar reaction and treatment to that in Example 1(5) using 1-(2-chloro-4-fluorophenyl)piperazine dihydrochloride instead of phenylpiperazine, the title compound was obtained as pale-red crystals.

m.p.=255–257° C.; $^1$H-NMR(CDCl$_3$)$\delta$: 2.03(3H, s), 2.62 (4H, t, J=4.6 Hz), 3.00(4H, t, J=4.6 Hz), 3.57(2H, s), 4.43(2H, d, J=5.3 Hz), 5.71(1H, br.s), 6.89–7.03(2H, m), 7.11(1H, dd, J=8.6, 2.6 Hz), 7.25(2H, d, J=7.9 Hz), 7.34(2H, d, J=8.6 Hz). IR(KBr): 3277, 2949, 2821, 1633, 1556 cm$^{-1}$; MS(EI): 375(M$^+$); Elemental analysis: Calculated: C; 63.91, H; 6.17, N; 11.18; Found: C; 63.76, H; 6.26, N; 11.07.

Example 45

Synthesis of N-(4-((4-(2-Bromo-4-fluorophenyl)piperazin-1-yl)methyl)phenylmethyl)acetamide Dihydrochloride (1) Synthesis of 1-(2-Bromo-4-fluorophenyl)piperazine dihydrochloride

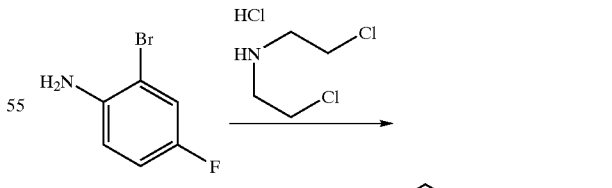

By similar reaction and treatment to that in Example 40(3) using 2-bromo-4-fluoroaniline instead of 4-fluoro-2- methoxyaniline, the title compound was obtained as pale-brown crystals, m.p.=208–210° C.

$^1$H-NMR(DMSO-$d_6$)δ: 3.17(8H, dd, J=8.6, 5.3 Hz), 7.26 (2H, d, J=5.9 Hz), 7.60(1H, d, J=8.6 Hz), 9.47(2H, br.s). IR(KBr): 2945, 2796, 2725, 1741, 1591 cm$^{-1}$; MS(EI): 258(M$^+$); Elemental analysis: Calculated: C; 40.63, H; 4.43, N; 9.48; Found: C; 40.99, H; 4.54, N; 9.22.

(2) Synthesis of N-(4-((4-(2-Bromo-4-fluorophenyl)piperazin-1-yl )methyl )phenylmethyl)acetamide Dihydrochloride

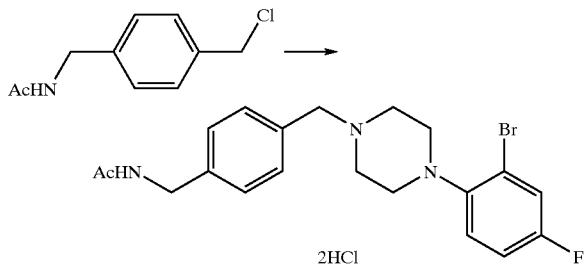

By similar reaction and treatment to that in Example 1(5) using 1-(2-bromo-4-fluorophenyl)piperazine dihydrochloride instead of phenylpiperazine, the title compound was obtained as pale-brown crystals.

m.p.=231–235° C.; $^1$H-NMR(DMSO-$d_6$)δ: 1.89(3H, s), 3.13–3.38(8H, m), 4.28(2H, d, J=5.9 Hz), 4.37(2H, d, J=4.6 Hz), 7.19–7.57(2H, m), 7.33(2H, d, J=7.9 Hz), 7.58–7.65 (1H, m), 7.63(2H, d, J=7.9 Hz), 8.46(1H, t, J=5.9 Hz), 11.5(1H, d, J=2.6 Hz). IR(KBr): 3228, 2979, 2958, 1753, 1668 cm$^{-1}$; MS(EI): 419(M$^+$−1); Elemental analysis: Calculated: C; 48.70, H; 5.11, N; 8.52; Found: C; 48.67, H; 5.19, N; 8.47.

Example 46

Synthesis of N-(4-((4-(4-Fluoro-2-methylphenyl)piperazin-1-yl)methyl)phenylmethyl)acetamide Dihydrochloride (1) Synthesis of 1-(4-Fluoro-2-methylphenyl)piperazine Dihydrochloride

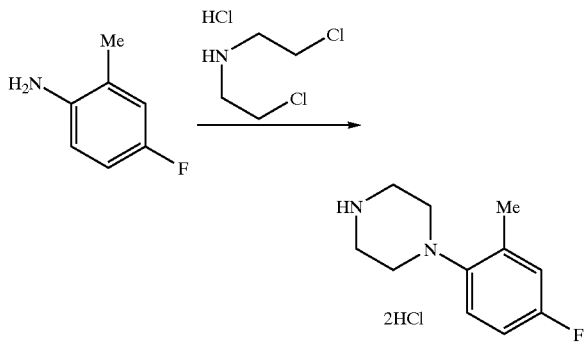

By similar reaction and treatment to that in Example 40(3) using 4-fluoro-2-methylaniline instead of 4-fluoro-2-methoxyaniline, the title compound was obtained as pale-brown crystals, m.p.=258–260° C.

$^1$H-NMR(DMSO-$d_6$)δ: 2.27(3H, s), 3.45(8H, dd, J=5.1, 4.4 Hz), 3.19(4H, br.s), 6.97–7.10(3H, m), 9.64(2H, br.s). IR(KBr): 3007, 2925, 2792, 1622, 1593 cm$^{-1}$; MS(EI): 194(M$^+$); Elemental analysis: Calculated: C; 49.45, H; 6.41, N; 10.49; Found: C; 49.23, H; 6.51, N; 10.51.

(2) Synthesis of N-(4-((4-(4-Fluoro-2-methylphenyl)piperazin-1-yl)methyl)phenylmethyl)acetamide Dihydrochloride

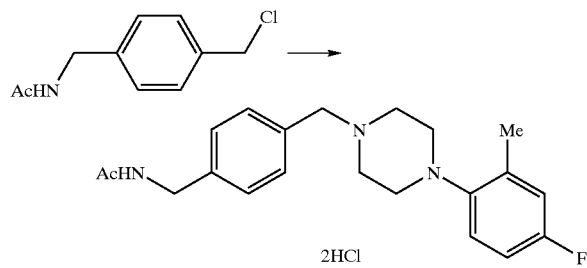

By similar reaction and treatment to that in Example 1(5) using 1-(4-fluoro-2-methylphenyl)piperazine dihydrochloride instead of phenylpiperazine, the title compound was obtained as white crystals.

m.p.=115–117° C.; $^1$H-NMR(CDCl$_3$)δ: 2.02(3H, s), 2.28 (3H, s), 2.58(4H, br.s), 2.86(4H, t, J=4.6 Hz), 3.56(2H, s), 4.42(2H, d, J=5.9 Hz), 5.76(1H, br.s), 6.78–6.99(3H, m), 7.24(2H, d, J=7.9 Hz), 7.32(2H, d, J=7.9 Hz). IR(KBr): 3278, 2949, 2821, 1651, 1552 cm$^{-1}$; MS(EI): 355(M$^+$); Elemental analysis: Calculated: C; 70.96, H; 7.37, N; 11.82; Found: C; 70.64, H; 7.44, N; 11.61.

Example 47

Synthesis of N-(4-((4-(2,4,6-Trifluorophenyl)piperazin-1-yl)methyl)phenylmethyl)acetamide Dihydrochloride (1) Synthesis of 1-(2,4,6-Trifluorophenyl)piperazine Dihydrochloride

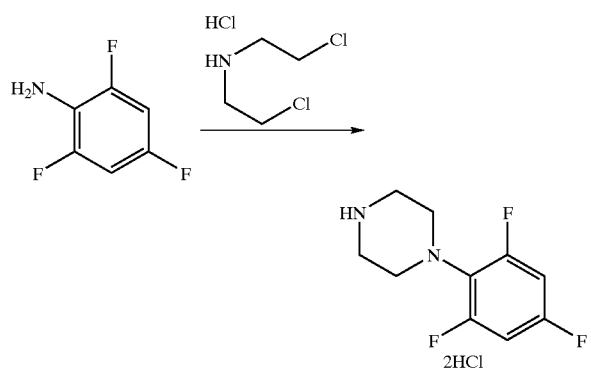

To a solution of 2,4,6-trifluoroaniline (4.4 g) an bis(2-chloroethyl)amine hydrochloride (6.4 g) in water (4.2 ml) was added dropwise a solution of sodium carbonate (3.8 g) in water (8.9 ml) over 40 min under reflux under heating and the mixture was further refluxed under heating for 5.5 hr. To the reaction mixture was added an aqueous solution (8.9 ml) of sodium hydroxide (3.6 g) and the mixture was further refluxed under heating for 2.5 hr. The reaction mixture was extracted with ethyl acetate. The extract was washed with water and saturated brine, and dried over anhydrous magnesium sulfate. The solvent was evaporated to give a dark brown oil. The oil was subjected to silica gel column chromatography (developing solvent; chloroform:methanol=9:1) to give the title compound (0.61 g) as a pale-brown solid.

$^1$H-NMR(DMSO-$d_6$)δ: 2.86(2H, br.s), 3.03(2H, br.s), 4.07(4H, br.s), 7.13(2H, t, J=9.5 Hz). IR(KBr): 3205, 2954, 2846, 1633, 1594 cm$^{-1}$; MS(EI): 216(M$^+$).

(2) Synthesis of N-(4-((4-(2,4,6-Trifluorophenyl)piperazin-1-yl)methyl)phenylmethyl)acetamide Dihydrochloride

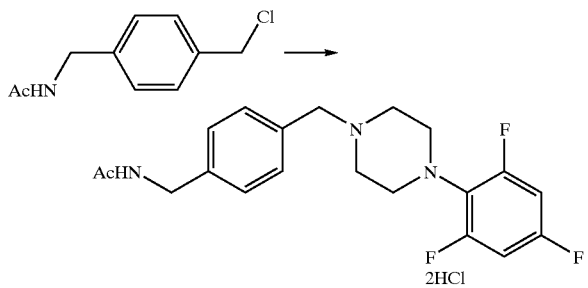

By similar reaction and treatment to that in Example 1(5) using 1-(2,4,6-trifluorophenyl)piperazine dihydrochloride instead of phenylpiperazine, the title compound was obtained as white crystals.

m.p.=235–240° C. (decomposition); $^1$H-NMR(DMSO-$d_6$)δ: 1.89(3H, s), 3.09–3.31(6H, m), 3.58(2H, t, J=12 Hz), 4.28(2H, d, J=5.9 Hz), 4.34(2H, d, J=4.6 Hz), 7.19(2H, t, J=9.2 Hz), 7.32(2H, d, J=7.9 Hz), 7.62(2H, d, J=7.9 Hz), 8.47(1H, t, J=5.9 Hz), 11.5(1H, br.s). IR(KBr): 3259, 2926, 2856, 1635, 1598 cm$^{-1}$; Elemental analysis: Calculated: C; 53.34, H; 5.37, N; 9.33; Found: C; 53.35, H; 5.59, N; 9.34.

Example 48

Synthesis of N-(1-(4-((4-(4-Fluorophenyl)piperazin-1-yl)methyl)phenyl)ethyl)acetamide (1) Synthesis of 4-Chloromethylacetophenone

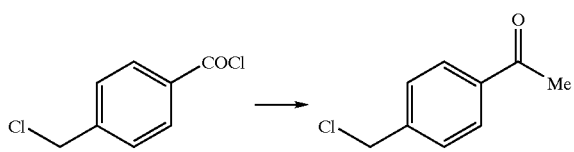

To a solution of 4-chloromethylbenzoyl chloride (40 g) and tris(acetylacetonato) iron (0.75 g) in tetrahydrofuran (400 ml) was added dropwise methylmagnesium bromide (3M, tetrahydrofuran solution)(70 ml) under ice-cooling and the mixture was stirred at 0° C. for 2 hr. The reaction mixture was poured into water and passed through Celite. The Celite was washed with ethyl acetate and the filtrate was combined. The mixture was extracted with ethyl acetate. The extract was washed with water and saturated brine, and dried over anhydrous magnesium sulfate. The solvent was evaporated to give a black red oil. The oil was subjected to silica gel column chromatography (developing solvent; hexane:ethyl acetate=9:1, then ethyl acetate) to give the title compound (19 g) as a pale-brown oil.

$^1$H-NMR(CDCl$_3$)δ: 2.60(3H, s), 4.61(2H, s), 7.48(2H, d, J=7.9 Hz), 7.95(2H, d, J=7.9 Hz). IR(KBr): 3005, 2964, 1683, 1609, 1574 cm$^{-1}$; MS(EI): 168(M$^+$);

(2) Synthesis of 1-(4-Chloromethylphenyl)ethanol

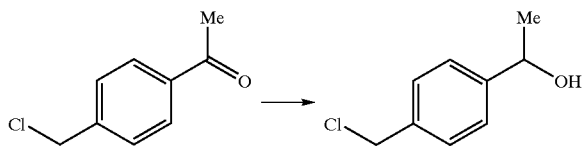

To a solution of sodium borohydride (4.9 g) in methanol (70 ml) was added dropwise a solution of 4-chloromethylacetophenone (22 g) in methanol(60 ml) under ice-cooling, and the mixture was stirred at room temperature for 1 hr. The reaction mixture was poured into water and extracted with ethyl acetate. The extract was washed with saturated brine and dried over anhydrous magnesium sulfate. The solvent was evaporated to give a pale-brown substance. The substance was subjected to silica gel column chromatography (developing solvent; hexane-:ethyl acetate=2:1) to give the title compound (17 g) as a colorless oil.

$^1$H-NMR(CDCl$_3$)δ: 1.49(3H, d, J=6.6 Hz), 4.59(2H, s), 4.91(1H, q, J=6.6 Hz), 7.73(4H, s). IR(KBr): 3360, 2974, 1513, 1445 cm$^{-1}$; MS(EI): 170(M$^+$).

(3) Synthesis of N-(1-(4-Chloromethylphenyl)ethyl)acetamide

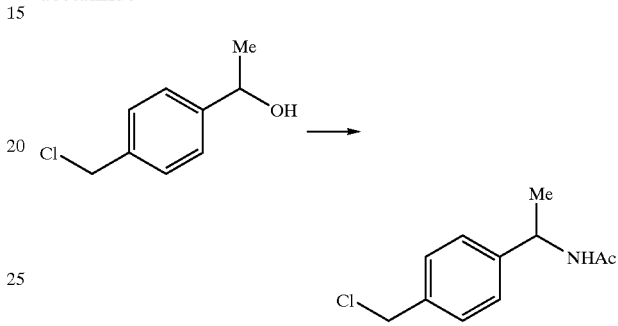

To a solution of 1-(4-chloromethylphenyl)ethanol (17 g) in acetonitrile (102 ml) was added dropwise conc. sulfuric acid (5.7 ml) under ice-cooling. The mixture was stirred at 0° C. for 3.5 hr and left standing overnight. The reaction mixture was poured into water and extracted with ethyl acetate. The extract was washed with an aqueous sodium hydrogencarbonate solution and saturated brine, and dried over anhydrous magnesium sulfate. The solvent was evaporated to give a white solid. This solid was recrystallized from ethyl acetate-isopropyl ether to give the title compound (17 g) as white crystals.

$^1$H-NMR(CDCl$_3$)δ: 1.48(3H, d, J=6.6 Hz), 1.98(3H, s), 4.57(2H, s), 5.12(1H, dq, J=7.3, 6.6 Hz), 5.77(1H, br.s), 7.30(2H, d, J=7.9 Hz), 7.36(2H, d, J=7.9 Hz). IR(KBr): 3267, 3061, 2978, 1631, 1540 cm$^{-1}$; MS(EI): 211(M$^+$).

(4) Synthesis of N-(1-(4-((4-(4-Fluorophenyl)piperazin-1-yl)methyl)phenyl)ethyl)acetamide

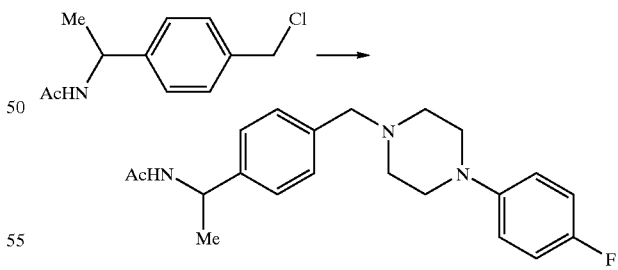

By similar reaction and treatment to that in Example 1(5) using 1-(4-fluorophenyl)piperazine instead of phenylpiperazine and N-(1-(4-chloromethylphenyl)ethyl)acetamide instead of N-(4-chloromethylphenylmethyl)acetamide, the title compound was obtained as white crystals, m.p.= 101–103° C.

$^1$H-NMR(CDCl$_3$)δ: 1.49(3H, d, J=6.6 Hz), 1.99(3H, s), 2.60(4H, dd, J=5.3, 4.6 Hz), 3.11(4H, dd, J=5.3, 4.6 Hz), 3.55(2H, s), 5.13(1H, dq, J=7.3, 6.6 Hz), 5.65(1H, d, J=7.3 Hz), 6.83–6.98(4H, m), 7.27(2H, d, J=7.9 Hz), 7.32(2H, d,

J=7.9 Hz). IR(KBr): 3355, 2943, 2816, 1645, 1507 cm$^{-1}$; MS(EI): 355(M$^+$); Elemental analysis: Calculated: C; 70.96, H; 7.37, N; 11.82; Found: C; 70.88, H; 7.51, N; 11.79.

Example 49

Synthesis of N-(1-(4-((4-(2,4-Difluorophenyl)piperazin-1-yl)methyl)phenyl)ethyl)acetamide

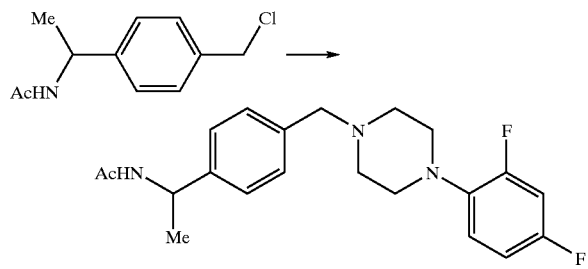

By similar reaction and treatment to that in Example 1(5) using 1-(2,4-difluorophenyl)piperazine dihydrochloride instead of phenylpiperazine and N-(1-(4-chloromethylphenyl)ethyl)acetamide instead of N-(4-chloromethylphenylmethyl)acetamide, the title compound was obtained as white crystals, m.p.=109–111° C.

$^1$H-NMR(CDCl$_3$)δ: 1.49(3H, d, J=6.6 Hz), 1.99(3H, s), 2.62(4H, t, J=4.6 Hz), 3.04(4H, t, J=4.6 Hz), 3.56(2H, s), 5.13(1H, quintet, J=7.3 Hz), 5.65(1H, d, J=7.9 Hz), 6.74–6.94(3H, m), 7.27(2H, d, J=7.9 Hz), 7.32(2H, d, J=7.9 Hz). IR(KBr): 3351, 2946, 2811, 1644, 1505 cm$^{-1}$; MS(EI): 373(M$^+$); Elemental analysis: Calculated: C; 67.54, H; 6.75, N; 11.25; Found: C; 67.38, H; 6.80, N; 11.21.

Example 50

Synthesis of N-(1-Methyl-1-(4-((4-phenylpiperazin-1-yl)methyl)phenyl)ethyl)acetamide
(1) Synthesis of 1-(4-Chloromethylphenyl)-1-methylethanol

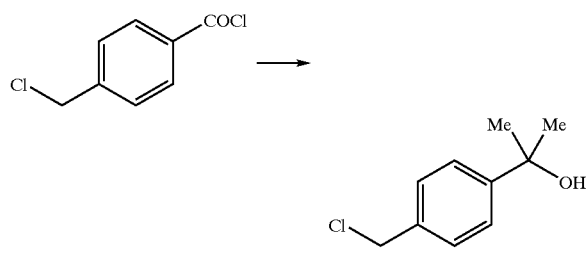

To a solution of 4-chloromethylbenzoyl chloride (40 g) in tetrahydrofuran (400 ml) was added dropwise methylmagnesium bromide (3M, tetrahydrofuran solution) (70 ml) under ice-cooling and the mixture was stirred at 0° C. for 4 hr. The reaction mixture was poured into an aqueous ammonium chloride solution and extracted with ethyl acetate. The extract was washed with saturated brine and dried over anhydrous magnesium sulfate and the solvent was evaporated to give a yellow oil. The oil was subjected to silica gel column chromatography (developing solvent; hexane:ethyl acetate=9:1) to give an orange oil. The oil was subjected to silica gel column chromatography (developing solvent; hexane:ethyl acetate=4:1) to give the title compound (10 g) as a pale-brown oil, m.p.=101–103° C.

$^1$H-NMR(CDCl$_3$)δ: 1.58(6H, s), 4.58(2H, s), 7.36(2H, d, J=8.6 Hz), 7.48(2H, d, J=8.6 Hz). IR(KBr): 3407, 2976, 2932, 1677, 1610 cm$^{-1}$; MS(EI): 184(M$^+$).

(2) Synthesis of N-(1-(4-Chloromethylphenyl)-1-methylethyl)acetamide

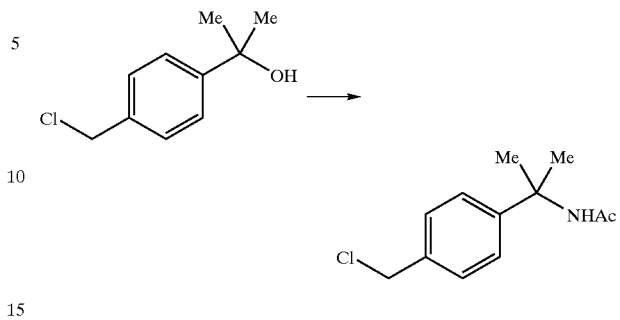

By similar reaction and treatment to that in Example 48(3) using 1-(4-chloromethylphenyl)-1-methylethanol instead of 1-(4-chloromethylphenyl)ethanol, the title compound was obtained as a pale-brown substance, m.p.=101–103° C.

$^1$H-NMR(CDCl$_3$)δ: 1.66(6H, s), 1.95(3H, s), 4.56(2H, s), 5.82(1H, br.s), 7.33(2H, d, J=8.6 Hz), 7.37(2H, d, J=8.6 Hz). IR(KBr): 3317, 3074, 2974, 1658, 1553 cm$^{-1}$; MS(EI): 225(M$^+$).

(3) Synthesis of N-(1-Methyl-1-(4-((4-phenylpiperazin-1-yl)methyl)phenyl)ethyl)acetamide

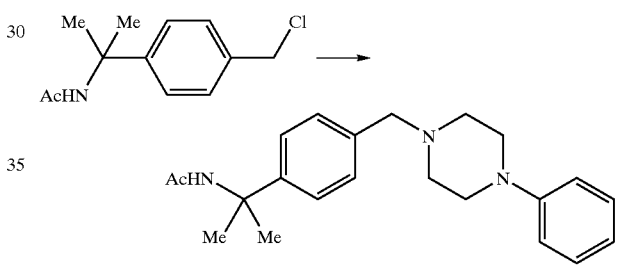

By similar reaction and treatment to that in Example 1(5) using N-(1-(4-chloromethylphenyl)-1-methylethyl)acetamide instead of N-(4-chloromethylphenylmethyl)acetamide, the title compound was obtained as white crystals, m.p.=110–111° C.

$^1$H-NMR(CDCl$_3$)δ: 1.70(6H, s), 1.97(3H, s), 2.60(4H, dd, J=5.3, 4.6 Hz), 3.19(4H, dd, J=5.3, 4.6 Hz), 3.54(2H, s), 5.70(1H, br.s), 6.84(1H, t, J=7.3 Hz), 6.91(2H, d, J=7.9 Hz), 7.25(2H, ddd, J=5.3, 4.6, 2.0 Hz), 7.30(2H, d, J=8.6 Hz), 7.35(2H, d, J=8.6 Hz). IR(KBr): 3325, 2923, 2810, 1659, 1601 cm$^{-1}$; MS(EI): 351(M$^+$); Elemental analysis: Calculated: C; 75.18, H; 8.32, N; 11.96; Found: C; 75.10, H; 8.28, N; 11.87.

Example 51

Synthesis of N-(1-Methyl-1-(4-((4-(4-fluorophenyl)-piperazin-1-yl)methyl)phenyl)ethyl)acetamide

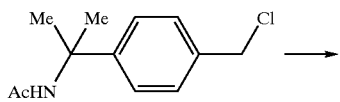

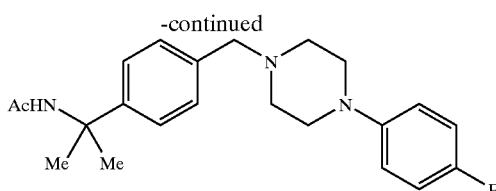

By similar reaction and treatment to that in Example 1(5) using 1-(4-fluorophenyl)piperazine instead of phenylpiperazine and N-(1-(4-chloromethylphenyl)-1-methylethyl)acetamide instead of N-(4-chloromethylphenylmethyl)acetamide, the title compound was obtained as pale-brown crystals, m.p.=104.5–106° C.

$^1$H-NMR(CDCl$_3$)δ: 1.70(6H, s), 1.97(3H, s), 2.60(4H, dd, J=5.3, 4.6 Hz), 3.11(4H, dd, J=5.3, 4.6 Hz), 3.54(2H, s), 5.70(1H, br.s), 6.83–7.02(4H, m), 7.29(2H, d, J=8.6 Hz), 7.32(2H, d, J=8.6 Hz). IR(KBr): 3323, 3002, 2811, 1658, 1549 cm$^{-1}$; MS(EI): 369(M$^+$); Elemental analysis: Calculated: C; 71.52, H; 7.64, N; 11.37; Found: C; 71.43, H; 7.65, N; 11.25.

Example 52

Synthesis of N-(1-Methyl-1-(4-((4-(2,4-difluorophenyl)piperazin-1-yl)methyl)phenyl)ethyl)acetamide Hydrochloride 1/4 Hydrate

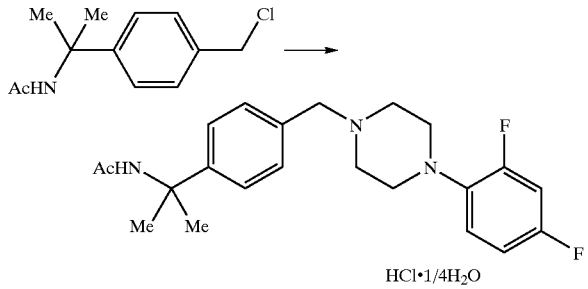

By similar reaction and treatment to that in Example 1(5) using 1-(2,4-difluorophenyl)piperazine dihydrochloride instead of phenylpiperazine and N-(1-(4-chloromethylphenyl)-1-methylethyl)acetamide instead of N-(4-chloromethylphenylmethyl)acetamide, the title compound was obtained as pale-brown crystals.

m.p.=240.5–242° C.; $^1$H-NMR(DMSO-d$_6$)δ: 1.54(6H, s), 1.85(3H, s), 3.21–3.41(8H, m), 4.32(2H, d, J=4.0 Hz), 6.80–7.28(3H, m), 7.38(2H, d, J=7.9 Hz), 7.59(2H, d, J=7.9 Hz), 8.17(1H, s), 11.6(1H, br.s). IR(KBr): 3287, 2976, 2468, 1645, 1596 cm$^{-1}$; MS(EI): 387(M$^+$); Elemental analysis: Calculated: C; 61.68, H; 6.71, N; 9.81; Found: C; 61.42, H; 6.62, N; 9.65.

Example 53

Synthesis of N-(1-(4-((4-Phenylpiperazin-1-yl)methyl)phenyl)propyl)acetamide (1) Synthesis of (4-Chloromethylphenyl)ethyl Ketone

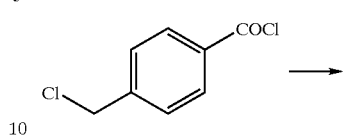

By similar reaction and treatment to that in Example 48(1) using ethylmagnesium bromide (3M, ether solution) instead of methylmagnesium bromide (3M, tetrahydrofuran solution), the title compound was obtained as a pale-yellow substance. $^1$H-NMR(CDCl$_3$)δ: 1.23(3H, t, J=7.3 Hz), 3.00 (2H, q, J=7.3 Hz), 4.61(2H, s), 7.48(2H, d, J=8.6 Hz), 7.96(2H, d, J=8.6 Hz). IR(KBr): 2980, 2939, 1716, 1687, 1574 cm$^{-1}$; MS(EI): 182(M$^+$).

(2) Synthesis of 1-(4-Chloromethylphenyl)propanol

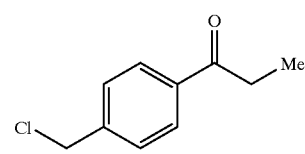

By similar reaction and treatment to that in Example 48(2) using (4-chloromethylphenyl)ethyl ketone instead of 4-chloromethylacetophenone, the title compound was obtained as a colorless oil.

$^1$H-NMR(CDCl$_3$)δ: 0.92(3H, t, J=7.3 Hz), 1.65–1.89(2H, m), 4.58(2H, s), 4.60(1H, t, J=6.6 Hz), 7.33(2H, d, J=8.6 Hz), 7.37(2H, d, J=8.6 Hz). IR(KBr): 3371, 2964, 2933, 1614, 1514 cm$^{-1}$; MS(EI): 184(M$^+$).

(3) Synthesis of N-(1-(4-Chloromethylphenyl)propyl)acetamide

By similar reaction and treatment to that in Example 48(3) using 1-(4-chloromethylphenyl)propanol instead of 1-(4- chloromethylphenyl)ethanol, the title compound was obtained as a white substance.

¹H-NMR(CDCl₃)δ: 0.89(3H, t, J=7.3 Hz), 1.70–1.93(2H, m), 1.98(3H, s), 4.57(2H, s), 4.88(1H, q, J=7.9 Hz), 5.68 (1H, d, J=7.3 Hz), 7.27(2H, d, J=7.9 Hz), 7.35(2H, d, J=7.9 Hz). IR(KBr): 3299, 2964, 2933, 1639, 1553 cm⁻¹; MS(EI): 225(M⁺).

(4) Synthesis of N-(1-(4-((4-Phenylpiperazin-1-yl)methyl) phenyl)propyl)acetamide

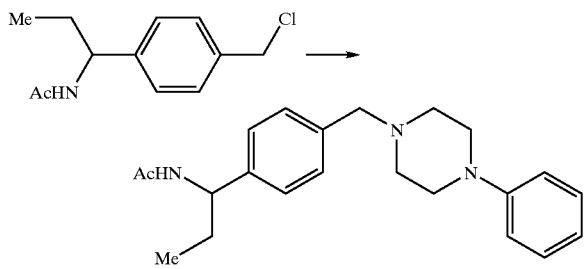

By similar reaction and treatment to that in Example 1(5) using N-(1-(4-chloromethylphenyl)propyl)acetamide instead of N-(4-chloromethylphenylmethyl)acetamide, the title compound was obtained as pale-brown crystals, m.p.= 109–110.5° C.

¹H-NMR(CDCl₃)δ: 0.89(3H, dd, J=7.9, 7.3 Hz), 1.74–1.91(2H, m), 1.99(3H, s), 2.60(4H, dd, J=5.3, 4.6 Hz), 3.20(4H, dd, J=5.3, 4.6 Hz), 3.55(2H, s), 4.88(1H, dt, J=7.9, 7.3 Hz), 5.65(1H, d, J=7.9 Hz), 6.84(1H, t, J=7.3 Hz), 6.92(2H, d, J=7.9 Hz), 7.24(2H, d, J=7.9 Hz), 7.31(2H, d, J=7.9 Hz). IR(KBr): 3310, 2924, 2812, 1649, 1540 cm⁻¹; MS(EI): 351(M⁺); Elemental analysis: Calculated: C; 75.18, H; 8.32, N; 11.96; Found: C; 75.00, H; 8.41, N; 11.86.

Example 54

Synthesis of N-(1-(4-((4-(4-Fluorophenyl)piperazin-1-yl)methyl)phenyl)propyl)acetamide

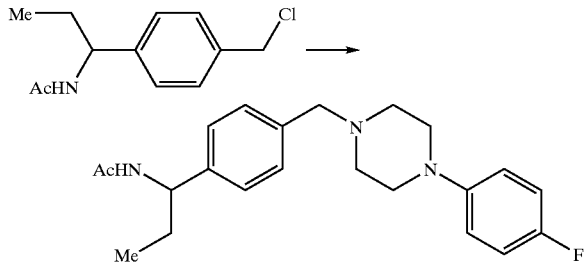

By similar reaction and treatment to that in Example 1(5) using 1-(4-fluorophenyl)piperazine instead of phenylpiperazine and N-(1-(4-chloromethylphenyl)propyl)acetamide instead of N-(4-chloromethylphenylmethyl)acetamide, the title compound was obtained as pale-brown crystals, m.p.= 113–114° C.

¹H-NMR(CDCl₃)δ: 0.89(3H, dd, J=7.9, 7.3 Hz), 1.74–1.90(2H, m), 1.99(3H, s), 2.60(4H, dd, J=5.3, 4.6 Hz), 3.11(4H, dd, J=5.3, 4.6 Hz), 3.54(2H, s), 4.88(1H, dt, J=7.9, 7.3 Hz), 5.66(1H, d, J=7.9 Hz), 6.83–6.99(4H, m), 7.23(2H, d, J=7.9 Hz), 7.32(2H, d, J=7.9 Hz). IR(KBr): 3308, 2960, 2811, 1647, 1510 cm⁻¹; MS(EI): 369(M⁺); Elemental analysis: Calculated: C; 71.52, H; 7.64, N; 11.37; Found: C; 71.48, H; 7.75, N; 11.35.

Example 55

Synthesis of N-(1-(4-((4-(2,4-Difluorophenyl) piperazin-1-yl)methyl)phenyl)propyl)acetamide

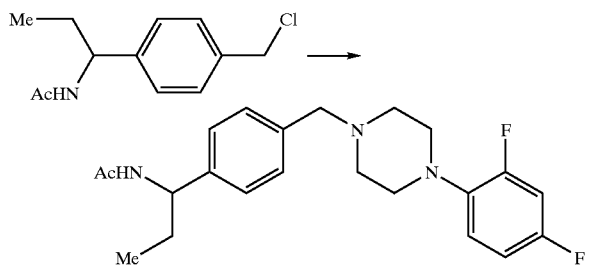

By similar reaction and treatment to that in Example 1(5) using 1-(2,4-difluorophenyl)piperazine instead of phenylpiperazine and N-(1-(4-chloromethylphenyl)propyl) acetamide instead of N-(4-chloromethylphenylmethyl) acetamide, the title compound was obtained as pale-brown crystals, m.p.=137–138° C.

¹H-NMR(CDCl₃)δ: 0.89(3H, t, J=7.3 Hz), 1.74–1.90(2H, m), 1.99(3H, s), 2.62(4H, t, J=4.6 Hz), 3.04(4H, t, J=4.6 Hz), 3.55(2H, s), 4.88(1H, dt, J=7.8, 7.3 Hz), 5.69(1H, d, J=7.8 Hz), 6.74–6.94(3H, m), 7.23(2H, d, J=7.9 Hz), 7.31(2H, d, J=7.9 Hz). IR(KBr): 3316, 2946, 2828, 1647, 1508 cm⁻¹; MS(EI): 387(M⁺); Elemental analysis: Calculated: C; 68.20, H; 7.02, N; 10.84; Found: C; 68.26, H; 7.08, N; 10.79.

Example 56

Synthesis of N-(1-Ethyl-1-(4-((4-phenylpiperazin-1-yl)methyl)phenyl)propyl)acetamide (1) Synthesis of 1-(4-Chloromethylphenyl)-1-ethylpropanol

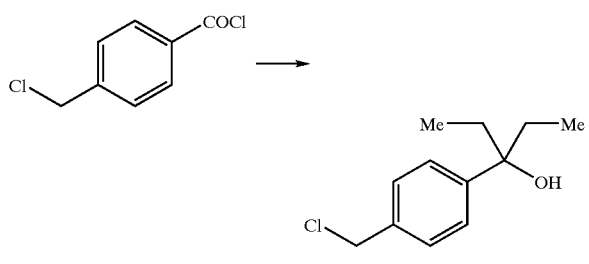

By similar reaction and treatment to that in Example 50(1) using ethylmagnesium bromide (3M, ether solution) instead of methylmagnesium bromide (3M, tetrahydrofuran solution), the title compound was obtained as a brown oil.

¹H-NMR(CDCl₃)δ: 0.76(6H, dd, J=7.9, 7.3 Hz), 1.73–1.93(4H, m), 4.59(2H, s), 7.36(4H, s). IR(KBr): 3473, 2968, 2937, 1612, 1511 cm⁻¹; MS(EI): 183(M+−Et).

(2) Synthesis of N-(1-(4-Chloromethylphenyl)-1-ethylpropyl)acetamide

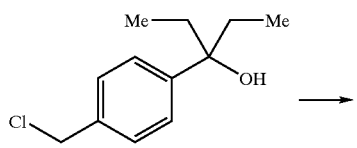

-continued

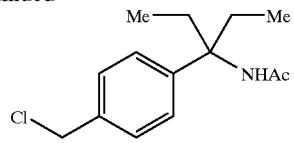

By similar reaction and treatment to that in Example 48(3) using 1-(4-chloromethylphenyl)-1-ethylpropanol instead of 1-(4-chloromethylphenyl)ethanol, the title compound was obtained as a pale-brown oil.

$^1$H-NMR(CDCl$_3$)δ: 0.73(6H, dd, J=7.9, 7.3 Hz), 1.91–2.21(4H, m), 2.01(3H, s), 4.57(2H, s), 5.54(1H, s), 7.29(2H, d, J=8.6 Hz), 7.35(2H, d, J=8.6 Hz). IR(KBr): 3288, 2979, 2966, 1644, 1551 cm$^{-1}$; MS(EI): 254(M++1).

(3) Synthesis of N-(1-Ethyl-1-(4-((4-Phenylpiperazin-1-yl)methyl)phenyl)propyl)acetamide

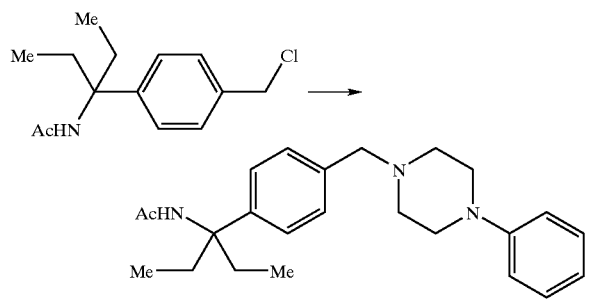

By similar reaction and treatment to that in Example 1(5) using N-(1-(4-chloromethylphenyl)-1-ethylpropyl)acetamide instead of N-(4-chloromethylphenylmethyl)acetamide, the title compound was obtained as white crystals, m.p.=139–140° C.

$^1$H-NMR(CDCl$_3$)δ: 0.73(6H, dd, J=7.9, 7.3 Hz), 1.93–2.22(4H, m), 2.03(3H, s), 2.61(4H, dd, J=5.3, 4.6 Hz), 3.20(4H, dd, J=5.3, 4.6 Hz), 3.54(2H, s), 5.51(1H, br.s), 6.84(1H, t, J=7.3 Hz), 6.92(2H, d, J=7.9 Hz), 7.21–7.33(6H, m). IR(KBr): 3269, 2973, 2827, 1648, 1602 cm$^{-1}$; MS(EI): 379(M$^+$); Elemental analysis: Calculated: C; 75.95, H; 8.76, N; 11.07; Found: C; 75.96, H; 8.96, N; 10.92.

Example 57

Synthesis of N-(1-(4-((4-Phenylpiperazin-1-yl)methyl)-phenyl)cyclopropyl)acetamide (1) Synthesis of Methyl 1-Phenylcyclopropanecarboxylate

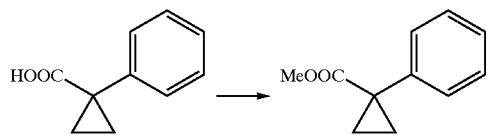

To a solution of 1-phenylcyclopropanecarboxylic acid (9.8 g) in methanol (121 ml) was added conc. sulfuric acid (0.1 ml) and the mixture was refluxed under heating for 8 hr. The reaction mixture was neutralized by adding an aqueous potassium carbonate solution and concentrated under reduced pressure. The concentrate was extracted with ethyl acetate. The extract was washed with an aqueous sodium hydrogencarbonate solution and saturated brine, and dried over anhydrous magnesium sulfate. The solvent was evaporated to give the title compound (8.5 g) as a colorless oil.

$^1$H-NMR(CDCl$_3$)δ: 1.20(2H, dd, J=6.6, 3.7 Hz), 1.61(2H, dd, J=6.6, 3.7 Hz), 3.62(3H, s), 7.24–7.36(5H, m). IR(KBr): 3059, 2953, 1724, 1603 cm$^{-1}$; MS(EI): 176(M$^+$).

(2) Synthesis of Methyl 1-(4-Chloromethylphenyl)cyclopropanecarboxylate

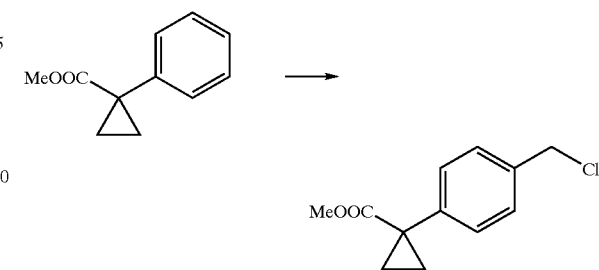

To a solution of methyl 1-phenylcyclopropanecarboxylate (8.5 g) in methylene chloride (70 ml) was added titanium tetrachloride (8.0 ml) under ice-cooling. To this solution was added dropwise a solution of methoxymethyl chloride (5.5 ml) in methylene chloride (30 ml) under ice-cooling. The mixture was stirred at room temperature for 5 hr and left standing overnight. The reaction mixture was poured into water and extracted with ethyl acetate. The extract was washed with an aqueous sodium hydrogencarbonate solution and saturated brine, and dried over anhydrous magnesium sulfate. The solvent was evaporated to give a pale-brown oil. The oil was subjected to silica gel column chromatography (developing solvent; hexane:ethyl acetate=4:1) to give the title compound (7.9 g) as a colorless oil.

$^1$H-NMR(CDCl$_3$)δ: 1.19–1.21(2H, m), 1.58–1.64(2H, m), 3.62(3H, s), 4.57(2H, s), 7.33(4H, s). IR(KBr): 3016, 2954, 1717, 1604 cm$^{-1}$; MS(EI): 224(M$^+$).

(3) Synthesis of Methyl 1-(4-((4-Phenylpiperazin-1-yl)methyl)phenyl)cyclopropanecarboxylate

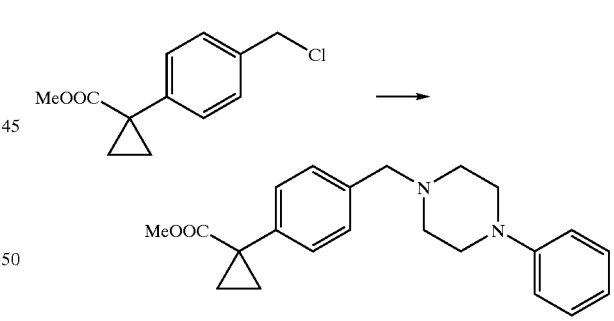

By similar reaction and treatment to that in Example 1(5) using methyl 1-(4-chloromethylphenyl)cyclopropanecarboxylate instead of N-(4-chloromethylphenylmethyl)acetamide, the title compound was obtained as a pale-yellow solid.

$^1$H-NMR(CDCl$_3$)δ: 1.19(2H, dt, J=4.0, 3.3 Hz), 1.60(2H, dt, J=4.0, 3.3 Hz), 2.61(4H, dd, J=5.3, 4.6 Hz), 3.20(4H, dd, J=5.3, 4.6 Hz), 3.55(2H, s), 3.62(3H, s), 6.84(1H, t, J=7.3 Hz), 6.91(2H, d, J=8.6 Hz), 7.25–7.32(6H, m). IR(KBr): 2934, 2923, 1713, 1601 cm$^{-1}$; MS(EI): 350(M$^+$).

(4) Synthesis of (4-((4-Phenylpiperazin-1-yl)methyl) phenylcyclopropanecarboxylic Acid

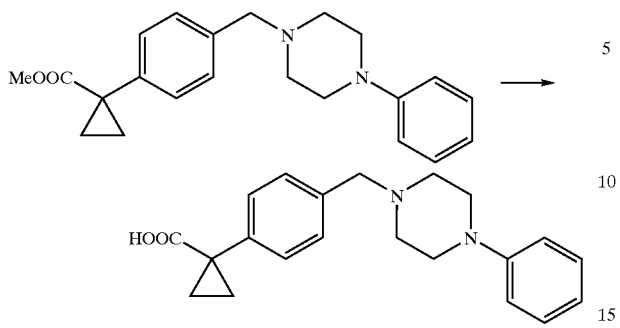

Methyl 1-(4-((4-phenylpiperazin-1-yl)methyl)phenyl)-cyclopropanecarboxylate (1.9 g) was dissolved in a mixed solution of methanol (50 ml) and tetrahydrofuran (10 ml) and lithium hydroxide monohydrate (0.46 g) was added. The mixture was refluxed under heating for 4 hr. The reaction mixture was neutralized with hydrochloric acid, and concentrated under reduced pressure and extracted with ethyl acetate. The extract was washed with saturated brine and dried over anhydrous magnesium sulfate. The solvent was evaporated to give the title compound (1.2 g) as a pale-brown solid.

$^1$H-NMR(CDCl$_3$)δ: 1.07(2H, t, J=3.3 Hz), 1.40(2H, t, J=3.3 Hz), 2.50(4H, t, J=4.6 Hz), 3.11(4H, t, J=4.6 Hz), 3.48(2H, s), 3.73(1H, br.s), 6.76(1H, t, J=7.3 Hz), 6.91(2H, d, J=8.6 Hz), 7.16–7.29(6H, m). IR(KBr): 2934, 2822, 1697, 1600 cm$^{-1}$; MS(EI): 336(M$^+$).

(5) Synthesis of N-(1-(4-((4-Phenylpiperazin-1-yl)methyl)phenyl)cyclopropyl)acetamide

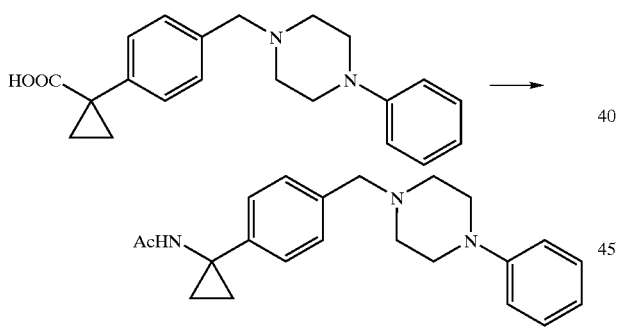

To a solution of (4-((4-phenylpiperazin-1-yl)methyl)-phenylcyclopropanecarboxylic acid (1.0 g) and triethylamine (0.42 ml) in tetrahydrofuran (70 ml) was added ethyl chlorocarbonate (0.29 ml) under ice-cooling and the mixture was stirred at 0° C. for 1 hr and 20 min. To this solution was added a solution of sodium azide (0.2 g) in water (3 ml) under ice-cooling, and the mixture was stirred for 30 min and left standing overnight. The reaction mixture was poured into water and extracted with ethyl acetate. The extract was washed with saturated brine and dried over anhydrous magnesium sulfate. The solvent was evaporated to give a brown oil. The oil was dissolved in benzene (20 ml) and refluxed under heating for 40 min. The reaction mixture was ice-cooled and methylmagnesium bromide (3M, tetrahydrofuran solution) (0.93 ml) was added dropwise. The mixture was stirred at room temperature for 1 hr. The reaction mixture was poured into water and extracted with ethyl acetate. The extract was washed with saturated brine and dried over anhydrous magnesium sulfate. The solvent was evaporated to give a colorless oil. The oil was subjected to silica gel column chromatography (developing solvent; ethyl acetate:methanol=20:1) to give a white solid. This solid was recrystallized from ethyl acetate-isopropyl ether to give the title compound (0.52 g) as white crystals, m.p.= 129–139.5° C.

$^1$H-NMR(CDCl$_3$)δ: 1.26(4H, br.s), 1.99(3H, s), 2.58(4H, dd, J=5.3, 4.6 Hz), 3.18(4H, dd, J=5.3, 4.6 Hz), 3.51(2H, s), 6.15(1H, br.s), 6.84(1H, t, J=7.3 Hz), 6.91(2H, d, J=7.9 Hz), 7.09–7.32(6H, m). IR(KBr): 3308, 2824, 1658, 1603, 1517 cm$^{-1}$; MS(EI): 349(M$^+$); Elemental analysis: Calculated: C; 75.61, H; 7.99, N; 12.05; Found: C; 75.36, H; 7.79, N; 11.85.

Example 58

Synthesis of N-(1-(4-((4-Phenylpiperazin-1-yl)methyl)phenyl)ethyl)acetamide Dihydrochloride 1/4 Hydrate (1) N-(1-Phenylethyl)acetamide

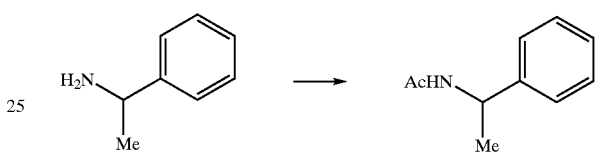

To a solution of 1-phenylethylamine (10.45 g) and triethylamine (14.4 ml) in dichloromethane (100 ml) was added dropwise acetic anhydride (9.0 ml) at room temperature. The mixture was stirred at room temperature for 5 hr. The reaction mixture was poured into ice water (200 ml) and extracted with chloroform. The organic layer was dried over anhydrous sodium sulfate and the solvent was evaporated. The obtained residue was left standing at room temperature for 3 hr. The obtained crude crystals were washed several times with hexane to give the title compound (14.0 g) as white crystals.

$^1$H-NMR(CDCl$_3$)δ: 1.46(3H, d, J=6.6 Hz), 1.95(3H, s), 5.10(1H, dt, J=5.4, 5.4 Hz), 6.10(1H, brs), 7.30(5H, m). IR(KBr): 3282, 3062, 2979, 1645, 1552 cm$^{-1}$; MS(EI): 163(M$^+$).

(2) N-(1-(4-Formylphenyl)ethyl)acetamide

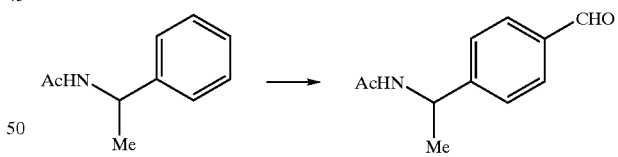

To a solution of N-(1-phenylethyl)acetamide (5.0 g) in dichloromethane (100 ml) was added dropwise titanium tetrachloride (16.7 ml) at below 5° C. over 30 min. Thereto was added dropwise a solution of dichloromethyl methyl ether (14.1 ml) in dichloromethane (30 ml) solution at below 5° C. over 30 min. The mixture was stirred at 25° C. for 3 hr, at room temperature for 12 hr, and then at 25° C. for 3 hr, and poured into ice water (800 ml) and extracted with ethyl acetate. The extract was washed successively with a saturated sodium hydrogencarbonate solution (500 ml) and saturated brine (500 ml), and dried over anhydrous sodium sulfate. The solvent was evaporated and the obtained residue was purified by silica gel column chromatography (elution solvent; hexane:ethyl acetate=1:3) to give the title compound (0.35 g) as a colorless oil.

¹H-NMR(CDCl₃)δ: 1.48(3H, d, J=7.3 Hz), 2.01(3H, s), 5.17(1H, dt, J=7.1, 7.1 Hz), 6.04(1H, brs), 7.47(2H, d, J=7.9 Hz), 7.84(2H, d, J=8.6 Hz), 9.98(1H, s); MS(EI): 191(M⁺).

(3) N-(1-(4-((4-Phenylpiperazin-1-yl)methyl)phenyl)ethyl)acetamide Dihydrochloride 1/4 Hydrate

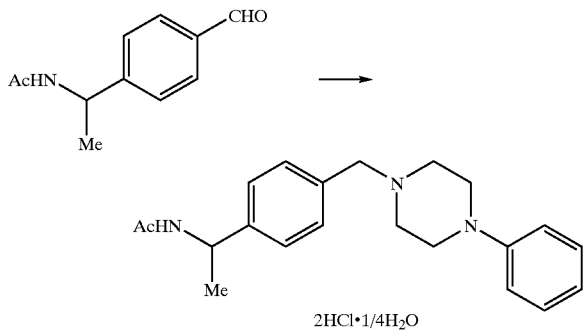

A solution of N-(1-(4-formylphenyl)ethyl)acetamide (0.32 g) and sodium borohydride (63 mg) in ethanol (10 ml) was stirred at room temperature for 1 hr. Thereto was added 2N hydrochloric acid (1 ml) to stop the reaction, and the reaction mixture was poured into ice water (100 ml) and extracted with ethyl acetate. The extract was washed successively with saturated sodium hydrogencarbonate solution (500 ml) and saturated brine (500 ml) and dried over anhydrous sodium sulfate. The solvent was evaporated and the obtained residue was purified by silica gel column chromatography (elution solvent; hexane:ethyl acetate=2:5, later 1:4) to give N-(1-(4-hydroxymethylphenyl)ethyl)acetamide (100 mg) as a colorless oil. A solution of the obtained N-(1-(4-hydroxymethylphenyl)ethyl)acetamide (100 mg) and thionyl chloride (0.050 ml) in chloroform (5 ml) was stirred at 60° C. for 1 hr. This was diluted with ethyl acetate (100 ml) and poured into a saturated sodium hydrogencarbonate solution (100 ml) to separate the organic layer. The aqueous layer was extracted with ethyl acetate (100 ml) and combined with the organic layer obtained earlier. The organic layer was washed with saturated brine and dried over anhydrous sodium sulfate. The solvent was evaporated and the obtained residue was purified by silica gel column chromatography (elution solvent; ethyl acetate alone) to give N-(1-(4-chloromethylphenyl)ethyl)acetamide (92 mg) as yellow crystals.

By similar reaction and treatment to that in Example 1(5) using the obtained N-(1-(4-chloromethylphenyl)ethyl)acetamide instead of N-(4-chloromethylphenylmethyl)acetamide, and treatment with a solution of 1M hydrochloric acid in ether, the title compound (40 mg) was obtained as white crystals, m.p.=196–200° C.

¹H-NMR(DMSO-d₆)δ: 1.34(3H, s), 1.85(3H, s), 3.20(4H, m), 3.33(2H, m), 3.78(2H, m), 4.34(2H, s), 6.86(1H, t, J=7.3 Hz), 6.97(2H, d, J=8.6 Hz), 7.26(1H, t, J=7.9 Hz), 7.38(2H, d, J=8.6 Hz), 7.61(2H, d, J=8.6 Hz), 8.40(2H, d, J=7.9 Hz), 11.41(1H, brs). IR(KBr): 3437, 3244, 3055, 2987, 1639 cm⁻¹; MS(EI): 337(M⁺); Elemental analysis: Calculated: C; 60.79, H; 7.17, N; 10.13; Found: C; 60.69, H; 7.27, N; 9.84.

Example 59

Synthesis of N-(4-(1-(4-(4-Fluorophenyl)piperazin-1-yl)ethyl)phenylmethyl)acetamide (1) (4-Azidomethylphenyl)methyl Ketone

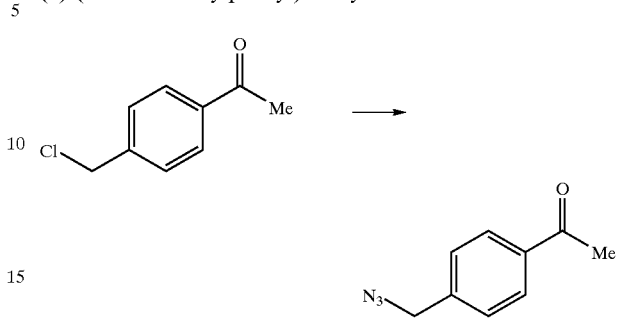

A solution of 4-chloromethylacetophenone (8.8 g) obtained in Example 48(1) and sodium azide in dimethylformamide (52 ml) was stirred at 50° C. for 3 hr. The reaction mixture was poured into ice water (200 ml) and extracted with ethyl acetate. The extract was washed with saturated brine and dried over anhydrous sodium sulfate. The solvent was evaporated and the obtained residue was purified by silica gel column chromatography (elution solvent; hexane:ethyl acetate=4:1) to give the title compound (8.61 g) as a yellow oil.

¹H-NMR(CDCl₃)δ: 2.61(3H, s), 4.42(2H, s), 7.42(2H, d, J=7.9 Hz), 7.97(2H, d, J=8.6 Hz). IR(neat): 2102, 1684, 1608 cm⁻¹.

(2) N-(4-(1-Hydroxyethyl)phenylmethyl)acetamide

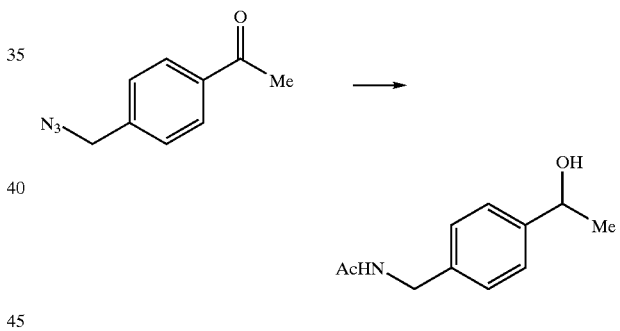

To a suspension of aluminum lithium hydride (5.31 g) in tetrahydrofuran (500 ml) was added dropwise a solution of (4-azidomethylphenyl) methyl ketone (8.18 g) in tetrahydrofuran (100 ml) at below 5° C. over 30 min. The mixture was stirred at 30° C. for 2 hr. A saturated aqueous sodium sulfate solution (30 ml) was added and the mixture was stirred for 1 hr. The insoluble matter was filtered off and the solvent was evaporated. The obtained residue was dissolved in ethyl acetate (100 ml), 2N aqueous sodium hydroxide solution (30 ml) and water (70 ml). Thereto was added dropwise acetic anhydride (4.8 ml) with vigorous agitation at 10–15° C. over 10 min. The mixture was stirred at room temperature for 1 hr. The organic layer was separated and the aqueous layer was extracted with ethyl acetate and combined with the organic layer. The organic layer was washed with saturated brine and dried over anhydrous sodium sulfate. The solvent was evaporated and the obtained residue was purified by silica gel column chromatography (elution solvent; methanol:chloroform=3:97, later 5:95) to give the title compound (5.37 g) as a rather brown oil.

¹H-NMR(CDCl₃)δ: 1.46(3H, d, J=6.6 Hz), 1.98(3H, s), 2.21(1H, brs), 4.36(2H, d, J=5.3 Hz), 4.87(1H, q, J=6.4 Hz), 6.88(1H, brs), 7.22(2H, d, J=8.6 Hz), 7.32(2H, d, J=7.9 Hz). IR(neat): 3296, 2972, 2821, 1653, 1556 cm⁻¹; MS(EI): 193(M⁺).

(3) N-(4-(1-Chloroethyl)phenylmethyl)acetamide

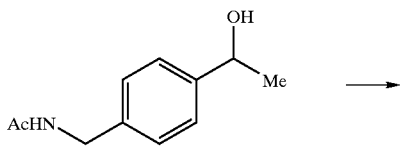

To a solution of N-(4-(1-hydroxyethyl)phenylmethyl)acetamide (5.26 g) in chloroform (40 ml) was added dropwise a solution of thionyl chloride (2.1 ml) in chloroform (10 ml) at below 5° C. over 20 min. The mixture was stirred at 30° C. for 1 hr. The mixture was poured into a saturated sodium hydrogencarbonate solution and extracted with chloroform. The organic layer was dried over anhydrous sodium sulfate and the solvent was evaporated. The obtained residue was purified by silica gel column chromatography (elution solvent; methanol:chloroform=4:96) to give the title compound (4.08 g) as white crystals.

m.p.=58–62° C. $^1$H-NMR(CDCl$_3$)δ: 1.83(3H, d, J=6.6 Hz), 1.99(3H, s), 4.39(2H, d, J=5.9 Hz), 5.07(1H, q, J=6.8 Hz), 6.12(1H, brs), 7.25(2H, d, J=7.9 Hz), 7.37(2H, d, J=7.9 Hz). IR(KBr): 3286, 1649, 1547 cm⁻¹; MS(EI): 211((M+1)+); Elemental analysis: Calculated: C; 62.41, H; 6.67, N; 6.62; Found: C; 62.68, H; 6.81, N; 6.59.

(4) N-(4-(1-(4-(4-Fluorophenyl)piperazin-1-yl)ethyl)phenylmethyl)acetamide

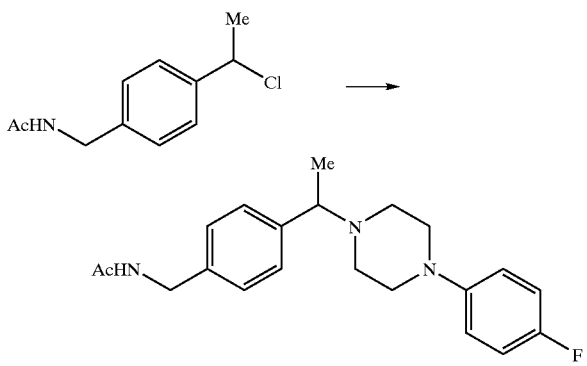

By similar reaction and treatment to that in Example 1(5) using 1-(4-fluorophenyl)piperazine dihydrochloride instead of phenylpiperazine and N-(4-(1-chloroethyl)phenylmethyl)acetamide instead of N-(4-chloromethylphenylmethyl)acetamide, the title compound was obtained as white crystals, m.p.=128–130° C.

$^1$H-NMR(DMSO-d$_6$)δ: 1.30(3H, d, J=6.6 Hz), 1.87(3H, s), 2.37–2.77(4H, m), 3.03(4H, t, J=5.0 Hz), 3.39(1H, q, J=7.3 Hz), 4.23(2H, d, J=5.3 Hz), 6.86–7.05(4H, m), 7.21 (2H, d, J=7.9 Hz), 7.27(2H, d, J=8.6 Hz), 8.30(1H, t, J=5.6 Hz). IR(KBr): 3323, 2818, 1651, 1535, 1510 cm⁻¹; MS(EI): 355(M⁺); Elemental analysis: Calculated: C; 70.96, H; 7.37, N; 11.82; Found: C; 71.09, H; 7.41, N; 11.74.

Example 60

Synthesis of N-(1-(4-(1-(4-(4-Fluorophenyl)piperazin-1-yl)ethyl)phenyl)-1-methylethyl)acetamide (1) N-(1-(4-(1-Hydroxyethyl)phenyl)-1-methylethyl)acetamide

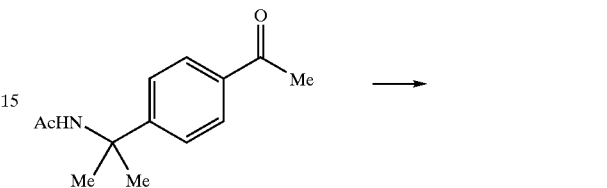

To a solution of N-(1-(4-acetylphenyl)-1-methylethyl)acetamide (50.0 g) in methanol (400 ml) was added dropwise sodium borohydride (4.3 g) at below 5° C. over 30 min. The mixture was stirred at room temperature for 2 hr and 2N hydrochloric acid (60 ml) was added. The mixture was treated by a conventional method and the obtained crude crystals were recrystallized from ethanol to give the title compound (42.17 g) as white crystals.

m.p.=146–149° C.; $^1$H-NMR(DMSO-d$_6$)δ: 1.30(3H, d, J=6.6 Hz), 1.52(6H, s), 1.81(3H, s), 4.67(1H, q, J=6.4 Hz), 7.23(4H, s), 7.99(1H, s). MS(EI): 221(M⁺);

(2) N-(1-(4-(1-Chloroethyl)phenyl)-1-methylethyl)acetamide

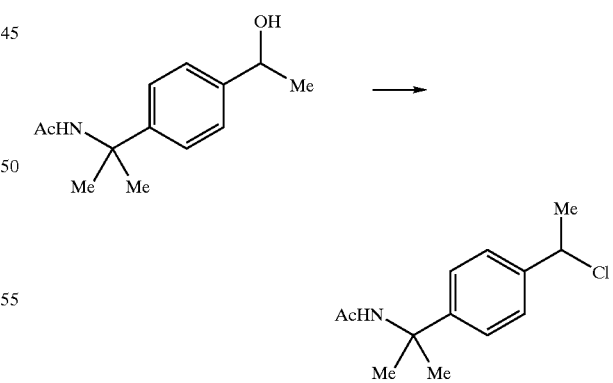

N-(1-(4-(1-Hydroxyethyl)phenyl)-1-methylethyl)acetamide was chlorinated in the same manner as in Example 59(3) to give the title compound as white crystals.

$^1$H-NMR(CDCl$_3$)δ: 1.67(6H, s), 1.83(3H, d, J=6.6 Hz), 1.95(3H, s), 5.07(1H, q, J=6.8 Hz), 5.88(1H, brs), 7.39(4H, s). MS(EI): 239(M⁺).

(3) N-(1-(4-(1-(4-(4-Fluorophenyl)piperazin-1-yl)ethyl)phenyl)-1-methylethyl)acetamide

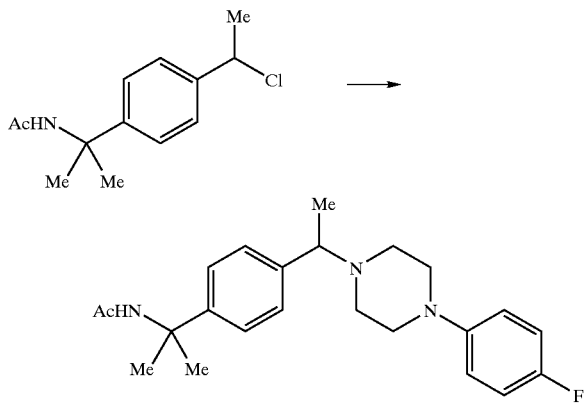

By similar reaction and treatment to that in Example 1(5) using 1-(4-fluorophenyl)piperazine dihydrochloride instead of phenylpiperazine and N-(1-(4-(1-chloroethyl)phenyl)-1-methylethyl)acetamide instead of N-(4-chloromethylphenylmethyl)acetamide, the title compound was obtained as white crystals.

m.p.=156–157° C. $^1$H-NMR(DMSO-$d_6$)δ: 1.30(3H, d, J=6.6 Hz), 1.53(6H, s), 1.83(3H, s), 2.40–2.56(4H, m), 3.03(4H, t, J=4.6 Hz), 3.38(1H, m), 6.87–7.05(4H, m), 7.21(2H, d, J=8.6 Hz), 7.26(2H, d, J=8.6 Hz), 7.98(1H, s) IR(KBr): 3327, 2818, 1659, 1547, 1512 cm$^{-1}$; MS(EI): 383(M$^+$); Elemental analysis: Calculated: C; 72.03, H; 7.88, N; 10.96; Found: C; 71.90, H; 7.99, N; 10.76.

Example 61

Synthesis of N-(1-(4-(1-(4-(2,4-Difluorophenyl)-piperazin-1-yl)ethyl)phenyl)-1-methylethyl)acetamide

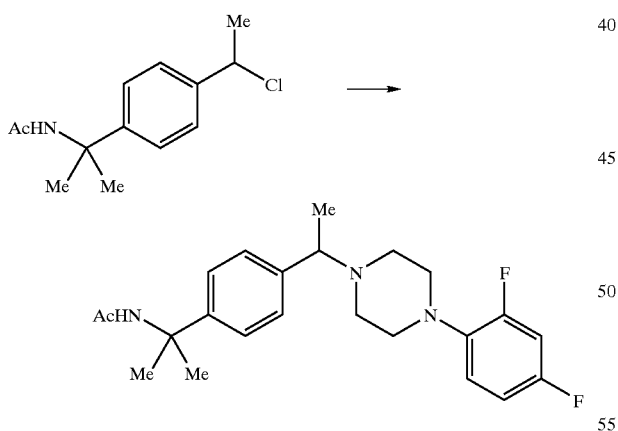

By similar reaction and treatment to that in Example 1(5) using 1-(2,4-difluorophenyl)piperazine dihydrochloride instead of phenylpiperazine and N-(1-(4-(1-chloroethyl)phenyl)-1-methylethyl)acetamide obtained in Example 60(2) instead of N-(4-chloromethylphenylmethyl) acetamide, the title compound was obtained as a white amorphous solid.

$^1$H-NMR(DMSO-$d_6$)δ: 1.30(3H, d, J=6.6 Hz), 1.53(6H, s), 1.83(3H, s), 2.42–2.57(4H, m), 2.93(4H, m), 3.39(1H, q, J=6.6 Hz), 6.92–7.18(3H, m), 7.21(2H, d, J=8.6 Hz), 7.27(2H, d, J=8.6 Hz), 7.99(1H, s). IR(KBr): 3331, 2975, 2821, 1659, 1547, 1508 cm$^{-1}$; MS(EI): 401(M$^+$); Elemental analysis: Calculated: C; 68.80, H; 7.28, N; 10.47; Found: C; 68.76, H; 7.38, N; 10.28.

Example 62

Synthesis of N-(1-(4-(1-(4-Phenylpiperazin-1-yl)ethyl)-phenyl)-1-methylethyl)acetamide

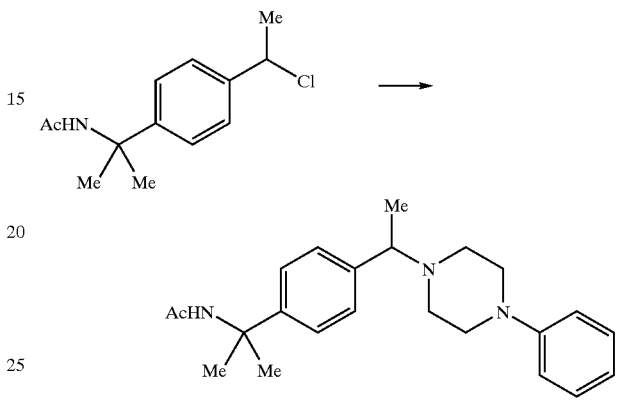

By similar reaction and treatment to that in Example 1(5) using N-(1-(4-(1-chloroethyl)phenyl)-1-methylethyl)acetamide obtained in Example 103(2) instead of N-(4-chloromethylphenylmethyl) acetamide, the title compound was obtained as white crystals.

m.p.=169–171° C.; $^1$H-NMR(DMSO-$d_6$)δ: 1.31(3H, d, J=7.3 Hz), 1.53(6H, s), 1.83(3H, s), 2.38–2.58 (4H, m), 3.09(4H, t, J=4.6 Hz), 3.38(1H, q, J=6.6 Hz), 6.75(1H, t, J=7.3 Hz), 6.88(2H, d, J=7.9 Hz), 7.18(2H, t, J=7.3 Hz), 7.22(2H, d, J=8.6 Hz), 7.27(2H, d, J=8.6 Hz), 7.98(1H, s); IR(KBr): 3286, 2974, 2823, 1655, 1603 cm$^{-1}$; MS(EI): 365(M$^+$); Elemental analysis: Calculated: C; 75.58, H; 8.55, N; 11.50; Found: C; 75.28, H; 8.60, N; 11.41.

Example 63

Synthesis of N-(4-(1-(4-(2,4-Difluorophenyl)piperazin-1-yl)ethyl)phenylmethyl)acetamide

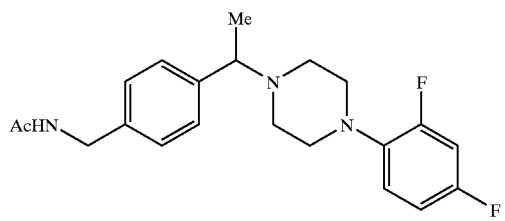

By similar reaction and treatment to that in the above-mentioned Examples, the title compound was obtained.

m.p.=96–97° C.

Example 64

Synthesis of N-(4-(1-(4-(4-Fluorophenyl)piperazin-1-yl)propyl)phenylmethyl)acetamide

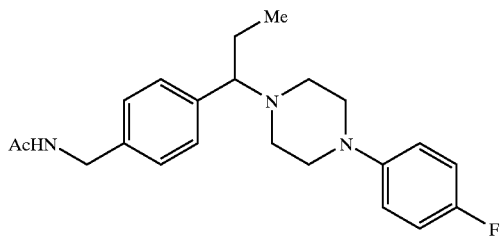

By similar reaction and treatment to that in the above-mentioned Examples, the title compound was obtained.

m.p.=134–135° C.

Example 65

Synthesis of N-(1-(4-((4-(4-Fluorophenyl)piperazin-1-yl)methyl)phenyl)cyclopropyl)acetamide (1) Synthesis of Methyl 1-(4-((4-(4-Fluorophenyl)piperazin-1-yl)methyl)phenyl)cyclopropanecarboxylate

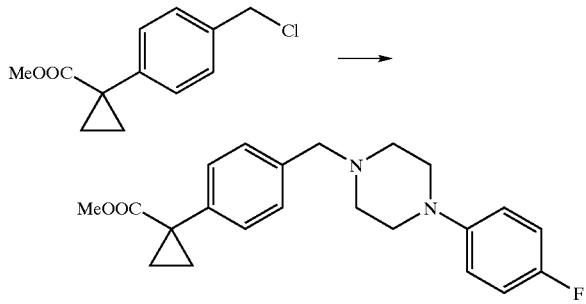

By similar reaction and treatment to that in Example 1(5) using methyl 1-(4-chloromethylphenyl)cyclopropanecarboxylate obtained in Example 75(2) instead of N-(4-chloromethylphenylmethyl)acetamide and 1-(4-fluorophenyl)piperazine dihydrochloride instead of phenylpiperazine, the title compound was obtained as a pale-yellow oil.

$^1$H-NMR(CDCl$_3$)δ: 1.16–1.20(2H, m), 1.58–1.62(2H, m), 2.59–2.63(4H, m), 3.09–3.13(4H, m), 3.55(2H, s), 3.62 (3H, s), 6.83–6.98(4H, m), 7.25–7.32(4H, m). MS(EI): 368(M$^+$).

(2) Synthesis of 1-(4-((4-(4-Fluorophenyl)piperazin-1-yl)methyl)phenyl)cyclopropanecarboxylic Acid

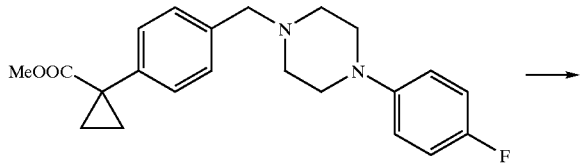

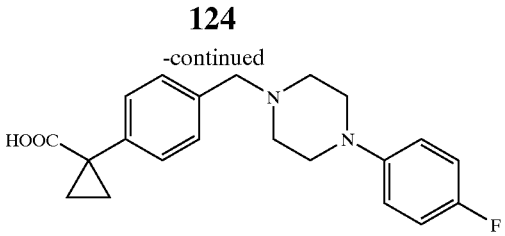

Methyl 1-(4-((4-(4-fluorophenyl)piperazin-1-yl)methyl)phenyl)cyclopropanecarboxylate (2.26 g) was dissolved in ethanol (18 ml) and a solution of sodium hydroxide (0.49 g) in water (4.6 ml) was added, and the mixture was heated at 70° C. for 2 hr. The solvent was evaporated, and the residue was dissolved in water (200 ml). The solution was neutralized with hydrochloric acid and extracted with ethyl acetate (300 ml). The extract was washed with saturated brine and dried over anhydrous magnesium sulfate. The solvent was evaporated to give the title compound (1.73 g) as white crystals, m.p.=74–77° C.

$^1$H-NMR(CDCl$_3$)δ: 1.13–1.17(2H, m), 1.57–1.65(2H, m), 2.76–2.79(4H, m), 3.11–3.12(4H, m), 3.62(2H, s), 6.81–6.98(4H, m), 7.22–7.34(4H, m), 7.70(1H, br.s). MS(EI): 354(M$^+$).

(3) Synthesis of N-(1-(4-((4-(4-Fluorophenyl)piperazin-1-yl)methyl)phenyl)cyclopropyl)acetamide

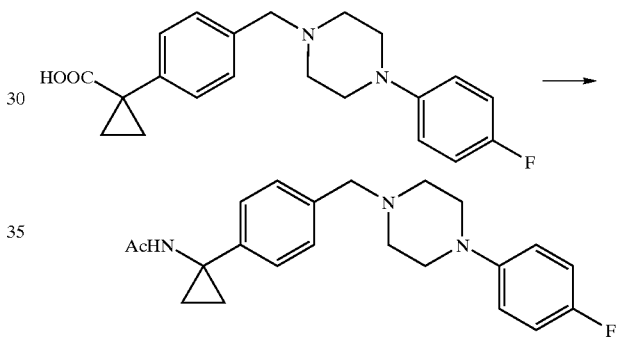

To a suspension of 1-(4-((4-(4-fluorophenyl)piperazin-1-yl)methyl)phenyl)cyclopropanecarboxylic acid (1.73 g) in water (1.7 ml) was added acetone (7 ml) and dissolved therein. A solution of triethylamine (0.75 ml) in acetone (10 ml) was added under ice-cooling and a solution of ethyl chlorocarbonate (0.56 ml) in acetone (4 ml) was added dropwise over 15 min. The mixture was stirred at 0° C. for 30 min. To this solution was added dropwise a solution of sodium azide (0.48 g) in water (3 ml) under ice-cooling over 10 min. The mixture was stirred for 30 min. The reaction mixture was poured into ice water (100 ml) and extracted with diethyl ether. The extract was dried over anhydrous magnesium sulfate and the solvent was evaporated to give an oil. The oil was dissolved in toluene (17 ml) and heated at 100° C. for 1 hr. The reaction mixture was ice-cooled and methylmagnesium iodide (1M, diethyl ether solution) (4.3 ml) was added. The mixture was stirred at room temperature for 30 min. The reaction mixture was poured into aqueous ammonium chloride and extracted with water and ethyl acetate (100 ml). The extract was washed with saturated brine and dried over anhydrous magnesium sulfate. The solvent was evaporated and the obtained residue was purified by silica gel column chromatography (developing solvent; ethyl acetate:methanol=100:1) and recrystallized from ethyl acetate-isopropyl ether to give the title compound (0.52 g) as white crystals.

m.p.=124–126° C. $^1$H-NMR(CDCl$_3$)δ: 1.26 and 1.36(4H, s and d, J=4.0 Hz), 2.00(3H, s), 2.56–2.62(4H, m), 3.08–3.13(4H, m), 3.51 and 3.54(2H, s and s), 6.09 and 6.12(1H, s and s), 6.83–6.98(4H, m), 7.10–7.32(4H, m). MS(EI): 367(M⁺); Elemental analysis: Calculated: C; 71.91, H; 7.13, N; 11.44; Found: C; 71.57, H; 7.23, N; 11.41.

Example 66

Synthesis of N-(1-(4-((4-(2,4-Difluorophenyl)-piperazin-1-yl)methyl)phenyl)cyclopropyl)acetamide (1) Synthesis of Methyl 1-(4-((4-(2,4-difluorophenyl) piperazin-1-yl)methyl)phenyl)cyclopropanecarboxylate

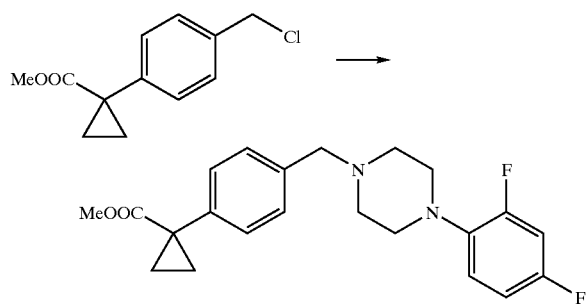

By similar reaction and treatment to that in Example 1(5) using methyl 1-(4-chloromethylphenyl)cyclopropanecarboxylate obtained in Example 75(2) instead of N-(4-chloromethylphenylmethyl)acetamide and 1-(2,4-difluorophenyl)piperazine dihydrochloride instead of phenylpiperazine, the title compound was obtained as an orange oil.

¹H-NMR(CDCl₃)δ: 1.11–1.20(2H, m), 1.58–1.62(2H, m), 2.61–2.65(4H, m), 3.02–3.06(4H, m), 3.56(2H, s), 3.62(3H, s), 6.74–6.94(3H, m), 7.25–7.32(4H, m). MS(EI): 386(M⁺).

(2) Synthesis of 1-(4-((4-(2,4-Difluorophenyl)piperazin-1-yl)methyl)phenyl)cyclopropanecarboxylic Acid

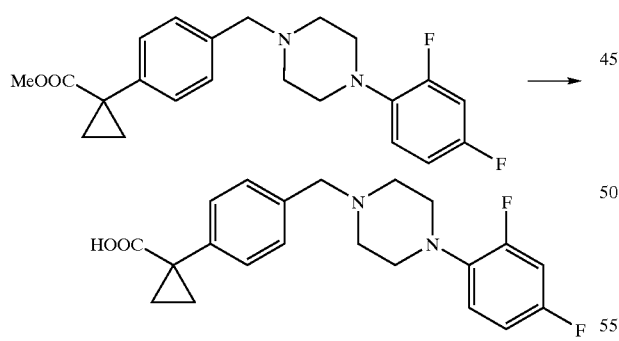

By similar reaction and treatment to that in Example 65(2) using methyl 1-(4-((4-(2,4-difluorophenyl)piperazin-1-yl)methyl)phenyl)cyclopropanecarboxylate instead of methyl 1-(4-((4-(4-fluorophenyl)piperazin-1-yl)methyl)phenyl)cyclopropanecarboxylate, the title compound was obtained as white crystals.

m.p.=70–74° C.; ¹H-NMR(CDCl₃)δ: 1.13–1.19(2H, m), 1.57–1.65(2H, m), 2.81(4H, m), 3.04–3.05(4H, m), 3.62(2H, s), 6.73–7.36(8H, m); MS(EI): 372(M⁺).

(3) Synthesis of N-(1-(4-((4-(2,4-Difluorophenyl)piperazin-1-yl)methyl)phenyl)cyclopropyl)acetamide

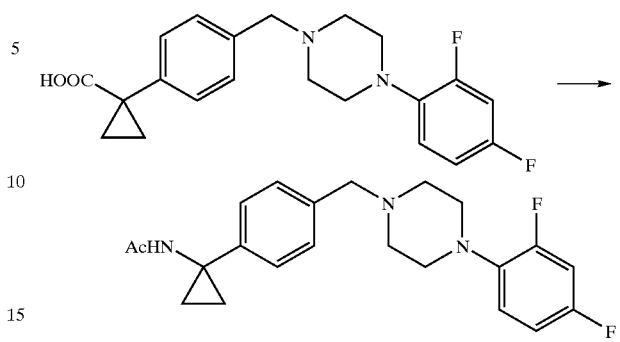

By similar reaction and treatment to that in Example 65(3) using 1-(4-((4-(2,4-difluorophenyl)piperazin-1-yl)methyl)phenyl)cyclopropanecarboxylic acid instead of 1-(4-((4-(4-fluorophenyl)-piperazin-1-yl)methyl)phenyl)cyclopropanecarboxylic acid, the title compound was obtained as white crystals.

m.p.=124–125° C.; ¹H-NMR(CDCl₃)δ: 1.26 and 1.32 (4H, s and d, J=4.0 Hz), 2.00(3H, s), 2.58–2.63(4H, m), 3.00–3.04(4H, m), 3.52 and 3.55(2H, s and s), 6.11 and 6.13(1H, s and s), 6.75–6.93(3H, m), 7.09–7.32(4H, m). MS(EI): 385(M⁺); Elemental analysis: Calculated: C; 68.55, H; 6.54, N; 10.90; Found: C; 68.50, H; 6.61, N; 10.96.

Example 67

Synthesis of N-(1-(4-(1-(4-(4-Fluorophenyl) piperazin-1-yl) ethyl)phenyl)cyclopropyl)acetamide (1) Synthesis of N-(1-Phenylcyclopropyl)acetamide

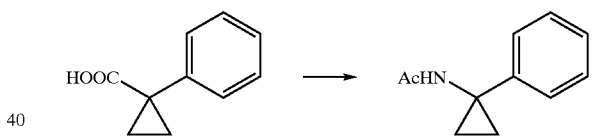

By similar reaction and treatment to that in Example 65(3) using 1-phenylcyclopropanecarboxylic acid instead of 1-(4-((4-(4-fluorophenyl)piperazin-1-yl)methyl)phenyl)cyclopropanecarboxylic acid, the title compound was obtained as pale-yellow crystals, m.p.=94–95° C.

¹H-NMR(CDCl₃)δ: 1.24 and 1.33–1.36(4H, s and m), 1.96 and 1.97(3H, s and s), 6.36(1H, br.s), 7.13–7.35(5H, m). MS(EI): 175(M⁺).

(2) Synthesis of N-(1-(4-Acetylphenyl)cyclopropyl)acetamide

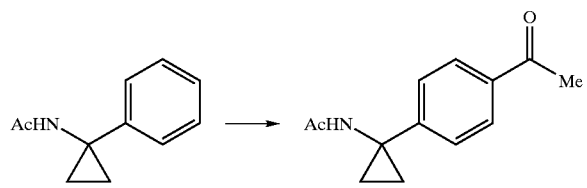

By similar reaction and treatment to that in Example 16(2) using N-(1-phenylcyclopropyl)acetamide instead of N-phenylmethylacetamide, the title compound was obtained as white crystals, m.p.=128–131° C.

¹H-NMR(CDCl₃)δ: 1.33 and 1.46(4H, s and s), 1.96 and 2.02(3H, s and s), 2.56 and 2.59(3H, s and s), 6.26 and 6.36(1H, br.s and br.s), 7.21–7.28(2H, m), 7.84–7.93(2H, m). MS(EI): 217(M+).

(3) Synthesis of N-(1-(4-(1-Hydroxyethyl)phenyl)cyclopropyl)acetamide

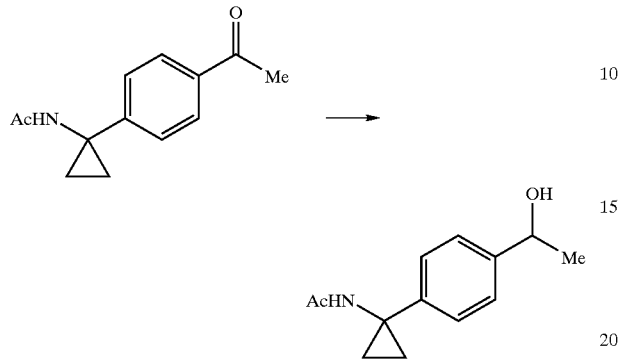

By similar reaction and treatment to that in Example 16(3) using N-(1-(4-acetylphenyl)cyclopropyl)acetamide instead of N-((4-acetylphenyl)methyl) acetamide, the title compound was obtained as white crystals, m.p.=114–116° C.

$^1$H-NMR(CDCl$_3$)δ: 1.25 and 1.35(4H, s and d, J=3.3 Hz), 1.46 and 1.50(3H, d, J=6.6 Hz and s), 1.87 and 1.92(1H, d, J=4.0 Hz and d, J=3.3 Hz), 1.97 and 1.98(3H, s and s), 4.82–4.90(1H, m), 6.17(1H, br.s), 7.11–7.35(4H, m). MS(EI): 219(M+).

(4) Synthesis of N-(1-(4-(1-Chloroethyl)phenyl)cyclopropyl)acetamide

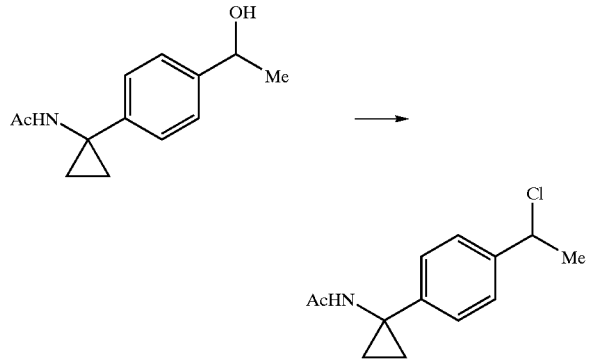

By similar reaction and treatment to that in Example 16(4) using N-(1-(4-(1-hydroxyethyl)phenyl)cyclopropyl)acetamide instead of N-((4-(1-hydroxyethyl)phenyl)methyl)acetamide, the title compound was obtained as white crystals, m.p.=104–107° C.

$^1$H-NMR(CDCl$_3$)δ: 1.25 and 1.35–1.38(4H, s and m), 1.81 and 1.85(3H, d, J=6.6 Hz and s), 1.98(1H, s), 5.06(1H, q, J=6.6 Hz), 6.25 and 6.29(1H, br.s and br.s), 7.11–7.40(4H, m). MS(EI): 237(M+).

(5) Synthesis of N-(1-(4-(1-(4-(4-Fluorophenyl)piperazin-1-yl)ethyl)phenyl)cyclopropyl)acetamide

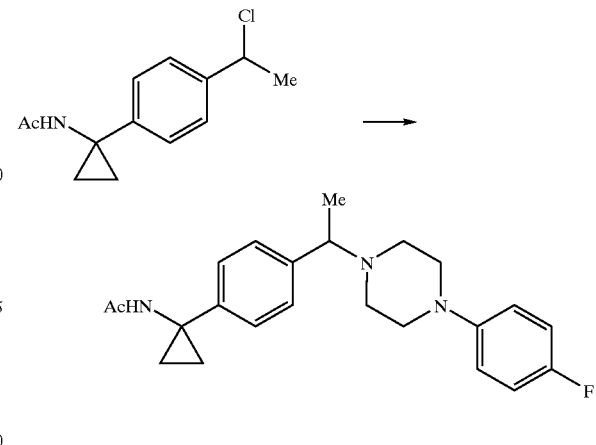

By similar reaction and treatment to that in Example 1(5) using N-(1-(4-(1-chloroethyl)phenyl)cyclopropyl)acetamide instead of N-(4-chloromethylphenylmethyl)acetamide and 1-(4-fluorophenyl)piperazine dihydrochloride instead of phenylpiperazine, the title compound was obtained as white crystals, m.p.=149–150° C.

$^1$H-NMR(CDCl$_3$)δ: 1.26(3H, s), 1.35–1.39(4H, m), 2.00 (3H, s), 2.48–2.66(4H, m), 3.05–3.10(4H, m), 3.32–3.45 (1H, m), 6.12–6.14(1H, m), 6.81–6.98(4H, m), 7.08–7.30 (4H, m). MS(EI): 381(M+); Elemental analysis: Calculated: C; 72.41, H; 7.40, N; 11.01; Found: C; 72.33, H; 7.39, N; 10.94.

Example 68

Synthesis of N-(4-(1-(4-(4-Fluorophenyl)piperazin-1-yl)-1-methylethyl)phenylmethyl)acetamide dihydrochloride monohydrate (1) Synthesis of 2-(4-Methylphenyl)-2-methylpropionitrile

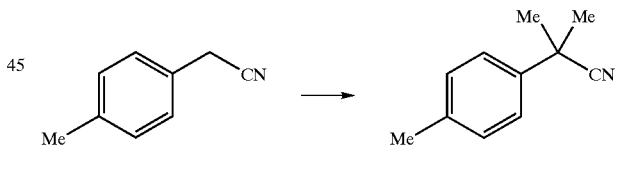

A suspension of 60% sodium hydride (50 g) and tetrahydrofuran (225 ml) was heated to 40° C. and a solution of 4-methylphenylacetonitrile (74.5 g) in tetrahydrofuran (75 ml) was added dropwise over 30 min. The mixture was stirred at 40° C. for 30 min and a solution of methyl iodide (78 ml) in tetrahydrofuran (75 ml) was added dropwise over 30 min. The mixture was stirred at 40° C. for 1 hr. The reaction mixture was poured into water (2000 ml) and extracted with ethyl acetate. The extract was washed with saturated brine and dried over anhydrous magnesium sulfate. The solvent was evaporated and the obtained residue was purified by distillation under reduced pressure to give the title compound (83.66 g) as a colorless oil.

Boiling point=88–91° C./4 mmHg; $^1$H-NMR(CDCl$_3$)δ: 1.70(6H, s), 2.34(3H, s), 7.19(2H, d, J=7.9 Hz), 7.35(2H, d, J=7.9 Hz). MS(EI): 159(M+).

(2) Synthesis of 2-(4-Methylphenyl)-2-methylpropionic Acid

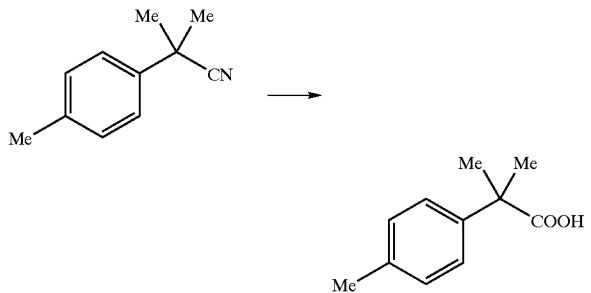

A solution of 2-(4-methylphenyl)-2-methylpropionitrile (53.61 g), sodium hydroxide (40.4 g), diethylene glycol (160.8 ml) and water (60.6 ml) was refluxed for 18 hr. The reaction mixture was poured into water (3000 ml) and conc. hydrochloric acid (90 ml) was added. The generated crystals were collected by filtration to give the title compound (60.0 g) as pale-brown crystals, m.p.=78–81° C.

$^1$H-NMR(CDCl$_3$)δ: 1.57(6H, s), 2.32(3H, s), 7.14(2H, d, J=8.6 Hz), 7.28(2H, d, J=8.6 Hz). MS(EI): 178(M$^+$).

(3) Synthesis of Methyl 2-(4-Methylphenyl)-2-methylpropionate

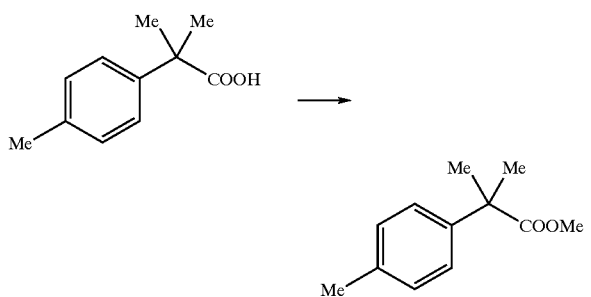

A solution of 2-(4-methylphenyl)-2-methylpropionic acid (60.0 g), sulfuric acid (0.6 ml) and methanol (300 ml) was refluxed for 19 hr. The solvent was evaporated, and water (200 ml) was added and the mixture was extracted with chloroform. The extract was washed with saturated brine and dried over anhydrous magnesium sulfate. The solvent was evaporated to give the title compound (61.52 g) as a pale-brown oil. $^1$H-NMR(CDCl$_3$)δ:1.56(6H, s), 2.32(3H, s), 3.64(3H, s), 7.13(2H, d, J=8.6 Hz), 7.22(2H, d, J=8.6 Hz). MS(EI): 192(M$^+$).

(4) Synthesis of Methyl 2-(4-Azidomethylphenyl)-2-methylpropionate

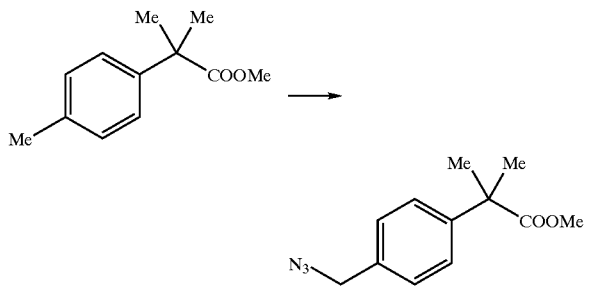

A solution of methyl 2-(4-methylphenyl)-2-methylpropionate (58.5 g), N-bromosuccinimide (54.2 g), benzoyl peroxide (1.2 g) and carbon tetrachloride (300 ml) was refluxed for 40 min. After being cooled, the reaction mixture was filtrated. The filtrate was washed with an aqueous sodium sulfite solution and saturated brine, and dried over anhydrous magnesium sulfate. The solvent was evaporated to give methyl 2-(4-bromomethylphenyl)-2-methylpropionate (80.0 g) as a pale-brown oil. To a solution of this oil in dimethylformamide (500 ml) was added sodium azide (21.14 g) and the mixture was stirred at 80° C. for 40 min. The reaction mixture was poured into water (1000 ml) and extracted with ethyl acetate. The extract was washed with saturated brine and dried over anhydrous magnesium sulfate. The solvent was evaporated and the obtained residue was purified by silica gel column chromatography (developing solvent; hexane,hexane:ethyl acetate=20:1) to give the title compound (48.1 g) as a pale-yellow oil.

$^1$H-NMR(CDCl$_3$)δ: 1.58(6H, s), 3.64(3H, s), 4.31(2H, s), 7.25–7.37(4H, m).

(5) Synthesis of Methyl 2-(4-Aminomethylphenyl)-2-methylpropionate

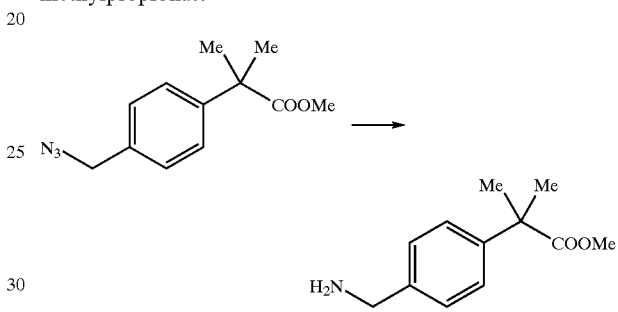

A solution of methyl 2-(4-azidomethylphenyl)-2-methylpropionate (48.1 g)and triphenylphosphine (59.5 g) in a mixed solvent of tetrahydrofuran (480 ml) and water (24 ml) was refluxed for 30 min. The solvent was evaporated, and the obtained residue was purified by silica gel column chromatography (developing solvent; chloroform:methanol=10:1, chloroform:methanol:aqueous ammonia=10:1:0.3) to give the title compound (29.4 g) as a pale-yellow oil.

$^1$H-NMR(CDCl$_3$)δ: 1.57(6H, s), 2.42(3H, s), 3.63(3H, s), 3.83(2H, s), 7.25–7.32(4H, m).

(6) Synthesis of Methyl 2-(4-Acetamidomethylphenyl)-2-methylpropionate

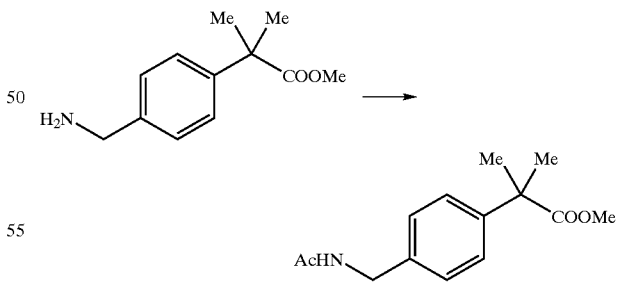

To a solution of methyl 2-(4-aminomethylphenyl)-2-methylpropionate (29.4 g) and triethylamine (23.8 ml) indichloroethane (300 ml) was added dropwise acetyl chloride (11.1 ml) at 5° C. over 30 min. The mixture was stirred at room temperature for 30 min. The reaction mixture was poured into water and the organic layer was separated. The organic layer was washed with saturated brine and dried over anhydrous magnesium sulfate. The solvent was evaporated and the obtained residue was purified by silica gel column chromatography (developing solvent; ethyl acetate:hexane=3:1, ethyl acetate) to give the title compound (23.47 g) as a pale-yellow oil.

$^1$H-NMR(CDCl$_3$)δ: 1.56(6H, s), 1.98(3H, s), 3.63(3H, s), 4.37(2H, d, J=5.3 Hz), 7.21–7.31(4H, m). MS(EI): 249(M$^+$).

(7) Synthesis of 2-(4-Acetamidomethylphenyl)-2-methylpropionic Acid

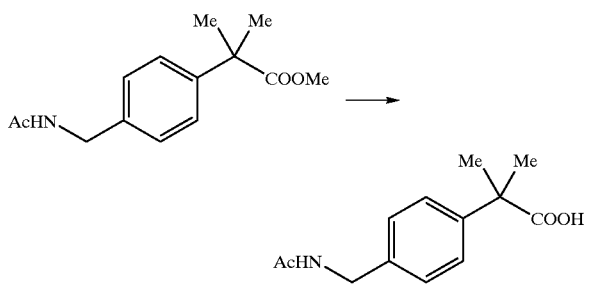

To a solution of methyl 2-(4-acetylaminomethylphenyl)-2-methylpropionate (23.47 g) in ethanol (160 ml) was added a solution of sodium hydroxide (7.53 g) in water (94 ml) and the mixture was stirred at 70° C. for 1 hr. The solvent was evaporated, and conc. hydrochloric acid was added. The resulting crystals were collected by filtration to give the title compound (14.0 g) as pale-yellow crystals, m.p.=166–169° C.

$^1$H-NMR(DMSO-d$_6$)δ: 1.45(6H, s), 1.85(3H, s), 4.21(2H, d, J=5.9 Hz), 7.20(2H, d, J=8.6 Hz), 7.29(2H, d, J=8.6 Hz), 8.28(1H, br), 12.27(1H, br.s). MS(EI): 235(M$^+$).

(8) Synthesis of N-(4-(1-Benzyloxycarbonylamino-1-methylethyl)phenylmethyl)acetamide

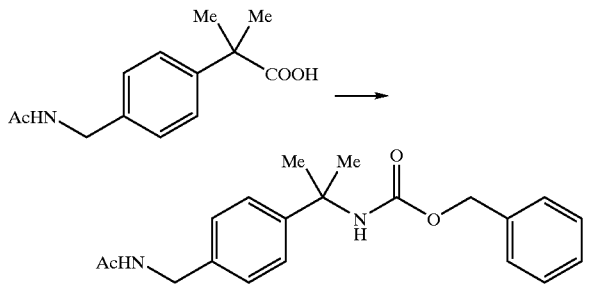

To a solution of 2-(4-acetylaminomethylphenyl)-2-methylpropionic acid (14 g) in a mixed solvent of acetone (40 ml) and dimethylformamide (30 ml) was added triethylamine (8.75 ml) under ice-cooling and a solution of ethyl chlorocarbonate (6.76 g) in acetone (20 ml) was added dropwise over 10 min. The mixture was stirred at 0° C. for 15 min. To this solution was added dropwise a solution of sodium azide (4.26 g) in water (28 ml) under ice-cooling over 10 min, and the mixture was stirred for 30 min. The reaction mixture was poured into ice water (500 ml) and extracted with ethyl acetate. The extract was washed with saturated brine and dried over anhydrous magnesium sulfate. The solvent was evaporated and the obtained oil was dissolved in toluene (100 ml) and heated at 80° C. for 2 hr. To this solution was added benzyl alcohol (6.77 ml) and the mixture was stirred at 80° C. for 42 hr. To the reaction mixture was added isopropyl alcohol to allow crystallization to give the title compound (14.62 g) as white crystals, m.p.=132–135° C.

$^1$H-NMR(DMSO-d$_6$)δ: 1.51(6H, s), 1.86(3H, s), 4.21(4H, d, J=5.3 Hz), 4.93(2H, m), 7.14–7.42(9H, m), 7.65(1H, br.s), 8.26–8.30(1H, br).

(9) Synthesis of N-(4-(1-Amino-1-methylethyl)phenylmethyl)acetamide

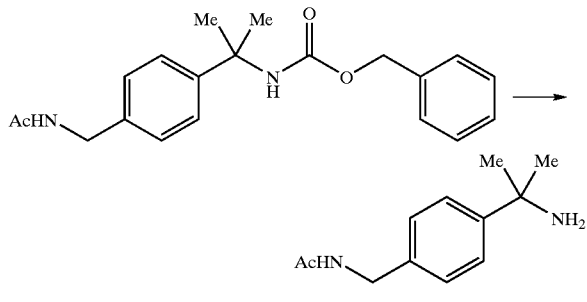

To a solution of N-(4-(1-benzyloxycarbonylamino-1-methylethyl)phenylmethyl)acetamide (9.57 g) in methanol (200 ml) and chloroform (200 ml) was added 10% palladium-carbon (5.0 g) and the mixture was stirred for 5 hr while introducing a hydrogen gas. The reaction mixture was passed through Celite and the solvent was evaporated to give the title compound (5.8 g) as a pale-yellow amorphous solid.

$^1$H-NMR(DMSO-d$_6$)δ: 1.63(6H, s), 1.87(3H, s), 4.23(2H, d, J=5.9 Hz), 7.28(2H, d, J=7.9 Hz), 7.52(2H, d, J=7.9 Hz), 8.47(1H, br), 8.77(2H, br.s).

(10) Synthesis of Ethyl N-Ethoxycarbonylmethyl-N-(4-fluorophenyl)aminoacetate

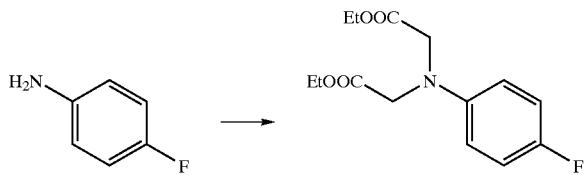

To a solution of 4-fluoroaniline (10 g) and bromoethyl acetate (31.56 g) in dimethylformamide (120 ml) was added potassium carbonate (31.09 g) and the mixture was stirred at 80° C. for 1.5 hr. Bromoethyl acetate (13.5 g) and potassium carbonate (6.22 g) were further added and the mixture was stirred for 3 hr. The reaction mixture was poured into water (500 ml) and extracted with ethyl acetate. The extract was washed with saturated brine and dried over anhydrous magnesium sulfate. The solvent was evaporated and the obtained residue was purified by silica gel column chromatography (developing solvent; hexane:ethyl acetate=7:1, ethyl acetate) to give the title compound (13.51 g) as a yellow oil.

$^1$H-NMR(CDCl$_3$)δ: 1.26(6H, t, J=7.3 Hz), 4.10(2H, s), 4.20(4H, q, J=7.3 Hz), 6.51–6.61(2H, m), 6.86–6.96(2H, m). MS(EI): 283(M$^+$).

(11) Synthesis of N,N-bis(2-Hydroxyethyl)-4-fluorophenylamine

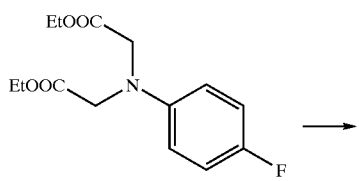

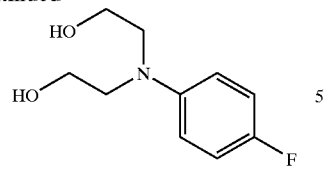

To a solution of N-ethoxycarbonylmethyl-N-(4-fluorophenyl)-aminoethyl acetate (13.51 g) in tetrahydrofuran (135 ml) was added lithium borohydride (4.15 g) and the mixture was stirred at 60° C. for 1 hr. The reaction mixture was poured into water (300 ml) and extracted with ethyl acetate. The extract was washed with saturated brine and dried over anhydrous magnesium sulfate. The solvent was evaporated to give the title compound (9.2 g) as a yellow oil.

$^1$H-NMR(CDCl$_3$)δ: 3.42–3.46(4H, m), 3.71–3.74(4H, m), 4.24(2H, br.s), 6.56–6.64(2H, m), 6.87–6.94(2H, m). MS(EI): 199(M$^+$).

(12) Synthesis of N,N-bis(2-Chloroethyl)-4-fluorophenylamine

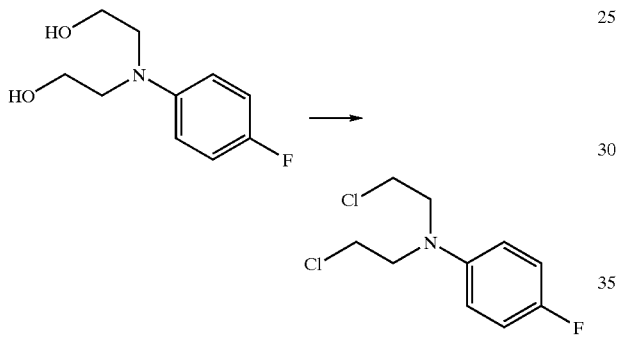

To a solution of N,N-bis(2-hydroxyethyl)-4-fluorophenylamine (9.2 g) in methylene chloride (92 ml) was added dropwise thionyl chloride (7.1 ml) over 10 min under ice-cooling. The mixture was stirred at room temperature for 1 hr and the reaction mixture was further refluxed for 1.5 hr. The mixture was poured into aqueous sodium hydrogencarbonate to make it alkaline and the organic layer was separated. The organic layer was washed with saturated brine and dried over anhydrous magnesium sulfate. The solvent was evaporated and the obtained residue was purified by silica gel column chromatography (developing solvent; hexane:ethyl acetate=10:1) to give the title compound (4.88 g) as an organge oil.

$^1$H-NMR(CDCl$_3$)δ: 3.56–3.70(8H, m), 6.60–6.67(2H, m), 6.91–7.00(2H, m).

(13) Synthesis of N-(4-(1-(4-(4-Fluorophenyl)piperazin-1-yl)-1-methylethyl)phenylmethyl)acetamide Dihydrochloride Monohydrate

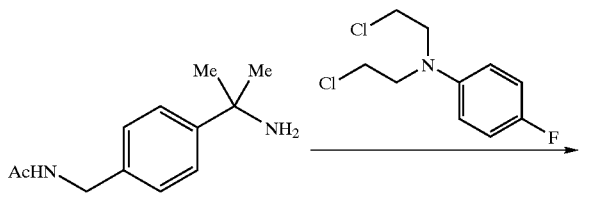

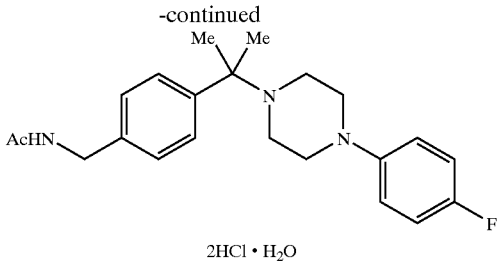

To a solution of N-(4-(1-amino-1-methylethyl)phenylmethyl)-acetamide (1.55 g) and N,N-di(2-chloroethyl)-4-fluoroaniline (1.5 g) in dimethyl sulfoxide (30 ml) were added potassium carbonate (3.12 g) and potassium iodide (2.50 g) and the mixture was stirred at 80° C. for 24 hr. The reaction mixture was poured into water (300 ml) and extracted with ethyl acetate. The extract was washed with saturated brine and dried over anhydrous sodium sulfate. The solvent was evaporated and the obtained residue was purified by silica gel chromatography (developing solvent; ethyl acetate:hexane=3:1) and treated with 1M hydrochloric acid-ether in ethanol to give the title compound (0.33 g) as white crystals.

m.p.=179–181° C.; $^1$H-NMR(DMSO-d$_6$)δ: 1.87 and 1.89 (9H, s and s), 2.88–2.96(2H, m), 3.35–3.44(4H, m), 3.61–3.66(2H, m), 4.28(2H, d, J=5.9 Hz), 6.95–7.12(4H, m), 7.36(2H, d, J=8.6 Hz), 7.82(2H, d, J=8.6 Hz), 8.48(1H, t, J=5.9 Hz). MS(EI): 369(M$^+$); Elemental analysis: Calculated: C; 57.39, H; 7.01, N; 9.13; Found: C; 57.63, H; 6.96, N; 9.19.

Example 69

Synthesis of N-(1-(4-((4-(Pyrimidin-2-yl)piperazin-1-yl)methyl)phenyl)ethyl)acetamide

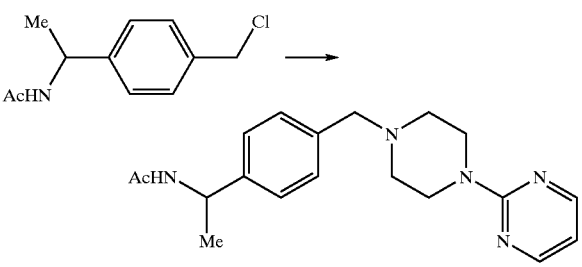

By similar reaction and treatment to that in Example 1(5) using 1-(2-pyrimidyl)piperazine instead of phenylpiperazine and N-(1-(4-chloromethylphenyl)ethyl)acetamide obtained in Example 66(3) instead of N-(4-chloromethylphenylmethyl)acetamide, the title compound was obtained as white crystals.

m.p.=124–126° C.; $^1$H-NMR(DMSO-d$_6$)δ: 1.33(3H, d, J=7.3 Hz), 1.84(3H, s), 2.40(4H, t, J=5.3 Hz), 3.47(2H, s), 3.72(4H, t, J=5.0 Hz), 4.91(1H, dq, J=7.3, 7.3 Hz), 6.60(1H, t, J=5.0 Hz), 7.27(4H, s), 8.25(1H, d, J=7.9 Hz), 8.34(2H, d, J=4.6 Hz). IR(KBr): 3309, 1643, 1587, 1547 cm$^{-1}$; MS(EI): 339(M$^+$); Elemental analysis: Calculated: C; 67.23, H; 7.42, N; 20.63; Found: C; 67.18, H; 7.50, N; 20.52.

Example 70

Synthesis of N-(1-(4-(1-(4-(Pyrimidin-2-yl)piperazin-1-yl)ethyl)phenyl)cyclopropyl)acetamide

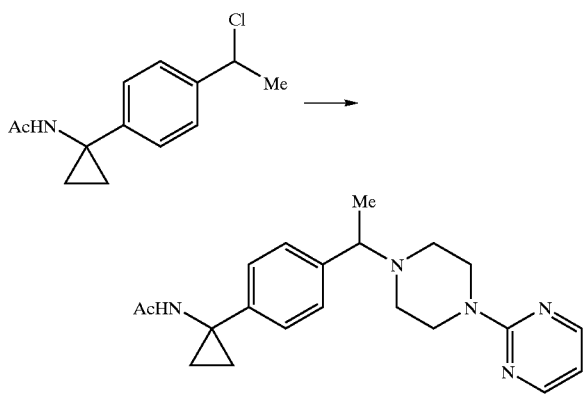

By similar reaction and treatment to that in Example 1(5) using N-(1-(4-(1-chloroethyl)phenyl)cyclopropyl)acetamide instead of N-(4-chloromethylphenylmethyl)acetamide and 1-(2-pyrimidyl)piperazine dihydrochloride instead of phenylpiperazine, the title compound was obtained as white crystals, m.p.=124–125° C.

$^1$H-NMR(CDCl$_3$)δ: 1.26(3H, s), 1.34–1.41(4H, m), 2.00 (3H, s), 2.38–2.54(4H, m), 3.33–3.45(1H, m), 3.76–3.81 (4H, m), 6.10 and 6.16(1H, s and s), 6.42–6.46(1H, m), 7.08–7.30(4H, m), 8.27(2H, d, J=4.6 Hz). MS(EI): 365(M$^+$); Elemental analysis: Calculated: C; 69.01, H; 7.45, N; 19.16; Found: C; 68.97, H; 7.47, N; 19.05.

Example 71

Synthesis of N-(1-(4-((4-(Pyrimidin-2-yl)piperazin-1-yl)methyl)phenyl)cyclopropyl)acetamide (1) Synthesis of N-(1-(4-Chloromethylphenyl)cyclopropyl)acetamide

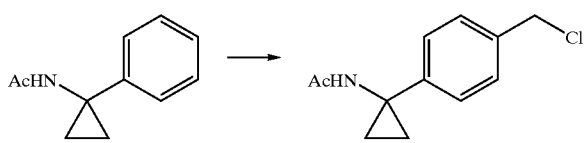

To a solution of N-(1-phenylcyclopropyl)acetamide (5.0 g) in methylene chloride (35 ml) was added titanium tetrachloride (6.26 ml) under ice-cooling and to this solution was added dropwise a solution of methoxymethyl chloride (4.33 ml) in methylene chloride (15 ml) over 10 min under ice-cooling. The mixture was stirred at room temperature for 14 hr. The reaction mixture was poured into ice water and extracted with chloroform (50 ml). The extract was washed with saturated brine and dried over anhydrous magnesium sulfate. The solvent was evaporated and the obtained residue was purified by silica gel column chromatography (developing solvent; ethyl acetate) to give the title compound (3.71 g) as white crystals, m.p.=124–127° C.

$^1$H-NMR(CDCl$_3$)δ: 1.25 and 1.37(4H, s and s), 1.98(3H, s), 4.54 and 4.57(2H, s and s), 6.17–6.28(1H, m), 7.12–7.36 (4H, m). MS(EI): 223(M$^+$).

(2) Synthesis of N-(1-(4-((4-(Pyrimidin-2-yl)piperazin-1-yl)methyl)phenyl)cyclopropyl)acetamide

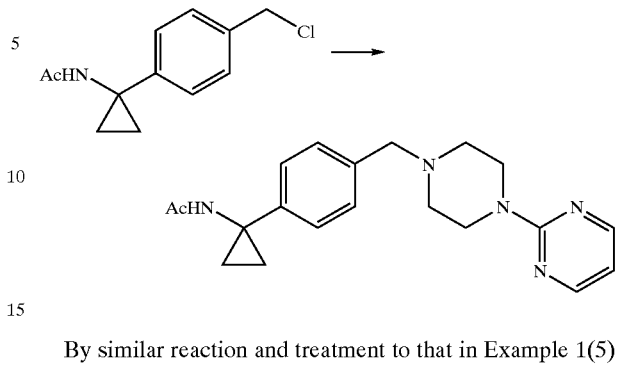

By similar reaction and treatment to that in Example 1(5) using N-(1-(4-chloromethylphenyl)cyclopropyl)acetamide instead of N-(4-chloromethylphenylmethyl)acetamide and 1-(2-pyrimidyl)piperazine dihydrochloride instead of phenylpiperazine, the title compound was obtained as white crystals, m.p.=145–146° C.

$^1$H-NMR(CDCl$_3$)δ: 1.26 and 1.36(4H, s and d, J=5.3 Hz), 2.00(3H, s), 2.45–2.51(4H, m), 3.49 and 3.52(2H, s and s), 3.79–3.84(4H, m), 6.14(1H, s), 6.44–6.48(1H, m), 7.09–7.32(4H, m), 8.29(2H, d, J=4.6 Hz). MS(EI): 351(M$^+$); Elemental analysis: Calculated: C; 68.35, H; 7.17, N; 19.93; Found: C; 68.30, H; 7.07, N; 19.77.

Example 72

Synthesis of N-(4-((4-(Pyrimidin-2-yl)piperazin-1-yl)methyl)phenylmethyl)acetamide (1) 4-Acetamidomethylbenzoic Acid

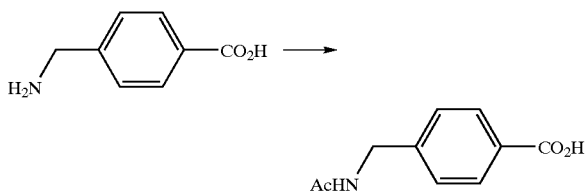

To a solution of 4-(aminomethyl)benzoic acid (20.46 g) in ethyl acetate (100 ml) was added an aqueous solution (100 ml) of sodium hydroxide (12 g) and acetic anhydride (14 ml) was further added at 5–7° C. The reaction mixture was stirred at room temperature for 1 hr. The reaction mixture was made acidic with 10% hydrochloric acid and extracted with ethyl acetate:ethanol (10:1). The extract was washed with saturated brine and dried over anhydrous sodium sulfate. The solvent was evaporated to give a pale-yellow solid (27.2 g). The obtained solid was crystallized from ethyl acetate:ethanol (1:1, 500 ml) to give the title compound (16.7 g) as white crystals, m.p.=200–202° C.

$^1$H-NMR(DMSO-d$_6$)δ: 1.89(3H, s), 4.32(2H, d, J=5.9 Hz), 7.36(2H, d, J=7.9 Hz), 7.89(2H, d, J=8.6 Hz), 8.41(1H, m), 12.84(1H, br.s); IR(KBr): 3298, 1691, 1646, 1539 cm$^{-1}$; MS(EI): 193(M$^+$); Elemental analysis: Calculated: C; 62.17, H; 5.74, N; 7.25; Found: C; 62.01, H; 5.71, N; 7.21.

(2) Methyl 4-Acetamidomethylbenzoate

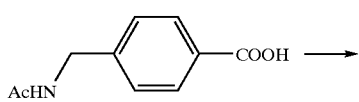

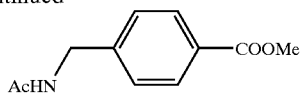

4-Acetamidomethylbenzoic acid (4.0 g) was dissolved in 0.5% hydrogen chloride-methanol solution (100 ml). The mixture was stirred at 40° C. for 3.5 hr and poured into ice water (300 ml) and extracted with ethyl acetate. The extract was washed with a saturated aqueous sodium hydrogencarbonate solution and saturated brine, and dried over anhydrous sodium sulfate. The solvent was evaporated to give a pale-yellow solid (4.3 g). The obtained solid was crystallized from ethyl acetate (50 ml) to give the title compound (3.2 g) as a pale-yellow white crystals, m.p.=110–111° C.

$^1$H-NMR(DMSO-$d_6$)δ: 1.90(3H, s), 3.84(3H, s), 4.33(2H, d, J=5.9 Hz), 7.39(2H, d, J=8.6 Hz), 7.92(2H, d, J=7.9 Hz), 8.43(1H, m); IR(KBr): 3277, 1727, 1643, 1556 cm$^{-1}$; MS(EI): 207(M$^+$); Elemental analysis: Calculated: C; 63.76, H; 6.32, N; 6.76; Found: C; 63.76, H; 6.38, N; 6.76.

(3) N-(4-Hydroxymethylphenylmethyl)acetamide

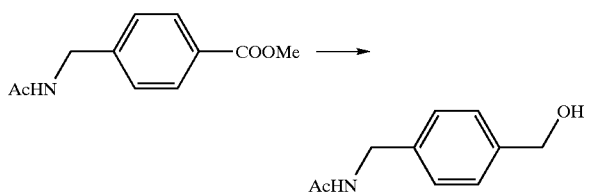

To a suspension of aluminum lithium hydride (570 mg) in tetrahydrofuran (80 ml) was added a solution of methyl 4-acetamidomethylbenzoate (3.1 g) in tetrahydrofuran (20 ml) under ice-cooling. The reaction mixture was stirred at room temperature for 1.5 hr. A saturated aqueous sodium sulfate solution (7 ml) was added at 10° C., and the mixture was stirred at room temperature for 1 hr. The sediment was filtered off and the solvent was evaporated to give the title compound (2.8 g) as a white solid.

$^1$H-NMR(DMSO-$d_6$)δ: 1.86(3H, s), 4.22(2H, d, J=5.9 Hz), 4.46(2H, s), 5.13(1H, br.s), 7.19(2H, d, J=7.9 Hz), 7.25(2H, d, J=8.6 Hz), 8.30(1H, m); MS(EI): 179(M$^+$).

(4) N-(4-Chloromethylphenylmethyl)acetamide

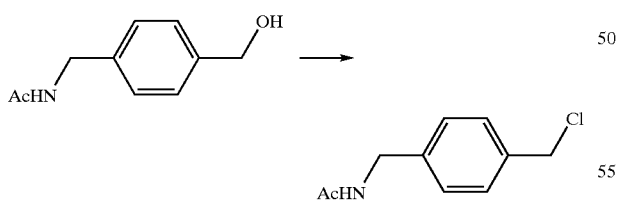

To a solution of N-(4-hydroxymethylphenylmethyl) acetamide (1.5 g) in chloroform (50 ml) was added thionyl chloride (0.73 ml) and the mixture was refluxed under heating for 1 hr. The solvent was evaporated and the obtained residue was crystallized from ethyl acetate to give the title compound (1.8 g) as pale-yellow crystals.

m.p.=116–118° C.; $^1$H-NMR(CDCl$_3$)δ: 2.01(3H, s), 4.40 (2H, d, J=5.9 Hz), 4.56(2H, s), 6.20(1H, br.s), 7.26(2H, d, J=8.6 Hz), 7.34(2H, d, J=7.9 Hz); MS(EI): 197(M$^+$).

(5) N-(4-((4-(Pyrimidin-2-yl)piperazin-1-yl)methyl) phenylmethyl)acetamide

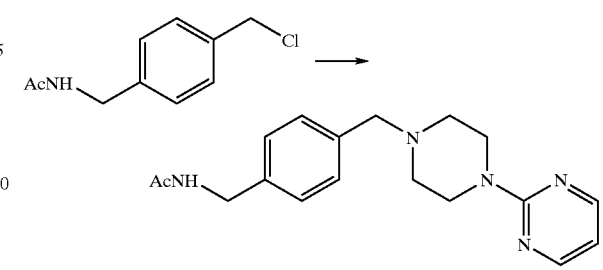

A solution of N-(4-chloromethylphenylmethyl)acetamide (15.0 g), 1-(2-pyrimidyl)piperazine dihydrochloride (19.8 g) and potassium carbonate (42.0 g) in dimethylformamide (200 ml) was stirred at 80° C. for 8.5 hr. The reaction mixture was poured into water (500 ml) and extracted with ethyl acetate. The extract was washed with saturated brine and dried over anhydrous sodium sulfate. The solvent was evaporated to give a brown oil (24.0 g). The obtained brown oil was purified by silica gel column chromatography (developing solvent; chloroform:methanol=20:1) to give a pale-brown oil (18.7 g). The obtained pale-brown oil was crystallized from ethyl acetate: hexane (5:1, 100 ml) and the crystals were recrystallized from ethyl acetate:hexane (10:1, 100 ml) to give the title compound (12.8 g) as white crystals, m.p.=120–121° C. $^1$H-NMR(DMSO-$d_6$)δ: 1.87(3H, s), 2.38–2.42(4H, m), 3.47(2H, s), 3.70–3.73(4H, m), 4.24(2H, d, J=5.9 Hz), 6.60(1H, t, J=4.6 Hz), 7.20–7.29(4H, m), 8.30(1H, t, J=5.3 Hz), 8.34(2H, d, J=4.6 Hz); IR(KBr): 3292, 2792, 1651, 1587 cm$^{-1}$; MS(EI): 325(M$^+$); Elemental analysis: Calculated: C; 66.44, H; 7.12, N; 21.52; Found: C; 66.48, H; 7.19, N; 21.72.

Example 73

Synthesis of N-(4-((4-(Pyrimidin-2-yl)piperazin-1-yl)methyl)phenylmethyl)acetamide Dihydrochloride Monohydrate

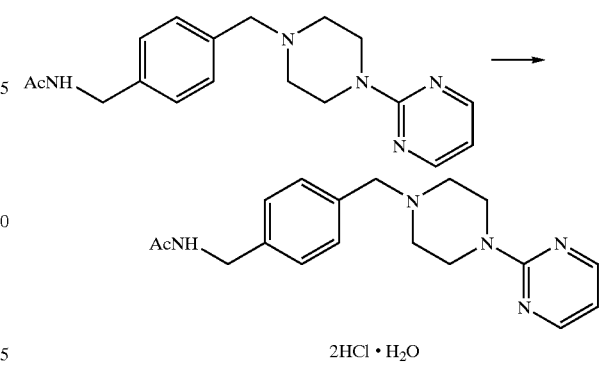

To a solution of N-(4-((4-(pyrimidin-2-yl)piperazin-1-yl) methyl)phenylmethyl)acetamide (5.1 g) in ethanol (40 ml) was added 1M hydrogen chloride—ether (40 ml) and the solvent was evaporated under reduced pressure to give a pale-brown substance (7.2 g). The obtained pale-brown substance was crystallized and recrystallized from ethyl acetate/ethanol to give the title compound (3.8 g) as white crystals, m.p.=194–195° C.

$^1$H-NMR(DMSO-$d_6$)δ: 1.89(3H, s), 2.95–3.10(2H, m), 3.25–3.35(2H, m), 3.40–3.55(2H, m), 4.25–4.32(4H, m), 4.65–4.71(2H, m), 5.20–5.40(3H, m), 6.78(1H, t, J=5.3 Hz), 7.32(2H, d, J=7.9 Hz), 7.61(2H, d, J=7.9 Hz), 8.45(2H, d, J=4.6 Hz), 8.50(1H, t, J=5.9 Hz), 11.80(1H, brs); IR(KBr): 3417, 3290, 1627, 1544 cm$^{-1}$; MS(EI): 325(M$^+$); Elemental analysis: Calculated: C; 51.93, H; 6.54, N; 16.82; Found: C; 52.26, H; 6.40, N; 16.86.

Example 74

Synthesis of 2-(4-(4-(Aminomethyl)phenylmethyl)-piperazin-1-yl)pyrimidine

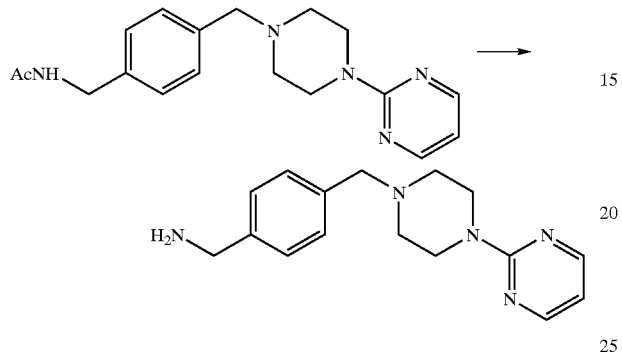

N-(4-((4-(Pyrimidin-2-yl)piperazin-1-yl)methyl)phenylmethyl)acetamide (4.0 g) was dissolved in 10% hydrochloric acid (50 ml) and the solution was refluxed under heating for 12.5 hr. To the reaction mixture was added 10% aqueous sodium hydroxide solution to make it alkaline, and the mixture was extracted with ethyl acetate. The extract was washed with saturated brine and dried over anhydrous sodium sulfate. The solvent was evaporated and the obtained residue was crystallized from diisopropyl ether to give the title compound (2.2 g) as pale-yellow crystals, m.p.=70–72° C.

$^1$H-NMR(DMSO-d$_6$)δ: 2.38–2.42(4H, m), 2.70–3.10(2H, brs), 3.47(2H, s), 3.70–3.73(6H, m), 6.62(1H, t, J=4.6 Hz), 7.23–7.30(4H, m), 8.34(2H, d, J=5.3 Hz); IR(KBr): 3358, 2939, 2817, 1585 cm$^{-1}$; MS(EI): 283(M$^+$); Elemental analysis: Calculated: C; 67.81, H; 7.47, N; 24.71; Found: C; 67.52, H; 7.42, N; 24.12.

Example 75

Synthesis of N-(4-((4-(Pyrimidin-2-yl)piperazin-1-yl)methyl)phenylmethyl)propionamide 1/4 Hydrate

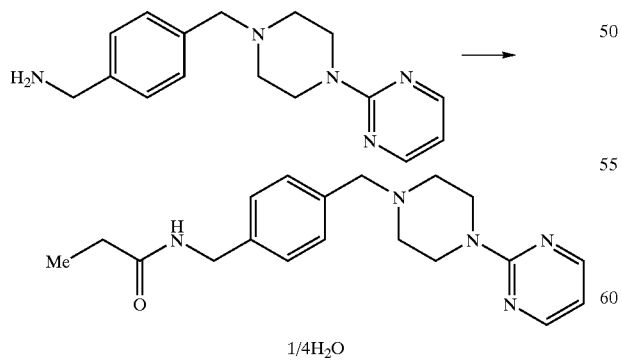

A solution of 2-(4-(4-(aminomethyl)phenylmethyl)piperazin-1-yl)pyrimidine (0.5 g), propionic chloride (0.18 ml) and triethylamine (0.3 ml) in methylene chloride (20 ml) was stirred at room temperature for 2 hr. The reaction mixture was washed with water and dried over anhydrous sodium sulfate. The solvent was evaporated under reduced pressure to give a pale-yellow substance (0.8 g). The obtained pale-yellow substance was crystallized from hexane/ethyl acetate (1:1, 50 ml) to give the title compound (0.5 g) as pale-yellow crystals.

m.p.=103–105° C.; $^1$H-NMR(DMSO-d$_6$)δ: 1.03(3H, t, J=7.9 Hz), 2.15(2H, q, J=7.9 Hz), 2.40–2.43(4H, m), 3.49 (2H, s), 3.70–3.74(4H, m), 4.25(2H, d, J=5.9 Hz), 6.60(1H, t, J=4.6 Hz), 7.19–7.30(4H, m), 8.25(1H, t, J=5.9 Hz), 8.34(2H, d, J=4.6 Hz); IR(KBr): 3290, 2935, 1635, 1587 cm$^{-1}$; MS(EI): 339(M$^+$); Elemental analysis: Calculated: C; 66.35, H; 7.47, N; 20.36; Found: C; 66.31, H; 7.50, N; 19.97.

Example 76

Synthesis of N-(4-((4-(Pyrimidin-2-yl)piperazin-1-yl)methyl)phenylmethyl)formamide

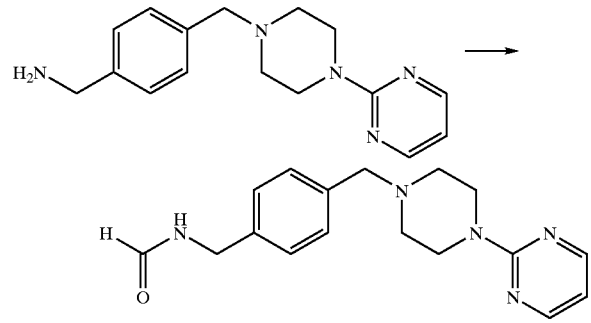

A mixture of acetic anhydride (0.30 ml) and formic acid (0.13 ml) was stirred at 50–60° C. for 1 hr. To the obtained acetic formic anhydride was added a solution of 2-(4-(4-(aminomethyl)phenylmethyl)piperazin-1-yl)pyrimidin (0.42 g) in methylene chloride (10 ml) under ice-cooling and the mixture was stirred at 5–10° C. for 2 hr. The reaction mixture was concentrated under reduced pressure and the obtained residue was purified by silica gel column chromatography (developing solvent; chloroform:methanol=9:1) to give a yellow oil. (0.46 g). The obtained yellow oil was crystallized from ethyl acetate/diisopropyl ether to give the title compound (0.45 g) as pale-yellow crystals, m.p.= 97–98° C.

$^1$H-NMR(DMSO-d$_6$)δ: 2.38–2.42(4H, m), 3.48(2H, s), 3.70–3.73(4H, m), 4.30(2H, d, J=5.9 Hz), 6.60(1H, t, J=4.6 Hz), 7.22–7.31(4H, m), 8.15(1H, s), 8.34(2H, d, J=4.6 Hz), 8.45–8.55(1H, m); IR(KBr): 3383, 2868, 1664, 1581 cm$^{-1}$; MS(EI): 311(M$^+$); Elemental analysis: Calculated:° C.; 65.57, H; 6.80, N; 22.49; Found: C; 65.38, H; 6.78, N; 22.27.

Example 77

Synthesis of Ethyl N-(4-((4-(Pyrimidin-2-yl)piperazin-1-yl)methyl)phenylmethyl)succinamide Dihydrochloride 1/2 Hydrate

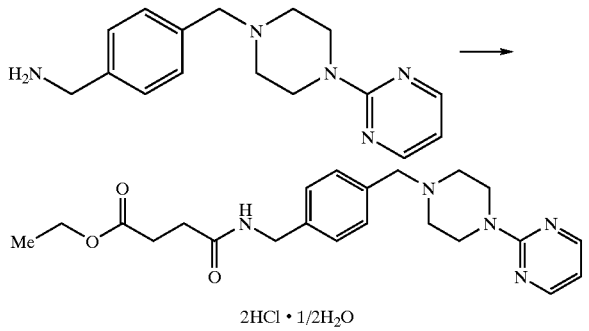

A solution of 2-(4-(4-(aminomethyl)phenylmethyl)piperazin-1-yl)pyrimidine (1.3 g), ethylsuccinyl chloride (0.7 ml) and triethylamine (0.7 ml) in methylene chloride (40 ml) was stirred at room temperature for 4.5 hr. To the reaction mixture was added chloroform (100 ml), washed with saturated brine and dried over anhydrous sodium sulfate. The solvent was evaporated under reduced pressure to give a brown oil (2.0 g). The obtained brown oil was purified by silica gel column chromatography (developing solvent; chloroform:methanol=9:1) to give a pale-brown oil (2.0 g). To the obtained pale-brown oil was added 1M hydrogen chloride—ether (12 ml) in ethanol and the mixture was concentrated under reduced pressure and crystallized from ethyl acetate/ethanol to give the title compound (1.4 g) as white crystals, m.p.=120–123° C.

$^1$H-NMR(DMSO-d$^6$)δ: 1.17(3H, t, J=7.3 Hz), 2.40–2.55 (4H, m), 2.95–3.10(2H, m), 3.30–3.35(2H, m), 3.45–3.55 (2H, m), 4.05(2H, q, J=7.3 Hz), 4.25–4.35(4H, m), 4.65–4.75(2H, m), 4.80–4.90(2H, m), 6.77(1H, t, J=4.6 Hz), 7.31(2H, d, J=7.9 Hz), 7.60(2H, d, J=7.9 Hz), 8.45(2H, d, J=4.6 Hz), 8.52(1H, t, J=5.9 Hz), 11.78(1H, brs); IR(KBr): 3421, 3292, 2981, 1728, 1626 cm$^{-1}$; MS(EI): 411(M$^+$); Elemental analysis: Calculated: C; 53.55, H; 6.54, N; 14.19; Found: C; 53.81, H; 6.66, N; 14.28.

Example 78

Synthesis of N-(4-((4-(4,6-Difluoropyrimidin-2-yl)piperazin-1-yl)methyl)phenylmethyl)acetamide (1) N-(4-((4-Acetylpiperazin-1-yl)methyl)phenylmethyl)acetamide

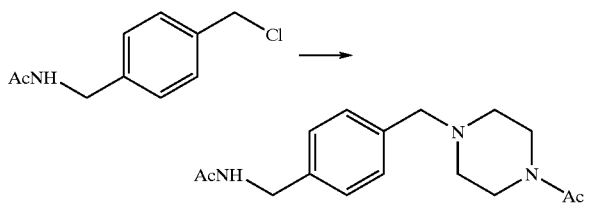

A solution of N-(4-chloromethylphenylmethyl)acetamide (7.7 g), 1-acetylpiperazine (5.0 g) and potassium carbonate (8.1 g) in dimethylformamide (50 ml) was stirred at 80° C. for 5 hr. The reaction mixture was poured into water (250 ml) and extracted with chloroform. The extract was washed with saturated brine and dried over anhydrous sodium sulfate. The solvent was evaporated to give a yellow oil. The obtained yellow oil was purified by silica gel column chromatography (developing solvent; chloroform:methanol=9:1) to give the title compound (11.5 g) as a colorless transparent oil.

$^1$H-NMR(CDCl$_3$)δ: 2.02(3H, s), 2.06(3H, s), 2.37–2.44 (4H, m), 3.43–3.46(2H, m), 3.50(2H, s), 3.58–3.61(2H, m), 4.41(2H, d, J=5.9 Hz), 6.00(1H, brs), 7.22–7.30(4H, m); MS(EI): 289(M$^+$).

(2) N-(4-((Piperazin-1-yl)methyl)phenylmethyl)acetamide

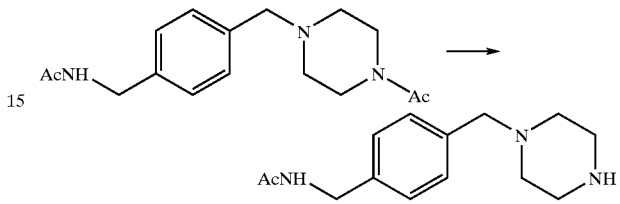

A solution of N-(4-((4-acetylpiperazin-1-yl)methyl)phenylmethyl)acetamide (11.5 g) and sodium hydroxide (4.0 g) in ethanol (20 ml)-water (20 ml) was refluxedunder heating for 18 hr. The reaction mixture was extracted with chloroform and the extract was dried over anhydrous sodium sulfate. The solvent was evaporated to give a pale-brown oil (9.1 g). The obtained pale-brown oil was purified by silica gel column chromatography (developing solvent; chloroform:methanol:aqueous ammonia=9:1:0.3) to give the title compound (7.4 g) as a pale-yellow oil.

$^1$H-NMR(CDCl$_3$)δ: 2.01(3H, s), 2.35–2.40(4H, m), 2.84–2.87(4H, m), 3.46(2H, s), 4.40(2H, d, J=5.30 Hz), 5.91(1H, brs), 7.20–7.30(4H, m); MS(EI): 247(M$^+$).

(3) N-(4-((4-(4,6-Difluoropyrimidin-2-yl)piperazin-1-yl)methyl)-phenylmethyl)acetamide

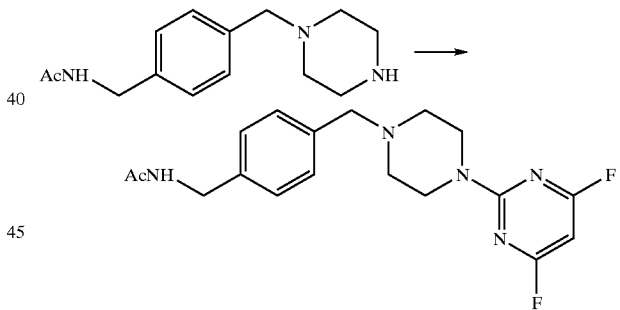

To a solution of 2,4,6-trifluoropyrimidine (1.4 g) and potassium carbonate (2.1 g) in acetonitrile (30 ml) was added a solution of N-(4-((piperazin-1-yl)methyl)phenylmethyl)acetamide (2.5 g) in acetonitrile (20 ml) over 5 min under ice-cooling. The mixture was stirred at the same temperature for 1.5 hr. The reaction mixture was poured into water (100 ml) and extracted with ethyl acetate. The extract was washed with brine and dried over anhydrous sodium sulfate. The solvent was evaporated to give a white solid (3.2 g). The obtained white solid was purified by silica gel column chromatography (developing solvent; chloroform:methanol=50:1) to give a crude purification product (1.3 g) of N-(4-((4-(4,6-difluoropyrimidin-2-yl)piperazin-1-yl)methyl)phenylmethyl)acetamide and a crude purification product (1.1 g) of N-(4-((4-(2,6-difluoropyrimidin-4-yl)piperazin-1-yl)methyl)phenylmethyl)acetamide. The crude purification product of N-(4-((4-(4,6-difluoropyrimidin-2-yl)piperazin-1-yl)

methyl)phenylmethyl)acetamide was crystallized from ethyl acetate:diisopropyl ether to give the title compound (1.0 g) as white crystals, m.p.=128–129° C.

$^1$H-NMR(CDCl$_3$)δ: 2.03(3H, s), 2.46(4H, t, J=5.3 Hz), 3.52(2H, s), 3.79(4H, t, J=5.3 Hz), 4.43(2H, d, J=5.3 Hz), 5.66(1H, t, J=1.3 Hz), 5.75(1H, brs), 7.23–7.32(4H, m); IR(KBr): 3288, 2918, 1635, 1552 cm$^{-1}$; MS(EI): 361(M$^+$); Elemental analysis: Calculated: C; 59.82, H; 5.86, N; 19.38; Found: C; 59.83, H; 5.85, N; 19.44.

Example 79

Synthesis of N-(4-((4-(2,6-Difluoropyrimidin-4-yl)piperazin-1-yl)methyl)phenylmethyl)acetamide

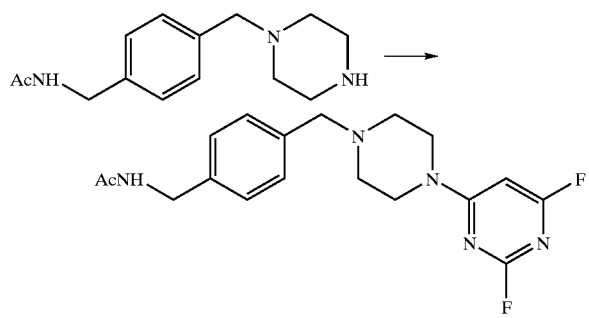

The roughly purified product (1.1 g) of N-(4-((4-(2,6-difluoropyrimidin-4-yl)piperazin-1-yl)methyl) phenylmethyl)acetamide obtained in Example 78(3) was crystallized from ethyl acetate:diisopropyl ether to give the title compound (1.0 g) as white crystals, m.p.=127–128° C.

$^1$H-NMR(CDCl$_3$)δ: 2.02(3H, s), 2.50(4H, t, J=5.3 Hz), 3.53(2H, s), 3.55–3.70(4H, m), 4.42(2H, d, J=5.9 Hz), 5.87(1H, d, J=2.0 Hz), 5.85–6.95(1H, brs), 7.23–7.31(4H, m); IR(KBr): 3259, 2946, 2823, 1624, 1560 cm$^{-1}$; MS(EI): 361(M$^+$); Elemental analysis: Calculated: C; 59.82, H; 5.86, N; 19.38; Found: C; 59.89, H; 5.86, N; 19.44.

Example 80

Synthesis of N-(4-((4-(4,6-Dichloropyrimidin-2-yl)piperazin-1-yl)methyl)phenylmethyl)acetamide

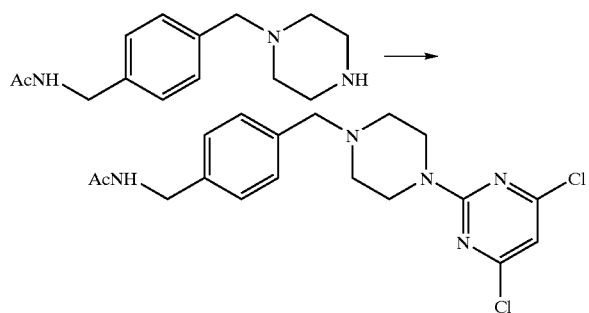

To a solution of 2,4,6-trichloropyrimidine (1.0 g) and potassium carbonate (0.84 g) in acetonitrile (20 ml) was added a solution of N-(4-((piperazin-1-yl)methyl)phenylmethyl)acetamide (1.0 g) obtained in Example 78(2) in acetonitrile (20 ml) under ice-cooling over 5 min. The mixture was stirred at the same temperature for 30 min. The reaction mixture was poured into water (100 ml) and extracted with ethyl acetate. The extract was washed with brine and dried over anhydrous sodium sulfate. The solvent was evaporated to give a pale-brown oil (1.6g). The obtained pale-brown oil was purified by silica gel column chromatography (developing solvent; chloroform:methanol=50:1) to give a crude purification product (0.28 g) of N-(4-((4-(4,6-dichloropyrimidin-2-yl)piperazin-1-yl)methyl) phenylmethyl)acetamide and a crude purification product (0.9 g) of N-(4-((4-(2,6-dichloropyriinidin-4-yl)piperazin-1-yl)methyl)phenylmethyl)acetamide. The crude purification product of N-(4-((4-(4,6-dichloropyrimidin-2-yl)piperazin-1-yl)methyl)phenylmethyl)acetamide was crystallized from ethyl acetate:hexane to give the title compound (0.2 g) as white crystals, m.p.=139–140° C.

$^1$H-NMR(DMSO-d$_6$)δ: 1.87(3H, s), 2.40–2.43(4H, m), 3.48(2H, s), 3.68–3.72(4H, m), 4.23(2H, d, J=5.9 Hz), 6.90(1H, s), 5.75(1H, brs), 7.19–7.29(4H, m), 8.30(1H, t, J=5.9 Hz); IR(KBr): 3259, 2858, 1639, 1570 cm$^{-1}$; MS(EI): 394(M$^+$); Elemental analysis: Calculated: C; 54.83, H; 5.37, N; 17.76; Found: c;54.93, H; 5.43, N; 17.37.

Example 81

Synthesis of N-(4-((4-(Thiazol-2-yl)piperazin-1-yl)methyl)phenylmethyl)acetamide Hydrochloride 1/2 Hydrate (1) 1-(Thiazol-2-yl)piperazine

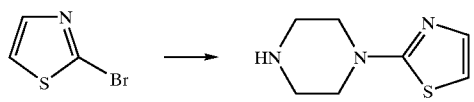

To piperazine (48 g) dissolved by heating at 110° C. was added dropwise 2-bromothiazole (5 ml) over 20 min. The mixture was stirred at 150° C. for 1 hr, poured into water (150 ml) and extracted with chloroform. The extract was washed with saturated brine and dried over anhydrous sodium sulfate. The solvent was evaporated to give the title compound (9.5 g) as a pale-yellow oil.

$^1$H-NMR(DMSO-d$_6$)δ: 2.78(4H, t, J=5.3 Hz), 3.29(4H, t, J=5.3 Hz), 6.80(1H, d, J=4.0 Hz), 7.15(1H, d, J=4.0 Hz); MS(EI): 169(M$^+$).

(2) N-(4-((4-(Thiazol-2-yl)piperazin-1-yl)methyl)phenylmethyl)acetamide Hydrochloride 1/2 Hydrate

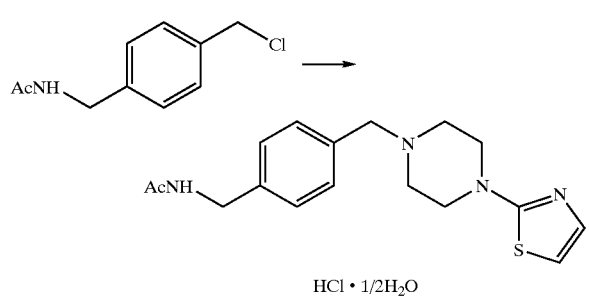

HCl · 1/2H$_2$O

A solution of N-(4-chloromethylphenylmethyl)acetamide (1.8 g), 1-(thiazol-2-yl)piperazine (1.5 g) and potassium carbonate (1.8 g) in dimethylformamide (20 ml) was stirred at 80° C. for 2.5 hr. The reaction mixture was poured into water (100 ml) and extracted with ethyl acetate. The extract was washed with saturated brine and dried over anhydrous sodium sulfate. The solvent was evaporated to give a brown oil. The obtained brown oil was purified by silica gel column chromatography (developing solvent; chloroform:methanol=9:1) to give a pale-brown oil (2.3 g).

The obtained pale-brown oil was dissolved in ethanol (200 ml) and 1M hydrogen chloride—ether (7 ml) was added. The solvent was evaporated under reduced pressure. The obtained residue was crystallized from ethyl acetate:ethanol (1:1, 100 ml) and the crystals were recrystallized from ethyl acetate:ethanol:methanol (1:1:1, 100 ml) to give the title compound (1.2 g) as white crystals, m.p.=120–121° C.

$^1$H-NMR(DMSO-d$_6$)δ: 1.89(3H, s), 3.00–3.35(4H, m), 3.50–3.65(2H, m), 3.70–3.80(4H, m), 3.90–4.10(2H, m), 4.28(2H, d, J=5.9 Hz), 4.35(2H, s), 6.99(1H, d, J=4.0 Hz), 7.24(1H, d, J=4.0 Hz), 7.32(1H, d, J=7.9 Hz), 7.61(1H, d, J=7.9 Hz), 8.48(1H, t, J=5.9 Hz), 11.86(1H, brs); IR(KBr): 3311, 2526, 2507, 1641, 1521 cm$^{-1}$; MS(EI): 330(M$^+$); Elemental analysis: Calculated: C; 54.32, H; 6.44, N; 14.90; Found: C; 54.10, H; 6.31, N; 14.73.

Example 82

Synthesis of N-(4-((4-(Pyridin-2-yl)piperazin-1-yl)methyl)phenylmethyl)acetamide

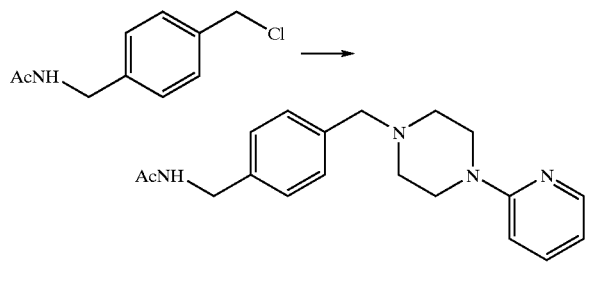

A solution of N-(4-chloromethylphenylmethyl)acetamide (1.0 g), 1-(2-pyridyl)piperazine (1.4 g) and potassium carbonate (4.2 g) in dimethylformamide (20 ml) was stirred at 60–70° C. for 2.5 hr. The reaction mixture was poured into water and extracted with ethyl acetate. The extract was washed with saturated brine and dried over anhydrous sodium sulfate. The solvent was evaporated to give a brown oil. The obtained brown oil was purified by silica gel column chromatography (developing solvent; chloroform:methanol=20:1) to give a pale-yellow oil (2.5 g). The obtained pale-yellow oil was crystallized from ethyl acetate and the crystals were recrystallized from ethyl acetate to give the title compound (1.4 g) as white crystals, m.p.=100–101° C.

$^1$H-NMR(DMSO-d$_6$)δ: 1.89(3H, s), 2.40–2.45(2H, m), 2.45–2.30(2H, m), 3.40–3.50(4H, m), 4.23(2H, d, J=5.9 Hz), 6.62(1H, dd, J=5.3, 7.3 Hz), 6.78(1H, d, J=8.6 Hz), 7.20–7.29(4H, m), 7.47–7.54(1H, m), 8.09(1H, dd, J=1.3, 4.6 Hz), 8.25–8.35(1H, m); IR(KBr): 3319, 2940, 2809, 1645, 1594 cm$^{-1}$; MS(EI): 324(M$^+$); Elemental analysis: Calculated: C; 70.34, H; 7.46, N; 17.27; Found: C; 70.10, H; 7.50, N; 17.05.

Example 83

Synthesis of N-(4-((4-(Pyridin-3-yl)piperazin-1-yl)methyl)phenylmethyl)acetamide 1/2 Hydrate (1) 1-(Pyridin-3-yl)piperazine

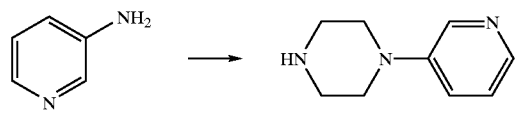

A suspension of 3-aminopyridine (2.0 g) and bis(2-chloroethyl)amine hydrochloride (3.8 g) in o-xylene (40 ml) was stirred at 140° C. for 20 hr. The reaction mixture was extracted with water and the aqueous layer was made alkaline with a 2N aqueous sodium hydroxide solution and extracted with chloroform. The extract was washed with saturated brine and dried over anhydrous sodium sulfate. The solvent was evaporated and the obtained residue was purified by silica gel column chromatography (developing solvent; chloroform:methanol:aqueous amnmonia=9:1:0.5) to give the title compound (0.55 g) as a black brown oil.

$^1$H-NMR(DMSO-d$_6$)δ: 2.83(4H, d, J=5.3 Hz), 3.08(4H, d, J=5.3 Hz), 7.17–7.21(1H, m), 7.26–7.30(1H, m), 7.97(1H, d, J=2.6 Hz), 8.27(1H, d, J=3.3 Hz); MS(EI): 163(M$^+$).

(2) N-(4-((4-(Pyridin-3-yl)piperazin-1-)methyl)phenylmethyl)acetamide 1/2 Hydrate

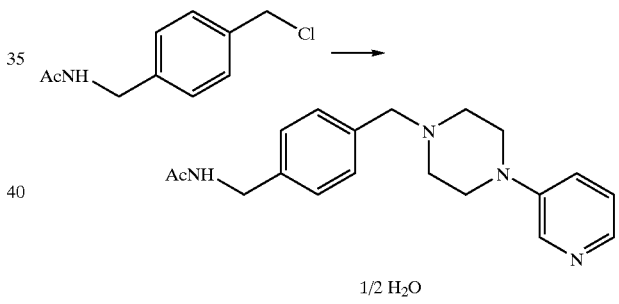

1/2 H$_2$O

A solution of N-(4-chloromethylphenylmethyl) acetamide (0.67 g), 1-(3-pyridyl)piperazine (0.55 g) and potassium carbonate (0.93 g) in dimethylformamide (10 ml) was stirred at 80° C. for 4 hr. The reaction mixture was poured into water and extracted with chloroform. The extract was washed with saturated brine and dried over anhydrous sodium sulfate. The solvent was evaporated to give a black oil. The obtained black oil was purified by silica gel column chromatography (developing solvent; chloroform:methanol=4:1) to give a brown solid. The obtained brown solid was crystallized from ethyl acetate-methanol to give the title compound (200 mg) as white crystals, m.p.=139–140° C.

$^1$H-NMR(DMSO-d$_6$)δ: 1.87(3H, s), 2.48–2.51(4H, m), 3.15–3.20(4H, m), 3.49(2H, s), 4.23(2H, d, J=5.9 Hz), 7.17–7.31(6H, m), 7.98(1H, d, J=3.3 Hz), 8.27(1H, d, J=2.6 Hz), 8.30(1H, t, J=5.9 Hz); IR(KBr): 3455, 3232, 3041, 1660, 1568 cm$^{-1}$; MS(EI): 324(M$^+$); Elemental analysis: Calculated: C; 68.44, H; 7.56, N; 16.80; Found: C; 68.32, H; 7.59, N; 16.72.

Example 84

Synthesis of N-(4-((4-(Pyridin-4-yl)piperazin-1-yl)methyl)phenylmethyl)acetamide (1) 1-(Pyridin-4-yl)piperazine

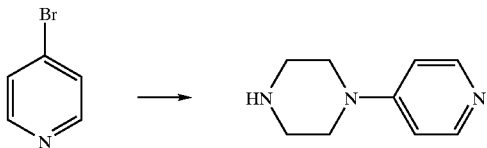

To piperazine (3.6 g) dissolved at 110° C. was added 4-bromopyridine (1.0 g) and the mixture was stirred at 140–150° C. for 1 hr. The reaction mixture was poured into water and extracted with chloroform. The extract was washed with saturated brine and dried over anhydrous sodium sulfate. The solvent was evaporated to give the title compound (0.64 g) as a pale-yellow solid.

$^1$H-NMR(DMSO-$d_6$)δ: 2.78(4H, t, J=5.3 Hz), 3.20(4H, t, J=5.3 Hz), 6.77(2H, dd, J=1.3, 6.6 Hz), 8.14(2H, d, J=6.6 Hz); MS(EI): 163(M$^+$).

(2) N-(4-((4-(Pyridin-4-yl)piperazin-1-yl)methyl)phenylmethyl)acetamide

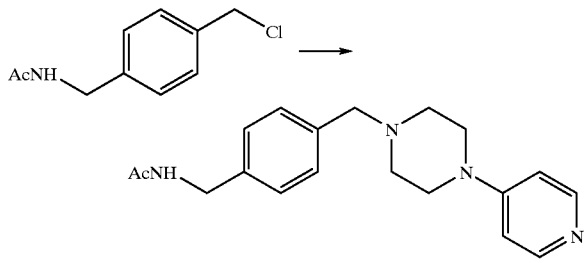

A solution of N-(4-chloromethylphenylmethyl) acetamide (0.85 g), 1-(pyridin-4-yl)piperazine (0.64 g) and potassium carbonate (0.81 g) in dimethylformamide (10 ml) was stirred at 60–70° C. for 5 hr. The reaction mixture was poured into water and extracted with chloroform. The extract was washed with saturated brine and dried over anhydrous sodium sulfate. The solvent was evaporated and the obtained residue was purified by silica gel column chromatography (developing solvent; chloroform:methanol=9:1)to give a yellow solid(0.6 g). The obtained yellow solid was crystallized from ethyl acetate-methanol to give the title compound (0.37 g) as white crystals, m.p.=164–166° C.

$^1$H-NMR(DMSO-$d_6$)δ: 1.89(3H, s), 2.43–2.46(2H, m), 2.49–2.51(2H, m), 3.27–3.30(4H, m), 3.49(2H, s), 4.23(2H, d, J=5.9 Hz), 6.78–6.79(2H, m), 7.20–7.28(4H, m), 8.13–8.15(2H, m), 8.32(1H, m); IR(KBr): 3033, 2952, 2931, 1664, 1599 cm$^{-1}$; MS(EI): 324(M$^+$); Elemental analysis: Calculated: C; 70.34, H; 7.46, N; 17.27; Found: C; 70.29, H; 7.37, N; 17.26.

Example 85

Synthesis of N-(4-((4-(6-Fluoropyridin-2-yl)piperazin-1-yl)methyl)phenylmethyl)acetamide Hydrochloride 1/2 Ethyl Acetate (1) 1-Acetyl-4-(6-fluoropyridin-2-yl)piperazine

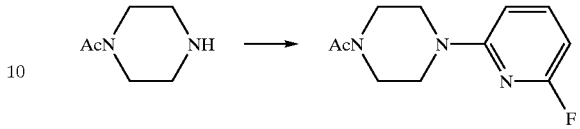

A solution of 2,6-difluoropyridine (9.0 g), 1-acetylpiperazine (5.0 g) and potassium carbonate (8.1 g) in acetonitrile (100 ml) was refluxed under heating for 18 hr. The reaction mixture was poured into water and extracted with ethyl acetate. The extract was washed with brine and dried over anhydrous sodium sulfate. The solvent was evaporated to give a pale-brown solid (8.7 g). The obtained pale-brown solid was crystallized from ethyl acetate-hexane to give the title compound (5.5 g) as pale-brown crystals.

m.p.=102–103° C.; $^1$H-NMR(CDCl$_3$)δ: 2.14(3H, s), 3.48–3.55(2H, m), 3.56–3.65(4H, m), 3.71–3.75(2H, m), 6.22(1H, dd, J=2.6, 7.9 Hz), 6.43(1H, dd, J=2.6, 8.6 Hz), 7.57(1H, dd, J=7.9, 16.5 Hz); IR(KBr): 3077, 2890, 2852, 1646, 1608 cm$^{-1}$; MS(EI): 223(M$^+$); Elemental analysis: Calculated: C; 59.18, H; 6.32, N; 18.82; Found: C; 59.25, H; 6.34, N; 18.83.

(2) 1-(6-Fluoropyridin-2-yl)piperazine

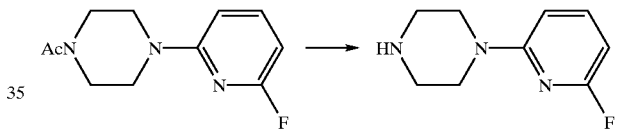

A solution of 1-acetyl-4-(6-fluoropyridin-2-yl)piperazine (5.5 g) and sodium hydroxide (3.0 g) in methanol (30 ml)—water (30 ml) was refluxed under heating for 5 hr. The reaction mixture was poured into water and extracted with ethyl acetate. The solvent was evaporated to give the title compound (4.6 g) as a pale-yellow oil.

$^1$H-NMR(CDCl$_3$)δ: 2.93–2.97(4H, m), 3.48–3.51(4H, m), 6.16(1H, dd, J=2.6, 7.9 Hz), 6.40(1H, dd, J=2.6, 7.9 Hz), 7.52(1H, dd, J=7.9, 16.5 Hz).

(3) N-(4-((4-(6-Fluoropyridin-2-yl)piperazin-1-yl)methyl)phenylmethyl)acetamide Hydrochloride 1/2 Ethyl Acetate

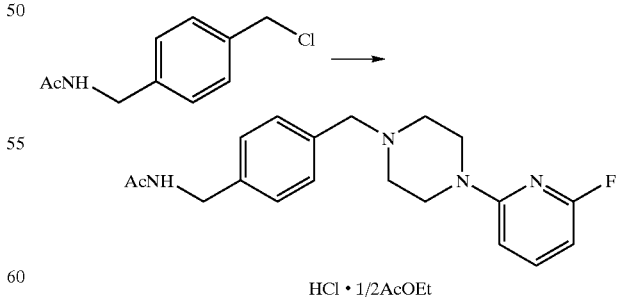

HCl · 1/2AcOEt

A solution of N-(4-chloromethylphenylmethyl)acetamide (1.5 g), 1-(6-fluoropyridin-2-yl)piperazine (1.3 g) and potassium carbonate (1.6 g) in dimethylformamide (20 ml) was stirred at 80° C. for 6 hr. The reaction mixture was poured into water and extracted with ethyl acetate. The extract was washed with saturated brine and dried over anhydrous sodium sulfate. The solvent was evaporated and the obtained residue was purified by silica gel column chromatography (developing solvent; chloroform:methanol=9:1) to give a pale-brown oil (2.9 g). The obtained pale-brown oil was treated with 1M hydrogen chloride—ether and crystallized from ethyl acetate-ethanol to give the title compound (2.2 g) as pale-yellow crystals.

m.p.=112–115° C. (decomposition); $^1$H-NMR(DMSO-d$_6$) δ: 1.78(1.5H, t, J=7.3 Hz), 1.90(3H, s), 1.99(1.5H, s), 2.95–3.13(2H, m), 3.25–3.45(4H, m), 4.03(1H, q, J=7.3 Hz), 4.25–4.35(6H, m), 6.39(1H, dd, J=2.6, 7.9 Hz), 6.78(1H, dd, J=2.6, 7.9 Hz), 7.32(2H, d, J=7.9 Hz), 7.60(2H, d, J=7.9 Hz), 7.75(1H, m), 8.47(1H, t, J=5.9 Hz), 11.69(1H, brs); IR(KBr): 3263, 2987, 2541, 1666, 1614 cm$^{-1}$; MS(EI): 342(M$^+$); Elemental analysis: Calculated: C; 57.46, H; 6.43, N; 12.76; Found: C; 57.85, H; 6.86, N; 12.67.

Example 86

Synthesis of N-(4-((4-(5-Chloropyridin-2-yl)piperazin-1-yl)methyl)phenylmethyl)acetamide (1) 1-(5-Chloropyridin-2-yl)piperazine

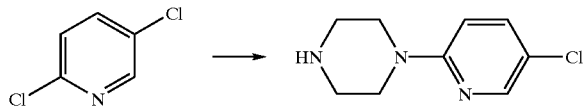

To piperazine (29.0 g) dissolved at 115° C. was added 2,5-dichloropyridine (5.1 g) and the mixture was stirred at 140–150° C. for 1 hr. The reaction mixture was poured into a 1N aqueous sodium hydroxide solution and extracted with ethyl acetate. The extract was washed with saturated brine and dried over anhydrous sodium sulfate. The solvent was evaporated to give the title compound (5.0 g) as a pale-brown solid.

$^1$H-NMR(DMSO-d$_6$)δ: 2.76(4H, t, J=5.3 Hz), 3.38(4H, t, J=5.3 Hz), 6.81(1H, d, J=8.6 Hz), 7.56(1H, dd, J=3.3, 8.6 Hz), 8.09(1H, d, J=2.6 Hz); MS(EI): 197(M$^+$).

(2) N-(4-((4-(5-Chloropyridin-2-yl)piperazin-1-yl)methyl)phenylmethyl)acetamide

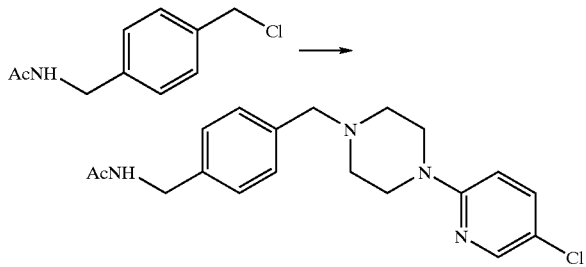

A solution of N-(4-chloromethylphenylmethyl)acetamide (1.5 g), 1-(5-chloropyridin-2-yl)piperazine (1.5 g) and potassium carbonate (1.6 g) in dimethylformamide (20 ml) was stirred at 70–80° C. for 8.5 hr. The reaction mixture was poured into water and extracted with ethyl acetate. The extract was washed with saturated brine and dried over anhydrous sodium sulfate. The solvent was evaporated to give a brown solid (3.1 g). The obtained brown solid was crystallized ethyl acetate to give the title compound (1.3 g) as pale-yellow crystals, m.p.=155–156° C.; $^1$H-NMR(DMSO-d$_6$)δ: 1.87(3H, s), 2.35–2.45(4H, m), 3.45–3.50(6H, m), 4.23(2H, d, J=5.9 Hz), 6.84(1H, d, J=9.2 Hz), 7.19–7.29(4H, m), 7.58(1H, dd, J=2.6, 9.2 Hz), 8.09(1H, d, J=2.6 Hz), 8.31(1H, t, J=5.3 Hz); IR(KBr): 3313, 2915, 2815, 1645, 1591 cm$^{-1}$; MS(EI): 358(M$^+$); Elemental analysis: Calculated: C; 63.59, H; 6.45, N; 15.61; Found: C; 63.55, H; 6.48, N; 15.48.

Example 87

Synthesis of N-(4-((4-(Pyrazin-2-yl)piperazin-1-yl)methyl)phenylmethyl)acetamide (1) 1-(Pyrazin-2-yl)piperazine

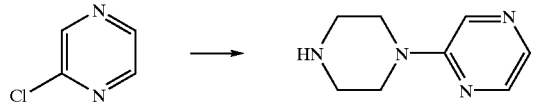

To piperazine (48.0 g) dissolved at 110° C. was added 2-chloropyrazine (5.0 ml) and the mixture was stirred at 150° C. for 2 hr. The reaction mixture was poured into an aqueous sodium hydroxide solution and extracted with chloroform. The extract was washed with saturated brine and dried over anhydrous sodium sulfate. The solvent was evaporated to give the title compound (6.4 g) as a brown oil.

$^1$H-NMR(DMSO-d$_6$)δ: 2.97–3.01(4H, m), 3.54–3.58(4H, m), 7.84(1H, d, J=2.6 Hz), 8.06(1H, dd, J=1.3, 2.6 Hz), 8.13(1H, d, J=1.3 Hz); MS(EI): 164(M$^+$).

(2) N-(4-((4-(Pyrazin-2-yl)piperazin-1-yl)methyl)phenylmethyl)acetamide

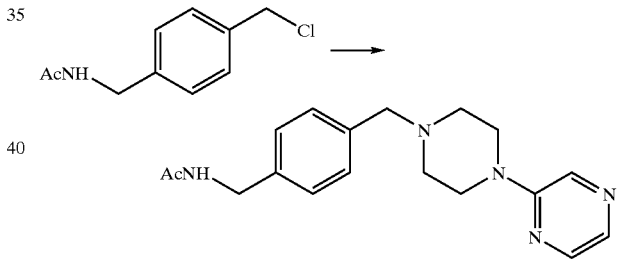

A solution of N-(4-chloromethylphenylmethyl)acetamide (1.6 g), 1-(pyrazin-2-yl)piperazine (1.3 g) and potassium carbonate (1.6 g) in dimethylformamide (20 ml) was stirred at 70–80° C. for 7 hr. The reaction mixture was poured into water and extracted with chloroform. The extract was washed with saturated brine and dried over anhydrous sodium sulfate. The solvent was evaporated and the obtained residue was purified by silica gel column chromatography (developing solvent; chloroform:methanol=20:1) to give a pale-yellow solid (1.8 g). The obtained pale-yellow solid was crystallized from hexane-ethyl acetate to give the title compound (1.2 g) as pale-yellow crystals, m.p.=118–119° C.

$^1$H-NMR(DMSO-d$_6$)δ: 1.87(3H, s), 2.40–2.45(4H, m), 3.49(2H, s), 3.50–3.55(4H, m), 4.24(2H, d, J=5.9 Hz), 7.20–7.29(4H, m), 7.82(1H, d, J=2.6 Hz), 8.06(1H, d, J=1.3 Hz), 8.29–8.35(2H, m); IR(KBr): 3307, 2929, 2845, 1639, 1578 cm$^{-1}$; MS(EI): 325(M$^+$); Elemental analysis: Calculated: C; 66.44, H; 7.12, N; 21.52; Found: C; 66.49, H; 7.10, N; 21.34.

Example 88

Synthesis of N-(4-((4-(5-Nitrothiazol-2-yl)piperazin-1-yl)methyl)phenylmethyl)acetamide (1) 1-(5-Nitrothiazol-2-yl)piperazine

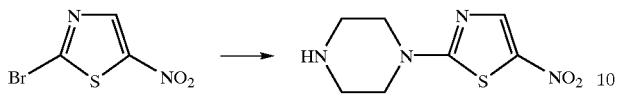

To a solution of piperazine (18.2 g) and potassium carbonate (12.6 g) in acetonitrile (150 ml) was added 2-bromo-5-nitrothiazole (14.7 g) at 40° C. and the mixture was stirred at 60° C. for 40 min. The reaction mixture was poured into water and extracted with chloroform. The extract was washed with saturated brine and dried over anhydrous sodium sulfate. The solvent was evaporated to give a brown solid (11.2 g). The obtained brown solid was purified by silica gel column chromatography (developing solvent; chloroform:methanol=9:1) to give the title compound (4.8 g) as yellow crystals.

$^1$H-NMR(DMSO-d$_6$)( δ: 2.80(4H, t, J=5.3 Hz), 3.55(4H, t, J=5.3 Hz), 8.37(1H, s); MS(EI): 214(M$^+$);

(2) N-(4-((4-(5-Nitrothiazol-2-yl)piperazin-1-yl)methyl)phenylmethyl)acetamide

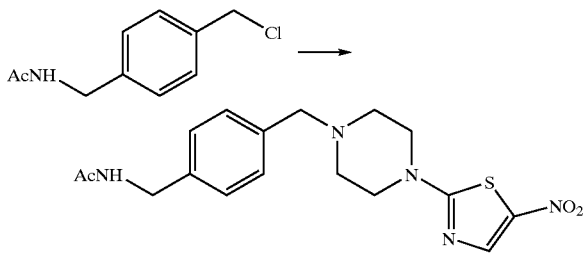

A solution of N-(4-chloromethylphenylmethyl)acetamide (0.5 g), 1-(5-nitrothiazol-2-yl) piperazine (0.5 g) and potassium carbonate (0.5 g) in dimethylformamide (15 ml) was stirred at 80° C. for 3.5 hr. The reaction mixture was poured into water and extracted with ethyl acetate. The extract was washed with saturated brine and dried over anhydrous sodium sulfate. The solvent was evaporated to give a yellow solid (1.5 g). The obtained pale-yellow solid was crystallized from ethyl acetate to give the title compound (0.5 g) as yellow crystals, m.p.=151–152° C.

$^1$H-NMR(DMSO-d$_6$)δ: 1.87(3H, s), 2.40–2.50(4H, m), 3.52(2H, s), 3.60–3.70(4H, m), 4.23(2H, d, J=5.9 Hz), 7.23–7.29(4H, m), 8.31(1H, t, J=5.3 Hz), 8.37(1H, s); IR(KBr): 3296, 2964, 1651, 1558, 1504 cm$^{-1}$; MS(EI): 375(M$^+$); Elemental analysis: Calculated: C; 54.38, H; 5.64, N; 18.65; Found: C; 54.26, H; 5.65, N; 18.38.

Example 89

Synthesis of N-(4-((4-(2,6-Dichloropyrimidin-4-yl)piperazin-1-yl)methyl)phenylmethyl)acetamide

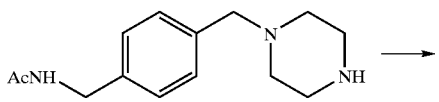

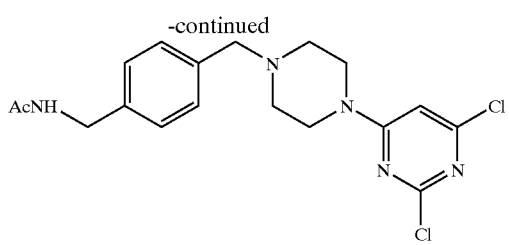

The roughly purified product (0.9 g) of N-(4-((4-(2,6-dichloropyrimidin-4-yl)piperazin-1-yl)methyl)phenylmethyl)acetamide obtained in Example 88(3) was crystallized from ethyl acetate to give the title compound (0.7 g) as white crystals,. m.p.=165–166° C.

$^1$H-NMR(DMSO-d$_6$)δ: 1.87(3H, s), 2.35–2.45(4H, m), 3.48(2H, s), 3.60–3.70(4H, m), 4.23(2H, d, J=5.9 Hz), 6.99(1H, s), 7.19–7.29(4H, m), 8.29(1H, t, J=5.9 Hz); IR(KBr): 3249, 2910, 1646, 1598 cm$^{-1}$; MS(EI): 394(M$^+$); Elemental analysis: Calculated: C; 54.83, H; 5.37, N; 17.76; Found: C; 54.88, H; 5.41, N; 17.60.

Example 90

Synthesis of N-(4-((4-(4,6-Dimethoxypyrimidin-2-yl)piperazin-1-yl)methyl)phenylmethyl)acetamide 1/2 Hydrate (1) 1-Acetyl-4-(4,6-difluoropyrimidin-2-yl)piperazine

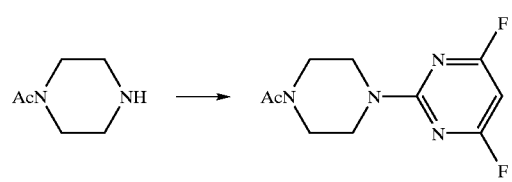

To a solution of 2,4,6-trifluoropyrimidine (2.0 g) and potassium carbonate (3.1 g) in acetonitrile (15 ml) was added a solution of 1-acetylpiperazine (1.9 g) in acetonitrile (5 ml) over 10 min under ice-cooling and the mixture was stirred at room temperature for 1 hr. The reaction mixture was poured into water and extracted with ethyl acetate. The extract was washed with brine and dried over anhydrous sodium sulfate. The solvent was evaporated to give a pale-yellow oil. The obtained pale-yellow oil was purified by silica gel column chromatography to give the title compound (1.8 g) and 1-acetyl-4-(2,6-difluoropyrimidin-4-yl)piperazine (1.7 g) both as a white solid.

$^1$H-NMR(CDCl$_3$)δ: 2.15(3H, s), 3.55–3.65(2H, m), 3.65–3.70(2H, m), 3.80–3.90(4H, m), 5.75(1H, t, J=2.0 Hz); MS(EI): 242(M$^+$);

(2) 1-(4,6-Dimethoxypyrimidin-2-yl)piperazine

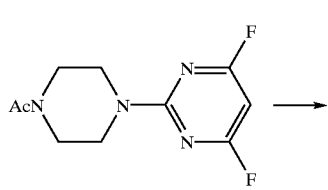

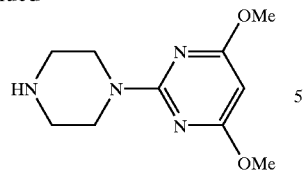

A solution of 1-acetyl-4-(4,6-difluoropyrimidin-2-yl)piperazine (1.7 g) and sodium hydroxide (0.84 g) in methanol (20 ml)—water (10 ml)was refluxed under heating for 7.5 hr. The reaction mixture was poured into water and extracted with chloroform. The extract was washed with brine and dried over anhydrous sodium sulfate. The solvent was evaporated to give a colorless transparent oil (2.5 g). The obtained colorless transparent oil was purified by silica gel column chromatography (developing solvent; chloroform:methanol=50:1) to give the title compound (1.0 g) as a pale-yellow solid.

$^1$H-NMR(CDCl$_3$)δ: 2.90(4H, t, J=5.3 Hz), 3.77(4H, t, J=5.3 Hz)., 3.85(6H, s), 5.36(1H, s); IR(KBr): 2985, 2944, 1583, 1564 cm$^{-1}$; MS(EI): 224(M$^+$); Elemental analysis: Calculated: C; 53.55, H; 7.19, N; 24.98; Found: C; 53.65, H; 7.24, N; 24.85.

(3) N-(4-((4-(4,6-Dimethoxypyrimidin-2-yl)piperazin-1-yl)methyl)phenylmethyl)acetamide 1/2 Hydrate

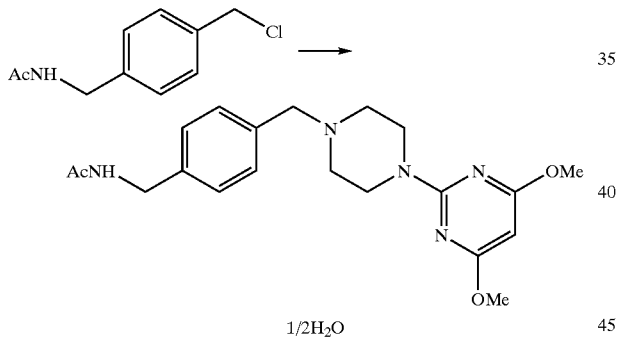

A solution of N-(4-chloromethylphenylmethyl) acetamide (0.93 g), 1-(4,6-dimethoxypyrimidin-2-yl)piperazine (0.94 g) and potassium carbonate (0.97 g) in dimethylformamide (10 ml) was stirred at 80° C. for 1.5 hr. The reaction mixture was poured into water and extracted with ethyl acetate. The extract was washed with saturated brine and dried over anhydrous sodium sulfate. The solvent was evaporated to give a brown oil (2.0 g). The obtained brown oil was crystallized from ethyl acetate:diisopropyl ether(1:3, 40 ml) to give the title compound (1.3 g) as pale-yellow crystals, m.p.=130–131° C.

$^1$H-NMR(DMSO-d$_6$)δ: 1.87(3H, s), 2.40–2.50(4H, m), 3.45–3.60(2H, m), 3.65–3.75(4H, m), 3.78(6H, s), 4.24(2H, d, J=5.9 Hz), 5.39(1H, s), 7.20–7.30(4H, m), 8.32(1H, t, J=5.3 Hz); IR(KBr): 3317, 2829, 1641, 1578 cm$^{-1}$; MS(EI): 385(M$^+$) Elemental analysis: Calculated: C; 60.90, H; 7.15, N; 17.75; Found: C; 61.13, H; 6.99, N; 17.75.

Example 91

Synthesis of N-(4-((4-(4,6-Dimethoxypyrimidin-2-yl)piperazin-1-yl)methyl)phenylmethyl)acetamide (Another Method)

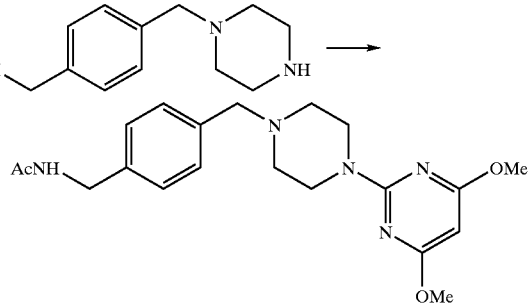

A solution of N-(4-((piperazin-1-yl)methyl)phenylmethyl)acetamide (5.0 g) obtained in Example 88(2), 2-chloro-4,6-dimethoxypyrimidine (3.9 g) and potassium carbonate (4.2 g) in acetonitrile (50 ml) was refluxed under heating for 5 hr. The reaction mixture was poured into ice water and extracted with ethyl acetate. The extract was washed with brine and dried over anhydrous sodium sulfate. The solvent was evaporated to give a pale-brown solid. The obtained pale-brown solid was purified by silica gel column chromatography (developing solvent; chloroform:methanol=9:1) and crystallized from diisopropyl ether to give the title compound (5.0 g) as white crystals.

$^1$H-NMR(DMSO-d6)δ: 1.87(3H, s), 2.40–2.50(4H, m), 3.45–3.60(2H, m), 3.65–3.75(4H, m), 3.78(6H, s), 4.24(2H, d, J=5.9 Hz), 5.39(1H, s), 7.20–7.30(4H, m), 8.32(1H, t, J=5.3 Hz).

Example 92

Synthesis of N-(4-((4-(2,6-Dimethoxypyrimidin-4-yl)piperazin-1-yl)methyl)phenylmethyl)acetamide 1/2 Hydrate (1) 1-Acetyl-4-(2,6-difluoropyrimidin-4-yl)piperazine

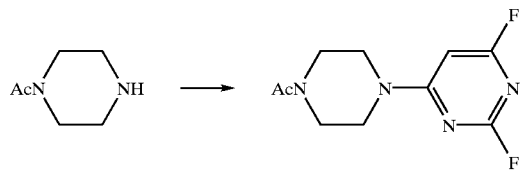

By the manipulation of Example 90(1), the title compound (1.7 g) was obtained as a white solid.

$^1$H-NMR(CDCl$_3$)δ: 2.15(3H, s), 3.55–3.70(4H, m), 3.70–3.85(4H, m), 5.95(1H, d, J=2.0 Hz); MS(EI): 242(M$^+$).

(2) 1-(2,6-Dimethoxypyrimidin-4-yl)piperazine

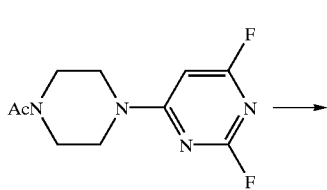

-continued

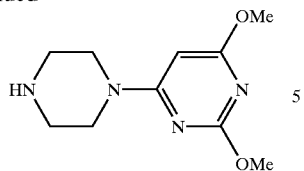

A solution of 1-acetyl-4-(2,6-difluoropyrimidin-4-yl)piperazine (1.5 g) and sodium hydroxide (0.8 g) in methanol (10 ml)-water (10 ml) was refluxed under heating for 4 hr. The reaction mixture was poured into water and extracted with chloroform. The extract was washed with brine and dried over anhydrous sodium sulfate. The solvent was evaporated to give a colorless transparent oil (1.8 g). The obtained colorless transparent oil was purified by silica gel column chromatography (developing solvent; chloroform:methanol=50:1) to give the title compound (1.2 g) as a colorless transparent oil.

$^1$H-NMR(CDCl$_3$)δ: 2.90–3.00(4H, m), 3.53–3.57(4H, m), 3.90(3H, s), 3.91(3H, s), 5.48(1H, s); MS(EI): 224(M$^+$);

(3) N-(4-((4-(2,6-Dimethoxypyrimidin-4-yl)piperazin-1-yl)methyl)phenylmethyl)acetamide 1/2 Hydrate

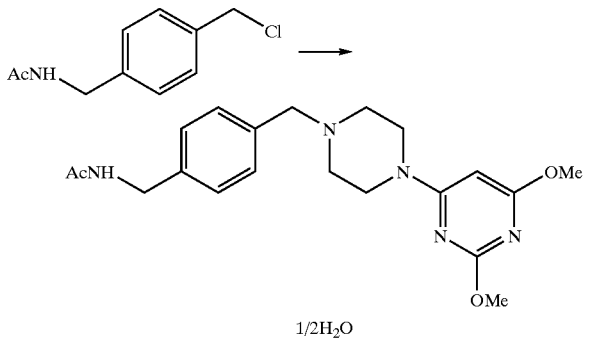

A solution of N-(4-chloromethylphenylmethyl)acetamide (1.0 g), 1-(2,6-dimethoxypyrimidin-4-yl)piperazine (1.1 g) and potassium carbonate (1.0 g) in dimethylformamide (10 ml) was stirred at 80° C. for 2 hr. The reaction mixture was poured into water and extracted with ethyl acetate. The extract was washed with saturated brine and dried over anhydrous sodium sulfate. The solvent was evaporated to give a brown oil (2.1 g). The obtained brown oil was purified by silica gel column chromatography (developing solvent; chloroform:methanol=9:1) and crystallized from ethyl acetate:diisopropyl ether (1:2, 30 ml) to give the title compound (1.0 g) as white crystals, m.p.=89–90° C.

$^1$H-NMR(DMSO-d$_6$)δ: 1.87(3H, s), 2.30–2.40(4H, m), 3.47(2H, s), 3.50–3.57(4H, m), 3.77(3H, s), 3.78(3H, s), 4.23(2H, d, J=5.9 Hz), 5.70(1H, s), 7.22–7.28(4H, m), 8.29(1H, t, J=5.9 Hz); IR(KBr): 3269, 1652, 1608, 1564 cm$^{-1}$; MS(EI): 385(M$^+$); Elemental analysis: Calculated: C; 60.90, H; 7.15, N; 17.75; Found: C; 60.78, H; 7.12, N; 17.67.

Example 93

Synthesis of N-(4-((4-(4,6-Dimethylpyrimidin-2-yl)piperazin-1-yl)methyl)phenylmethyl)acetamide (1) 2-Chloro-4,6-dimethylpyrimidine

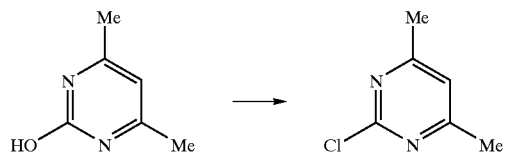

A solution of 2-hydroxy-4,6-dimethylpyrimidine (5.0 g) in phosphorous oxychloride (19 ml) was refluxed under heating for 9 hr. The reaction mixture was added dropwise to an aqueous sodium hydroxide solution and extracted with ethyl acetate. The extract was washed with saturated brine and dried over anhydrous sodium sulfate. The solvent was evaporated to give a yellow oil (3.0 g). The obtained yellow oil was purified by silica gel column chromatography (developing solvent; chloroform:methanol=30:1) to give the title compound (2.4 g) as a pale-yellow oil.

$^1$H-NMR(CDCl$_3$)δ: 2.49(6H, s), 6.98(1H, s).

(2) N-(4-((4-(4,6-dimethylpyrimidin-2-yl)piperazin-1-yl)methyl)phenylmethyl)acetamide A solution of N-(4-((piperazin-1-yl)methyl)phenylmethyl)acetamide (1.7 g) obtained in Example 88(2), 2-chloro-4,6-dimethylpyrimidine (1.0 g) and potassium carbonate (3.0 g) in acetonitrile (50 ml) was refluxed under heating for 7 hr. The reaction mixture was poured into water and extracted with ethyl acetate. The extract was washed with brine and dried over anhydrous sodium sulfate. The solvent was evaporated to give a yellow oil. The obtained yellow oil was purified by silica gel column chromatography (developing solvent; chloroform:methanol=20:1) and crystallized from diisopropyl ether and recrystallized from ethyl acetate-hexane to give the title compound (1.1 g) as white crystals.

m.p.=127–128° C.; $^1$H-NMR(CDCl$_3$)δ: 2.02(3H, s), 2.27 (6H, s), 2.47(4H, t, J=5.3 Hz), 3.52(2H, s), 3.83(4H, t, J=5.3 Hz), 4.42(2H, d, J=5.9 Hz), 5.79(1H, brs), 6.25(1H, s), 7.22–7.33(4H, m); IR(KBr): 3301, 1643, 1573 cm$^{-1}$; MS(EI): 353(M$^+$); Elemental analysis: Calculated: C; 67.96, H; 7.70, N; 19.81; Found: C; 68.03, H; 7.76, N; 19.73.

Example 94

Synthesis of N-(1-Methyl-1-(4-((4-(thiazol-2-yl)piperazin-1-yl)methyl)phenyl)ethyl)acetamide

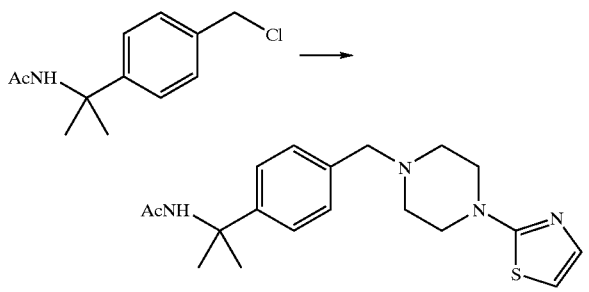

By similar reaction and treatment to that in Example 1(5) using N-(1-(4-chloromethylphenyl)-1-methylethyl)acetamide instead of N-(4-chloromethylphenylmethyl)acetamide and 1-(thiazol-2-yl)piperazine instead of phenylpiperazine, the title compound was obtained as pale-yellow crystals, m.p.=118–120° C.

$^1$H-NMR(CDCl$_3$)δ: 1.70(6H, s), 1.97(3H, s), 2.56(4H, t, J=5.3 Hz), 3.49(4H, t, J=5.3 Hz), 3.52(2H, s), 5.72(1H, br.s), 6.55(1H, d, J=3.3 Hz), 7.19(1H, d, J=4.0 Hz), 7.26–7.36(4H, m). MS(FAB): 359(M$^+$); Elemental analysis: Calculated: C; 63.66, H; 7.31, N; 15.63; Found: C; 63.70, H; 7.34, N; 15.65.

Example 95

Synthesis of N-(1-Methyl-1-(4-((4-(pyrimidin-2-yl)piperazin-1-yl)methyl)phenyl)ethyl)acetamide (1) Synthesis of 4-(1-Acetamide-1-methylethyl)benzoic Acid

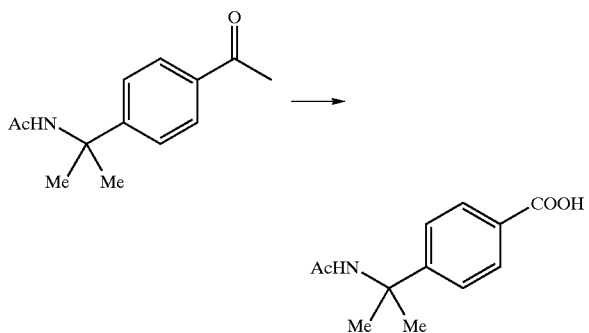

To a solution of sodium hydroxide (164.2 g) in water (500 ml) was added dropwise bromine (70 ml) over 30 min under ice-cooling. To this solution was added dropwise a solution of N-(1-(4-acetylphenyl)-1-methylethyl) acetamide (100 g) in dioxane (1000 ml) over 1 hr and the mixture was stirred at 10° C. for 30 min. To the reaction mixture was added a solution of sodium sulfite (19 g) in water (2000 ml) and stirred. Thereto was added hydrochloric acid and the resulting crystals were collected by filtration to give the title compound (73.4 g) as pale-brown crystals, m.p.=235–237° C.

$^1$H-NMR(DMSO-d$_6$)δ: 1.54(6H, s), 1.83(3H, s), 7.42(2H, d, J=8.6 Hz), 7.86(2H, d, J=8.6 Hz), 8.14(1H, s), 12.72(1H, br.s). MS(EI): 221(M$^+$).

(2) Synthesis of Methyl 4-(1-Acetamido-1-methylethyl)benzoate

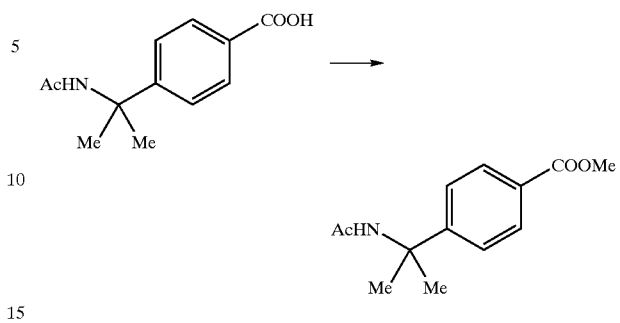

A suspension of 4-(1-acetamido-1-methylethyl)benzoic acid (73.4 g) and sulfuric acid (0.7 ml) in methanol (370 ml) was refluxed for 16 hr. The solvent was evaporated and 10% aqueous sodium hydrogencarbonate (500 ml) was added and the mixture was extracted with ethyl acetate (500 ml). The extract was washed with saturated brine and dried over anhydrous magnesium sulfate. The solvent was evaporated and the obtained residue was recrystallized from ethyl acetate-isopropyl ether to give the title compound (39.0 g) as pale-yellow crystals, m.p.=165–167° C.

$^1$H-NMR(DMSO-d$_6$)δ: 1.53(6H, s), 1.83(3H, s), 3.83(3H, s), 7.44(2H, d, J=8.6 Hz), 7.87(2H, d, J=8.6 Hz), 8.15(1H, s). MS(EI): 235(M$^+$).

(3) Synthesis of N-(1-(4-Hydroxymethylphenyl)-1-methylethyl)acetamide

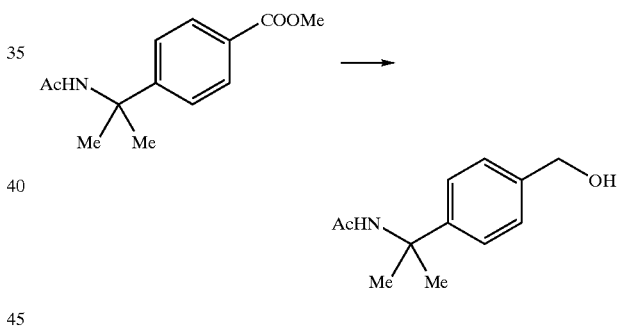

To a solution of methyl 4-(1-acetamido-1-methylethyl)benzoate (37.14g) in tetrahydrofuran (370 ml) was added lithium borohydride (6.88 g) and the mixture was refluxed for 19 hr. The reaction mixture was poured into water (1000 ml) and extracted with ethyl acetate (1000 ml). The extract was washed with saturated brine and dried over anhydrous magnesium sulfate. The solvent was evaporated and the obtained residue was recrystallized from ethyl acetate to give the title compound (18.24 m.p.=126–129° C.

$^1$H-NMR(DMSO-d$_6$)δ: 1.52(6H, s), 1.81(3H, s), 4.44(2H, d, J=5.3 Hz), 5.06(1H, t, J=5.3 Hz), 7.18–7.27(4H, m), 7.98(1H, br.s). MS(EI): 207(M$^+$).

(4) Synthesis of N-(1-(4-Chloromethylphenyl)-1-methylethyl)acetamide

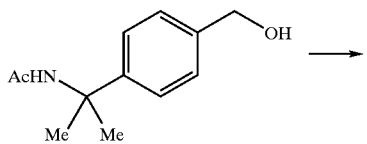

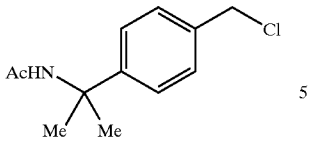

To a solution of N-(1-(4-hydroxymethylphenyl)-1-methylethyl)acetamide (18.24 g) in chloroform (180 ml) was added dropwise thionyl chloride (7.07 ml) over 10 min under ice-cooling and the mixture was stirred at room temperature for 20 hr. The reaction mixture was poured into water (1000 ml) and the organic layer was separated. The organic layer was washed with aqueous sodium hydrogencarbonate and saturated brine and dried over anhydrous magnesium sulfate. The solvent was evaporated to give the title compound (19.17 g) as pale-yellow crystals, m.p.=124–125° C.

$^1$H-NMR(DMSO-d$_6$)δ:1.52(6H, s), 1.82(3H, s), 4.71(2H, s), 7.28–7.35(4H, m), 8.05(1H, s). MS(EI): 225(M$^+$).

(5) Synthesis of N-(1-Methyl-1-(4-((4-(pyrimidin-2-yl)piperazin-1-yl)methyl)phenyl)ethyl)acetamide

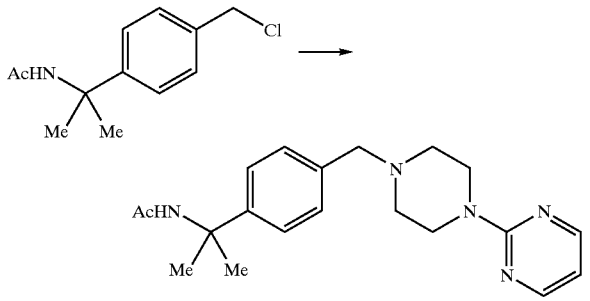

By similar reaction and treatment to that in Example 1(5) using N-(1-(4-chloromethylphenyl)-1-methylethyl)acetamide instead of N-(4-chloromethylphenylmethyl)acetamide and 1-(2-pyrimidyl)piperazine dihydrochloride instead of phenylpiperazine, the title compound was obtained as white crystals, m.p.=137–138° C.

$^1$H-NMR(CDCl$_3$)δ: 1.70(6H, s), 1.96(3H, s), 2.50(4H, t, J=5.3 Hz), 3.51(2H, s), 3.82(4H, t, J=5.3 Hz), 5.76(1H, br.s), 6.46(1H, t, J=4.6 Hz), 7.28–7.36(4H, m), 8.29(2H, t, J=4.6 Hz). MS(EI): 353(M$^+$). Elemental analysis: Calculated: C; 67.96, H; 7.70, N; 19.81; Found: C; 67.94, H; 7.65, N; 19.80.

Example 96

Synthesis of N-(1-(4-((4-(4,6-Dimethoxypyrimidin-2-yl)piperazin-1-yl)methyl)phenyl)-1-methylethyl)acetamide

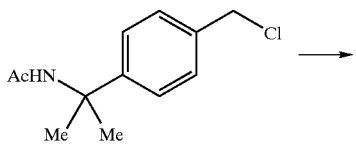

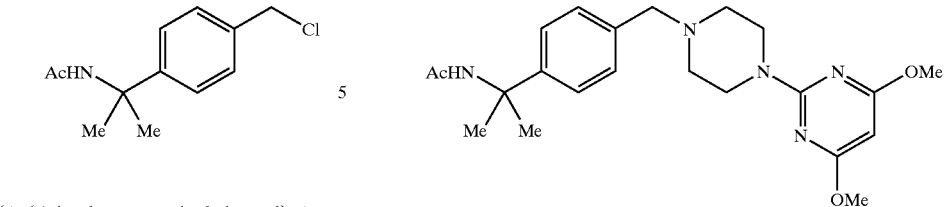

By similar reaction and treatment to that in Example 1(5) using N-(1-(4-chloromethylphenyl)-1-methylethyl)acetamide obtained in Example 95(4) instead of N-(4-chloromethylphenylmethyl)acetamide and 1-(4,6-dimethoxypyrimidin-2-yl)piperazine obtained in Example 90(2) instead of phenylpiperazine, the title compound was obtained as white crystals, m.p.=199–202° C.

$^1$H-NMR(DMSO-d$_6$)δ: 1.53(6H, s), 1.82(3H, s), 2.38–2.41(4H, m), 3.46(2H, s), 3.71(4H, m), 3.78(6H, s), 5.38(1H, s), 7.20–7.28(4H, m), 7.99(1H, s); MS(FAB): 414(M$^+$); Elemental analysis: Calculated: C; 63.90, H; 7.56, N; 16.94; Found: C; 63.73, H; 7.64, N; 16.82.

Example 97

Synthesis of N-(4-((4-(2-Chloropyrimidin-4-yl)piperazin-1-yl)methyl)phenylmethyl)acetamide and N-(4-((4-(4-chloropyrimidin-2-yl)piperazin-1-yl)methyl)phenylmethyl)acetamide

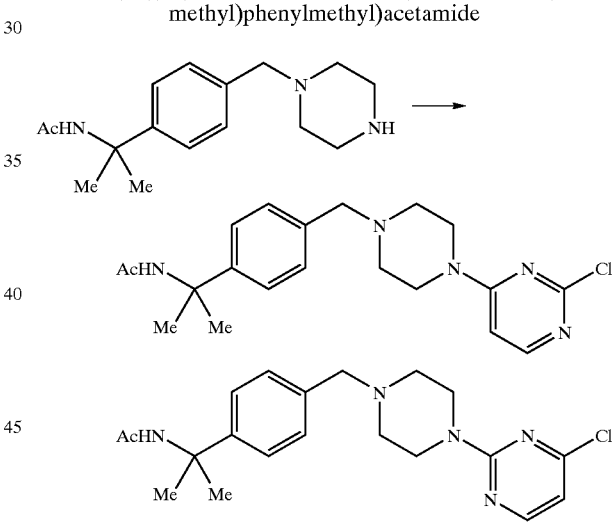

To a suspension of N-(4-((piperazin-1-yl)methyl)-phenylmethyl)acetamide (1.0 g) obtained in Example 78(2) and 2,4-dichloropyrimidine (0.60 g) in acetonitrile (20 ml) was added potassium carbonate (0.84 9) and the mixture was stirred at room temperature for 2 hr. The reaction mixture was poured into water (200 ml) and extracted with ethyl acetate (100 ml). The extract was washed with saturated brine and dried over anhydrous magnesium sulfate. The solvent was evaporated and the obtained residue was purified by silica gel column chromatography (developing solvent; ethyl acetate:methanol=20:1–10:1) to give N-(4-((4-(2-chloropyrimidin-4-yl)piperazin-1-yl)methyl)phenylmethyl)acetamide (0.61 g) as white crystals and N-(4-((4-(4-chloropyrimidin-2-yl)piperazin-1-yl)methyl)phenylmethyl)acetamide (10 mg) as white crystals. N-(4-((4-(2-chloropyrimidin-4-yl)piperazin-1-yl)methyl)phenylmethyl)acetamide.

m.p.=132–133° C.; ¹H-NMR(CDCl₃)δ: 2.02(3H, s), 2.49 (4H, t, J=5.3 Hz), 3.52(2H, s), 3.65(4H, br.), 4.42(2H, d, J=5.9 Hz), 5.96(1H, br.s), 6.36(1H, d, J=6.6 Hz), 7.23–7.31 (4H, m), 8.00(1H, d, J=6.6 Hz). MS(FAB): 360(M⁺); Elemental analysis: Calculated: C; 60.08, H; 6.16, N; 19.46; Found: C; 60.08, H; 6.11, N; 19.43.

N-(4-((4-(4-Chloropyrimidin-2-yl)piperazin-1-yl)methyl) phenylmethyl)acetamide m.p.=122–124° C.; ¹H-NMR(CDCl₃)δ: 2.01(3H, s), 2.47 (4H, t, J=5.3 Hz), 3.52(2H, s), 3.80–3.83(4H,t), 4.41(2H, d, J=5.3 Hz), 5.99(1H, br.s), 6.48(1H, d, J=4.6 Hz), 7.22–7.32 (4H, m), 8.13(1H, d, J=5.3 Hz). MS(FAB): 360(M⁺).

Example 98

Synthesis of N-(1-((4-(4-Methoxypyrimidin-2-yl) piperazin-1-yl)methyl)phenylmethyl)acetamide (1) Synthesis of 2-Chloro-4-methoxypyrimidine

To a solution of 2,4-dichloropyrimidine (32.4 g) in methanol (200 ml) was added dropwise a solution of sodium methoxide (11.7 g) in methanol (120 ml) over 40 min and the mixture was stirred for 30 min. The reaction mixture was poured into water (500 ml) and extracted with chloroform (300 ml). The extract was washed with saturated brine and dried over anhydrous magnesium sulfate. The solvent was evaporated and the obtained residue was recrystallized from hexane to give the title compound (21.5 g) as white crystals, m.p.=50–52° C.

¹H-NMR(CDCl₃)δ: 4.02(3H, s), 6.68(1H, d, J=5.3 Hz), 8.29(1H, d, J=5.3 Hz). MS(EI): 144(M⁺).

(2) Synthesis of 1-(4-Methoxypyrimidin-2-yl)piperazine

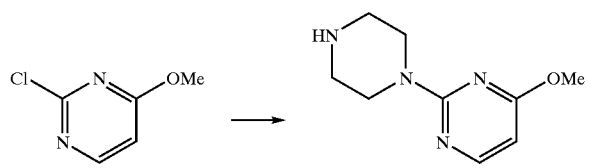

A suspension of 2-chloro-4-methoxypyrimidine (21.5 g) and piperazine (64.0 g) in acetonitrile (200 ml) was refluxed for 30 min. The reaction mixture was poured into water (500 ml) and extracted with chloroform (400 ml). The extract was washed with saturated brine and dried over anhydrous magnesium sulfate. The solvent was evaporated to give the title compound (26.0 g) as a pale-yellow oil.

¹H-NMR(CDCl₃)δ: 2.94(4H, m), 3.76–3.80(4H, m), 3.88 (3H, s), 5.97(1H, d, J=5.9 Hz), 8.05(1H, d, J=5.3 Hz). MS(EI): 194(M⁺).

(3) Synthesis of N-(1-((4-(4-Methoxypyrimidin-2-yl) piperazin-1-yl)methyl)phenylmethyl)acetamide

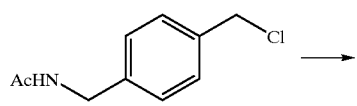

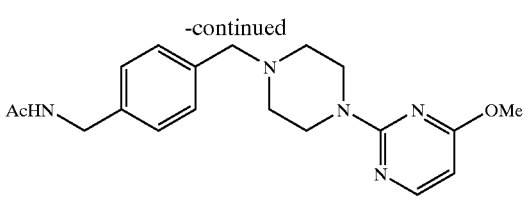

By similar reaction and treatment to that in Example 1(5) using 1-(4-methoxypyrimidin-2-yl)piperazine instead of phenylpiperazine, the title compound was obtained as white crystals, m.p.=144–145° C.

1H-NMR(CDCl₃)δ: 2.02(3H, s), 2.46–2.50(4H, m), 3.53 (2H, s), 3.79–3.82(4H, m), 3.86(3H, s), 4.42(2H, d, J=5.3 Hz), 5.84(1H, br.s), 5.96(1H, d, J=5.9 Hz), 7.23–7.33(4H, m), 8.03(1H, d, J=5.3 Hz). MS(EI): 355(M⁺); Elemental analysis: Calculated: C; 64.21, H; 7.09, N; 19.70; Found: C; 63.98, H; 6.93, N; 19.60.

Example 99

Synthesis of N-(4-((4-(4-(N,N-Dimethylamino) pyrimidin-2-yl)piperazin-1-yl)methyl)phenylmethyl) acetamide (1) Synthesis of 2-Chloro-4-(N,N-dimethylamino) pyrimidine

To a 20% dimethylamine-ethanol solution (15.4 g) of 2,4-dichloropyrimidine (3.0 g) was added triethylamine (3 ml) under ice-cooling, and the mixture was stirred for 30 min. The reaction mixture was poured into water (100 ml) and extracted with ethyl acetate (100 ml). The extract was washed with saturated brine and dried over anhydrous sodium sulfate. The solvent was evaporated and the obtained residue was purified by silica gel column chromatography (developing solvent; ethyl acetate:hexane=1:1) to give the title compound (1.90 g) as white crystals, m.p.=77–79° C.

¹H-NMR(CDCl₃)δ: 3.11(6H, s), 6.31(1H, d, J=5.9 Hz), 8.00(1H, d, J=5.9 Hz). MS(EI): 157(M⁺).

(2) Synthesis of N-(4-((4-(4-(N,N-Dimethylamino) pyrimidin-2-yl)piperazin-1-yl)methyl)phenylmethyl) acetamide

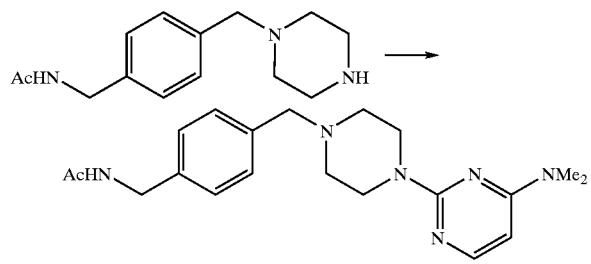

By similar reaction and treatment to that in Example 1(5) using N-(4-((piperazin-1-yl)methyl)phenylmethyl) acetamide obtained in Example 78(2) instead of N-(4-chloromethylphenylmethyl)acetamide and 2-chloro-4-(N,N-dimethylamino)pyrimidine instead of phenylpiperazine, the title compound was obtained as white crystals, m.p.= 152–155° C.

¹H-NMR(CDCl₃)δ: 1.99(3H, s), 2.44–2.48(4H, m), 3.02 (6H, s), 3.51(2H, s), 3.75–3.78(4H, m), 4.40(2H, d, J=5.3 Hz), 5.77(1H, d, J=5.9 Hz), 6.08(1H, br.s), 7.21–7.32(4H, m), 7.88(1H, d, J=5.9 Hz). MS(EI): 368(M⁺); Elemental analysis: Calculated: C; 65.19, H; 7.66, N; 22.81; Found: C; 64.84, H; 7.59, N; 22.53.

Example 100

Synthesis of N-(1-(4-((4-(Thiazol-2-yl)piperazin-1-yl)methyl)phenyl)cyclopropyl)acetamide

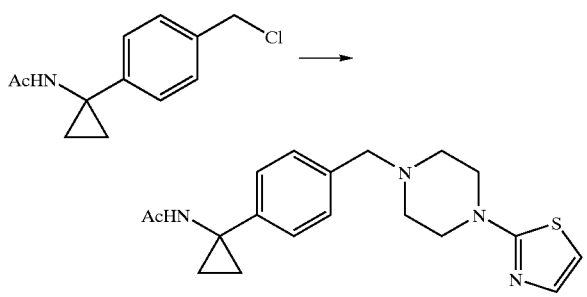

By similar reaction and treatment to that in Example 1(5) using N-(1-(4-chloromethylphenyl)cyclopropyl)acetamide obtained in Example 71(1) instead of N-(4-chloromethylphenylmethyl)acetamide and 1-(thiazol-2-yl)piperazine obtained in Example 81(1) instead of phenylpiperazine, the title compound was obtained as pale-yellow crystals, m.p.=184–185° C.

¹H-NMR(CDCl₃)δ: 1.26 and 1.36(4H, s and d, J=4.0 Hz), 1.99(3H, s), 2.51–2.57(4H, m), 3.46–3.53(6H, m), 6.21(1H, br), 6.54–6.56(1H, m), 7.09–7.31(5H, m). MS(EI): 356 (M⁺); Elemental analysis: Calculated: C; 64.02, H; 6.79, N; 15.72; Found: C; 63.83, H; 6.55, N; 15.58.

Example 101

Synthesis of N-(1-(4-((4-(Thiazol-2-yl)piperazin-1-yl)methyl)phenyl)ethyl)acetamide

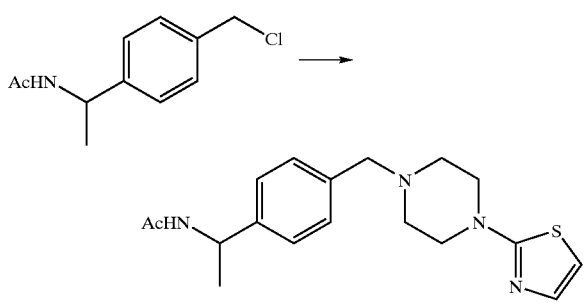

By similar reaction and treatment to that in Example 1(5) using N-(1-(4-chloromethylphenyl)ethyl)acetamide obtained in Example 48(3) instead of N-(4-chloromethylphenylmethyl)acetamide and 1-(thiazol-2-yl)piperazine obtained in Example 81(1) instead of phenylpiperazine, the title compound was obtained as white crystals, m.p.=136–137° C.

¹H-NMR(CDCl₃)δ: 1.49(3H, d, J=7.3 Hz), 1.98(3H, s), 2.55(4H, t, J=5.3 Hz), 3.49(4H, t, J=5.3 Hz), 3.53(2H, s), 5.12(1H, dt, J=7.3 Hz), 5.74–5.77(1H, br), 6.56(1H, d, J=3.3 Hz), 7.18(1H, d, J=3.3 Hz), 7.25–7.33(4H, m). MS(EI): 344(M⁺); Elemental analysis: Calculated: C; 62.76, H; 7.02, N; 16.26; Found: C; 62.74, H; 6.92, N; 16.21.

Example 102

Synthesis of N-(1-(4-((4-(6-Fluoropyridin-2-yl)piperazin-1-yl)methyl)phenyl)ethyl)acetamide

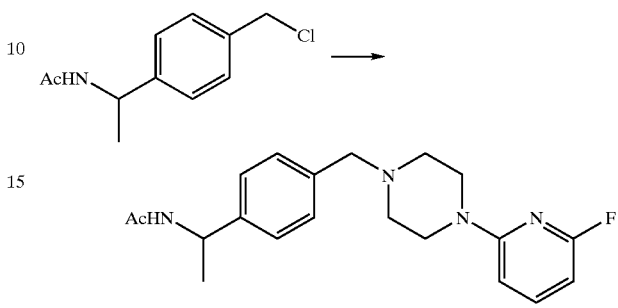

By similar reaction and treatment to that in Example 1(5) using N-(1-(4-chloromethylphenyl)ethyl)acetamide obtained in Example 48(3) instead of N-(4-chloromethylphenylmethyl)acetamide and 1-(6-fluoropyridin-2-yl)piperazine obtained in Example 85(2) instead of phenylpiperazine, the title compound was obtained as white crystals, m.p.=109–111° C.

¹H-NMR(CDCl₃)δ: 1.49(3H, d, J=7.3 Hz), 1.98(3H, s), 2.50–2.53(4H, m), 3.51–3.55(6H, m), 5.13(1H, dq, J=7.3 Hz), 5.73–5.75(1H, br), 6.13–6.17(1H, m), 6.37–6.41(1H, m), 7.26–7.33(4H, m), 7.46–7.55(1H, m). MS(EI): 356(M⁺); Elemental analysis: Calculated: C; 67.39, H; 7.07, N; 15.72; Found: C; 67.29, H; 7.00, N; 15.76.

Example 103

Synthesis of N-(1-(4-((4-(6-Fluoropyridin-2-5 yl)piperazin-1-yl)methyl)phenyl)-1-methylethyl)acetamide

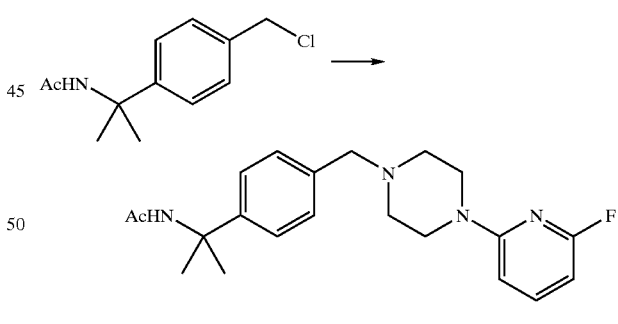

By similar reaction and treatment to that in Example 1(5) using N-(1-(4-chloromethylphenyl)-1-methylethyl)acetamide obtained in Example 95(4) instead of N-(4-chloromethylphenylmethyl)acetamide and 1-(6-fluoropyridin-2-yl)piperazine obtained in Example 85(2) instead of phenylpiperazine, the title compound was obtained as white crystals, m.p.=133–134° C.

¹H-NMR(CDCl₃)δ: 1.70(6H, s), 1.97(3H, s), 2.50–2.54 (4H, m), 3.51–3.55(6H, m), 5.71(1H, br.s), 6.13–6.16(1H, m), 6.36–6.41(1H, m), 7.26–7.36(4H, m), 7.46–7.55(1H, m). MS(EI): 370(M⁺); Elemental analysis: Calculated: C; 68.08, H; 7.35, N; 15.12; Found: C; 68.10, H; 7.15, N; 15.14.

Example 104

Synthesis of N-(1-(4-((4-(Pyridin-2-yl)piperazin-1-yl)methyl)phenyl)ethyl)acetamide

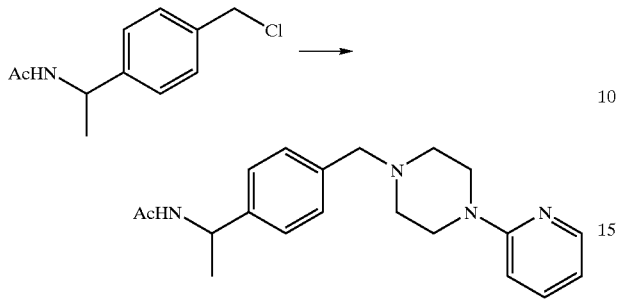

By similar reaction and treatment to that in Example 1(5) using N-(1-(4-chloromethylphenyl)ethyl)acetamide obtained in Example 48(3) instead of N-(4-chloromethylphenylmethyl)acetamide and 1-(2-pyridyl)piperazine instead of phenylpiperazine, the title compound was obtained as pale-yellow crystals, m.p.=120–121° C.

$^1$H-NMR(CDCl$_3$)δ: 1.70(6H, s), 1.97(3H, s), 2.50–2.54 (4H, m), 3.51–3.55(6H, m), 5.71(1H, br), 6.13–6.16(1H, m), 6.36–6.41(1H, m), 7.26–7.36(4H, m), 7.46–7.55(1H, m). MS(EI): 338(M$^+$); Elemental analysis: Calculated: C; 70.98, H; 7.74, N; 16.55; Found: C; 70.91, H; 7.70, N; 16.51.

Example 105

Synthesis of N-(1-Methyl-1-(4-((4-(pyridin-2-yl)piperazin-1-yl)methyl)phenyl)ethyl)acetamide

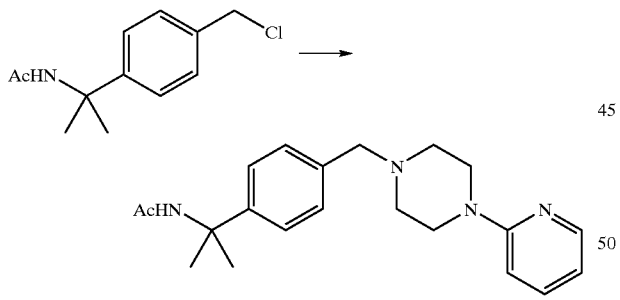

By similar reaction and treatment to that in Example 1(5) using N-(1-(4-chloromethylphenyl)-1-methylethyl)acetamide obtained in Example 95(4) instead of N-(4-chloromethylphenylmethyl)acetamide and 1-(2-pyridyl)piperazine instead of phenylpiperazine, the title compound was obtained as white crystals, m.p.=129–130° C.

$^1$H-NMR(CDCl$_3$)δ: 1.70(6H, s), 1.97(3H, s), 2.53–2.57 (4H, m), 3.52–3.55(6H, m), 5.71(1H, br.s), 6.58–6.64(2H, m), 7.26–7.36(4H, m), 7.42–7.49(1H, m), 8.17–8.18(1H, m). MS(EI): 352(M$^+$); Elemental analysis: Calculated: C; 71.56, H; 8.01, N; 15.90; Found: C; 71.59, H; 7.93, N; 15.88.

Example 106

Synthesis of N-(1-(4-((4-(4-Methoxypyrimidin-2-yl)piperazin-1-yl)methyl)phenyl)-1-methylethyl)acetamide

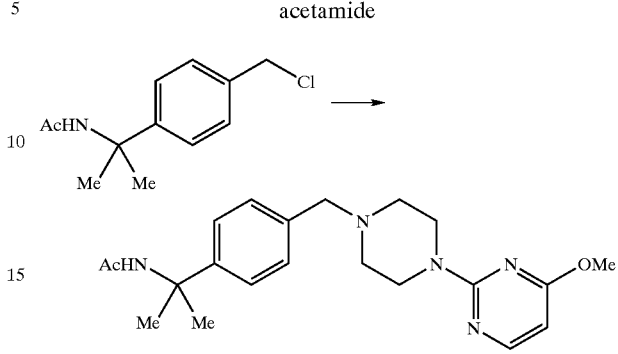

By similar reaction and treatment to that in Example 1(5) using N-(1-(4-chloromethylphenyl)-1-methylethyl)acetamide obtained in Example 95(4) instead of N-(4-chloromethylphenylmethyl)acetamide and 1-(4-methoxypyrimidin-2-yl)piperazine obtained in Example 98(2) instead of phenylpiperazine, the title compound was obtained as white crystals, m.p.=160–162° C.

$^1$H-NMR(CDCl$_3$)δ: 1.70(6H, s), 1.97(3H, s), 2.47–2.51 (4H, m), 3.52(2H, s), 3.79–3.83(4H, m), 3.87(3H, s), 5.71 (1H, br), 5.96(1H, d, J=5.3 Hz), 7.26–7.36(4H, m), 8.04(1H, d, J=5.3 Hz). MS(EI): 383(M$^+$); Elemental analysis: Calculated: C; 65.77, H; 7.62, N; 18.26; Found: C; 65.69, H; 7.46, N; 18.37.

Example 107

Synthesis of N-(1-(4-((4-(4-Methoxypyrimidin-2-yl)piperazin-1-yl)methyl)phenyl)ethyl)acetamide

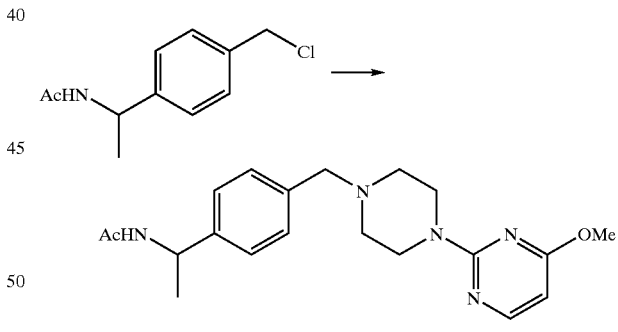

By similar reaction and treatment to that in Example 1(5) using N-(1-(4-chloromethylphenyl)ethyl)acetamide obtained in Example 48(3) instead of N-(4-chloromethylphenylmethyl)acetamide and 1-(4-methoxypyrimidin-2-yl)piperazine obtained in Example 98(2) instead of phenylpiperazine, the title compound was obtained as pale-yellow crystals, m.p.=113–115° C.

$^1$H-NMR(CDCl$_3$)δ: 1.49(3H, d, J=7.3 Hz), 1.98(3H, s), 2.46–2.50(4H, m), 3.52(2H, s), 3.79–3.83(4H, m), 3.86(3H, s), 5.13(1H, dq, J=7.3 Hz), 5.70–5.72(1H, br), 5.96(1H, d, J=5.3 Hz), 7.26–7.34(4H, m), 8.03(1H, d, J=5.9 Hz). MS(EI): 369(M$^+$); Elemental analysis: Calculated: C; 65.02, H; 7.37, N; 18.96; Found: C; 64.90, H; 7.15, N; 19.21.

Example 108

Synthesis of N-(4-((4-(4,6-Diethoxypyrimidin-2-yl)piperazin-1-yl)methyl)phenylmethyl)acetamide (1) 1-Acetyl-4-(4,6-diethoxypyrimidin-2-yl)piperazine

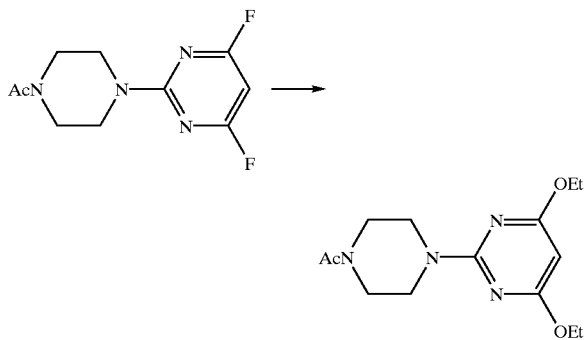

A solution of 1-acetyl-4-(4,6-difluoropyrimidin-2-yl)piperazine (1.5 g) and sodium ethoxide (1.3 g) in ethanol (15 ml) was refluxed under heating for 1 hr. The reaction mixture was poured into ice water and extracted with ethyl acetate. The extract was washed with brine and dried over anhydrous sodium sulfate. The solvent was evaporated to give the title compound (1.8 g) as a pale-brown solid.

$^1$H-NMR(CDCl$_3$)δ: 1.36(6H, t, J=7.3 Hz), 2.14(3H, s), 3.48–3.52(2H, m), 3.64–3.68(2H, m), 3.73–3.83(4H, m), 4.27(4H, q, J=7.3 Hz), 5.38(1H, s); MS(EI): 294(M$^+$).

(2) 1-(4,6-Diethoxypyrimidin-2-yl)piperazine

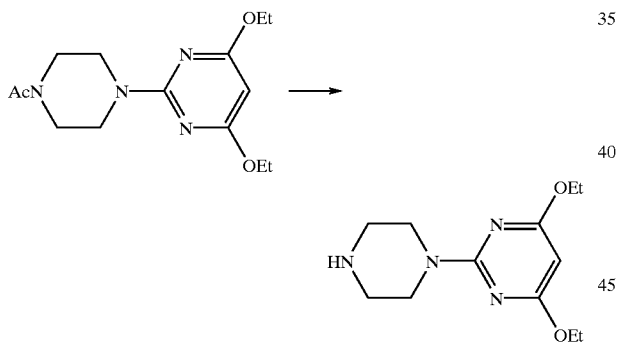

A solution of 1-acetyl-4-(4,6-diethoxypyrimidin-2-yl)piperazine (1.8 g) and sodium hydroxide (1.0 g) in ethanol (10 ml)—water (10 ml) was refluxed under heating for 11 hr. The reaction mixture was poured into water and extracted with chloroform. The extract was dried over anhydrous sodium sulfate and the solvent was evaporated to give the title compound (1.6 g) as a pale-brown oil.

$^1$H-NMR(CDCl$_3$)δ: 1.35(6H, t, J=7.3 Hz), 2.89(4H, t, J=5.3 Hz), 3.74(4H, t, J=5.3 Hz), 4.26(4H, q, J=7.3 Hz), 5.32(1H, s) MS(EI): 252(M$^+$).

(3) N-(4-((4-(4,6-Diethoxypyrimidin-2-yl)piperazin-1-yl)methyl)phenylmethyl)acetamide

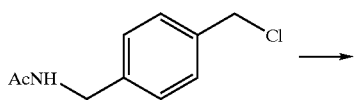

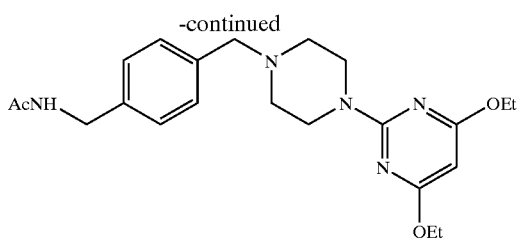

A solution of N-(4-chloromethylphenylmethyl)acetamide (1.2 g), 1-(4,6-diethoxypyrimidin-2-yl)piperazine (1.7 g) and potassium carbonate (1.3 g) in dimethylformamide (20 ml) was stirred at 80° C. for 4.5 hr. The reaction mixture was poured into water(150 ml) and extracted with ethyl acetate. The extract was washed with saturated brine and dried over anhydrous sodium sulfate. The solvent was evaporated to give a brown oil (2.9 g). The obtained brown oil was purified by silica gel column chromatography to give a pale-yellow oil (2.4 g). The obtained pale-yellow oil was crystallized from ethyl acetate/hexane (2:1, 30 ml) to give the title compound (1.7 g) as white crystals, m.p.=119–120° C.

$^1$H-NMR(CDCl$_3$)δ: 1.34(6H, t, J=7.3 Hz), 2.03(3H, s), 2.45(4H, t, J=5.3 Hz), 3.52(2H, s), 3.77(4H, t, J=5.3 Hz), 4.25(4H, q, J=7.3 Hz), 4.42(4H, d, J=5.9 Hz), 5.32(1H, s), 5.71(1H, brs), 7.22–7.33(4H, m); IR(KBr): 3288, 2977, 1643, 1578 cm$^{-1}$; MS(EI): 413(M$^+$); Elemental analysis: Calculated: C; 63.90, H; 7.56, N; 16.94; Found: C; 63.81, H; 7.47, N; 16.72.

Example 109

Synthesis of N-(4-((4-(4,6-bis(Dimethylamino)-pyrimidin-2-yl)piperazin-1-yl)methyl)phenylmethyl)acetamide (1) 1-Acetyl-4-(6-(dimethylamino)-4-fluoropyrimidin-2-yl)piperazine

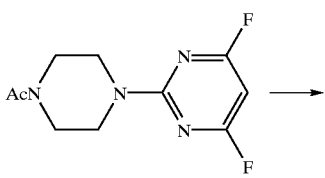

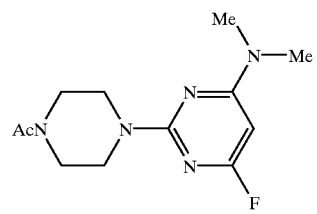

1-Acetyl-4-(4,6-difluoropyrimidin-2-yl)piperazine (1.9 g) was dissolved in 12% dimethylamine-ethanol solution (30 ml) and the mixture was stirred at room temperature for 1 hr. The reaction mixture was concentrated under reduced pressure. Water was added to the residue and the mixture was extracted with ethyl acetate. The extract was washed with brine and dried over anhydrous sodium sulfate. The solvent was evaporated to give the title compound (2.1 g) as a yellow solid.

$^1$H-NMR(CDCl$_3$)δ: 2.13(3H, s), 3.06(6H, s), 3.47–3.51(2H, m), 3.64–3.68(2H, m), 3.74–3.81(4H, m), 5.33(1H, d, J=1.3 Hz); MS(EI): 267(M$^+$).

(2) 1-Acetyl-4-(4,6-bis(dimethylamino)pyrimidin-2-yl)piperazine

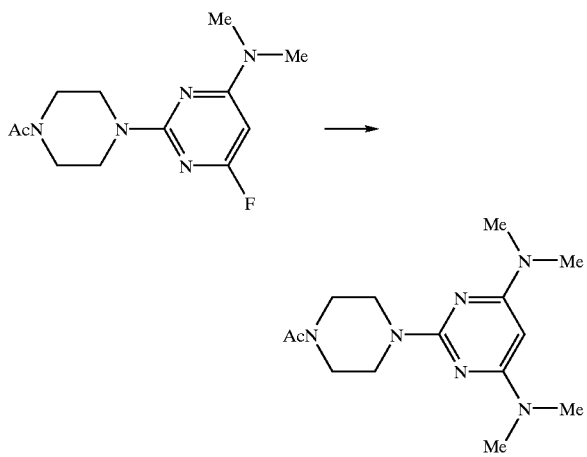

1-Acetyl-4-(6-(dimethylamino)-4-fluoropyrimidin-2-yl)piperazine (1.0 g) was dissolved in 12% dimethylamine-ethanol solution (30 ml) in an autoclave, and the mixture was stirred at 100° C. for 5 hr. The reaction mixture was concentrated under reduced pressure and chloroform was added to the reside. The chloroform solution was washed with brine and dried over anhydrous sodium sulfate. The solvent was evaporated to give the title compound (1.3 g) as a pale-yellow solid.

$^1$H-NMR(CDCl$_3$)δ: 2.13(3H, s), 3.02(12H, s), 3.48–3.52 (2H, m), 3.65–3.68(2H, m), 3.73–3.82(4H, m), 4.91(1H, s); MS(EI): 292(M$^+$).

(3) 1-(4,6-bis(Dimethylamino)pyrimidin-2-yl)piperazine

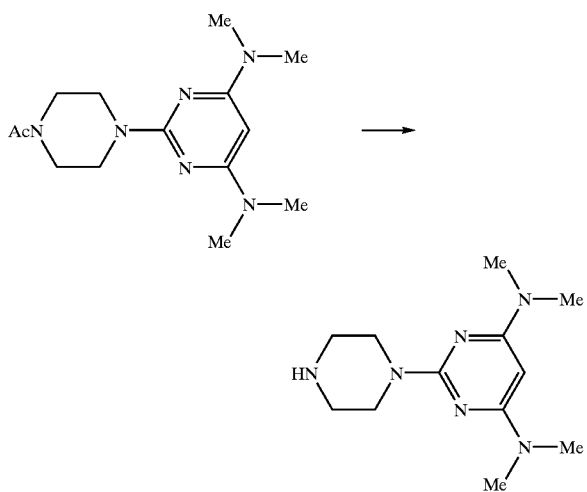

A solution of 1-acetyl-4-(4,6-bis(dimethylamino)pyrimidin-2-yl)piperazine (1.3 g) and sodium hydroxide (0.5 g) in ethanol (15 ml)—water (15 ml) was refluxed under heating for 9.5 hr. The reaction mixture was concentrated under reduced pressure, and ethyl acetate was added to the residue and the mixture was washed with brine. The organic layer was dried over anhydrous sodium sulfate and the solvent was evaporated to give the title compound (0.9 g) as a pale-brown oil.

$^1$H-NMR(CDCl$_3$)δ: 1.73(1H, s), 2.87–2.89(4H, m), 3.01 (12H, s), 3.70–3.74(4H, m), 4.89(1H, s); MS(EI): 250(M$^+$).

(4) N-(4-((4-(4,6-bis(Dimethylamino)pyrimidin-2-yl)piperazin-1-yl methyl)phenylmethyl)acetamide

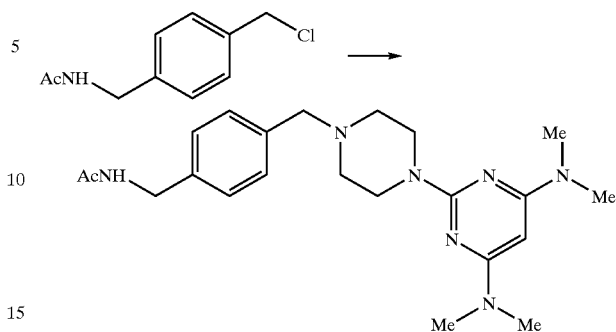

A solution of N-(4-chloromethylphenylmethyl)acetamide (0.7 g), 1-(4,6-bis(dimethylamino)pyrimidin-2-yl)piperazine (0.9 g) and potassium carbonate (0.7 g) in dimethylformamide (10 ml) was stirred at 80° C. for 6 hr. The reaction mixture was poured into water (100 ml) and extracted with ethyl acetate. The extract was washed with saturated brine and dried over anhydrous sodium sulfate. The solvent was evaporated to give a brown solid (1.6 g). The obtained brown solid was crystallized from ethyl acetate/ethanol (2:1, 30 ml) to give the title compound (0.9 g) as pale-yellow crystals.

m.p.=189–190° C. (decomposition); $^1$H-NMR(CDCl$_3$)(δ: 2.00(3H, s), 2.43–2.47(4H, m), 2.99(12H, s), 3.51(2H, s), 3.74–3.77(4H, m), 4.40(2H, d, J=5.3 Hz), 4.88(1H, s), 5.80(1H, brs), 7.21–7.32(4H, m); IR(KBr): 3291, 2935, 2819, 1645, 1578 cm$^{-1}$; MS(EI): 411(M$^+$); Elemental analysis: Calculated: C; 64.21, H; 8.08, N; 23.82; Found: C; 63.81, H; 7.79, N; 22.96.

Example 110

Synthesis of N-(4-((4-(4-Dimethylamino-6-methoxypyrimidin-2-yl)piperazin-1-yl)methyl)phenylmethyl)acetamide (1) 1-(4-Dimethylamino-6-methoxypyrimidin-2-yl)piperazine

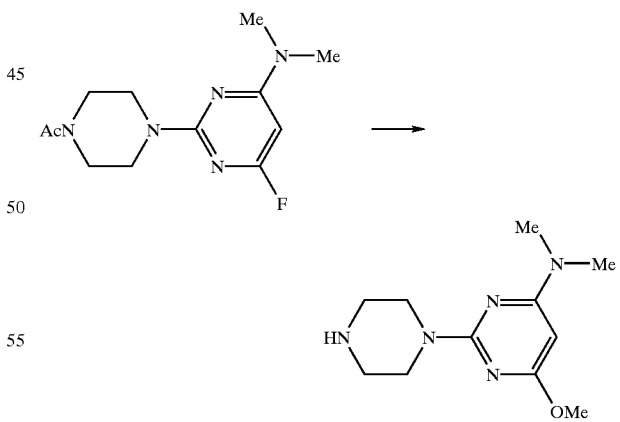

1-Acetyl-4-(6-(dimethylamino)-4-fluoropyrimidin-2-yl)piperazine (1.0 g) obtained in Example 109(1) and sodium methoxide (1.1 g) were refluxed under heating in methanol (10 ml) for 28 hr. The reaction mixture was poured into water (100 ml) and extracted with chloroform. The extract was dried over anhydrous sodium sulfate and the solvent was evaporated to give the title compound (1.1 g) as a pale-yellow oil.

$^1$H-NMR(CDCl$_3$)δ: 2.88–2.92(4H, m), 3.01(6H, s), 3.72–3.76(4H, m), 3.84(3H, s), 5.15(1H, s); MS(EI): 237 (M$^+$).

(2) N-(4-((4-(4-Dimethylamino-6-methoxypyrimidin-2-yl)piperazin-1-yl)methyl)phenylmethyl)acetamide

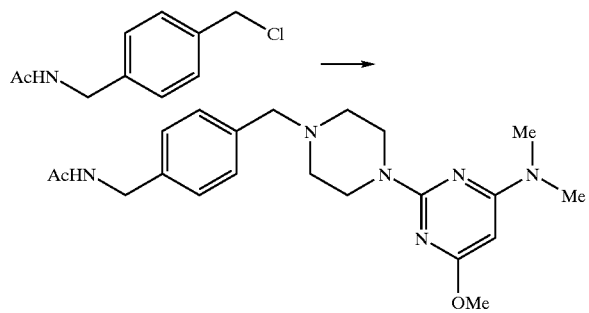

A solution of N-(4-chloromethylphenylmethyl)acetamide (0.9 g), 1-(4-dimethylamino-6-methoxypyrimidin-2-yl)piperazine (1.1 g) and potassium carbonate (1.0 g) in dimethylformamide (10 ml) was stirred at 80° C. for 8.5 hr. The reaction mixture was poured into water (100 ml) and extracted with ethyl acetate. The extract was washed with saturated brine and dried over anhydrous sodium sulfate. The solvent was evaporated to give a brown oil (1.9 g). The obtained brown oil was purified by silica gel column chromatography (developing solvent; chloroform:methanol=9:1) to give a yellow oil (1.6 g). The obtained yellow oil was crystallized from ethyl acetate/hexane (1:1, 20 ml) to give the title compound (1.0 g) as pale-yellow crystals.

m.p.=115–118° C.; $^1$H-NMR(CDCl$_3$)δ: 2.01(3H, s), 2.43–2.47(4H, m), 2.99(6H, s), 3.52(2H, s), 3.75–3.79(4H, m), 3.81(3H, s), 4.40(2H, d, J=5.9 Hz), 5.14(1H, s), 5.86 (1H, brs), 7.21–7.32(4H, m); IR(KBr): 3261, 2939, 2834, 1635, 1589 cm$^{-1}$; MS(EI): 398(M$^+$); Elemental analysis: Calculated: C; 63.29, H; 7.59, N; 21.09; Found: C; 63.38, H; 7.45, N; 20.64.

Example 111

Synthesis of N-(4-((4-(5-Bromothiazol-2-yl)piperazin-1-yl)methyl)phenylmethyl)acetamide (1) 4-Acetyl-1-(thiazol-2-yl)piperazine

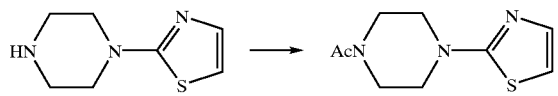

A solution of 1-(thiazol-2-yl)piperazine (6.7 g) obtained by similar manipulation to that in Example 81(1), acetic anhydride (5.6 ml) and sodium hydroxide (2.4 g) in water (50 ml)—ethyl acetate (50 ml) was stirred under ice-cooling for 1 hr. The reaction mixture was extracted with ethyl acetate and dried over anhydrous sodium sulfate. The solvent was evaporated to give a pale-yellow solid (6.9 g). The obtained pale-yellow solid was crystallized from ethyl acetate-hexane (1:1, 100 ml) to give the title compound (5.0 g) as white crystals.

$^1$H-NMR(CDCl$_3$)δ: 2.14(3H, s), 3.44–3.48(2H, m), 3.55–3.62(4H, m), 3.74–3.78(2H, m), 6.62(1H, d, J=3.3 Hz), 7.21(1H, d, J=3.3 Hz) MS(EI): 211(M$^+$).

(2) 4-Acetyl-1-(5-bromothiazol-2-yl)piperazine

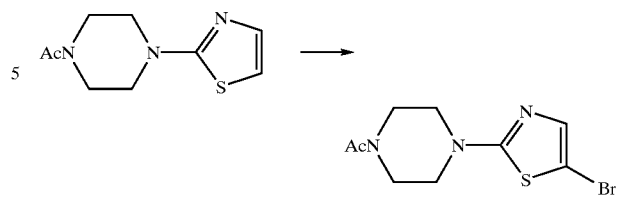

A solution of 4-acetyl-1-(thiazol-2-yl)piperazine (3.1 g) and N-bromosuccinimide (2.9 g) in acetic acid (14 ml) was stirred at room temperature for 1 hr. The reaction mixture was neutralized with 1N aqueous sodium hydroxide solution and extracted with ethyl acetate. The extract was washed with saturated brine and dried over anhydrous sodium sulfate. The solvent was evaporated to give a pale-brown solid (2.9 g). The obtained pale-brown solid was purified by silica gel column chromatography (developing solvent; chloroform:methanol=20:1) to give the title compound (2.1 g) as a pale-brown solid.

$^1$H-NMR(CDCl$_3$)δ: 2.14(3H, s), 3.37–3.41(2H, m), 3.48–3.51(2H, m), 3.56–3.60(2H, m), 3.72–3.76(2H, m), 7.09(1H, s); MS(EI): 291((M+1)+).

(3) 1-(5-Bromothiazol-2-yl)piperazine

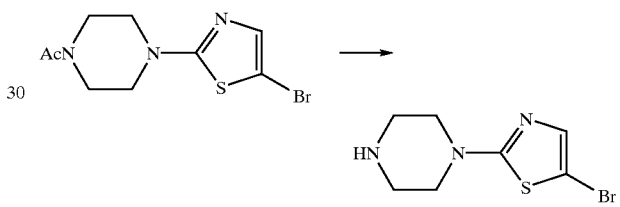

4-Acetyl-1-(5-bromothiazol-2-yl)piperazine (2.0 g) was dissolved in 6N hydrochloric acid and refluxed under heating for 4.5 hr. The reaction mixture was neutralized with 1N aqueous sodium hydroxide solution and extracted with ethyl acetate. The extract was washed with saturated brine and dried over anhydrous sodium sulfate. The solvent was evaporated to give a brown oil (1.5 g). The obtained brown oil was purified by silica gel column chromatography (developing solvent; chloroform:methanol=9:1) to give the title compound (1.1 g) as a pale-yellow solid.

$^1$H-NMR(CDCl$_3$)δ: 2.95–2.98(4H, m), 3.37–3.41(4H, m), 7.06(1H, s); MS(EI): 248((M+1)+).

(4) N-(4-((4-(5-Bromothiazol-2-yl)piperazin-1-yl)methyl)phenylmethyl)acetamide

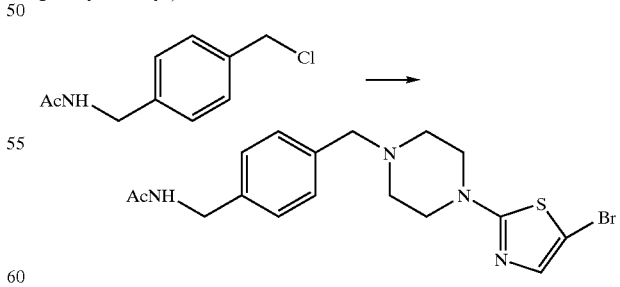

A solution of N-(4-chloromethylphenylmethyl)acetamide (0.9 g), 1-(5-bromothiazol-2-yl)piperazine (1.1 g) and potassium carbonate (0.9 g) in dimethylformamide (10 ml) was stirred at 70° C. for 9 hr. Water (100 ml) was poured into the reaction mixture to allow precipitation of crystals. The crystals were collected by filtration and washed with water to give the title compound (1.5 g) as yellow crystals, m.p.=160–163° C.

¹H-NMR(CDCl₃)δ: 2.01(3H, s), 2.50–2.54(4H, m), 3.40–3.44(4H, m), 3.52(2H, s), 4.41(2H, d, J=5.3 Hz), 5.91(1H, brs), 7.05(1H, s), 7.22–7.31(4H, m); IR(KBr): 3309, 2935, 2821, 1645, 1529 cm⁻¹; MS(EI): 410((M+1)+); Elemental analysis: Calculated: C; 49.88, H; 5.17, N; 13.69; Found: C; 49.94, H; 5.13, N; 13.54.

Example 112

Synthesis of N-(4-((4-(5-Chlorothiazol-2-yl) piperazin-1-yl )methyl)phenylmethyl)acetamide (1) 4-Acetyl-1-(5-chlorothiazol-2-yl)piperazine

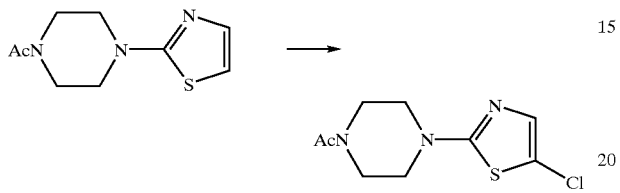

By similar reaction and treatment to that in Example 111(2) using N-chlorosuccinimide instead of N-bromosuccinimide, the title compound was obtained as pale-yellow crystals.

¹H-NMR(CDCl₃)δ: 2.14(3H, s), 3.36–3.40(2H, m), 3.47–3.50(2H, m), 3.57–3.60(2H, m), 3.72–3.76(2H, m), 7.00(1H, s); MS(EI): 245(M⁺).

(2) 1-(5-Chlorothiazol-2-yl)piperazine

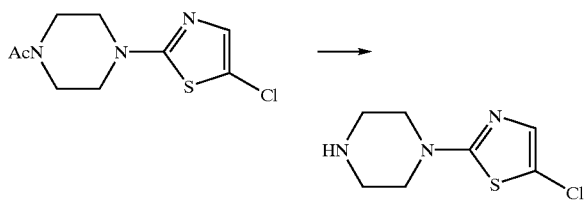

By similar reaction and treatment to that in Example 111(3) using 4-acetyl-1-(5-chlorothiazol-2-yl)piperazine instead of 4-acetyl-1-(5-bromothiazol-2-yl)piperazine, the title compound was obtained as a pale-brown oil.

¹H-NMR(CDCl₃)δ: 2.95–2.98(4H, m), 3.36–3.40(4H, m), 6.98(1H, s) MS(EI): 203(M⁺).

(3) N-(4-((4-(5-Chlorothiazol-2-yl)piperazin-1-yl)methyl) phenylmethyl)acetamide

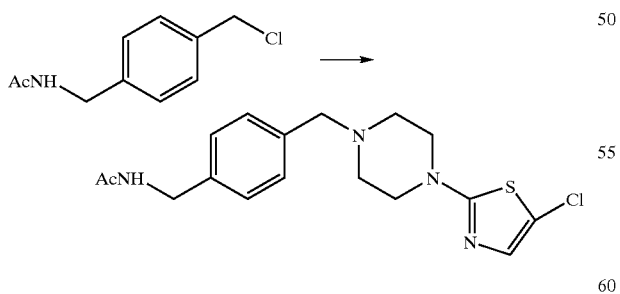

By similar reaction and treatment to that in Example 111(4) using 1-(5-chlorothiazol-2-yl)piperazine instead of 1-(5-bromothiazol-2-yl)piperazine, the title compound was obtained as pale-brown crystals, m.p.=142–145° C. (decomposition).

¹H-NMR(CDCl₃)δ: 2.02(3H, s), 2.51–2.54(4H, m), 3.39–3.43(4H, m), 3.53(2H, s), 4.41(2H, d, J=5.3 Hz), 5.88(1H, brs), 6.96(1H, s), 7.22–7.31(4H, m); MS(EI): 364(M⁺); Elemental analysis: Calculated: C; 55.96, H; 5.80, N; 15.35; Found: C; 55.81, H; 5.68, N; 15.38.

Example 113

Synthesis of N-(4-(1-(4-(Pyrimidin-2-yl)piperazin-1-yl)ethyl)phenylmethyl)acetamide Dihydrochloride 1/2 Hydrate

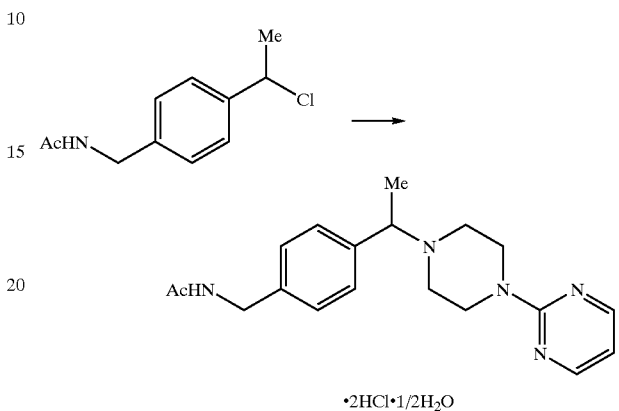

By similar reaction and treatment to that in Example 1(5) using 1-(2-pyrimidyl) piperazine dihydrochloride instead of phenylpiperazine and N-(4-(1-chloroethyl)phenylmethyl) acetamide instead of N-(4-chloromethylphenylmethyl) acetamide, the title compound was obtained as a yellow amorphous solid.

¹H-NMR(DMSO-d₆)δ: 1.72(3H, d, J=6.6 Hz), 1.89(3H, s), 2.75–3.15(3H, m), 3.30–3.90(3H, m), 4.27(2H, d, J=5.3 Hz), 4.45(1H, m), 4.66(2H, m), 6.76(1H, t, J=4.9 Hz), 7.33(2H, d, J=7.9 Hz), 7.63(2H, d, J=7.9 Hz), 8.44(2H, d, J=4.6 Hz), 8.47(1H, t, J=4.6 Hz). IR(KBr): 3244, 2920, 1659, 1626 cm⁻¹; Elemental analysis: Calculated: C; 54.16, H; 6.70, N; 16.62; Found: C; 53.92, H; 7.01, N; 16.39.

Example 114

Synthesis of N-(1-(4-(1-(4-(Pyrimidin-2-yl) piperazin-1-yl)ethyl)phenyl)-1-methylethyl) acetamide

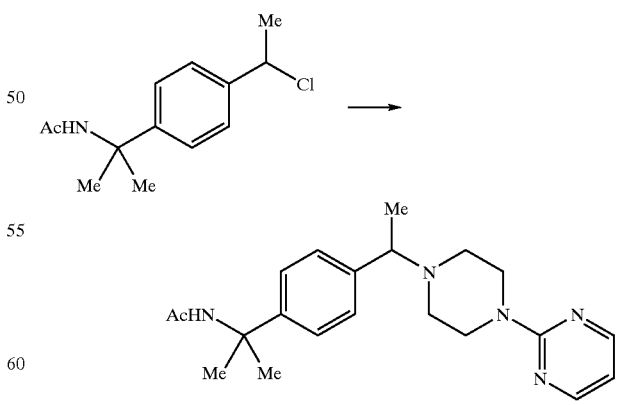

By similar reaction and treatment to that in Example 1(5) using 1-(2-pyrimidyl) piperazine dihydrochloride instead of phenylpiperazine and N-(1-(4-(1-chloroethyl)phenyl)-1-methylethyl)acetamide instead of N-(4- chloromethylphenylmethyl)acetamide, the title compound was obtained as a white amorphous solid.

$^1$H-NMR(DMSO-d$_6$)δ: 1.30(3H, d, J=6.6 Hz), 1.53(6H, s), 1.83(3H, s), 2.25–2.50(4H, m), 3.69(4H, m), 6.58(1H, t, J=4.6 Hz), 7.21(2H, d, J=8.6 Hz), 7.26(2H, d, J=7.9 Hz), 7.97(1H, s), 7.32(2H, s,J=5.3 Hz); IR(KBr): 3331, 2976, 1657, 1585 cm$^{-1}$; MS(EI): 367(M$^+$); Elemental analysis: Calculated: C; 68.63, H; 7.95, N; 19.06; Found: C; 68.23, H; 7.68, N; 18.82.

Example 115

Synthesis of N-(4-(1-(4-(Thiazol-2-yl)piperazin-1-yl)ethyl)phenylmethyl)acetamide 1/2 Ethanol 1/2 Hydrate

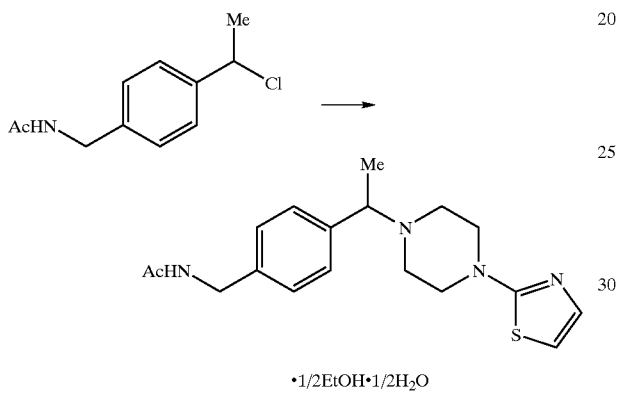

•1/2EtOH•1/2H$_2$O

By similar reaction and treatment to that in Example 1(5) using 1-(2-thiazolyl)piperazine instead of phenylpiperazine and N-(4-(1-chloroethyl)phenylmethyl)acetamide instead of N-(4-chloromethylphenylmethyl) acetamide, the title compound was obtained as a brown oil.

$^1$H-NMR(DMSO-d$_6$)δ: 1.30(3H, d, J=6.6 Hz), 1.87(3H, s), 2.38–2.50(4H, m), 3.37(4H, m), 3.45(1H, q, J=6.6 Hz), 4.23(2H, d, J=5.9 Hz), 6.81(2H, d, J=3.3 Hz), 7.13(2H, d, J=3.3 Hz), 7.20(2H, d, J=8.6 Hz), 7.27(2H, d, J=7.9 Hz), 8.29(1H, t, J=5.3 Hz). IR(neat): 3284, 2816, 1653 cm$^{-1}$; MS(EI): 344(M$^+$); Elemental analysis: Calculated: C; 60.61, H; 7.50, N; 14.88; Found: C; 60.61, H; 7.15, N; 14.98.

Example 116

Synthesis of N-(1-(4-(1-(4-(Pyridin-2-yl)piperazin-1-yl)ethyl)phenyl)-1-methylethyl)acetamide 1/4 Ethanol

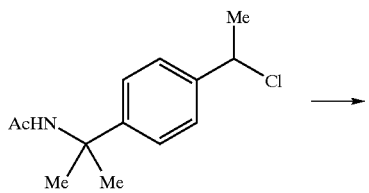

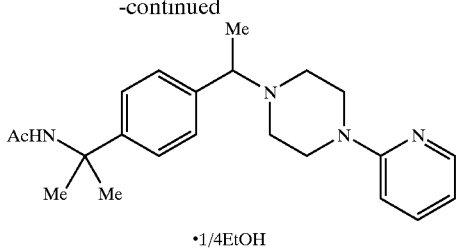

•1/4EtOH

By similar reaction and treatment to that in Example 1(5) using 1-(2-pyridyl)piperazine instead of phenylpiperazine and N-(1-(4-(1-chloroethyl)phenyl)-1-methylethyl) acetamide instead of N-(4-chloromethylphenylmethyl) acetamide, the title compound was obtained as white crystals.

$^1$H-NMR(DMSO-d$_6$)δ: 1.30(3H, d, J=6.6 Hz), 1.53(6H, s), 1.83(3H, s), 2.30–2.60(4H, m), 3.37(1H, m), 3.43(4H, m), 6.60(1H, d, J=4.6, 6.6 Hz), 6.75(1H, d, J=8.6 Hz), 7.22(2H, d, J=8.6 Hz), 7.27(2H, d, J=8.6 Hz), 7.49(1H, m), 7.98(1H, s), 8.09(1H, m); IR(KBr): 3329, 3066, 1659, 1594 cm$^{-1}$; MS(EI): 366(M$^+$); Elemental analysis: Calculated: C; 71.49, H; 8.37, N; 14.91; Found: C; 71.89, H; 8.07, N; 14.69.

Example 117

Synthesis of N-(1-(4-((4-(6-Fluoropyridin-2-yl)piperazin-1-yl)methyl)phenyl)cyclopropyl)acetamide

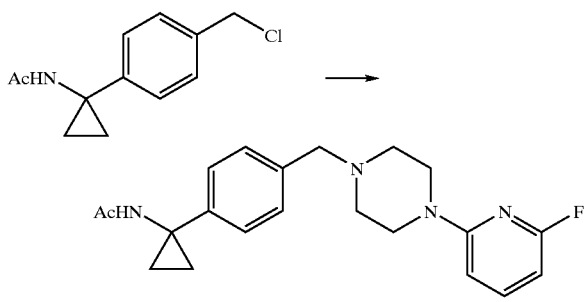

By similar reaction and treatment to that in Example 1(5) using N-(1-(4-chloromethylphenyl)cyclopropyl)acetamide obtained in Example 71(1) instead of N-(4-chloromethylphenylmethyl)acetamide and 1-(6-fluoropyridin-2-yl)piperazine obtained in Example 85(2) instead of phenylpiperazine, the title compound was obtained as white crystals, m.p.=135–136° C.

$^1$H-NMR(CDCl$_3$)δ: 1.26 and 1.36(4H, s and d,J=4.6 Hz), 1.99(3H, s), 2.48–2.53(4H, m), 3.49–3.55(6H, m), 6.12–6.17(2H, m), 6.36–6.40(1H, m), 7.10–7.31(4H, m), 7.45–7.55(1H, m). MS(EI): 368(M$^+$); Elemental analysis: Calculated: C; 68.46, H; 6.84, N; 15.21; Found: C; 68.51, H; 6.92, N; 15.18.

Example 118

Synthesis of N-(1-(4-((4-(Pyridin-2-yl)piperazin-1-yl)methyl)phenyl)cyclopropyl)acetamide

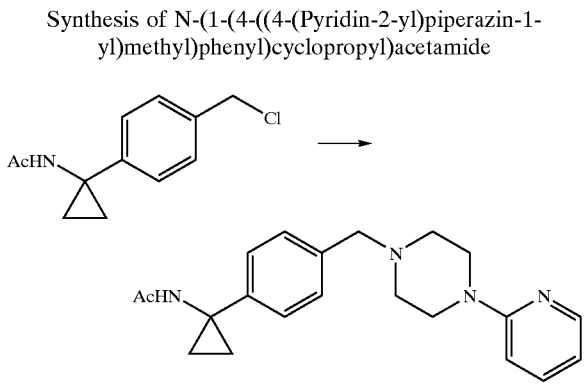

By similar reaction and treatment to that in Example 1(5) using N-(1-(4-chloromethylphenyl)cyclopropyl)acetamide obtained in Example 71(1) instead of N-(4-chloromethylphenylmethyl)acetamide and 1-(2-pyridyl) piperazine instead of phenylpiperazine, the title compound was obtained as white crystals, m.p.=145–147° C.

$^1$H-NMR(CDCl$_3$)δ: 1.26 and 1.36(4H, s and d, J=5.3 Hz), 2.00(3H, s), 2.51–2.56(4H, m), 3.50–3.56(6H, m), 6.13(1H, br), 6.58–6.64(1H, m), 7.10–7.32(4H, m), 7.42–7.49(1H, m), 8.16–8.19(1H, m). MS(EI): 350(M$^+$); Elemental analysis: Calculated: C; 71.97, H; 7.48, N; 15.99; Found: C; 72.10, H; 7.52, N; 15.94.

Example 119

Synthesis of (S)-N-(1-(4-((4-(6-Fluoropyridin-2-yl) piperazin-1-yl)methyl)phenyl)ethyl)acetamide (1) Synthesis of (S)-N-(1-Phenylethyl)acetamide

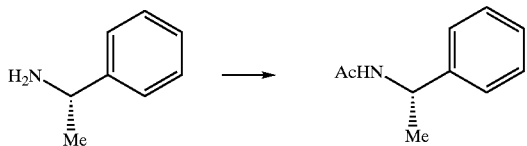

To a solution of (S)-(−)-1-phenylethylamine (121 g) and triethylamine (168 ml) in dichloroethane (1200 ml) was added dropwise acetyl chloride (78.2 ml) over 1 hr under ice-cooling and the mixture was stirred at room temperature for 2 hr. The reaction mixture was poured into water (1000 ml) and the organic layer was separated. The organic layer was washed with saturated brine and dried over anhydrous magnesium sulfate. The solvent was evaporated to give the title compound (143.4 g) as pale-yellow crystals, m.p.= 99–101° C.

$^1$H-NMR(CDCl$_3$)δ: 1.44(3H, d, J=6.6 Hz), 1.92(3H, s), 5.08(1H, dq, J=7.3 Hz), 6.37(1H, br), 7.20–7.34(5H, m). MS(EI): 163(M$^+$).

(2) Synthesis of (S)-N-(1-(4-Acetylphenyl)ethyl)acetamide

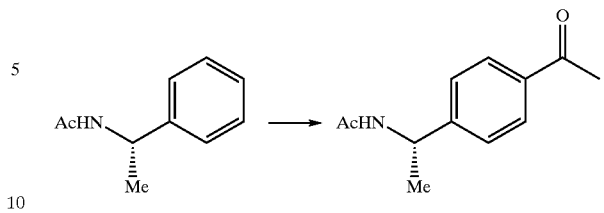

To a solution of (S)-1-phenylethylacetamide (143.4 g) and acetyl chloride (93.7 ml) in dichloroethane (700 ml) was added aluminum chloride (257.7 g) over 30 min under ice-cooling. The mixture was stirred at 10° C. for 30 min and at 60° C. for 3 hr. The reaction mixture was poured into icewater (1500ml) and the organic layer was separated. The organic layer was washed with saturated brine and dried over anhydrous magnesium sulfate. The solvent was evaporated and the obtained residue was purified by silica gel column chromatography (developing solvent; ethyl acetate) and recrystallized from ethyl acetate-hexane to give the title compound (76.4 g) as white crystals, m.p.=125–128° C.

$^1$H-NMR(CDCl$_3$)δ: 1.48(3H, d, J=6.6 Hz), 2.00(3H, s), 2.58(3H, s), 5.15(1H, dq, J=7.3 Hz), 5.98(1H, br.d, J=6.6 Hz), 7.40(2H, d, J=8.6 Hz), 7.92(2H, d, J=7.9 Hz). MS(EI): 205(M$^+$).

(3) Synthesis of (S)-4-(1-Acetamidoethyl)benzoic Acid

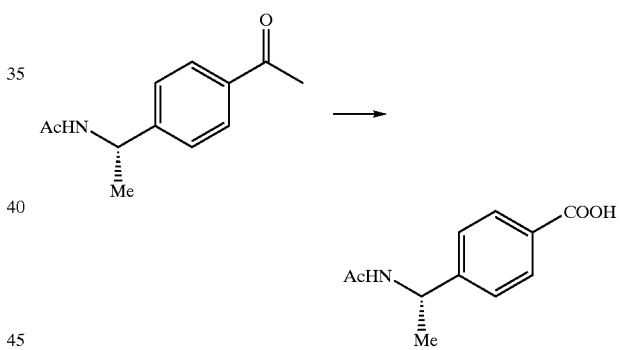

By similar reaction and treatment to that in Example 95(1) using (S)-N-(1-(4-acetylphenyl)ethyl)acetamide instead of N-(1-(4-acetylphenyl)-1-methylethyl) acetamide, the title compound was obtained as yellow crystals, m.p.=186–190° C.

$^1$H-NMR(DMSO-d$_6$)δ: 1.35(3H, d, J=7.3 Hz), 1.86(3H, s), 4.96(1H, dq, J=7.3 Hz), 7.42(2H, d, J=8.6 Hz), 7.91(2H, d, J=7.9 Hz), 8.36(1H, d, J=7.9 Hz), 12.87(1H, br.s). MS(EI): 207(M$^+$).

(4) Synthesis of Methyl (S)-4-(1-Acetamidoethyl)benzoate

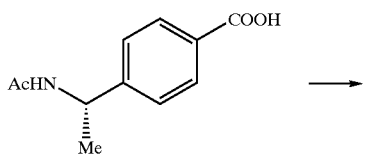

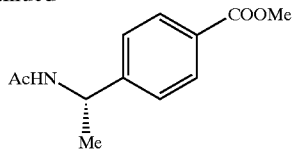

By similar reaction and treatment to that in Example 95(2) using (S)-4-(1-acetamidoethyl)benzoic acid instead of 4-(1-acetamido-1-methylethyl)benzoic acid, the title compound was obtained as white crystals.

m.p.=125–127° C.; $^1$H-NMR(CDCl$_3$)δ: 1.48(3H, d, J=7.3 Hz), 2.00(3H, s), 3.91(3H, s), 5.16(1H, dq, J=7.3 Hz), 5.85–5.87(1H, br), 7.36–7.39(2H, m), 7.98–8.01(2H, m). MS(EI): 221(M$^+$).

(5) Synthesis of (S)-N-(1-(4-Hydroxymethylphenyl)ethyl)acetamide

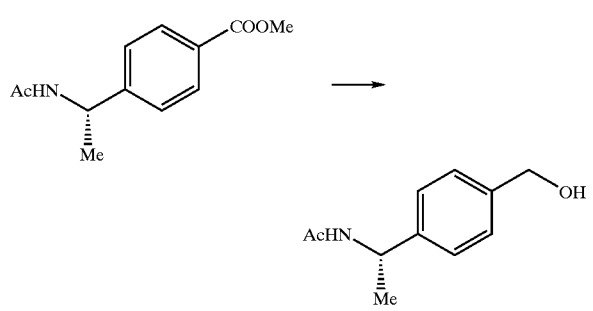

By similar reaction and treatment to that in Example 1(3) using methyl (S)-4-(1-acetamidoethyl)benzoate instead of methyl 4-acetamidomethylbenzoate, the title compound was obtained as white crystals, m.p.=103–104° C.

$^1$H-NMR(CDCl$_3$)δ: 1.45(3H, d, J=7.3 Hz), 1.93(3H, s), 2.53(1H, br.s), 4.63(2H, s), 5.07(1H, dq, J=7.3 Hz), 6.02(1H, br.d, J=7.3 Hz), 7.24–7.32(4H, m). MS(EI): 193(M$^+$).

(6) Synthesis of (S)-N-(1-(4-Chloromethylphenyl)ethyl)acetamide

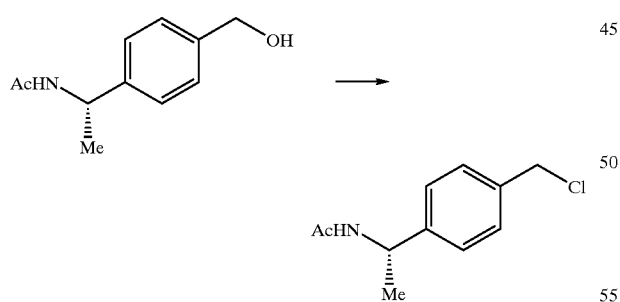

By similar reaction and treatment to that in Example 95(4) using (S)-N-(1-(4-hydroxymethylphenyl)ethyl)acetamide instead of N-(1-(4-hydroxymethylphenyl)-1-methylethyl)acetamide, the title compound was obtained as white crystals, m.p.=114–116° C.

$^1$H-NMR(CDCl$_3$)δ: 1.48(3H, d, J=7.3 Hz), 1.98(3H, s), 4.57(2H, s), 5.12(1H, dq, J=7.3 Hz), 5.70(1H, br), 7.29–7.38 (4H, m). MS(EI): 211(M$^+$); [α]$_D^{25}$-145.0° (c=1.00, CHCl$_3$).

(7) Synthesis of (S)-N-(1-(4-((4-(6-Fluoropyridin-2-yl)piperazin-1-yl)methyl)phenyl)ethyl)acetamide

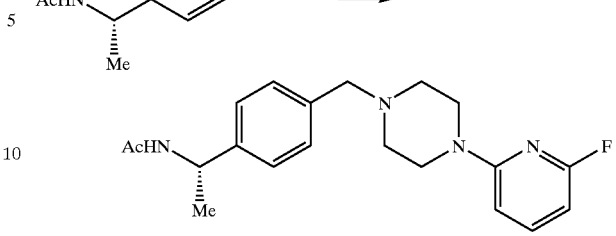

By similar reaction and treatment to that in Example 1(5) using (S)-N-(1-(4-chloromethylphenyl)ethyl)acetamide instead of N-(4-chloromethylphenylmethyl)acetamide and 1-(6-fluoropyridin-2-yl)piperazine obtained in Example 85(2) instead of phenylpiperazine, the title compound was obtained as a pale-yellow oil.

$^1$H-NMR(CDCl$_3$)δ: 1.48(3H, d, J=6.6 Hz), 1.97(3H, s), 2.49–2.53(4H, m), 3.50–3.54(6H, m), 5.12(1H, dq, J=7.3 Hz), 5.84–5.87(1H, br), 6.12–6.16(1H, m), 6.36–6.40(1H, m), 7.25–7.32(4H, m), 7.46–7.55(1H, m). MS(EI): 356(M$^+$).

Example 120

Synthesis of (R)-N-(1-(4-((4-(6-Fluoropyridin-2-yl)piperazin-1-yl)methyl)phenyl)ethyl)acetamide (1) Synthesis of (R)-N-(1-Phenylethyl)acetamide

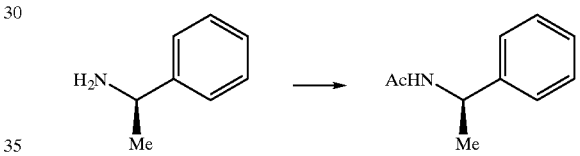

By similar reaction and treatment to that in Example 119(1) using (R)-(+)-1-phenylethylamine instead of (S)-(−)-1-phenylethylamine, the title compound was obtained as white crystals.

m.p.=100–102° C.; $^1$H-NMR(CDCl$_3$)δ: 1.47(3H, d, J=7.3 Hz), 1.96(3H, s), 5.11(1H, dq, J=7.3 Hz), 5.95(1H, br), 7.22–7.36(5H, m). MS(EI): 163(M$^+$).

(2) Synthesis of (R)-N-(1-(4-Acetylphenyl)ethyl)acetamide

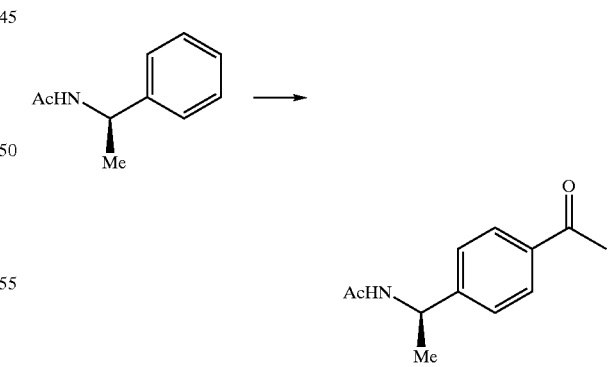

By similar reaction and treatment to that in Example 119(2) using (R)-1-phenylethylacetamide instead of (S)-1-phenylethylacetamide, the title compound was obtained as white crystals, m.p.=125–127° C.

$^1$H-NMR(CDCl$_3$)δ: 1.48(3H, d, J=6.6 Hz), 1.99(3H, s), 2.58(3H, s), 5.14(1H, dq, J=7.3 Hz), 6.17(1H, br.d, J=6.6 Hz), 7.39(2H, d, J=7.9 Hz), 7.91(2H, d, J=7.9 Hz). MS(EI): 205(M$^{30}$).

(3) Synthesis of (R)-4-(1-Acetamidoethyl)benzoic Acid

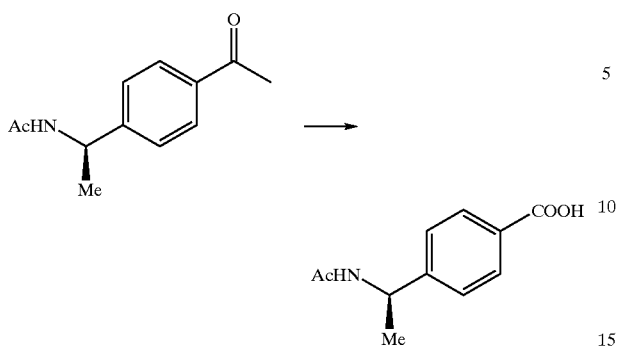

By similar reaction and treatment to that in Example 95(1) using (R)-N-(1-(4-acetylphenyl)ethyl)acetamide instead of N-(1-(4-acetylphenyl)-1-methylethyl) acetamide, the title compound was obtained as pale-yellow crystals, m.p.= 189–192° C.
$^1$H-NMR(DMSO-d$_6$)δ: 1.35(3H, d, J=7.3 Hz), 1.86(3H, s), 4.96(1H, dq, J=7.3 Hz), 7.42(2H, d, J=8.6 Hz), 7.91(2H, d, J=7.9 Hz), 8.36(1H, d, J=7.9 Hz), 12.85(1H, br.s). MS(EI): 207(M$^+$).

(4) Synthesis of Methyl (R)-4-(1-Acetamidoethyl)benzoate

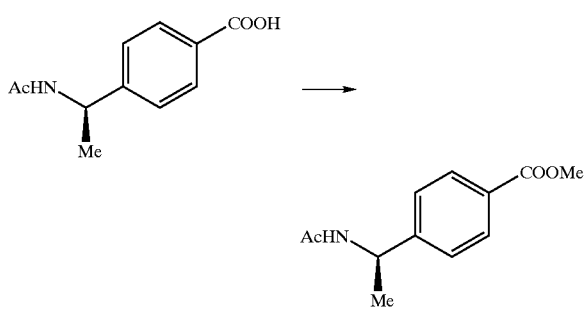

By similar reaction and treatment to that in Example 95(2) using (R)-4-(1-acetamidoethyl)benzoic acid instead of 4-(1-acetamido-1-methylethyl)benzoic acid, the title compound was obtained as white crystals.
m.p.=126–128° C.; $^1$H-NMR(CDCl$_3$)δ: 1.48(3H, d, J=7.3 Hz), 2.00(3H, s), 3.91(3H, s), 5.16(1H, dq, J=7.3 Hz), 5.85–5.87(1H, br), 7.36–7.39(2H, m), 7.98–8.01(2H, m). MS(EI): 221(M$^+$).

(5) Synthesis of (R)-N-(1-(4-Hydroxymethylphenyl)ethyl)acetamide

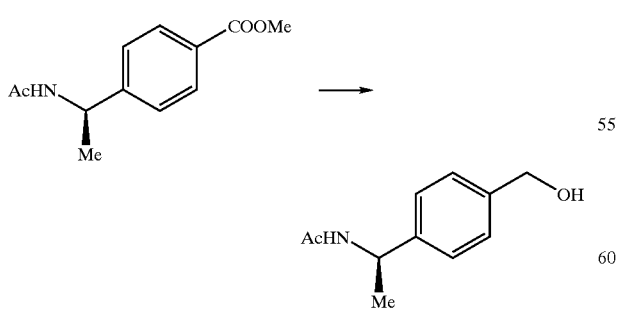

By similar reaction and treatment to that in Example 1(3) using methyl (R)-4-(1-acetamidoethyl)benzoate instead of methyl 4-acetamidomethylbenzoate, the title compound was obtained as white crystals, m.p.=102–104° C.

$^1$H-NMR(CDCl$_3$)δ: 1.44(3H, d, J=6.6 Hz), 1.92(3H, s), 2.67(1H, br.s), 4.62(2H, s), 5.06(1H, dq, J=7.3 Hz), 6.09(1H, br.d, J=7.3 Hz), 7.23–7.31(4H, m). MS(EI): 193(M$^+$).

(6) Synthesis of (R)-N-(1-(4-Chloromethylphenyl)ethyl)acetamide

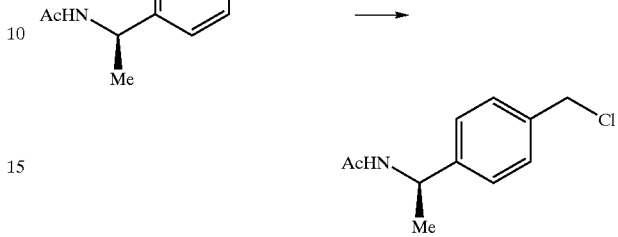

By similar reaction and treatment to that in Example 95(4) using (R)-N-(1-(4-hydroxymethylphenyl)ethyl)acetamide instead of N-(1-(4-hydroxymethylphenyl)-1-methylethyl) acetamide, the title compound was obtained as white crystals, m.p.=113–114° C.
$^1$H-NMR(CDCl$_3$)δ: 1.46(3H, d, J=7.3 Hz), 1.96(3H, s), 4.56(2H, s), 5.11(1H, dq, J=7.3 Hz), 5.88(1H, br), 7.28–7.37 (4H, m). MS(EI): 211(M$^+$); $[\alpha]_D^{25}$ 145.80° (c=1.00, CHCl$_3$).

(7) Synthesis of (R)-N-(1-(4-((4-(6-Fluoropyridin-2-yl) piperazin-1-yl)methyl)phenyl)ethyl)acetamide

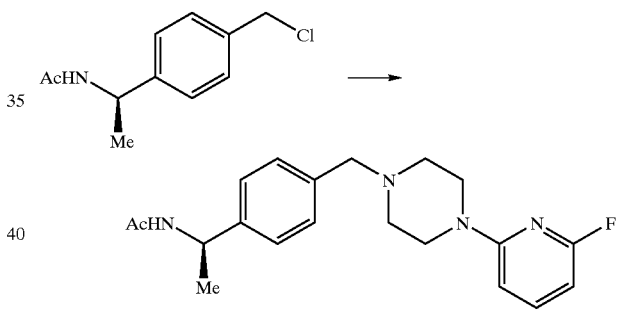

By similar reaction and treatment to that in Example 1(5) using (R)-N-(1-(4-chloromethylphenyl)ethyl)acetamide instead of N-(4-chloromethylphenylmethyl)acetamide and 1-(6-fluoropyridin-2-yl)piperazine obtained in Example 85(2) instead of phenylpiperazine, the title compound was obtained as a pale-yellow oil.
$^1$H-NMR(CDCl$_3$)δ: 1.48(3H, d, J=6.6 Hz), 1.97(3H, s), 2.49–2.53(4H, m), 3.50–3.54(6H, m), 5.12(1H, dq, J=7.3 Hz), 5.90–5.93(1H, br), 6.12–6.16(1H, m), 6.36–6.40(1H, m), 7.25–7.32(4H, m), 7.46–7.55(1H, m). MS(EI): 356(M$^+$).

Example 121

Synthesis of (S)-N-(1-(4-((4-(4-Fluorophenyl) piperazin-1-yl)methyl)phenyl)ethyl)acetamide

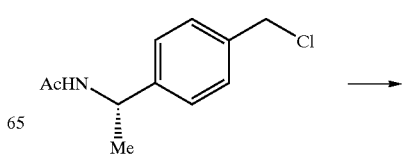

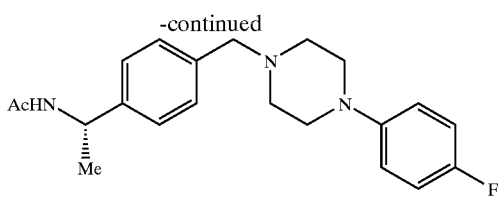

By similar reaction and treatment to that in Example 1(5) using (S)-N-(1-(4-chloromethylphenyl)ethyl)acetamide instead of N-(4-chloromethylphenylmethyl)acetamide and 1-(4-fluorophenyl)piperazine dihydrochloride instead of phenylpiperazine, the title compound was obtained as white crystals, m.p.=114–115° C.

¹H-NMR(CDCl₃)δ: 1.48(3H, d, J=6.6 Hz), 1.98(3H, s), 2.57–2.61(4H, m), 3.09–3.12(4H, m), 3.54(2H, s), 5.12(1H, dq, J=7.3 Hz), 5.73(1H, br.d, J=7.3 Hz), 6.83–6.98(4H, m), 7.25–7.33(4H, m). MS(EI): 355(M⁺); Elemental analysis: Calculated: C; 70.96, H; 7.37, N; 11.82; Found: C; 70.97, H; 7.37, N; 11.76; $[\alpha]_D^{25}$ −87.0° (c=1.00, CHCl₃).

Example 122

Synthesis of (R)-N-(1-(4-((4-(4-fluorophenyl)piperazin-1-yl)methyl)phenyl)ethyl)acetamide

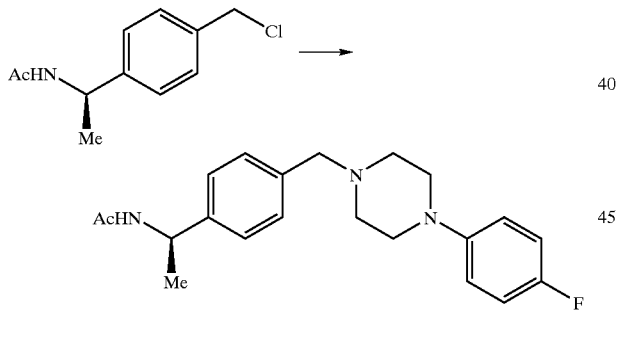

By similar reaction and treatment to that in Example 1(5) using (R)-N-(1-(4-chloromethylphenyl)ethyl)acetamide instead of N-(4-chloromethylphenylmethyl)acetamide and 1-(4-fluorophenyl)piperazine dihydrochloride instead of phenylpiperazine, the title compound was obtained as white crystals, m.p.=114–115° C.

¹H-NMR(CDCl₃)δ: 1.48(3H, d, J=7.3 Hz), 1.98(3H, s), 2.57–2.61(4H, m), 3.09–3.12(4H, m), 3.54(2H, s), 5.12(1H, dq, J=7.3 Hz), 5.72(1H, br.d, J=7.3 Hz), 6.83–6.98(4H, m), 7.25–7.33(4H, m). MS(EI): 355(M⁺); Elemental analysis: Calculated: C; 70.96, H; 7.37, N; 11.82; Found: C; 71.03, H; 7.35, N; 11.79; $[\alpha]_D^{25}$ 87.40 (c=1.00, CHCl₃).

Example 123

Synthesis of N-(1-(4-(1-(4-(6-fluoropyridin-2-yl)piperazin-1-yl)ethyl)phenyl)-1-methylethyl)acetamide

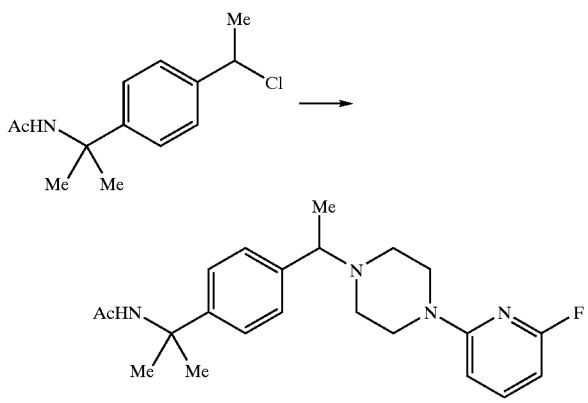

By similar reaction and treatment to that in Example 1(5) using 1-(6-fluoropyridin-2-yl)piperazine obtained in Example 85(2) instead of phenylpiperazine and N-(1-(4-(1-chloroethyl)phenyl)-1-methylethyl)acetamide instead of N-(4-chloromethylphenylmethyl)acetamide, the title compound can be obtained.

Example 124

Synthesis of N-(4-(1-(4-(Pyridin-2-yl)piperazin-1-yl)ethyl)phenylmethyl)acetamide

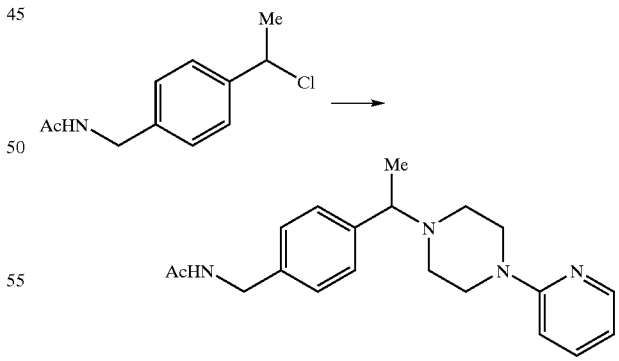

By similar reaction and treatment to that in Example 1(5) using 1-(2-pyridyl)piperazine instead of phenylpiperazine and N-(4-(1-chloroethyl)phenylmethyl)acetamide instead of N-(4-chloromethylphenylmethyl)acetamide, the title compound can be obtained.

Example 125

Synthesis of N-(1-(4-(1-(4-(6-Fluoropyridin-2-yl)piperazin-1-yl)ethyl)phenyl)methyl)acetamide

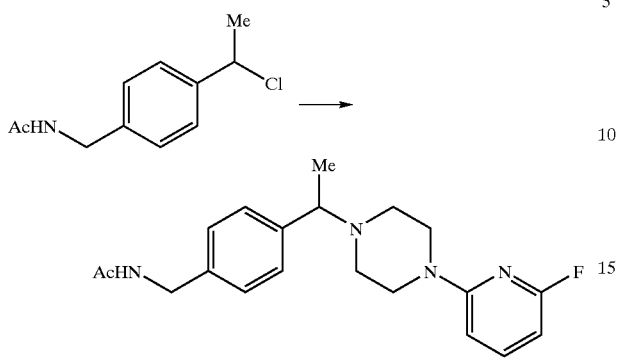

By similar reaction and treatment to that in Example 1(5) using 1-(6-fluoropyridin-2-yl)piperazine instead of phenylpiperazine and N-((4-(1-chloroethyl)phenyl)methyl)acetamide instead of N-(4-chloromethylphenylmethyl)acetamide, the title compound can be obtained.

Example 126

Synthesis of (S)-N-(4-(1-(4-(4-Fluorophenyl)piperazin-1-yl)ethyl)phenylmethyl)acetamide (1) Synthesis of (S)-4-(1-Aminoethyl)benzoic Acid

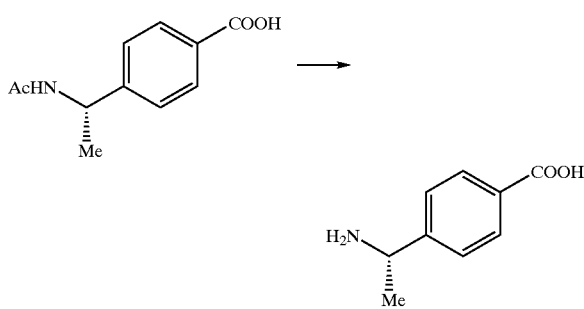

By similar reaction and treatment to that in Example 68(2) using (S)-4-(1-acetamidoethyl)benzoic acid obtained in Example 119(3) instead of 2-(4-methylphenyl)-2-methylpropionitrile, the title compound can be obtained.

(2) Synthesis of Methyl (S)-4-(1-Aminoethyl)benzoate

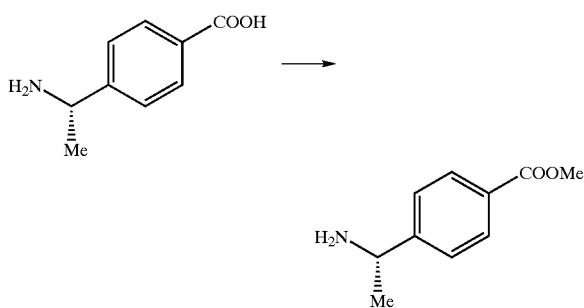

By similar reaction and treatment to that in Example 95(2) using (S)-4-(1-aminoethyl)benzoic acid instead of 4-(1-acetamido-1-methylethyl)benzoic acid, the title compound can be obtained.

(3) Synthesis of methyl (S)-4-(1-(4-(4-Fluorophenyl)piperazin-1-yl)ethyl)benzoate

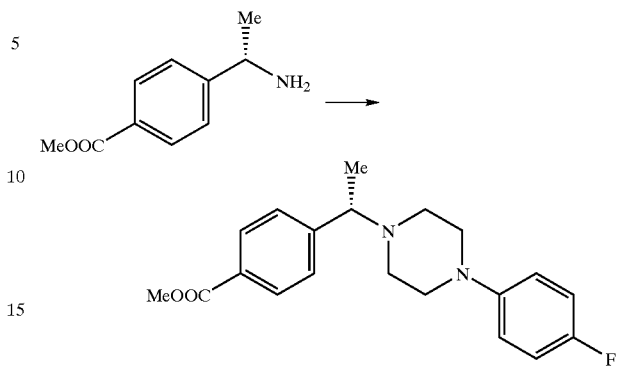

By similar reaction and treatment to that in Example 68(13) using methyl (S)-4-(1-aminoethyl)benzoate instead of N-(4-(1-amino-1-methylethyl)phenylmethyl)acetamide, the title compound can be obtained.

(4) Synthesis of (S)-4-(1-(4-Hydroxymethylphenyl)ethyl)-1-(4-fluorophenyl)piperazine

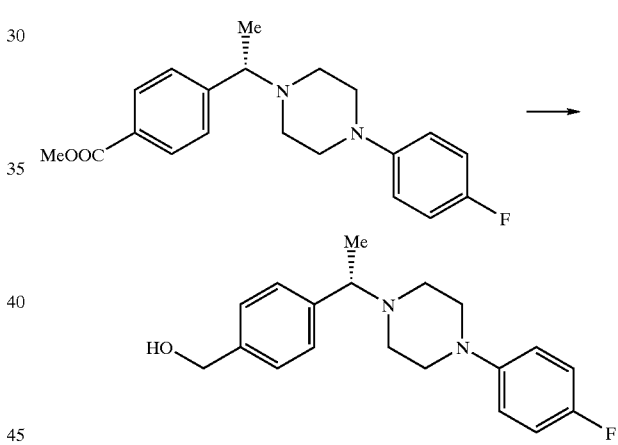

By similar reaction and treatment to that in Example 1(3) using methyl (S)-4-(1-(4-(4-fluorophenyl)piperazin-1-yl)ethyl)benzoate instead of methyl 4-acetamidomethylbenzoate, the title compound can be obtained.

(5) Synthesis of (S)-4-(1-(4-Chloromethylphenyl)ethyl)-1-(4-fluorophenyl)piperazine

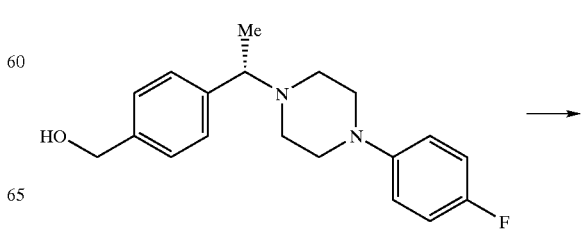

-continued

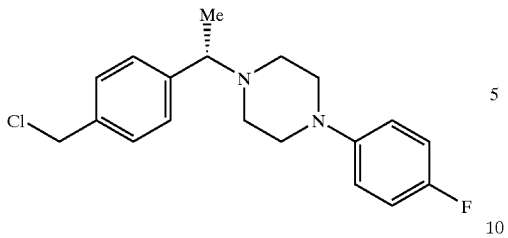

By similar reaction and treatment to that in Example 95(4) using (S)-4-(1-(4-hydroxymethylphenyl)ethyl)-1-(4-fluorophenyl)piperazine instead of N-(1-(4-hydroxymethylphenyl)-1-methylethyl)acetamide, the title compound can be obtained.

(6) Synthesis of (S)-4-(1-(4-Azidomethylphenyl)ethyl)-1-(4-fluorophenyl)piperazine

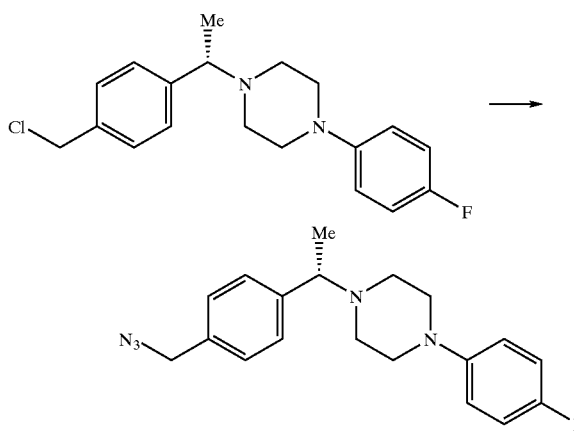

By similar reaction and treatment to that in Example 59(1) using ((S)-4-(1-(4-chloromethylphenyl)ethyl)-1-(4-fluorophenyl)piperazine instead of 4-chloromethylacetophenone, the title compound can be obtained.

(7) Synthesis of (S)-4-(1-(4-Aminomethylphenyl)ethyl)-1-(4-fluorophenyl)piperazine

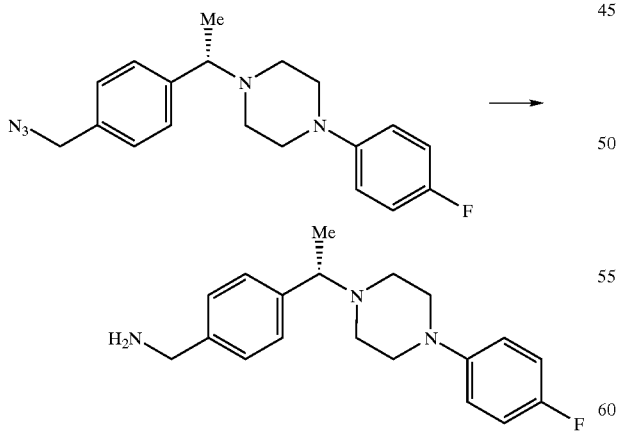

By similar reaction and treatment to that in Example 68(5) using (S)-4-(1-(4-azidomethylphenyl)ethyl)-1-(4-fluorophenyl)piperazine instead of methyl 2-(4-azidomethylphenyl)-2-methylpropionate, the title compound can be obtained.

(8) Synthesis of (S)-N-(4-(1-(4-(4-Fluorophenyl)piperazin-1-yl)ethyl)phenylmethyl)acetamide

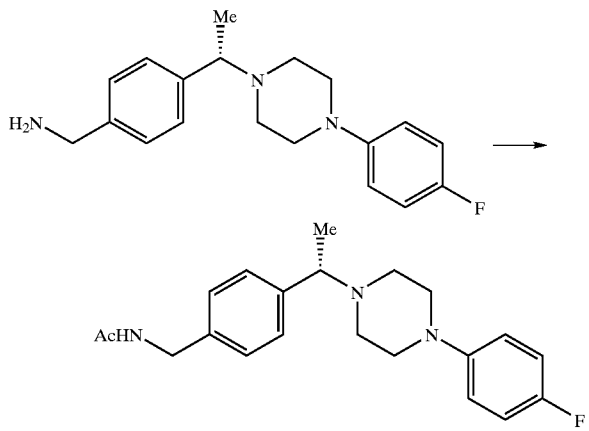

By similar reaction and treatment to that in Example 68(6) using (S)-4-(1-(4-aminomethylphenyl)ethyl)-1-(4-fluorophenyl)piperazine instead of methyl 2-(4-aminomethylphenyl)-2-methylpropionate, the title compound can be obtained.

Example 127

Synthesis of (R)-N-(4-(1-(4-(4-fluorophenyl)piperazin-1-yl)ethyl)phenylmethyl)acetamide (1) Synthesis of (R)-4-(1-Aminoethyl)benzoic Acid

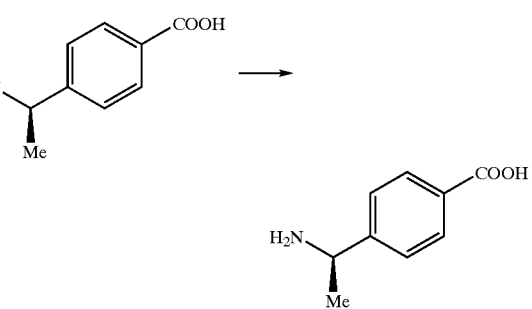

By similar reaction and treatment to that in Example 68(2) using (R)-4-(1-acetamideethyl)benzoic acid obtained in Example 120(3) instead of 2-(4-methylphenyl)-2-methylpropionitrile, the title compound can be obtained.

(2) Synthesis of Methyl (R)-4-(1-Aminoethyl)benzoate

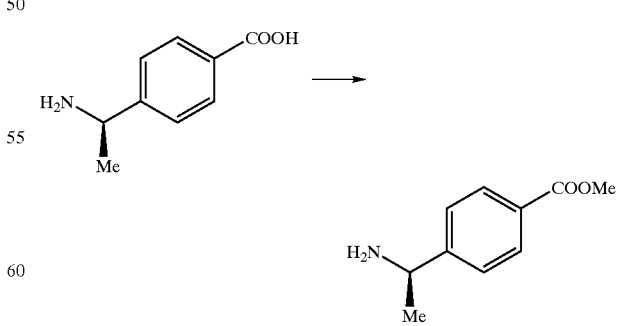

By similar reaction and treatment to that in Example 95(2) using (R)-4-(1-aminoethyl)benzoic acid instead of 4-(1-acetamido-1-methylethyl)benzoic acid, the title compound can be obtained.

(3) Synthesis of Methyl (R)-4-(1-(4-(4-Fluorophenyl)piperazin-1-yl)ethyl)benzoate

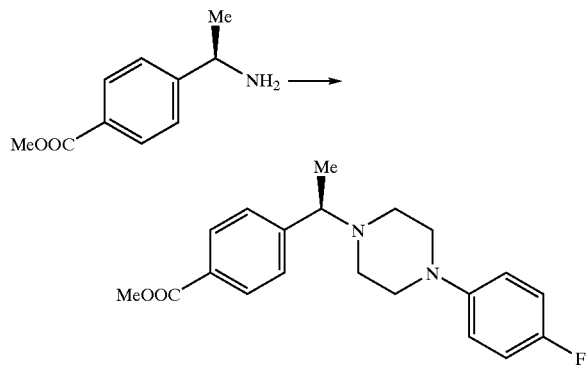

By similar reaction and treatment to that in Example 68(13) using methyl (R)-4-(1-aminoethyl)benzoate instead of N-(4-(1-amino-1-methylethyl)phenylmethyl)acetamide, the title compound can be obtained.

(4) Synthesis of (R)-4-(1-(4-Hydroxymethylphenyl)ethyl)-1-(4-fluorophenyl)piperazine

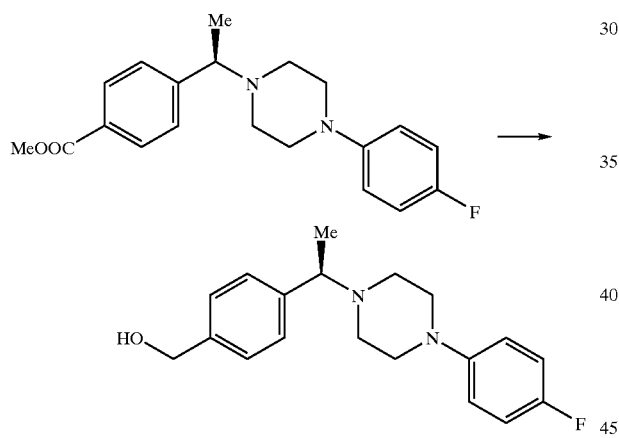

By similar reaction and treatment to that in Example 1(3) using imethyl (R)-4-(1-(4-(4-fluorophenyl)piperazin-1-yl)ethyl)benzoate instead of methyl 4-acetamidomethylbenzoate, the title compound can be obtained.

(5) Synthesis of (R)-4-(1-(4-Chloromethylphenyl)ethyl)-1-(4-fluorophenyl)piperazine

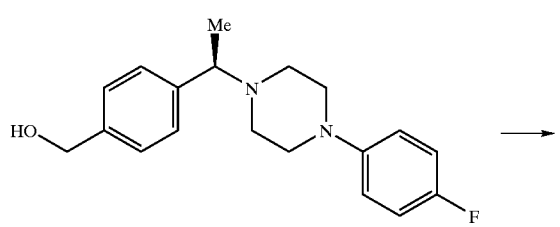

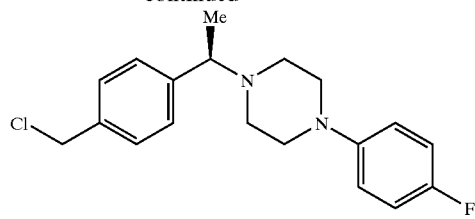

By similar reaction and treatment to that in Example 95(4) using (R)-4-(1-(4-hydroxymethylphenyl)ethyl)-1-(4-fluorophenyl)piperazine instead of N-(1-(4-hydroxymethylphenyl)-1-methylethyl)acetamide, the title compound can be obtained.

(6) Synthesis of (R)-4-(1-(4-Azidomethylphenyl)ethyl)-1-(4-fluorophenyl)piperazine

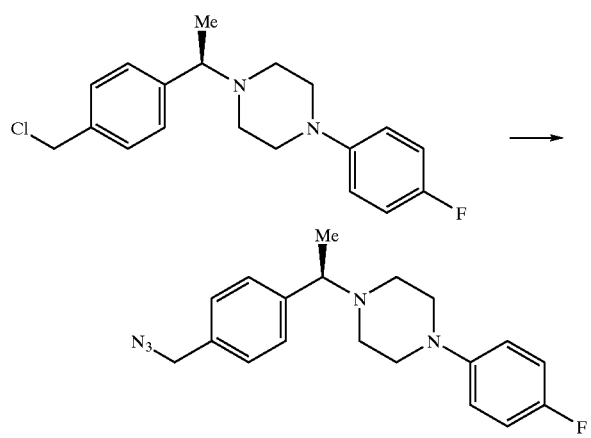

By similar reaction and treatment to that in Example 59(1) using (R)-4-(1-(4-chloromethylphenyl)ethyl)-1-(4-fluorophenyl)piperazine instead of 4-chloromethylacetophenone, the title compound can be obtained.

(7) Synthesis of (R)-4-(1-(4-Aminomethylphenyl)ethyl)-1-(4-fluorophenyl)piperazine

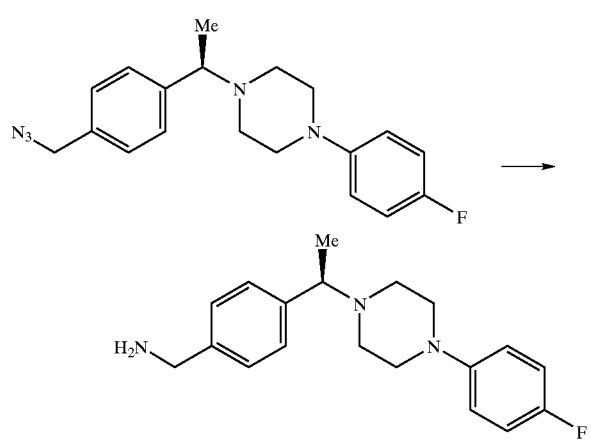

By similar reaction and treatment to that in Example 68(5) using (R)-4-(1-(4-azidomethylphenyl)ethyl)-1-(4-fluorophenyl)piperazine instead of methyl 2-(4-azidomethylphenyl)-2-methylpropionate, the title compound can be obtained.

(8) Synthesis of (R)-N-(4-(1-(4-(4-Fluorophenyl)piperazin-1-yl)ethyl)phenylmethyl)acetamide By similar reaction and treatment to that in Example 68(6) using (R)-4-(1-(4-aminomethylphenyl)ethyl)-1-(4-fluorophenyl)piperazine instead of methyl 2-(4-aminomethylphenyl)-2-methylpropionate, the title compound can be obtained.

In the same manner as in the above Examples, the following compounds can be produced.

Example 128

N-(4-((4-(1-Methylimidazol-2-yl)piperazin-1-yl)methyl)phenylmethyl)acetamide

Example 129

N-(1-(4-((4-(1-Methylimidazol-2-yl)piperazin-1-yl)methyl)phenyl-1-methylethyl)acetamide

Example 130

N-(1-(4-((4-(1-Methylimidazol-2-yl)piperazin-1-yl)methyl)phenyl)ethyl)acetamide

Example 131

N-(4-(1-(4-(1-Methylimidazol-2-yl)piperazin-1-yl)ethyl)phenylmethyl)acetamide

Example 132

N-(1-(4-(1-(4-(1-Methylimidazol-2-yl)piperazin-1-yl)ethyl)phenyl)-1-methylethyl)acetamide

Example 133

N-(1-(4-((4-(1-Methylimidazol-2-yl)piperazin-1-yl)methyl)phenyl)cyclopropyl)acetamide Example 134

N-(4-((4-(5-Methylthiazol-2-yl)piperazin-1-yl)methyl)phenylmethyl)acetamide

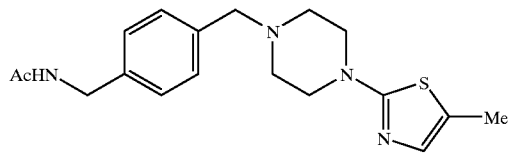

Example 135

N-(4-((4-(4-Methylthiazol-2-yl)piperazin-1-yl)methyl)phenylmethyl)acetamide

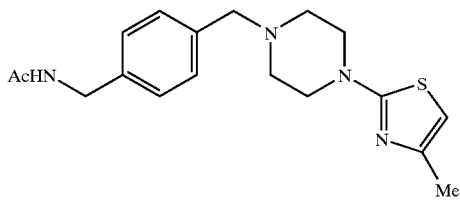

Example 136

N-(4-((4-(4,5-Dimethylthiazol-2-yl)piperazin-1-yl)methyl)phenylmethyl)acetamide

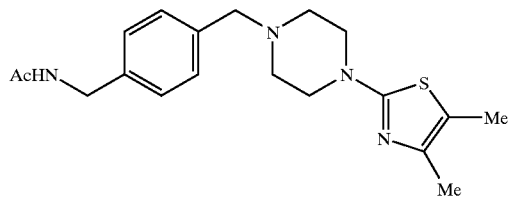

Example 137

N-(1-(4-((4-(5-Methylthiazol-2-yl)piperazin-1-yl)methyl)phenyl)ethyl)acetamide

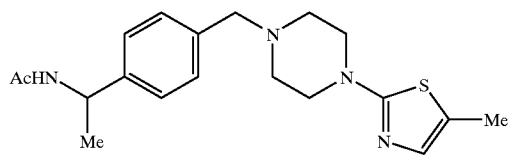

Example 138

N-(1-(4-((4-(5-Methylthiazol-2-yl)piperazin-1-yl)methyl)phenyl)-1-methylethyl)acetamide

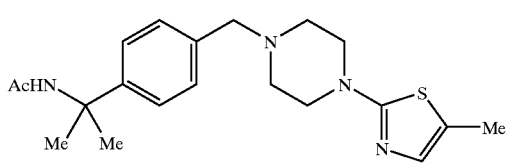

Example 139

N-(1-(4-((4-(4-Methylthiazol-2-yl)piperazin-1-yl)methyl)phenyl)-1-methylethyl)acetamide

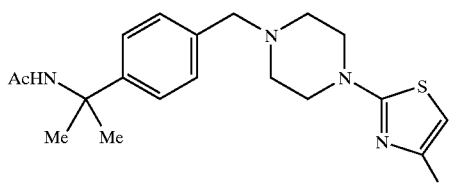

Example 140

N-(1-(4-((4-(4,5-Dimethylthiazol-2-yl)piperazin-1-yl)methyl)phenyl)-1-methylethyl)acetamide

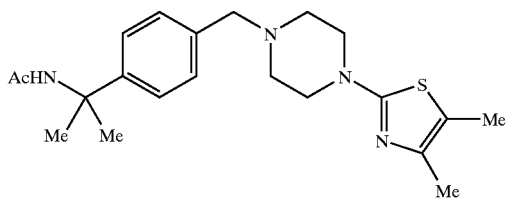

Example 141

N-(1-(4-((4-(5-Methylthiazol-2-yl)piperazin-1-yl methyl)phenyl)cyclopropyl)acetamide

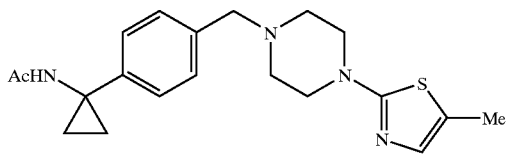

The action and effect of the present invention is explained in more detail in the following by Experimental Examples.

Experimental Example 1

Effect on TNF-α, IL-10 Production in Mice (In Vivo)

To female BALB/c mice (purchased from Japan Charles River) was intraperitoneally administered LPS (lipopolysaccharide: 500 μg/kg, derived from *Escherichia coli* 055:B5, manufactured by Difco). Since the TNF-α concentration in serum reaches a peak at 90 min after LPS administration, the TNF-α concentration in the serum at this point was measured using FACTOR TEST mTNF-α (manufactured by Genzyme) and the IL-10 concentration at the same point of time was also measured using Murine IL-10 ELISA Kit (manufactured by Endogen). The test compound was orally administered at 30 min before LPS administration, and the TNF-α concentration and IL-10 concentration were measured in the same manner. The results are shown in Table 1. The effect of the test compound on the TNF-α production and IL-10 production was calculated by the following formula as the ratio relative to the test compound non-administration group.

TABLE 1

$$\frac{\text{Concentration on administration of test compound}}{\text{Concentration without administration of test compound}} \times 100(\%)$$

| Example | TNF-α production (%) | IL-10 production (%) |
|---|---|---|
| 20 | 17 | 770 |
| 48 | 12 | 888 |
| 51 | 16 | 533 |
| 58 | 19 | 499 |
| 72 | 20 | 510 |
| 81 | 11 | 1035 |
| 82 | 11 | 742 |

Experimental Example 2

Effect on TNF-α, IL-10 Production by Human Monocyte (In Vitro)

Blood is taken from healthy volunteers and monocytes are separated using a lymphocyte separation medium (Flow Laboratories). The cells are suspended in RPMI-1640 medium supplemented with 10% FCS (fetal calf serum: manufactured by Gibco). Monocytes ($5 \times 10^6$/ml) are stimulated using LPS (1 μg/ml) and PMA (phorbol 12-myristate 13-acetate, 10 ng/ml, manufactured by Sigma) and incubated with test compounds having various concentrations at 37° C. under humid conditions containing 5% $CO_2$. After incubation for 24 hr, the TNF-α concentrations in the supernatant are measured using Cytoscreen human TNF-α ELISA Kit (manufactured by Biosource).

Experimental Example 3

Effect on Endotoxin Shock (Life and Death)

To female BALB/c mice (purchased from Japan Charles River) was intraperitoneally administered LPS (*E. coli* O55 B5, 10 mg/kg). The test compound was orally administered at 30 min before LPS administration. The survival of the mice was monitored for 3 days from the next day. As the test compound, the compound of Example 20 was used. As a result, all mice in the test compound non-administration group (9 mice per group) died but 8 mice in the test compound administration group (9 mice per group) survived, showing markedly significant effect.

Experimental Example 4

Therapeutic Effect on Adjuvant Arthritis

Killed *Mycobacterium tuberculosis* was inoculated to male Lewis rats (purchased from Seac Yoshitomi, Ltd.) at the tail base to cause adjuvant arthritis. For 6 days from day 15 to day 20 when arthritis was developed, the test compound was orally administered at 30 mg/kg. The volume of the limb was measured with the lapse of time from day 15.

As the test compound, the compound of Example 20 was used. The changes in the volume of the limb from day 15 to day 20 were measured. As a result, the volume of the limb increased by 0.344 ml in the test compound non-administration rats and decreased by 0.186 ml in the test compound administered rats. It was clarified that the inventive compound markedly inhibited the onset of adjuvant arthritis.

Experimental Example 5

Therapeutic Effect on Collagen Arthritis

Bovine-derived type II collagen (purchased from Koragen gijutsu kenkyukai) is intradermally injected twice to DBA/1J mice (purchased from Seac Yoshitomi, Ltd.) at the tail base, together with complete Freund's adjuvant H37Rv (purchased from Wako Pure Chemical Industries, Ltd.) at day 0 and day 21. From day 22 to day 33 after the injection, the test compound is orally administered. The swelling of the joints of the four limbs is observed and scored in 0 (no change)—3 (edema of 5 fingers). The joint swelling score of each mouse is the total scores of the four limbs.

Experimental Example 6

Affinity for Dopamine $D_2$ Receptor; $^3$H-spiperone Binding

Preparation of crude synaptic membranes and a binding test were performed according to the method of I. Creese et al. [European Journal of Pharmacology, vol. 46, p. 377 (1977)]. The crude synaptic membranes were prepared from freeze preserved rat corpus striatum, and the membrane specimen and $^3$H-spiperone were reacted in the presence of the test compound at 37° C. for 20 min. After the completion of the reaction, the reaction mixtures were immediately filtered by suction on Whatman GF/B filter (trademark) and the radioactivity on the filter was measured by Top Count. Every reaction was carried out in the presence of 100 nM ketanserin. The non-specific binding was determined in the presence of 100 μM(±)-sulpiride. The 50% inhibition concentration ($IC_{50}$) of the test compound was calculated by two-point interpolation, from which inhibitory constant (Ki value) was determined.

Experimental Example 7

Affinity for Serotonin 2 Receptor; $^3$H-ketanserin Binding

Preparation of crude synaptic membranes and a binding test were performed according to the method of Leysen J. E. et al. [Molecular Pharmacology, vol. 21, p. 301 (1982)]. The crude synapse membranes were prepared from freeze preserved rat cerebral cortex, and the membrane specimen and $^3$H-ketanserin were incubated in the presence of the test compounds at 37° C. for 20 min. After the completion of the reaction, the reaction mixture was immediately filtered by suction on Whatman GF/B filter (trademark) and the radioactivity on the filter was measured by Top Count. The non-specific binding was determined in the presence of 10 μM ritanserin. The 50% inhibition concentration ($IC_{50}$) of the test compound was calculated by two-point interpolation, from which inhibitory constant (Ki value) was determined.

Experimental Example 8

Affinity for Adrenalin α1 Receptor; $^3$H-prazosin Binding

Preparation of crude synaptic membranes and a binding test were performed according to European Journal of Pharmacology, vol. 55, p. 323 (1979). The crude synaptic membranes were prepared from freeze preserved rat cerebral tissue, and the membrane specimen and $^3$H-prazosin were incubated in the presence of the test compound at 25° C. for 30 min. After the completion of the reaction, the reaction mixture was immediately filtered by suction on whatman GF/B filter (trademark) and the radioactivity on the filter was measured by Top Count. The non-specific binding was determined in the presence of 100 μM WB4101. The 50% inhibition concentration (IC$_{50}$) of the test compound was calculated by two-point interpolation, from which inhibitory constant (Ki value) was determined.

Experimental Example 9

Affinity for serotonin 1A receptor; $^3$H-8-OH-DPAT Binding

The specific serotonin 1A (5-HT$_{1A}$) receptor binding test was performed according to the method described in J. Neurochem., 44, 1685 (1985). The crude synaptosome fractions were prepared from the hippocampus of 9 to 10-week-old Wistar rats and suspended in 50 mM Tris-hydrochloric acid buffer (pH 7.4) containing 1 mM manganese chloride and used for the test. To the synaptosome suspension were added several concentrations of the test compounds and tritium-labeled 8-hydroxy-2-dipropylaminotetralin (8-OH-DPAT: final concentration 1 nM) and the mixture was reacted at 37° C. for 12 min. After the completion of the reaction, the reaction mixture was immediately filtered by suction on Whatman GF/B filter (trademark), the filter was washed with 50 mM Tris-hydrochloric acid buffer (pH 7.4) and the radioactivity on the filter was measured by Top Count. The non-specific binding was determined in the presence of 1 μM WAY-100635. The 50% inhibition concentration (IC$_{50}$) of the test compound was calculated by two-point interpolation, from which inhibitory constant (Ki value) was determined.

The results of Experimental Examples 6–9 are shown in Table 2. In the Table, * shows IC$_{50}$ value.

TABLE 2

| Example | D$_2$ | 5-HT$_{1A}$ | 5-HT$_2$ | α1 |
|---|---|---|---|---|
| 20 | >1000* | >1000* | >1000* | >1000* |
| 48 | >1000* | >1000* | >1000* | >1000* |
| 51 | >1000* | >1000* | >1000* | >1000* |
| 58 | >1000* | >1000* | >1000* | >1000* |
| 72 | >1000* | >1000* | >1000* | >1000* |
| 81 | >1000* | >1000* | >1000* | >1000* |

Experimental Example 10

Toxicity Test

In a single administration toxicity test, the test compound is administered to male and female SD rats (3 rats/group) and beagle (1 dog/group) and the toxicity by single administration is evaluated using the incidence of death, general condition and body weight as indices. In a repeat administration toxicity test, the test compound is repeatedly administered to male and female SD rats (6 rats/group) and male and female beagles (2 dogs/group) for 2 weeks and the toxicity by repeat administration is evaluated using the general condition, body weight, intake, hematological test, blood biochemiocal test, organ weight and autopsy (inclusive of histopathological test) as indices.

Experimental Example 11

Evaluation of Bioavailability in Rats

The test compound is intravenously and orally administered to SD female rats (5 rats per group). The blood is taken with the lapse of time and the drug concentration in plasma is measured by High Performance Liquid Chromatography. The bioavailability (BA) is calculated by the following formula.

$$\frac{\text{AUC on oral administration}}{\text{AUC on intravenous administration}} \times \frac{\text{dose of intravenous administration}}{\text{dose of oral administration}} \times 100(\%)$$

AUC: area under plasma concentration – time curve

Industrial Applicability

As is evident from the above-mentioned pharmacological experiment and various experiments, since the compound (I) of the present invention and a pharmaceutically acceptable salt thereof are free of or show only strikingly reduced expression of an effect on the central nervous system, they have highly safe and superior TNF-α production inhibitory effect and/or IL-10 production promoting effect, and are useful for the prophylaxis or treatment of various diseases caused by abnormal TNF-α production, diseases curable with IL-10, such as chronic inflammatory diseases, acute inflammatory diseases, inflammatory diseases due to infection, autoimmune diseases, allergic diseases, and TNF-α mediated diseases.

This application is based on application Nos. 280880/1997 and 261100/1998 filed in Japan, the contents of which are incorporated hereinto by reference.

What is claimed is:
1. A piperazine compound of the formula

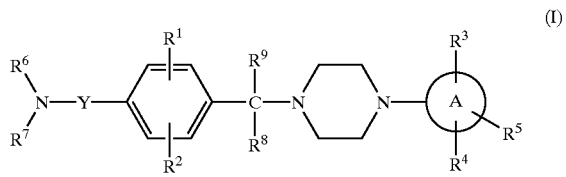

wherein
R$^1$ and R$^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;

R$^3$, R$^4$ and R$^5$ are the same or different and each is hydrogen, halogen, lower alkyl, lower alkoxy, nitro, amino, hydroxy or amino mono- or di-substituted by a group selected from the group consisting of lower alkyl and lower acyl;

R$^6$ and R$^7$ are the same or different and each is hydrogen, lower alkyl, lower alkyl substituted by 1 to 3 halogen(s), aralkyl, acyl or lower acyl substituted by 1 to 3 halogen(s);

R$^8$ and R$^9$ are the same or different and each is hydrogen or lower alkyl;

Y is a group of the formula

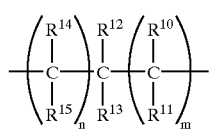

wherein $R^{10}$ and $R^{11}$ are the same or different and each is hydrogen or lower alkyl, $R^{12}$ and $R^{13}$ are the same or different and each is hydrogen or lower alkyl, or $R^{12}$ and $R^{13}$ in combination form alkylene, $R^{14}$ and $R^{15}$ are the same or different and each is hydrogen or lower alkyl, m is an integer of 0–2, n is an integer of 0–2, and 0≦m+n ≦2; and ring A is pyrimidyl, or a pharmaceutically acceptable salt thereof.

2. The piperazine compound of claim 1, wherein $R^3$, $R^4$ and $R^5$ are the same or different and each is hydrogen, halogen or lower alkoxy, or a pharmaceutically acceptable salt thereof.

3. The piperazine compound of claim 1, which has the following formula (I-d)

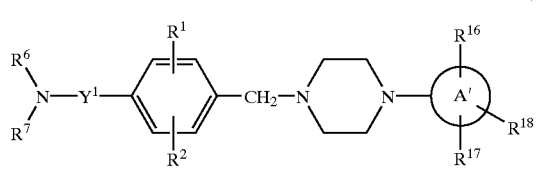

wherein $R^1$ and $R^2$ are the same or different and each is hydrogen, halogen, lower alkyl, lower alkoxy, amino, amino mono-or di-substituted by a group selected from the group consisting of lower alkyl and lower acyl, nitro, hydroxy or cyano;

ring A' is a group of the formula

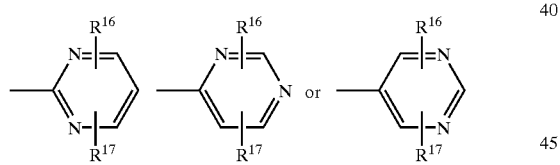

wherein $R^{16}$ and $R^{17}$ are the same or different and each is hydrogen, halogen, lower alkyl, lower alkoxy or amino mono- or di-substituted by a group selected from the group consisting of lower alkyl and lower acyl, and $R^{18}$ is hydrogen or lower alkyl;

$R^6$ and $R^7$ are the same or different and each is hydrogen, lower alkyl, lower alkyl substituted by 1 to 3 halogen(s), aralkyl, acyl or lower acyl substituted by 1 to 3 halogen(s); and $Y^1$ is a group of the formula

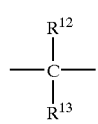

wherein $R^{12}$ and $R^{13}$ are the same or different and each is hydrogen or lower alkyl, or $R^{12}$ and $R^{13}$ in combination form alkylene, or a pharmaceutically acceptable salt thereof.

4. The piperazine compound of claim 1, which has the following formula (I-e)

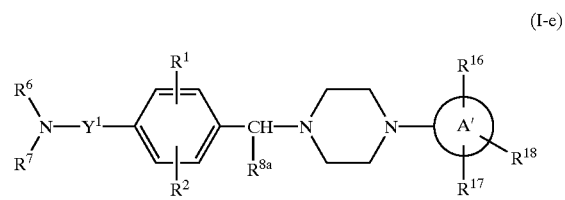

wherein $R^1$ and $R^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;

ring A' is a group of the formula

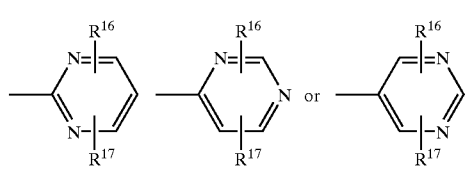

wherein $R^{16}$ and $R^{17}$ are the same or different and each is hydrogen, halogen, lower alkyl, lower alkoxy, amino mono- or di-substituted by a group selected from the gor ip consisting of lower alkyl and lower acyl, and $R^{18}$ is hydrogen or lower alkyl;

$R^6$ and $R^7$ are the same or different and each is hydrogen, lower alkyl, lower alkyl substituted by 1 to 3 halogen(s), aralkyl, acyl or lower acyl substituted by 1 to 3 halogen(s);

$R^{8a}$ is lower alkyl; and $Y^1$ is a group of the formula

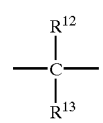

wherein $R^{12}$ and $R^{13}$ are the same or different and each is hydrogen or lower alkyl, or $R1^2$ and $R^{13}$ in combination form alkylene, or a pharmaceutically acceptable salt thereof.

5. The piperazine compound of claim 4, wherein $R^{8a}$ is methyl, or a pharmaceutically acceptable salt thereof.

6. The piperazine compound of claim 1, which has the following formula (I-f)

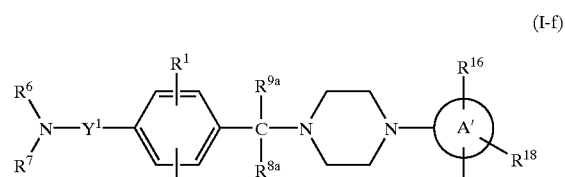

wherein $R^1$ and $R^2$ are the same or different and each is hydrogen, halogen, lower alkyl, lower alkoxy, amino, amino mono- or di-substituted by a group selected from the group consisting of lower alkyl and lower acyl, nitro, hydroxy or cyano;

ring A' is a group of the formula

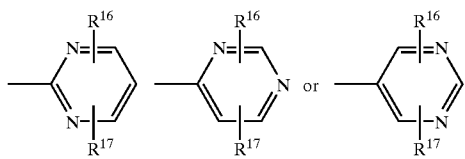

wherein R[16] and R[17] are the same or different and each is hydrogen, halogen, lower alkyl, lower alkoxy or amino mono- or di-substituted by a group selected from the group consisting or lower alkyl and lower acyl, and R[18] is hydrogen or lower alkyl;

R[6] and R[7] are the same or different and each is hydrogen, lower alkyl, lower alkyl substituted by 1 to 3 halogen (s), aralkyl, acyl or lower acyl substituted by 1 to 3 halogen(s);

R[8a] and R[9a] are the same or different and each is lower alkyl; and

Y[1] is a group of the formula

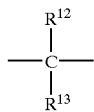

wherein R[12] and R[13] are the same or different and each is hydrogen or lower alkyl, or R[12] and R[13] in combination form alkylene, or a pharmaceutically acceptable salt thereof.

7. The piperazine compound of claim 6, wherein R[8a] and R[9a] are both methyl, or a pharmaceutically acceptable salt thereof.

8. The piperazine compound of any one of claims 3–7, wherein one of R[6] and R[7] is hydrogen and the other is acyl, or a pharmaceutically acceptable salt thereof.

9. The piperazine compound of any one of claims 3–7, wherein R[12] and R[13] are the same or different and each is hydrogen or methyl, or R[12] and R[13] in combination form ethylene, or a pharmaceutically acceptable salt thereof.

10. The piperazine compound of any one of claims 1, 2, and 3, which is a member selected from the group consisting of N-(4-((4-(pyrimidin-2-yl)piperazin-1-yl)methyl) phenylmethyl)-acetamide, N-( 1-(4-((4-(pyrimidin-2-yl)piperazin-1-yl)methyl) phenyl)ethyl)-acetamide, N-(1-(4-((4-(pyrimidin-2-yl)piperazin-1-yl)methyl) phenyl)-cyclopropyl)acetamide, N-(4-((4-(pyrimidin-2-yl)piperazin-1-yl)methyl) phenylmethyl)-formamide, N-(4-((4-(pyrimidin-2-yl)piperazin-1-yl)methyl) phenylmethyl)-propionamide, and N-( 1-(4-(1-(4-(pyrimidin-2-yl)piperazin-1-yl)ethyl)- phenyl)cyclopropyl)acetamide, or a pharmaceutically acceptable salt thereof.

11. N-(1-(4-(1-(4-(pyrimidin-2-yl)piperazin-1-yl) ethyl)- phenyl)cyclopropyl)acetamide, or a pharmaceutically acceptable salt thereof.

12. The piperazine compound of claim 2, wherein one of R[6] and R[7] is hydrogen and the other is acyl, or a pharmaceutically acceptable salt thereof.

13. The piperazine compound of claim 2, wherein R[12] and R[13] are the same or different and each is hydrogen or methyl, or R[12] and R[13] in combination form ethylene, or a pharmaceutically acceptable salt thereof.

14. The piperazine compound of claim 8, wherein R[12] and R[13] are the same or different and each is hydrogen or methyl, or R[12] and R[13] in combination form ethylene, or a pharmaceutically acceptable salt thereof.

15. The piperazine compound of any one of claims 1, 2–7, 11, and 12–14 herein the pharmaceutically acceptable salt is selected from the group consisting of salts of hydrochloric acid, hydrobromic acid, hydroiodic acid, sulfuric acid, nitric acid, phosphoric acid, acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, and 10-camphorsulfonic acid.

16. The piperazine compound of claim 10, wherein the pharmaceutically acceptable salt is selected from the group consisting of salts of hydrochloric acid, hydrobromic acid, hydroiodic acid, sulfuric acid, nitric acid, phosphoric acid, acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, and 10-camphorsulfonic acid.

17. The piperazine compound of claim 11, wherein the pharmaceutically acceptable salt is selected from the group consisting of salts of hydrochloric acid, hydrobromic acid, hydroiodic acid, sulfuric acid, nitric acid, phosphoric acid, acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, and 10-camphorsulfonic acid.

18. The piperazine compound of claim 10, which is N-(1-(4-((4-(pyrimidin-2-yl)piperazin-1-yl)methyl)phenyl) cyclopropyl)acetamide or a pharmaceutically acceptable salt thereof.

19. The piperazine compound of claim 18, wherein the pharmaceutically acceptable salt is a salt of hydrochloric acid.

20. A pharmaceutical composition containing the piperazine compound of any one of claims 1, 2–7, 11, 18, and 19, or a pharmaceutically acceptable salt thereof, as an active ingredient.

21. The piperazine compound of claim 20, wherein the pharmaceutically acceptable salt is selected from the group consisting of salts of hydrochloric acid, hydrobromic acid, hydroiodic acid, sulfuric acid, nitric acid, phosphoric acid, acetic acid, maleic acid, fumaric acid, benzoic acid, citric acid, succinic acid, tartaric acid, malic acid, mandelic acid, methanesulfonic acid, benzenesulfonic acid, p-toluenesulfonic acid, and 10-camphorsulfonic acid.

22. A pharmaceutical composition containing the piperazine compound of claim 10, or a pharmaceutically acceptable salt thereof, as an active ingredient.

* * * * *